US012037604B2

(12) United States Patent
Boyle et al.

(10) Patent No.: US 12,037,604 B2
(45) **Date of Patent: *Jul. 16, 2024**

(54) MODIFIED B CELLS AND METHODS OF USE THEREOF

(71) Applicant: Walking Fish Therapeutics, South San Francisco, CA (US)

(72) Inventors: Kathleen Boyle, South San Francisco, CA (US); Hangil Park, South San Francisco, CA (US); Srinivas Kothakota, South San Francisco, CA (US); Mark Selby, South San Francisco, CA (US); Thomas Brennan, South San Francisco, CA (US); Lewis T. Williams, South San Francisco, CA (US)

(73) Assignee: Walking Fish Therapeutics, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/316,198

(22) Filed: May 11, 2023

(65) Prior Publication Data

US 2024/0034995 A1 Feb. 1, 2024

Related U.S. Application Data

(63) Continuation of application No. 17/465,759, filed on Sep. 2, 2021, which is a continuation of application No. PCT/US2021/025273, filed on Mar. 31, 2021.

(60) Provisional application No. 63/073,799, filed on Sep. 2, 2020, provisional application No. 63/003,120, filed on Mar. 31, 2020.

(51) Int. Cl.

| | |
|---|---|
| ***C12N 5/0781*** | (2010.01) |
| ***A61K 35/17*** | (2015.01) |
| ***C07K 16/30*** | (2006.01) |

(52) U.S. Cl.

CPC ............ *C12N 5/0635* (2013.01); *A61K 35/17* (2013.01); *C07K 16/303* (2013.01); *C07K 16/3069* (2013.01); *C07K 2317/53* (2013.01); *C07K 2317/622* (2013.01); *C07K 2319/03* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 9,175,072 | B2 | 11/2015 | Hyde et al. |
| 9,512,213 | B2 | 12/2016 | Hyde et al. |
| 10,233,424 | B2 | 3/2019 | Hyde et al. |
| 10,597,442 | B2 | 3/2020 | Hyde et al. |
| 10,745,468 | B2 | 8/2020 | Hyde et al. |
| 2006/0165668 | A1 | 7/2006 | Liu et al. |
| 2006/0247191 | A1 | 11/2006 | Finney et al. |
| 2006/0263340 | A1 | 11/2006 | Andrian et al. |
| 2013/0004456 | A1 | 1/2013 | Weinschenk et al. |
| 2016/0158285 | A1 | 6/2016 | Cooper et al. |
| 2016/0289637 | A1 | 10/2016 | Goldberg et al. |
| 2017/0368098 | A1 | 12/2017 | Chen et al. |
| 2018/0002664 | A1 | 1/2018 | Scholz et al. |
| 2019/0218299 | A1 | 7/2019 | Pradines et al. |
| 2019/0321403 | A1 | 10/2019 | Levitsky |
| 2020/0061117 | A1 | 2/2020 | Kitchen et al. |
| 2020/0281973 | A1 | 9/2020 | Dranoff |
| 2021/0077532 | A1 | 3/2021 | Xiao et al. |
| 2021/0161954 | A1 | 6/2021 | Smith et al. |
| 2021/0301024 | A1 | 9/2021 | Yu et al. |
| 2022/0073876 | A1 | 3/2022 | Boyle et al. |
| 2022/0184123 | A1 | 6/2022 | Naso et al. |
| 2022/0275334 | A1 | 9/2022 | Delaney et al. |
| 2022/0372101 | A1 | 11/2022 | Roybal et al. |

FOREIGN PATENT DOCUMENTS

| | | | |
|---|---|---|---|
| WO | WO 02/092792 | A2 | 11/2002 |
| WO | WO 2017/174329 | A1 | 10/2017 |
| WO | WO 2018/140573 | A1 | 8/2018 |
| WO | WO 2018/200585 | A1 | 11/2018 |

OTHER PUBLICATIONS

Marks et al., Retinoic Acid Signaling in B Cells Is Required for the Generation of an Effective T-Independent Immune Response. Front Immunol. Dec. 23, 2016;7:643.

Pesch et al., Molecular Design, Optimization, and Genomic Integration of Chimeric B Cell Receptors in Murine B Cells. Front Immunol. Nov. 14, 2019;10:2630(16 pages).

*Primary Examiner* — Michail A Belyavskyi

(74) *Attorney, Agent, or Firm* — McDermott Will & Emery LLP

(57) ABSTRACT

The present invention relates to genetically modified B cells and their uses thereof, for example, for the treatment of a variety of diseases and disorders, including cancer, heart disease, inflammatory disease, muscle wasting disease, neurological disease, and the like. In certain embodiments, the invention relates to an isolated modified B cell ("CAR-B cell"), capable of expressing a chimeric receptor ("CAR-B receptor"), wherein said chimeric receptor comprises (a) an extracellular domain; (b) a transmembrane domain; and (c) a cytoplasmic domain that comprises at least one signaling domain. In various embodiments, the invention comprises an isolated modified B cell, wherein said B cell is capable of expressing and secreting a payload, wherein the payload is not naturally expressed in a B cell or is expressed at higher levels than is naturally expressed in a B cell. In various embodiments, the payload is an antibody or fragment thereof.

17 Claims, 18 Drawing Sheets

Specification includes a Sequence Listing.

Example of cBCR on cell membrane vH: heavy chain variable region
vL: light chain variable region
H: hinge region
M: transmembrane domain
E: cytoplasmic signaling domain Examples of cBCR (chimeric B cell receptor)

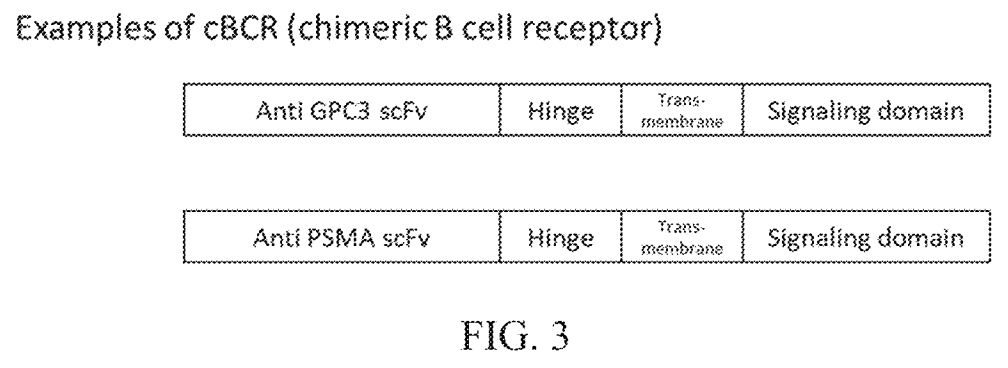

| Anti GPC3 scFv | Hinge | Trans-membrane | Signaling domain |
|---|---|---|---|

| Anti PSMA scFv | Hinge | Trans-membrane | Signaling domain |
|---|---|---|---|

FIG. 3

| | Sample Name | Geometric Mean : BL1-H |
|---|---|---|
| | No-PSMA Control.fcs | 97.5 |
| | With PSMA Control.fcs | 102 |
| | 82.fcs | 246 |
| | 83.fcs | 240 |
| | 84.fcs | 347 |
| | 85.fcs | 422 |
| | 86.fcs | 119 |
| | 87.fcs | 126 |
| | 88.fcs | 251 |
| | 89.fcs | 176 |

| | Sample Name | Subset Name | Count |
|---|---|---|---|
| | 0.fcs | CD19-Brilliant Violet 421-H+ | 32219 |
| | 1.fcs | CD19-Brilliant Violet 421-H+ | 17032 |
| | 3.fcs | CD19-Brilliant Violet 421-H+ | 12890 |
| | 10.fcs | CD19-Brilliant Violet 421-H+ | 4620 |

| pWF-506 | pmRNA_d7_13_anti-hGPC3 scFv-hIgG1 Fc [TM + cyto] A-1 |
|---|---|
| pWF-507 | pmRNA_d7_13_anti-hGPC3 vl-hcLambda G-1 |
| pWF-508 | pmRNA_d7_13_anti-hGPC3 vH-hIgHg1 [TM + cyto] H-3 |
| pWF-509 | pmRNA_d7_13_anti-hGPC3 scFv-hCD8H-hCD28M-hCD79bE P-1 |
| pWF-510 | pmRNA_d7_13_anti-hGPC3 scFv-hCD8H-hCD28M-hCD79aE O-3 |

SEQUENCE LISTING

```
Sequence total quantity: 150
SEQ ID NO: 1            moltype = DNA  length = 81
FEATURE                 Location/Qualifiers
source                  1..81
                        mol_type = unassigned DNA
                        organism = Mus musculus
SEQUENCE: 1
ttctgggccc ttgtggtggt tgccggagtg ctgttttgct atgggctcct ggttaccgtt  60
gccctttgtg tgatttggac c                                            81

SEQ ID NO: 2            moltype = AA  length = 27
FEATURE                 Location/Qualifiers
source                  1..27
                        mol_type = protein
                        organism = Mus musculus
SEQUENCE: 2
FWALVVVAGV LFCYGLLVTV ALCVIWT                                      27

SEQ ID NO: 3            moltype = DNA  length = 81
FEATURE                 Location/Qualifiers
source                  1..81
                        mol_type = unassigned DNA
                        organism = Homo sapiens
SEQUENCE: 3
ttttgggtat tggtagtggt gggcggagtt ttagcctgct acagcctcct ggtaacagtg  60
gcttttatca tcttttgggt g                                            81

SEQ ID NO: 4            moltype = AA  length = 27
FEATURE                 Location/Qualifiers
source                  1..27
                        mol_type = protein
                        organism = Homo sapiens
SEQUENCE: 4
```

```
FWVLVVVGGV LACYSLLVTV AFIIFWV                                27

SEQ ID NO: 5            moltype = DNA  length = 729
FEATURE                 Location/Qualifiers
source                  1..729
                        mol_type = unassigned DNA
                        organism = Homo sapiens
SEQUENCE: 5
cagcgggctt tagtcttgcg gcgtaaacgt aaaagaatga cagatccaac tcgcaggttc  60
ttcaaagtga cccccccacc tgggtccgga ccgcagaacc aatatgggaa tgtcctgtct  120
ctgcctacgc ctacaagtgg actgggtagg gctcagaggt gggctgccgg tctcggcgga  180
actgcgccat cttacggaaa tccctcctcc gacgttcagg cagacggggc cctggggtct  240
cgatccccgc ctggtgttgg accagaagag gaagagggcg agggctacga agagcccgac  300
tccgaagagg acagtgagtt ttacgagaac gacagcaacc tggggcagga tcagctgtca  360
caggatggct caggatatga aaaccctgag gacgagcctt tggggcctga agatgaggac  420
tccttttcta atgcagagtc atatgagaat gaggacgaag aattgactca acccgtggca  480
agaacaatgg atttcctcag tccacacggg agtgcatggg acccctccag agaggctact  540
agcctcggtt ctcaaagcta tgaggacatg aggggtattc tgtacgcagc gcctcagttg  600
aggtccatcc gcggccagcc aggcccaaac catgaggaag atgccgattc ttacgaaaac  660
atggacaacc ccgatggtcc tgaccccgca tggggggggcg gcgggaggat gggcacctgg  720
tctactcgc                                                    729

SEQ ID NO: 6            moltype = AA  length = 243
FEATURE                 Location/Qualifiers
source                  1..243
                        mol_type = protein
                        organism = Homo sapiens
SEQUENCE: 6
QRALVLRRKR KRMTDPTRRF FKVTPPPGSG PQNQYGNVLS LPTPTSGLGR AQRWAAGLGG  60
TAPSYGNPSS DVQADGALGS RSPPGVGPEE EEGEGYEEPD SEEDSEFYEN DSNLGQDQLS  120
QDGSGYENPE DEPLGPEDED SFSNAESYEN EDEELTQPVA RTMDFLSPHG SAWDPSREAT  180
SLGSQSYEDM RGILYAAPQL RSIRGQPGPN HEEDADSYEN MDNPDGPDPA WGGGGRMGTW  240
STR                                                          243

SEQ ID NO: 7            moltype = DNA  length = 186
FEATURE                 Location/Qualifiers
source                  1..186
                        mol_type = unassigned DNA
                        organism = Homo sapiens
SEQUENCE: 7
aagaaggttg caaaaaaacc tactaataag gctccccatc ctaagcaaga gccccaagaa  60
attaactttc ccgatgatct tccgggttct aacacggcag ccccggtgca ggagaccctg  120
catggttgtc aacccgtcac tcaggaggac gggaaagagt ctcgtatctc cgtccaggag  180
agacag                                                       186

SEQ ID NO: 8            moltype = AA  length = 62
FEATURE                 Location/Qualifiers
source                  1..62
                        mol_type = protein
                        organism = Homo sapiens
SEQUENCE: 8
KKVAKKPTNK APHPKQEPQE INFPDDLPGS NTAAPVQETL HGCQPVTQED GKESRISVQE  60
RQ                                                           62

SEQ ID NO: 9            moltype = DNA  length = 330
FEATURE                 Location/Qualifiers
source                  1..330
                        mol_type = unassigned DNA
                        organism = Homo sapiens
SEQUENCE: 9
aagaaggttg caaaaaaacc tactaataag gctccccatc ctaagcaaga gccccaagaa  60
attaactttc ccgatgatct tccgggttct aacacggcag ccccggtgca ggagaccctg  120
catggttgtc aacccgtcac tcaggaggac gggaaagagt ctcgtatctc cgtccaggag  180
agacaggaca aggacgatag taaagcaggg atggaggagg accatacata cgagggactg  240
gatatcgatc agacagccac gtacgaagac attgtgacac tgagaactgg cgaggtgaag  300
tggtcagtgg gagaacatcc ggggcaggaa                             330

SEQ ID NO: 10           moltype = AA  length = 110
FEATURE                 Location/Qualifiers
source                  1..110
                        mol_type = protein
                        organism = Homo sapiens
SEQUENCE: 10
KKVAKKPTNK APHPKQEPQE INFPDDLPGS NTAAPVQETL HGCQPVTQED GKESRISVQE  60
RQDKDDSKAG MEEDHTYEGL DIDQTATYED IVTLRTGEVK WSVGEHPGQE            110

SEQ ID NO: 11           moltype = DNA  length = 312
FEATURE                 Location/Qualifiers
source                  1..312
```

```
                        mol_type = unassigned DNA
                        organism = Homo sapiens
SEQUENCE: 11
aagaaggttg caaaaaaacc tactaataag gctccccatc ctaagcaaga gccccaagaa  60
attaactttc ccgatgatct tccgggttct aacacggcag ccccggtgca ggagaccctg  120
catggttgtc aacccgtcac tcaggaggac gggaaagagt ctcgtatctc cgtccaggag  180
agacagaaaa gaggccgaaa aaagctgctg tacatcttca aacaaccctt catgcgacct  240
gttcagacga cacaggagga ggacggctgc agctgtaggt ttcccgaaga agaggaggga  300
ggatgcgaac tt                                                      312

SEQ ID NO: 12           moltype = AA  length = 104
FEATURE                 Location/Qualifiers
source                  1..104
                        mol_type = protein
                        organism = Homo sapiens
SEQUENCE: 12
KKVAKKPTNK APHPKQEPQE INFPDDLPGS NTAAPVQETL HGCQPVTQED GKESRISVQE  60
RQKRGRKKLL YIFKQPFMRP VQTTQEEDGC SCRFPEEEEG GCEL                   104

SEQ ID NO: 13           moltype = DNA  length = 126
FEATURE                 Location/Qualifiers
source                  1..126
                        mol_type = unassigned DNA
                        organism = Homo sapiens
SEQUENCE: 13
aaaagaggcc gaaaaaagct gctgtacatc ttcaaacaac ccttcatgcg acctgttcag  60
acgacacagg aggaggacgg ctgcagctgt aggtttcccg aagaagagga gggaggatgc  120
gaactt                                                             126

SEQ ID NO: 14           moltype = AA  length = 42
FEATURE                 Location/Qualifiers
source                  1..42
                        mol_type = protein
                        organism = Homo sapiens
SEQUENCE: 14
KRGRKKLLYI FKQPFMRPVQ TTQEEDGCSC RFPEEEEGGC EL                     42

SEQ ID NO: 15           moltype = DNA  length = 414
FEATURE                 Location/Qualifiers
source                  1..414
                        mol_type = unassigned DNA
                        organism = Homo sapiens
SEQUENCE: 15
aagaaggttg caaaaaaacc tactaataag gctccccatc ctaagcaaga gccccaagaa  60
attaactttc ccgatgatct tccgggttct aacacggcag ccccggtgca ggagaccctg  120
catggttgtc aacccgtcac tcaggaggac gggaaagagt ctcgtatctc cgtccaggag  180
agacagcgca aaaaacgtat aagcgcaaac tctacagatc cagtaaaagc cgcgcaattc  240
gagcctcccg gccgccagat gattgcaata cggaaacgtc aactggagga aactaataat  300
gactatgaga cggccgacgg tggatacatg acccttaatc cccgcgcgcc aaccgacgat  360
gataagaaca tatatctgac gctccccct aacgatcacg ttaacagtaa taat        414

SEQ ID NO: 16           moltype = AA  length = 138
FEATURE                 Location/Qualifiers
source                  1..138
                        mol_type = protein
                        organism = Homo sapiens
SEQUENCE: 16
KKVAKKPTNK APHPKQEPQE INFPDDLPGS NTAAPVQETL HGCQPVTQED GKESRISVQE  60
RQRKKRISAN STDPVKAAQF EPPGRQMIAI RKRQLEETNN DYETADGGYM TLNPRAPTDD  120
DKNIYLTLPP NDHVNSNN                                                138

SEQ ID NO: 17           moltype = DNA  length = 228
FEATURE                 Location/Qualifiers
source                  1..228
                        mol_type = unassigned DNA
                        organism = Homo sapiens
SEQUENCE: 17
cgcaaaaaac gtataagcgc aaactctaca gatccagtaa aagccgcgca attcgagcct  60
cccggccgcc agatgattgc aatacggaaa cgtcaactgg aggaaactaa taatgactat  120
gagacggccg acggtggata catgaccctt aatccccgcg cgccaaccga cgatgataag  180
aacatatatc tgacgctccc ccctaacgat cacgttaaca gtaataat               228

SEQ ID NO: 18           moltype = AA  length = 76
FEATURE                 Location/Qualifiers
source                  1..76
                        mol_type = protein
                        organism = Homo sapiens
SEQUENCE: 18
RKKRISANST DPVKAAQFEP PGRQMIAIRK RQLEETNNDY ETADGGYMTL NPRAPTDDDK  60
```

```
NIYLTLPPND HVNSNN                                          76

SEQ ID NO: 19          moltype = DNA  length = 681
FEATURE                Location/Qualifiers
source                 1..681
                       mol_type = unassigned DNA
                       organism = Homo sapiens
SEQUENCE: 19
atggcggcgg gcgggcccgg cgccggaagc gccgcgccag tctcatctac gtccagtctg  60
ccactggctg ccctgaacat gagagtgaga cgccgtttat ccctcttcct gaatgtgcgg  120
acccaggtcg ccgctgattg gaccgccctg gccgaagaga tggactttga atacttggaa  180
atcagacagc tggaaacaca ggcagaccca accgggagac tgcttgacgc ctggcaggga  240
cgcccagggg caagtgttgg tcggttactg gagcttttaa ctaagttggg ccgcgatgac  300
gtgctgttgg agttaggacc cagtatcgag gaggattgtc agaaatacat cttgaaacag  360
cagcaggagg aggcggaaaa gcccctgcag gtggcggccg ttgacagcag tgtacccaga  420
acagctgagc tggccggcat cacaaccctg gatgatcccc tgggccacat gcctgagagg  480
ttcgacgctt tcataaagaa ggttgcaaaa aaacctacta ataaggctcc ccatcctaag  540
caagagcccc aagaaattaa ctttcccgat gatcttccgg gttctaacac ggcagccccg  600
gtgcaggaga ccctgcatgg ttgtcaaccc gtcactcagg aggacgggaa agagtctcgt  660
atctccgtcc aggagagaca g                                          681

SEQ ID NO: 20          moltype = AA  length = 227
FEATURE                Location/Qualifiers
source                 1..227
                       mol_type = protein
                       organism = Homo sapiens
SEQUENCE: 20
MAAGGPGAGS AAPVSSTSSL PLAALNMRVR RRLSLFLNVR TQVAADWTAL AEEMDFEYLE  60
IRQLETQADP TGRLLDAWQG RPGASVGRLL ELLTKLGRDD VLLELGPSIE EDCQKYILKQ  120
QQEEAEKPLQ VAAVDSSVPR TAELAGITTL DDPLGHMPER FDAFIKKVAK KPTNKAPHPK  180
QEPQEINFPD DLPGSNTAAP VQETLHGCQP VTQEDGKESR ISVQERQ             227

SEQ ID NO: 21          moltype = DNA  length = 495
FEATURE                Location/Qualifiers
source                 1..495
                       mol_type = unassigned DNA
                       organism = Homo sapiens
SEQUENCE: 21
atggcggcgg gcgggcccgg cgccggaagc gccgcgccag tctcatctac gtccagtctg  60
ccactggctg ccctgaacat gagagtgaga cgccgtttat ccctcttcct gaatgtgcgg  120
acccaggtcg ccgctgattg gaccgccctg gccgaagaga tggactttga atacttggaa  180
atcagacagc tggaaacaca ggcagaccca accgggagac tgcttgacgc ctggcaggga  240
cgcccagggg caagtgttgg tcggttactg gagcttttaa ctaagttggg ccgcgatgac  300
gtgctgttgg agttaggacc cagtatcgag gaggattgtc agaaatacat cttgaaacag  360
cagcaggagg aggcggaaaa gcccctgcag gtggcggccg ttgacagcag tgtacccaga  420
acagctgagc tggccggcat cacaaccctg gatgatcccc tgggccacat gcctgagagg  480
ttcgacgctt tcata                                                 495

SEQ ID NO: 22          moltype = AA  length = 165
FEATURE                Location/Qualifiers
source                 1..165
                       mol_type = protein
                       organism = Homo sapiens
SEQUENCE: 22
MAAGGPGAGS AAPVSSTSSL PLAALNMRVR RRLSLFLNVR TQVAADWTAL AEEMDFEYLE  60
IRQLETQADP TGRLLDAWQG RPGASVGRLL ELLTKLGRDD VLLELGPSIE EDCQKYILKQ  120
QQEEAEKPLQ VAAVDSSVPR TAELAGITTL DDPLGHMPER FDAFI                165

SEQ ID NO: 23          moltype = DNA  length = 183
FEATURE                Location/Qualifiers
source                 1..183
                       mol_type = unassigned DNA
                       organism = Homo sapiens
SEQUENCE: 23
aggaaacgat ggcagaacga gaagctcggg ttggatgccg gggatgaata tgaagatgaa  60
aacctttatg aaggcctgaa cctggacgac tgctccatgt atgaggacat ctcccggggc  120
ctccagggca cctaccagga tgtgggcagc ctcaacatag gagatgtcca gctggagaag  180
ccg                                                              183

SEQ ID NO: 24          moltype = AA  length = 61
FEATURE                Location/Qualifiers
source                 1..61
                       mol_type = protein
                       organism = Homo sapiens
SEQUENCE: 24
RKRWQNEKLG LDAGDEYEDE NLYEGLNLDD CSMYEDISRG LQGTYQDVGS LNIGDVQLEK  60
P                                                                61

SEQ ID NO: 25          moltype = DNA  length = 147
```

```
FEATURE                Location/Qualifiers
source                 1..147
                       mol_type = unassigned DNA
                       organism = Homo sapiens
SEQUENCE: 25
ctggacaagg atgacagcaa ggctggcatg gaggaagatc acacctacga gggcctggac  60
attgaccaga cagccaccta tgaggacata gtgacgctgc ggacagggga agtgaagtgg  120
tctgtaggtg agcacccagg ccaggag                                      147

SEQ ID NO: 26          moltype = AA  length = 49
FEATURE                Location/Qualifiers
source                 1..49
                       mol_type = protein
                       organism = Homo sapiens
SEQUENCE: 26
LDKDDSKAGM EEDHTYEGLD IDQTATYEDI VTLRTGEVKW SVGEHPGQE             49

SEQ ID NO: 27          moltype = DNA  length = 165
FEATURE                Location/Qualifiers
source                 1..165
                       mol_type = unassigned DNA
                       organism = Homo sapiens
SEQUENCE: 27
ttcgtgcctg tgttcctccc agctaagccc actaccaccc ccgctccaag gccgcccacg  60
cccgctccta ctattgctag tcagccttta agtttacgac ccgaagcttg caggcccgcc  120
gccggcggcg ctgtgcacac caggggggctt gatttgcct gcgac                   165

SEQ ID NO: 28          moltype = AA  length = 55
FEATURE                Location/Qualifiers
source                 1..55
                       mol_type = protein
                       organism = Homo sapiens
SEQUENCE: 28
FVPVFLPAKP TTTPAPRPPT PAPTIASQPL SLRPEACRPA AGGAVHTRGL DFACD       55

SEQ ID NO: 29          moltype = DNA  length = 189
FEATURE                Location/Qualifiers
misc_feature           1..189
                       note = Synthetic
source                 1..189
                       mol_type = other DNA
                       organism = synthetic construct
SEQUENCE: 29
ggcgctggta gtggcggtaa ctggagccac cctcaatttg agaagggcgg gtcaggcgga  60
tcaggtggta gtggtgggtc caactggagc catccgcaat ttgaaaaggg cggaagcggc  120
ggttccggcg gttcaggcgg tagcaactgg tcacatccgc aatttgagaa aggcgggtca  180
ggcggcggg                                                          189

SEQ ID NO: 30          moltype = AA  length = 63
FEATURE                Location/Qualifiers
REGION                 1..63
                       note = Synthetic
source                 1..63
                       mol_type = protein
                       organism = synthetic construct
SEQUENCE: 30
GAGSGGNWSH PQFEKGGSGG SGGSGGSNWS HPQFEKGGSG GSGGSGGSNW SHPQFEKGGS  60
GGG                                                                63

SEQ ID NO: 31          moltype = DNA  length = 903
FEATURE                Location/Qualifiers
source                 1..903
                       mol_type = unassigned DNA
                       organism = Homo sapiens
SEQUENCE: 31
cccaagagct gcgacaagac ccacacctgc ccccccctgcc cagccccaga gctgctgggc  60
ggaccctccg tgttcctgtt cccccccaag cccaaggaca ccctgatgat cagcaggacc  120
cccgaggtga cctgcgtggt ggtggacgtg agccacgagg acccagaggt gaagttcaac  180
tggtacgtgg acggcgtgga ggtgcacaac gccaagacca agcccagaga ggagcagtac  240
aacagcacct acagggtggt gtccgtgctg accgtgctgc accaggactg gctgaacggc  300
aaggaataca agtgcaaggt ctccaacaag gccctgccag cccccatcga aaagaccatc  360
agcaaggcca agggccagcc acgggagccc caggtgtaca ccctgccccc ctcccgggag  420
gagatgacca agaaccaggt gtccctgacc tgtctggtga agggcttcta ccccagcgac  480
atcgccgtgg agtgggagag caacggccag cccgagaaca actacaagac caccccccca  540
gtgctggaca gcgacggcag cttcttcctg tacagcaagc tgaccgtgga caagtccagg  600
tggcagcagg gcaacgtgtt cagctgcagc gtgatgcacg aggccctgca caaccactac  660
acccagaaga gcctgagcct gtcccccgag ctgcaactgg aggagagctg tgcggaggcg  720
caggacgggg agctggacgg gctgtggacg accatcacca tcttcatcac actcttcctg  780
ttaagcgtgt gctacagtgc caccgtcacc ttcttcaagg tgaagtggat cttctcctcg  840
```

```
gtggtggacc tgaagcagac catcatcccc gactacagga acatgatcgg acagggggcc  900
tga                                                                903

SEQ ID NO: 32          moltype = AA  length = 300
FEATURE                Location/Qualifiers
source                 1..300
                       mol_type = protein
                       organism = Homo sapiens
SEQUENCE: 32
PKSCDKTHTC PPCPAPELLG GPSVFLFPPK PKDTLMISRT PEVTCVVVDV SHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPE LQLEESCAEA  240
QDGELDGLWT TITIFITLFL LSVCYSATVT FFKVKWIFSS VVDLKQTIIP DYRNMIGQGA  300

SEQ ID NO: 33          moltype = DNA  length = 726
FEATURE                Location/Qualifiers
misc_feature           1..726
                       note = Synthetic
source                 1..726
                       mol_type = other DNA
                       organism = synthetic construct
SEQUENCE: 33
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca aggactcttt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaa                                                             726

SEQ ID NO: 34          moltype = AA  length = 242
FEATURE                Location/Qualifiers
REGION                 1..242
                       note = Synthetic
source                 1..242
                       mol_type = protein
                       organism = synthetic construct
SEQUENCE: 34
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IK                                                                 242

SEQ ID NO: 35          moltype = DNA  length = 735
FEATURE                Location/Qualifiers
misc_feature           1..735
                       note = Synthetic
source                 1..735
                       mol_type = other DNA
                       organism = synthetic construct
SEQUENCE: 35
gaagtccaat tggttgaaag cggtggtgga ctcgtcaaac ctggcggtag ccttaaactt  60
tcatgtgccg caagcggctt cacgtttagt aactatgcta tgagttgggt ccgccaaagt  120
ccagaaaagc gcctcgaatg ggtggcggag atctctggag gaggaacata tacatattat  180
ccagacacca tgaccggtag gtttacaatc tcaagagaca acgctaagaa caccctgtac  240
ctggaaatgt caagcctgag atcagaagat acggccatgt attattgtac gcgcctactc  300
gactattggg gtcaaggaac ttccgtgacg gtgtcaagcg gaggaggtgg gagcggagga  360
ggcggaagtg gcggtggtgg ctctggtggc ggtggaagtg atatagtgat gacgcaagct  420
gccttttcaa accctgttac tttggggact agcgcatcaa tctcctgtag gtccagcaaa  480
tctttgctgc acagtaatgg aatcacctat cttttctggt atttgcaaaa gcctgggcag  540
agcccgcaac tgctgatcta tcaaatgtca aatcttgctt ccggagttcc agaccgcttc  600
tcaagttccg ggtccggcac tgattttacc ttgagaattt ctagggtcga agctgaagac  660
gtcggtgtct attattgcgc gcaaaacctt gagcttccat acaccttcgg ggggggcaca  720
aaacttgaga tcaag                                                   735

SEQ ID NO: 36          moltype = AA  length = 245
FEATURE                Location/Qualifiers
REGION                 1..245
                       note = Synthetic
source                 1..245
                       mol_type = protein
```

```
                          organism = synthetic construct
SEQUENCE: 36
EVQLVESGGG LVKPGGSLKL SCAASGFTFS NYAMSWVRQS PEKRLEWVAE ISGGGTYTYY  60
PDTMTGRFTI SRDNAKNTLY LEMSSLRSED TAMYYCTRLL DYWGQGTSVT VSSGGGGSGG  120
GGSGGGGSGG GGSDIVMTQA AFSNPVTLGT SASISCRSSK SLLHSNGITY LFWYLQKPGQ  180
SPQLLIYQMS NLASGVPDRF SSSGSGTDFT LRISRVEAED VGVYYCAQNL ELPYTFGGGT  240
KLEIK                                                              245

SEQ ID NO: 37             moltype = DNA  length = 759
FEATURE                   Location/Qualifiers
misc_feature              1..759
                          note = Synthetic
source                    1..759
                          mol_type = other DNA
                          organism = synthetic construct
SEQUENCE: 37
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggttctagag gtggtggtgg tagcggcggc  360
ggcggctctg gtggtggtgg atccctcgag atggcccagg tgcagctggt ggagtctggg  420
ggaggcttgg tacagcctgg ggggtccctg agactctcct gtgcagcctc tggattcacc  480
tttagcagct atgccatgag ctgggtccgc caggctccag ggaaggggct ggagtgggtc  540
tcagttattt atagcggtgg tagtagcaca tactatgcag actccgtgaa gggccggttc  600
accatctcca gagataattc caagaacacg ctgtatctgc aaatgaacag cctgagagcc  660
gaggacacgg ccgtatatta ctgtgcgcgc acttcttacc tgaaccatgg tgattactgg  720
ggtcaaggta ctctggtgac cgtgtctagc gccgctgca                         759

SEQ ID NO: 38             moltype = AA  length = 253
FEATURE                   Location/Qualifiers
REGION                    1..253
                          note = Synthetic
source                    1..253
                          mol_type = protein
                          organism = synthetic construct
SEQUENCE: 38
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GSRGGGGSGG  120
GGSGGGGSLE MAQVQLVESG GGLVQPGGSL RLSCAASGFT FSSYAMSWVR QAPGKGLEWV  180
SVIYSGGSST YYADSVKGRF TISRDNSKNT LYLQMNSLRA EDTAVYYCAR TSYLNHGDYW  240
GQGTLVTVSS AAA                                                     253

SEQ ID NO: 39             moltype = DNA  length = 1704
FEATURE                   Location/Qualifiers
misc_feature              1..1704
                          note = Synthetic
source                    1..1704
                          mol_type = other DNA
                          organism = synthetic construct
SEQUENCE: 39
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgcagcgggc tttagtcttg cggcgtaaac gtaaaagaat gacagatcca  1020
actcgcaggt tcttcaaagt gacccccccca cctgggtccg gaccgcagaa ccaatatggg  1080
aatgtcctgt ctctgcctac gcctacaagt ggactgggta gggctcagag gtgggctgcc  1140
ggtctcggcg gaactgcgcc atcttacgga aatccctcct ccgacgttca ggcagacggg  1200
gccctggggt ctcgatcccc gcctggtgtt ggaccagaag aggaagaggg cgagggctac  1260
gaagagcccg actccgaaga ggacagtgag ttttacgaga acgacagcaa cctggggcag  1320
gatcagctgt cacaggatgg ctcaggatat gaaaaccctg aggacgagcc tttggggcct  1380
gaagatgagg actccttttc taatgcagag tcatatgaga atgaggacga agaattgact  1440
caacccgtgg caagaacaat ggatttcctc agtccacacg ggagtgcatg ggacccctcc  1500
agagaggcta ctagcctcgg ttctcaaagc tatgaggaca tgaggggtat tctgtacgca  1560
gcgcctcagt tgaggtccat ccgcggccag ccaggcccaa accatgagga agatgccgat  1620
```

```
tcttacgaaa acatggacaa ccccgatggt cctgaccccg catggggggg cggcgggagg  1680
atgggcacct ggtctactcg ctag                                         1704

SEQ ID NO: 40          moltype = AA  length = 567
FEATURE                Location/Qualifiers
REGION                 1..567
                       note = Synthetic
source                 1..567
                       mol_type = protein
                       organism = synthetic construct
SEQUENCE: 40
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVQRALVL RRKRKRMTDP TRRFFKVTPP PGSGPQNQYG  360
NVLSLPTPTS GLGRAQRWAA GLGGTAPSYG NPSSDVQADG ALGSRSPPGV GPEEEEGEGY  420
EEPDSEEDSE FYENDSNLGQ DQLSQDGSGY ENPEDEPLGP EDEDSFSNAE SYENEDEELT  480
QPVARTMDFL SPHGSAWDPS REATSLGSQS YEDMRGILYA APQLRSIRGQ PGPNHEEDAD  540
SYENMDNPDG PDPAWGGGGR MGTWSTR                                      567

SEQ ID NO: 41          moltype = DNA  length = 1122
FEATURE                Location/Qualifiers
misc_feature           1..1122
                       note = Synthetic
source                 1..1122
                       mol_type = other DNA
                       organism = synthetic construct
SEQUENCE: 41
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgctggacaa ggatgacagc aaggctggca tggaggaaga tcacacctac  1020
gagggcctgg acattgacca gacagccacc tatgaggaca tagtgacgct gcggacaggg  1080
gaagtgaagt ggtctgtagg tgagcaccca ggccaggagt ga                     1122

SEQ ID NO: 42          moltype = AA  length = 373
FEATURE                Location/Qualifiers
REGION                 1..373
                       note = Synthetic
source                 1..373
                       mol_type = protein
                       organism = synthetic construct
SEQUENCE: 42
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVLDKDDS KAGMEEDHTY EGLDIDQTAT YEDIVTLRTG  360
EVKWSVGEHP GQE                                                     373

SEQ ID NO: 43          moltype = DNA  length = 1305
FEATURE                Location/Qualifiers
misc_feature           1..1305
                       note = Synthetic
source                 1..1305
                       mol_type = other DNA
                       organism = synthetic construct
SEQUENCE: 43
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
```

```
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgaagaaggt tgcaaaaaaa cctactaata aggctcccca tcctaagcaa  1020
gagccccaag aaattaactt tcccgatgat cttccgggtt ctaacacggc agccccggtg  1080
caggagaccc tgcatggttg tcaacccgtc actcaggagg acgggaaaga gtctcgtatc  1140
tccgtccagg agagacagga caaggacgat agtaaagcag ggatggagga ggaccataca  1200
tacgagggac tggatatcga tcagacagcc acgtacgaag acattgtgac actgagaact  1260
ggcgaggtga agtggtcagt gggagaacat ccggggcagg aataa                  1305

SEQ ID NO: 44          moltype = AA  length = 434
FEATURE                Location/Qualifiers
REGION                 1..434
                       note = Synthetic
source                 1..434
                       mol_type = protein
                       organism = synthetic construct
SEQUENCE: 44
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVKKVAKK PTNKAPHPKQ EPQEINFPDD LPGSNTAAPV  360
QETLHGCQPV TQEDGKESRI SVQERQDKDD SKAGMEEDHT YEGLDIDQTA TYEDIVTLRT  420
GEVKWSVGEH PGQE                                                    434

SEQ ID NO: 45          moltype = DNA  length = 1287
FEATURE                Location/Qualifiers
misc_feature           1..1287
                       note = Synthetic
source                 1..1287
                       mol_type = other DNA
                       organism = synthetic construct
SEQUENCE: 45
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgaagaaggt tgcaaaaaaa cctactaata aggctcccca tcctaagcaa  1020
gagccccaag aaattaactt tcccgatgat cttccgggtt ctaacacggc agccccggtg  1080
caggagaccc tgcatggttg tcaacccgtc actcaggagg acgggaaaga gtctcgtatc  1140
tccgtccagg agagacagaa aagaggccga aaaaagctgc tgtacatctt caaacaaccc  1200
ttcatgcgac ctgttcagac gacacaggag gaggacggct gcagctgtag gtttcccgaa  1260
gaagaggagg gaggatgcga actttaa                                      1287

SEQ ID NO: 46          moltype = AA  length = 428
FEATURE                Location/Qualifiers
REGION                 1..428
                       note = Synthetic
source                 1..428
                       mol_type = protein
                       organism = synthetic construct
SEQUENCE: 46
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
```

```
LVVVGGVLAC YSLLVTVAFI IFWVKKVAKK PTNKAPHPKQ EPQEINFPDD LPGSNTAAPV  360
QETLHGCQPV TQEDGKESRI SVQERQKRGR KKLLYIFKQP FMRPVQTTQE EDGCSCRFPE  420
EEEGGCEL                                                          428

SEQ ID NO: 47          moltype = AA  length = 462
FEATURE                Location/Qualifiers
REGION                 1..462
                       note = Synthetic
source                 1..462
                       mol_type = protein
                       organism = synthetic construct
SEQUENCE: 47
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVKKVAKK PTNKAPHPKQ EPQEINFPDD LPGSNTAAPV  360
QETLHGCQPV TQEDGKESRI SVQERQRKKR ISANSTDPVK AAQFEPPGRQ MIAIRKRQLE  420
ETNNDYETAD GGYMTLNPRA PTDDDKNIYL TLPPNDHVNS NN                    462

SEQ ID NO: 48          moltype = DNA  length = 1656
FEATURE                Location/Qualifiers
misc_feature           1..1656
                       note = Synthetic
source                 1..1656
                       mol_type = other DNA
                       organism = synthetic construct
SEQUENCE: 48
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgatggcggc gggcgggccc ggcgccggaa gcgccgcgcc agtctcatct  1020
acgtccagtc tgccactggc tgccctgaac atgagagtga gacgccgttt atccctcttc  1080
ctgaatgtgc ggacccaggt cgccgctgat tggaccgccc tggccgaaga gatggacttt  1140
gaatacttgg aaatcagaca gctggaaaca caggcagacc caaccgggag actgcttgac  1200
gcctggcagg gacgcccagg ggcaagtgtt ggtcggttac tggagctttt aactaagttg  1260
ggccgcgatg acgtgctgtt ggagttagga cccagtatcg aggaggattg tcagaaatac  1320
atcttgaaac agcagcagga ggaggcggaa aagcccctgc aggtggcggc cgttgacagc  1380
agtgtaccca gaacagctga gctggccggc atcacaaccc tggatgatcc cctgggccac  1440
atgcctgaga ggttcgacgc tttcataaag aaggttgcaa aaaaacctac taataaggct  1500
ccccatccta agcaagagcc ccaagaaatt aactttcccg atgatcttcc gggttctaac  1560
acggcagccc cggtgcagga gaccctgcat ggttgtcaac ccgtcactca ggaggacggg  1620
aaagagtctc gtatctccgt ccaggagaga cagtga                            1656

SEQ ID NO: 49          moltype = AA  length = 551
FEATURE                Location/Qualifiers
REGION                 1..551
                       note = Synthetic
source                 1..551
                       mol_type = protein
                       organism = synthetic construct
SEQUENCE: 49
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVMAAGGP GAGSAAPVSS TSSLPLAALN MRVRRRLSLF  360
LNVRTQVAAD WTALAEEMDF EYLEIRQLET QADPTGRLLD AWQGRPGASV GRLLELLTKL  420
GRDDVLLELG PSIEEDCQKY ILKQQQEEAE KPLQVAAVDS SVPRTAELAG ITTLDDPLGH  480
MPERFDAFIK KVAKKPTNKA PHPKQEPQEI NFPDDLPGSN TAAPVQETLH GCQPVTQEDG  540
KESRISVQER Q                                                       551

SEQ ID NO: 50          moltype = DNA  length = 1158
FEATURE                Location/Qualifiers
```

```
misc_feature           1..1158
                       note = Synthetic
source                 1..1158
                       mol_type = other DNA
                       organism = synthetic construct
SEQUENCE: 50
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgaggaaacg atggcagaac gagaagctcg ggttggatgc cggggatgaa  1020
tatgaagatg aaaaccttta tgaaggcctg aacctggacg actgctccat gtatgaggac  1080
atctcccggg gcctccaggg cacctaccag gatgtgggca gcctcaacat aggagatgtc  1140
cagctggaga agccgtga                                                1158

SEQ ID NO: 51          moltype = AA  length = 385
FEATURE                Location/Qualifiers
REGION                 1..385
                       note = Synthetic
source                 1..385
                       mol_type = protein
                       organism = synthetic construct
SEQUENCE: 51
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVRKRWQN EKLGLDAGDE YEDENLYEGL NLDDCSMYED  360
ISRGLQGTYQ DVGSLNIGDV QLEKP                                        385

SEQ ID NO: 52          moltype = DNA  length = 1122
FEATURE                Location/Qualifiers
misc_feature           1..1122
                       note = Synthetic
source                 1..1122
                       mol_type = other DNA
                       organism = synthetic construct
SEQUENCE: 52
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgctggacaa ggatgacagc aaggctggca tggaggaaga tcacacctac  1020
gagggcctgg acattgacca gacagccacc tatgaggaca tagtgacgct gcggacaggg  1080
gaagtgaagt ggtctgtagg tgagcaccca ggccaggagt ga                     1122

SEQ ID NO: 53          moltype = AA  length = 373
FEATURE                Location/Qualifiers
REGION                 1..373
                       note = Synthetic
source                 1..373
                       mol_type = protein
                       organism = synthetic construct
SEQUENCE: 53
```

```
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKFVPVFLPA KPTTTPAPRP PTPAPTIASQ PLSLRPEACR PAAGGAVHTR GLDFACDFWV  300
LVVVGGVLAC YSLLVTVAFI IFWVLDKDDS KAGMEEDHTY EGLDIDQTAT YEDIVTLRTG  360
EVKWSVGEHP GQE                                                    373

SEQ ID NO: 54           moltype = DNA  length = 1143
FEATURE                 Location/Qualifiers
misc_feature            1..1143
                        note = Synthetic
source                  1..1143
                        mol_type = other DNA
                        organism = synthetic construct
SEQUENCE: 54
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaaggcg ctggtagtgg cggtaactgg agccaccctc aatttgagaa gggcgggtca  780
ggcggatcag gtggtagtgg tgggtccaac tggagccatc cgcaatttga aaagggcgga  840
agcggcggtt ccggcggttc aggcggtagc aactggtcac atccgcaatt tgagaaaggc  900
gggtcaggcg gcgggtttg ggctctcgtg gtggtggctg gagtgctttt ctgctatggc  960
ctgctggtaa ccgtggccct ttgtgtaatc tggaccgata aagacgatgg aaaagccggg  1020
atggaagaag accataccta cgaggggctc aatattgatc aaaccgccac gtatgaagac  1080
attgtaacac tgcgcacagg tgaggtcaag tggtccgtcg gtgaacaccc aggacaagaa  1140
taa                                                               1143

SEQ ID NO: 55           moltype = AA  length = 380
FEATURE                 Location/Qualifiers
REGION                  1..380
                        note = Synthetic
source                  1..380
                        mol_type = protein
                        organism = synthetic construct
SEQUENCE: 55
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKGAGSGGNW SHPQFEKGGS GGSGSGGSN WSHPQFEKGG SGGSGGSGGS NWSHPQFEKG  300
GSGGGFWALV VVAGVLFCYG LLVTVALCVI WTDKDDGKAG MEEDHTYEGL NIDQTATYED  360
IVTLRTGEVK WSVGEHPGQE                                             380

SEQ ID NO: 56           moltype = DNA  length = 1152
FEATURE                 Location/Qualifiers
misc_feature            1..1152
                        note = Synthetic
source                  1..1152
                        mol_type = other DNA
                        organism = synthetic construct
SEQUENCE: 56
gaagtccaat tggttgaaag cggtggtgga ctcgtcaaac ctggcggtag ccttaaactt  60
tcatgtgccg caagcggctt cacgtttagt aactatgcta tgagttgggt ccgccaaagt  120
ccagaaaagc gcctcgaatg ggtggcggag atctctggag gaggaacata tacatattat  180
ccagacacca tgaccggtag gtttacaatc tcaagagaca acgctaagaa caccctgtac  240
ctggaaatgt caagcctgag atcagaagat acggccatgt attattgtac gcgcctactc  300
gactattggg gtcaaggaac ttccgtgacg gtgtcaagcg gaggaggtgg gagcggagga  360
ggcggaagtg gcggtggtgg ctctggtggc ggtggaagtg atatagtgat gacgcaagct  420
gccttttcaa accctgttac tttggggact agcgcatcaa tctcctgtag gtccagcaaa  480
tctttgctgc acagtaatgg aatcacctat cttttctggt atttgcaaaa gcctgggcag  540
agcccgcaac tgctgatcta tcaaatgtca aatcttgctt ccggagttcc agaccgcttc  600
tcaagttccg ggtccggcac tgattttacc ttgagaattt ctagggtcga agctgaagac  660
gtcggtgtct attattgcgc gcaaaacctt gagcttccat acaccttcgg ggggggcaca  720
aaacttgaga tcaagggcgc tgggagcggc gggaattgga gtcatccaca attcgaaaag  780
ggtgggtccg gcggcagtgg tggaagcggc gggagtaact ggtcacatcc ccagtttgag  840
aaaggcggta gtggtggcag cggcggtagt ggtggcagta attggagcca tccccaattc  900
gaaaagggcg gttccggcgg cggattttgg gctcttgttg tggtggccgg agtattgttt  960
tgctatggcc tgctcgttac agtggcattg tgcgtaattt ggactgataa agacgacggc  1020
aaagccggga tggaagaaga tcacacctat gaggggctta atatagatca aacagccaca  1080
```

```
tatgaagata ttgtgactct aaggactgga gaggttaaat ggagtgtggg tgagcatcca  1140
ggacaagaat aa                                                      1152

SEQ ID NO: 57          moltype = AA  length = 383
FEATURE                Location/Qualifiers
REGION                 1..383
                       note = Synthetic
source                 1..383
                       mol_type = protein
                       organism = synthetic construct
SEQUENCE: 57
EVQLVESGGG LVKPGGSLKL SCAASGFTFS NYAMSWVRQS PEKRLEWVAE ISGGGTYTYY  60
PDTMTGRFTI SRDNAKNTLY LEMSSLRSED TAMYYCTRLL DYWGQGTSVT VSSGGGGSGG  120
GGSGGGGSGG GGSDIVMTQA AFSNPVTLGT SASISCRSSK SLLHSNGITY LFWYLQKPGQ  180
SPQLLIYQMS NLASGVPDRF SSSGSGTDFT LRISRVEAED VGVYYCAQNL ELPYTFGGGT  240
KLEIKGAGSG GNWSHPQFEK GGSGGSGGSG GSNWSHPQFE KGGSGGSGGS GGSNWSHPQF  300
EKGGSGGGFW ALVVVAGVLF CYGLLVTVAL CVIWTDKDDG KAGMEEDHTY EGLNIDQTAT  360
YEDIVTLRTG EVKWSVGEHP GQE                                          383

SEQ ID NO: 58          moltype = DNA  length = 1191
FEATURE                Location/Qualifiers
misc_feature           1..1191
                       note = Synthetic
source                 1..1191
                       mol_type = other DNA
                       organism = synthetic construct
SEQUENCE: 58
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggttctagag gtggtggtgg tagcggcggc  360
ggcggctctg gtggtggtgg atccctcgag atggcccagg tgcagctggt ggagtctggg  420
ggaggcttgg tacagcctgg ggggtccctg agactctcct gtgcagcctc tggattcacc  480
tttagcagct atgccatgag ctgggtccgc caggctccag ggaaggggct ggagtgggtc  540
tcagttattt atagcggtgg tagtagcaca tactatgcag actccgtgaa gggccggttc  600
accatctcca gagataattc caagaacacg ctgtatctgc aaatgaacag cctgagagcc  660
gaggacacgg ccgtatatta ctgtgcgcgc acttcttacc tgaaccatgg tgattactgg  720
ggtcaaggta ctctggtgac cgtgtctagc gccgctgcat tcgtgcctgt gttcctccca  780
gctaagccca ctaccacccc cgctccaagg ccgcccacgc ccgctcctac tattgctagt  840
cagcctttaa gtttacgacc cgaagcttgc aggcccgccg ccggcggcgc tgtgcacacc  900
agggggcttg attttgcctg cgacttttgg gtattggtag tggtgggcgg agttttagcc  960
tgctacagcc tcctggtaac agtggctttt atcatctttt gggtgaggaa acgatggcag  1020
aacgagaagc tcgggttgga tgccggggat gaatatgaag atgaaaacct ttatgaaggc  1080
ctgaacctgg acgactgctc catgtatgag gacatctccc ggggcctcca gggcacctac  1140
caggatgtgg gcagcctcaa cataggagat gtccagctgg agaagccgtg a           1191

SEQ ID NO: 59          moltype = AA  length = 396
FEATURE                Location/Qualifiers
REGION                 1..396
                       note = Synthetic
source                 1..396
                       mol_type = protein
                       organism = synthetic construct
SEQUENCE: 59
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GSRGGGGSGG  120
GGSGGGGSLE MAQVQLVESG GGLVQPGGSL RLSCAASGFT FSSYAMSWVR QAPGKGLEWV  180
SVIYSGGSST YYADSVKGRF TISRDNSKNT LYLQMNSLRA EDTAVYYCAR TSYLNHGDYW  240
GQGTLVTVSS AAAFVPVFLP AKPTTTPAPR PPTPAPTIAS QPLSLRPEAC RPAAGGAVHT  300
RGLDFACDFW VLVVVGGVLA CYSLLVTVAF IIFWVRKRWQ NEKLGLDAGD EYEDENLYEG  360
LNLDDCSMYE DISRGLQGTY QDVGSLNIGD VQLEKP                            396

SEQ ID NO: 60          moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 60
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggttctagag gtggtggtgg tagcggcggc  360
ggcggctctg gtggtggtgg atccctcgag atggcccagg tgcagctggt ggagtctggg  420
```

```
ggaggcttgg tacagcctgg ggggtccctg agactctcct gtgcagcctc tggattcacc  480
tttagcagct atgccatgag ctgggtccgc caggctccag ggaaggggct ggagtgggtc  540
tcagttattt atagcggtgg tagtagcaca tactatgcag actccgtgaa gggccggttc  600
accatctcca gagataattc caagaacacg ctgtatctgc aaatgaacag cctgagagcc  660
gaggacacgg ccgtatatta ctgtgcgcgc acttcttacc tgaaccatgg tgattactgg  720
ggtcaaggta ctctggtgac cgtgtctagc gccgctgcat tcgtgcctgt gttcctccca  780
gctaagccca ctaccacccc cgctccaagg ccgcccacgc ccgctcctac tattgctagt  840
cagcctttaa gtttacgacc cgaagcttgc aggcccgccg ccggcggcgc tgtgcacacc  900
agggggcttg attttgcctg cgacttttgg gtattggtag tggtgggcgg agttttagcc  960
tgctacagcc tcctggtaac agtggctttt atcatctttt gggtgctgga caaggatgac  1020
agcaaggctg gcatggagga agatcacacc tacgagggcc tggacattga ccagacagcc  1080
acctatgagg acatagtgac gctgcggaca ggggaagtga agtggtctgt aggtgagcac  1140
ccaggccagg agtga                                                    1155

SEQ ID NO: 61           moltype = AA  length = 384
FEATURE                 Location/Qualifiers
REGION                  1..384
                        note = Synthetic
source                  1..384
                        mol_type = protein
                        organism = synthetic construct
SEQUENCE: 61
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GSRGGGGSGG  120
GGSGGGGSLE MAQVQLVESG GGLVQPGGSL RLSCAASGFT FSSYAMSWVR QAPGKGLEWV  180
SVIYSGGSST YYADSVKGRF TISRDNSKNT LYLQMNSLRA EDTAVYYCAR TSYLNHGDYW  240
GQGTLVTVSS AAAFVPVFLP AKPTTTPAPR PPTPAPTIAS QPLSLRPEAC RPAAGGAVHT  300
RGLDFACDFW VLVVVGGVLA CYSLLVTVAF IIFWVLDKDD SKAGMEEDHT YEGLDIDQTA  360
TYEDIVTLRT GEVKWSVGEH PGQE                                          384

SEQ ID NO: 62           moltype = DNA  length = 1653
FEATURE                 Location/Qualifiers
misc_feature            1..1653
                        note = Synthetic
source                  1..1653
                        mol_type = other DNA
                        organism = synthetic construct
SEQUENCE: 62
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggttctagag gtggtggtgg tagcggcggc  360
ggcggctctg gtggtggtgg atccctcgag atggcccagg tgcagctggt ggagtctggg  420
ggaggcttgg tacagcctgg ggggtccctg agactctcct gtgcagcctc tggattcacc  480
tttagcagct atgccatgag ctgggtccgc caggctccag ggaaggggct ggagtgggtc  540
tcagttattt atagcggtgg tagtagcaca tactatgcag actccgtgaa gggccggttc  600
accatctcca gagataattc caagaacacg ctgtatctgc aaatgaacag cctgagagcc  660
gaggacacgg ccgtatatta ctgtgcgcgc acttcttacc tgaaccatgg tgattactgg  720
ggtcaaggta ctctggtgac cgtgtctagc cccaagagct gcgacaagac ccacacctgc  780
ccccctgcc cagccccaga gctgctgggc ggaccctccg tgttcctgtt cccccccaag  840
cccaaggaca ccctgatgat cagcaggacc cccgaggtga cctgcgtggt ggtggacgtg  900
agccacgagg acccagaggt gaagttcaac tggtacgtgg acggcgtgga ggtgcacaac  960
gccaagacca agcccagaga ggagcagtac aacagcacct acagggtggt gtccgtgctg  1020
accgtgctgc accaggactg gctgaacggc aaggaataca agtgcaaggt ctccaacaag  1080
gccctgccag cccccatcga aaagaccatc agcaaggcca agggccagcc acgggagccc  1140
caggtgtaca ccctgccccc ctcccgggag gagatgacca agaaccaggt gtccctgacc  1200
tgtctggtga agggcttcta ccccagcgac atcgccgtgg agtgggagag caacggccag  1260
cccgagaaca actacaagac cacccccca gtgctggaca gcgacggcag cttcttcctg  1320
tacagcaagc tgaccgtgga caagtccagg tggcagcagg gcaacgtgtt cagctgcagc  1380
gtgatgcacg aggccctgca caaccactac acccagaaga gcctgagcct gtcccccgag  1440
ctgcaactgg aggagagctg tgcggaggcg caggacgggg agctggacgg gctgtggacg  1500
accatcacca tcttcatcac actcttcctg ttaagcgtgt gctacagtgc caccgtcacc  1560
ttcttcaagg tgaagtggat cttctcctcg gtggtggacc tgaagcagac catcatcccc  1620
gactacagga acatgatcgg acagggggcc tga                                1653

SEQ ID NO: 63           moltype = AA  length = 550
FEATURE                 Location/Qualifiers
REGION                  1..550
                        note = Synthetic
source                  1..550
                        mol_type = protein
                        organism = synthetic construct
SEQUENCE: 63
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GSRGGGGSGG  120
GGSGGGGSLE MAQVQLVESG GGLVQPGGSL RLSCAASGFT FSSYAMSWVR QAPGKGLEWV  180
SVIYSGGSST YYADSVKGRF TISRDNSKNT LYLQMNSLRA EDTAVYYCAR TSYLNHGDYW  240
```

-continued

```
GQGTLVTVSS PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPE  480
LQLEESCAEA QDGELDGLWT TITIFITLFL LSVCYSATVT FFKVKWIFSS VVDLKQTIIP  540
DYRNMIGQGA                                                         550

SEQ ID NO: 64          moltype = DNA  length = 648
FEATURE                Location/Qualifiers
misc_feature           1..648
                       note = Synthetic
source                 1..648
                       mol_type = other DNA
                       organism = synthetic construct
SEQUENCE: 64
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggtcagccca aggccaaccc cactgtcact  360
ctgttcccgc cctcctctga ggagctccaa gccaacaagg ccacactagt gtgtctgatc  420
agtgacttct acccgggagc tgtgacagtg gcctggaagg cagatggcag ccccgtcaag  480
gcgggagtgg agaccaccaa accctccaaa cagagcaaca acaagtacgc ggccagcagc  540
tacctgagcc tgacgcccga gcagtggaag tcccacagaa gctacagctg ccaggtcacg  600
catgaaggga gcaccgtgga gaagacagtg gcccctacag aatgttca                648

SEQ ID NO: 65          moltype = AA  length = 216
FEATURE                Location/Qualifiers
REGION                 1..216
                       note = Synthetic
source                 1..216
                       mol_type = protein
                       organism = synthetic construct
SEQUENCE: 65
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                              216

SEQ ID NO: 66          moltype = DNA  length = 1554
FEATURE                Location/Qualifiers
misc_feature           1..1554
                       note = Synthetic
source                 1..1554
                       mol_type = other DNA
                       organism = synthetic construct
SEQUENCE: 66
caggtgcagc tggtggagtc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagtt atttatagcg gtggtagtag cacatactat  180
gcagactccg tgaagggccg gttcaccatc tccagagata attccaagaa cacgctgtat  240
ctgcaaatga acagcctgag agccgaggac acggccgtat attactgtgc gcgcacttct  300
tacctgaacc atggtgatta ctggggtcaa ggtactctgg tgaccgtgtc tagcgcctcc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga accacaagcc cagcaacacc aaggtggaca agagagtgga gcccaagagc  660
tgcgacaaga cccacacctg ccccccctgc ccagccccag agctgctggg cggaccctcc  720
gtgttcctgt tccccccaa gcccaaggac accctgatga tcagcaggac ccccgaggtg  780
acctgcgtgg tggtggacgt gagccacgag gacccagagg tgaagttcaa ctggtacgtg  840
gacggcgtgg aggtgcacaa cgccaagacc aagcccagag aggagcagta caacagcacc  900
tacagggtgg tgtccgtgct gaccgtgctg caccaggact ggctgaacgg caaggaatac  960
aagtgcaagg tctccaacaa ggccctgcca gcccccatcg aaaagaccat cagcaaggcc  1020
aagggccagc cacgggagcc ccaggtgtac accctgcccc cctcccggga ggagatgacc  1080
aagaaccagg tgtccctgac ctgtctggtg aagggcttct accccagcga catcgccgtg  1140
gagtgggaga gcaacggcca gcccgagaac aactacaaga ccaccccccc agtgctggac  1200
agcgacggca gcttcttcct gtacagcaag ctgaccgtgg acaagtccag gtggcagcag  1260
ggcaacgtgt tcagctgcag cgtgatgcac gaggccctgc acaaccacta cacccagaag  1320
agcctgagcc tgtcccccga gctgcaactg gaggagagct gtgcggaggc gcaggacggg  1380
gagctggacg ggctgtggac gaccatcacc atcttcatca cactcttcct gttaagcgtg  1440
tgctacagtg ccaccgtcac cttcttcaag gtgaagtgga tcttctcctc ggtggtggac  1500
ctgaagcaga ccatcatccc cgactacagg aacatgatcg gacagggggc ctga          1554

SEQ ID NO: 67          moltype = AA  length = 517
FEATURE                Location/Qualifiers
REGION                 1..517
                       note = Synthetic
```

```
source                  1..517
                        mol_type = protein
                        organism = synthetic construct
SEQUENCE: 67
QVQLVESGGG LVQPGGSLRL SCAASGFTFS SYAMSWVRQA PGKGLEWVSV IYSGGSSTYY  60
ADSVKGRFTI SRDNSKNTLY LQMNSLRAED TAVYYCARTS YLNHGDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPELQL EESCAEAQDG ELDGLWTTIT IFITLFLLSV  480
CYSATVTFFK VKWIFSSVVD LKQTIIPDYR NMIGQGA                          517

SEQ ID NO: 68           moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 68
atgagacttt caacagcaac actcctcctg ttgctggctt catgtctgag ccctggtcat  60
ggtattttgg aggcccacta tacaaatctc aaatgtcggt gttcaggcgt aatatccacc  120
gtagtcggcc tgaacattat cgataggatt caggttacac cccccgggaa cggatgtcct  180
aagaccgagg tggtgatttg gaccaagatg aagaaggtca tttgtgtgaa cccacgggct  240
aaatggctgc agcgtctttt gcgacacgtg cagtccaaga gcttgtccag cacacctcag  300
gccccagtta gcaagcgacg tgcagcc                                     327

SEQ ID NO: 69           moltype = AA  length = 109
FEATURE                 Location/Qualifiers
REGION                  1..109
                        note = Synthetic
source                  1..109
                        mol_type = protein
                        organism = synthetic construct
SEQUENCE: 69
MRLSTATLLL LLASCLSPGH GILEAHYTNL KCRCSGVIST VVGLNIIDRI QVTPPGNGCP  60
KTEVVIWTKM KKVICVNPRA KWLQRLLRHV QSKSLSSTPQ APVSKRRAA              109

SEQ ID NO: 70           moltype = DNA  length = 696
FEATURE                 Location/Qualifiers
misc_feature            1..696
                        note = Synthetic
source                  1..696
                        mol_type = other DNA
                        organism = synthetic construct
SEQUENCE: 70
atgacagtgc tggcccccgc gtggtctccc aatagctcac tcctcctctt gctgctactg  60
ctcagcccat gcctcagggg cacccccgat tgttacttca gccacagccc aatctcctcc  120
aacttcaaag tgaaatttag ggaactgacc gaccacctgc tgaaagatta tcctgtgact  180
gtggcagtga acctgcaaga cgaaaagcat tgtaaggcgc tatggagcct ctttcttgcc  240
caacgatgga ttgagcaact caaaactgta gccggaagca aaatgcagac gctactggag  300
gacgtgaata ctgagattca cttcgttacc agttgtactt tccagccact gccagagtgt  360
ctcaggtttg tgcagactaa tatcagccac ctgctgaagg atacttgcac ccagctcctg  420
gctctcaagc cttgtatagg caaggcttgt caaaatttta gcaggtgtct cgaagtccag  480
tgccagccag attcatccac actgctgccg ccccgaagcc ctatcgcact cgaagcgaca  540
gagttgccag agcctcgtcc cagacagctt ctgctgctgc tacttctgct gctgccgcta  600
actctggtgc tacttgctgc cgcctggggc ctcagatggc aacgcgccag acgccgaggc  660
gaactccacc ctggggtgcc actgccatcc caccca                           696

SEQ ID NO: 71           moltype = AA  length = 232
FEATURE                 Location/Qualifiers
REGION                  1..232
                        note = Synthetic
source                  1..232
                        mol_type = protein
                        organism = synthetic construct
SEQUENCE: 71
MTVLAPAWSP NSSLLLLLLL LSPCLRGTPD CYFSHSPISS NFKVKFRELT DHLLKDYPVT  60
VAVNLQDEKH CKALWSLFLA QRWIEQLKTV AGSKMQTLLE DVNTEIHFVT SCTFQPLPEC  120
LRFVQTNISH LLKDTCTQLL ALKPCIGKAC QNFSRCLEVQ CQPDSSTLLP PRSPIALEAT  180
ELPEPRPRQL LLLLLLLPL TLVLLAAAWG LRWQRARRRG ELHPGVPLPS HP           232

SEQ ID NO: 72           moltype = DNA  length = 342
FEATURE                 Location/Qualifiers
misc_feature            1..342
                        note = Synthetic
source                  1..342
```

```
                         mol_type = other DNA
                         organism = synthetic construct
SEQUENCE: 72
atgcgactct tgttgttgac ttttctcgga gtgtgctgcc tgacaccctg ggtcgtagag  60
ggagttggca ctgaagtact agaagagtcc tcctgcgtta acctgcagac acagcggctc  120
ccagtccaga aaattaagac ctacattata tgggaaggag caatgcgagc ggtgattttt  180
gtgaccaaga ggggtctcaa gatttgcgcg gaccctgagg ccaagtgggt caaagcagct  240
attaagacag tagacggaag agcctccacc aggaagaata tggcagaaac tgtaccgacc  300
ggtgcgcagc ggtcaacatc taccgcaatc acactcaccg gc                     342

SEQ ID NO: 73            moltype = AA  length = 114
FEATURE                  Location/Qualifiers
REGION                   1..114
                         note = Synthetic
source                   1..114
                         mol_type = protein
                         organism = synthetic construct
SEQUENCE: 73
MRLLLLTFLG VCCLTPWVVE GVGTEVLEES SCVNLQTQRL PVQKIKTYII WEGAMRAVIF  60
VTKRGLKICA DPEAKWVKAA IKTVDGRAST RKNMAETVPT GAQRSTSTAI TLTG        114

SEQ ID NO: 74            moltype = DNA  length = 1533
FEATURE                  Location/Qualifiers
misc_feature             1..1533
                         note = Synthetic
source                   1..1533
                         mol_type = other DNA
                         organism = synthetic construct
SEQUENCE: 74
atgagcaagg gccttctcct gctgtggcta gtaactgaat tgtggtggtt gtacctgaca  60
cctgccgcta gtgaggacac catcattggt ttccttgggc agcccgtcac cctcccttgc  120
cattacctaa gctggagcca gtcacggaac tctatgtgct ggggaaaggg gtcatgccct  180
aattccaagt gcaacgccga gctgttgcgc acggacggca ccagaataat ctcaagaaag  240
tccaccaagt atacgctgct cggcaaggtg caattcggtg aagtgagctt gaccataagt  300
aacaccaacc gcggtgactc cggagtttat tgttgcagga tcgaagtgcc aggctggttt  360
aacgacgtga agaaaaacgt gcggctggaa ctgaggaggg caactacgac caagaaacca  420
acaaccacga cgagacctac caccactcct tacgtgacaa ccacgacacc ggagctgttg  480
ccaactaccg tcatgacaac atctgtgttg ccaactacca cccccccca aacgctcgcg  540
acaactgcct tttccacagc cgttaccaca tgtccttcca ccaccccagg ctctttttct  600
caagaaacta ccaagggatc agcttttacc accgagtctg aaactctccc agcaagtaat  660
cactcacagc ggtcaatgat gaccatcagc acagacatcg ctgtcttgag acctactggc  720
agcaatccag gcattctgcc ctccacttca cagctgacta cccaaaagac tacactaacc  780
accagcgaaa gtctgcagaa aactacaaag agccatcaaa taaactcccg gcagactccc  840
agagggccca caatcaagcc ctgtcctcca tgcaaatgcc cagcacctaa cctcttgggt  900
ggaccatccg tcttcatctt ccctccaaag atcaaggatg tactcatgat ctccctgagc  960
cccatagtca catgtgtggt ggtggatgtg agcgaggatg acccagatgt ccagatcagc  1020
tggtttgtga acaacgtgga agtacacaca gctcagacac aaacccatag agaggattac  1080
aacagtactc tccgggtggt cagtgccctc cccatccagc accaggactg gatgagtggc  1140
aaggagttca aatgcaaggt caacaacaaa gacctcccag cgcccatcga gagaaccatc  1200
tcaaaaccca aagggtcagt aagagctcca caggtatatg tcttgcctcc accagaagaa  1260
gagatgacta agaaacaggt cactctgacc tgcatggtca cagacttcat gcctgaagac  1320
atttacgtgg agtggaccaa caacgggaaa acagagctaa actacaagaa cactgaacca  1380
gtcctggact ctgatggttc ttacttcatg tacagcaagc tgagagtgga aaagaagaac  1440
tgggtggaaa gaaatagcta ctcctgttca gtggtccacg agggtctgca caatcaccac  1500
acgactaaga gcttctcccg gactccgggt aaa                               1533

SEQ ID NO: 75            moltype = AA  length = 511
FEATURE                  Location/Qualifiers
REGION                   1..511
                         note = Synthetic
source                   1..511
                         mol_type = protein
                         organism = synthetic construct
SEQUENCE: 75
MSKGLLLLWL VTELWWLYLT PAASEDTIIG FLGQPVTLPC HYLSWSQSRN SMCWGKGSCP  60
NSKCNAELLR TDGTRIISRK STKYTLLGKV QFGEVSLTIS NTNRGDSGVY CCRIEVPGWF  120
NDVKKNVRLE LRRATTTKKP TTTTRPTTTP YVTTTTPELL PTTVMTTSVL PTTTPPQTLA  180
TTAFSTAVTT CPSTTPGSFS QETTKGSAFT TESETLPASN HSQRSMMTIS TDIAVLRPTG  240
SNPGILPSTS QLTTQKTTLT TSESLQKTTK SHQINSRQTP RGPTIKPCPP CKCPAPNLLG  300
GPSVFIFPPK IKDVLMISLS PIVTCVVVDV SEDDPDVQIS WFVNNVEVHT AQTQTHREDY  360
NSTLRVVSAL PIQHQDWMSG KEFKCKVNNK DLPAPIERTI SKPKGSVRAP QVYVLPPPEE  420
EMTKKQVTLT CMVTDFMPED IYVEWTNNGK TELNYKNTEP VLDSDGSYFM YSKLRVEKKN  480
WVERNSYSCS VVHEGLHNHH TTKSFSRTPG K                                 511

SEQ ID NO: 76            moltype = DNA  length = 927
FEATURE                  Location/Qualifiers
misc_feature             1..927
                         note = Synthetic
source                   1..927
```

```
                        mol_type = other DNA
                        organism = synthetic construct
SEQUENCE: 76
atggatcagc atacactgga cgtggaagat acagccgatg ccagacaccc tgctggaacg  60
tcctgtccca gcgacgctgc cctgctcaga gacaccgggc tgctcgcaga tgctgctctg  120
ctgagtgata ccgttcggcc aactaacgcg gccctaccca cagatgccgc atatcccgcg  180
gtaaatgtca gggaccggga agctgcctgg ccaccggccc tcaatttctg ctctagacat  240
ccgaaactgt acggtctggt cgcactggta ctgctgctac ttatagcagc ttgtgttccc  300
atatttaccc gcactgaacc cagacccgct ctcactatta caacttcacc aaacttgggc  360
acacgtgaaa acaatgcaga tcaggttacc cctgtaagtc atattggatg ccccaacacc  420
acacaacagg gaagtccggt gtttgcaaaa ctccttgcta agaatcaggc ttcactgtgt  480
aacactactc ttaattggca ctcacaagac ggggccggga gtagctatct cagccaaggt  540
ctccgctatg aagaagataa gaaagagttg gtggtggaca gcccaggact ctactacgtc  600
ttcctggagc taaaactaag ccccactttt actaacactg gacataaggt ccaaggttgg  660
gtgtccctcg tacttcaagc taaaccccag gtggacgact tcgataacct ggcgttgaca  720
gttgagctct ttccttgctc tatggaaaat aagctcgtgg atcggagctg gtctcaactg  780
ttgctgctta aagccggtca tcgtctgtct gttggactac gcgcatactt gcatggagcc  840
caggacgcat atcgtgattg ggaactgagc tacccgaata ccactagctt tggactattt  900
cttgttaaac cagataatcc ttgggag                                      927

SEQ ID NO: 77           moltype = AA  length = 309
FEATURE                 Location/Qualifiers
REGION                  1..309
                        note = Synthetic
source                  1..309
                        mol_type = protein
                        organism = synthetic construct
SEQUENCE: 77
MDQHTLDVED TADARHPAGT SCPSDAALLR DTGLLADAAL LSDTVRPTNA ALPTDAAYPA  60
VNVRDREAAW PPALNFCSRH PKLYGLVALV LLLLIAACVP IFTRTEPRPA LTITTSPNLG  120
TRENNADQVT PVSHIGCPNT TQQGSPVFAK LLAKNQASLC NTTLNWHSQD GAGSSYLSQG  180
LRYEEDKKEL VVDSPGLYYV FLELKLSPTF TNTGHKVQGW VSLVLQAKPQ VDDFDNLALT  240
VELFPCSMEN KLVDRSWSQL LLLKAGHRLS VGLRAYLHGA QDAYRDWELS YPNTTSFGLF  300
LVKPDNPWE                                                          309

SEQ ID NO: 78           moltype = DNA  length = 705
FEATURE                 Location/Qualifiers
misc_feature            1..705
                        note = Synthetic
source                  1..705
                        mol_type = other DNA
                        organism = synthetic construct
SEQUENCE: 78
atggagagcg tagtgcaacc cagcgtattt gtggtggatg gacagaccga catcccattc  60
agacgcttgg aacagaacca ccgaagaagg cggtgcggca ccgtccaggt gtccctcgct  120
ctcgtgctgc tgcttggtgc tggcctcgca acacaagggt ggtttctttt gagactccat  180
caacgcttgg gagacatagt ggcccacctg cctgatggtg ggaagggctc ttggcaggac  240
cagcgatcac accaggctaa ccccgccgct cacctgacag gggcgaatgc cagcttgatc  300
ggaataggtg ggccgctgct gtgggaaact aggcttggac ttgcctttct gagagggctt  360
acataccatg acggagccct cgtaacaatg gagcctggtt attactacgt gtacagtaag  420
gtgcagcttt ctggagtcgg gtgtccccag ggctggcta acggactgcc catcactcat  480
ggactataca aacgcacatc cagatatcct aaagagctgg aactgttggt gtcccgtagg  540
agcccgtgtg gcagggccaa ctcttcccgt gtgtggtggg actcctcttt tctgggcggc  600
gtggtccatc tggaagctgg tgaggaagtc gtcgtaagag tacctggaaa ccgtctggtt  660
cgcccccgcg atggcaccag gtcctacttc ggagctttca tggta                  705

SEQ ID NO: 79           moltype = AA  length = 235
FEATURE                 Location/Qualifiers
REGION                  1..235
                        note = Synthetic
source                  1..235
                        mol_type = protein
                        organism = synthetic construct
SEQUENCE: 79
MESVVQPSVF VVDGQTDIPF RRLEQNHRRR RCGTVQVSLA LVLLLGAGLA TQGWFLLRLH  60
QRLGDIVAHL PDGGKGSWQD QRSHQANPAA HLTGANASLI GIGGPLLWET RLGLAFLRGL  120
TYHDGALVTM EPGYYYVYSK VQLSGVGCPQ GLANGLPITH GLYKRTSRYP KELELLVSRR  180
SPCGRANSSR VWWDSSFLGG VVHLEAGEEV VVRVPGNRLV RPRDGTRSYF GAFMV       235

SEQ ID NO: 80           moltype = DNA  length = 1821
FEATURE                 Location/Qualifiers
misc_feature            1..1821
                        note = Synthetic
source                  1..1821
                        mol_type = other DNA
                        organism = synthetic construct
SEQUENCE: 80
atgtgcccac agaaactcac aatttcttgg ttcgcaatcg tcctgctggt gtcacccctg  60
atggcaatgt gggagttgga aaaggatgta tacgtcgtcg aggtcgactg gacacctgac  120
```

```
gctccgggtg aaactgtcaa cctcacttgc gatactcctg aagaggacga catcacgtgg  180
acgagcgacc agcgacatgg agtgataggg tctggcaaga cgcttactat cacggttaag  240
gaatttctcg acgcagggca gtacacatgt cacaagggcg gcgagactct gagccactcc  300
catttgctgc tgcacaagaa ggagaatggt atctggtcta ccgaaatcct gaagaatttt  360
aagaacaaga cttttctgaa atgcgaggcc ccaaattatt ccggacgttt cacttgcagt  420
tggctcgttc aaagaaatat ggacttgaaa tttaacatta aatccagctc ttcatctcct  480
gacagcaggg ccgtaacttg tggaatggct tcattgtcag ctgagaaagt tacgcttgac  540
caaagggatt atgagaaata cagcgtgagt tgccaggaag atgtgacatg tccaacggca  600
gaggaaacgt tgccaattga gctcgctttg gaagctcgtc aacaaaacaa gtatgaaaac  660
tatagtacta gcttcttcat acgggacatc atcaaaccag atccacctaa gaatttgcag  720
atgaagcctc tgaagaattc acaagtcgag gtatcctggg aatacccaga ttcatggtcc  780
actcctcata gttactttag cctgaaattc tttgtacgca tacagcggaa gaaggagaaa  840
atgaaggaga cggaagaagg ctgcaatcag aaaggcgctt ttcttgttga aaagacgagc  900
actgaggttc aatgcaaagg cggaatgta tgtgttcaag cccaagatag gtattataat  960
agctcctgct ctaagtgggc ttgcgtacca tgcagagtta gaagtggctc aacctcaggc  1020
tccggaaaac ctggttccgg tgaaggttcc acaaaagggc gtgtgattcc tgtgtccggc  1080
ccagctaggt gtctctccca gtcacggaat ctcctgaaaa ccacggatga catggtaaag  1140
acagctaggg agaaactcaa gcactactcc tgcacagctg aggatatcga tcatgaggac  1200
atcaccaggg accagacatc cactctgaaa acttgcctgc ctttggaact ccacaagaac  1260
gaatcttgtc tggcaacgcg tgaaacgagt tctactacaa gagggtcctg tcttccccct  1320
caaaagacaa gccttatgat gaccttgtgt ctcggtagca tttatgagga cctaaagatg  1380
tatcaaaccg agtttcaggc tatcaatgca gcgctccaga atcataacca tcagcagatc  1440
attcttgaca aggaatgct  cgtggccatt gatgaactaa tgcagagcct aaaccacaat  1500
ggcgagactc ttcgacagaa accgcctgtg ggcgaggccg atccatatag agtcaaaatg  1560
aaactgtgta ttctcctgca tgcatttagt actcgtgtag tgactattaa cagagtgatg  1620
ggttaccttt cctcagctaa tacacttgtc ctctttggcg ctgggttcgg cgccgtcata  1680
acggttgttg tcatcgtggt aataatcaag tgcttttgca agcacaggtc ttgttttcgc  1740
aggaatgaag cctctagaga aacaaataat tcactgacct ttggccccga agaagctctt  1800
gcagagcaaa cggtgtttct c                                               1821
```

```
SEQ ID NO: 81          moltype = AA  length = 607
FEATURE                Location/Qualifiers
REGION                 1..607
                       note = Synthetic
source                 1..607
                       mol_type = protein
                       organism = synthetic construct
SEQUENCE: 81
MCPQKLTISW FAIVLLVSPL MAMWELEKDV YVVEVDWTPD APGETVNLTC DTPEEDDITW  60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRSGSTSG SGKPGSGEGS TKGRVIPVSG  360
PARCLSQSRN LLKTTDDMVK TAREKLKHYS CTAEDIDHED ITRDQTSTLK TCLPLELHKN  420
ESCLATRETS STTRGSCLPP QKTSLMMTLC LGSIYEDLKM YQTEFQAINA ALQNHNHQQI  480
ILDKGMLVAI DELMQSLNHN GETLRQKPPV GEADPYRVKM KLCILLHAFS TRVVTINRVM  540
GYLSSANTLV LFGAGFGAVI TVVVIVVIIK CFCKHRSCFR RNEASRETNN SLTFGPEEAL  600
AEQTVFL                                                           607
```

```
SEQ ID NO: 82          moltype = DNA  length = 1716
FEATURE                Location/Qualifiers
misc_feature           1..1716
                       note = Synthetic
source                 1..1716
                       mol_type = other DNA
                       organism = synthetic construct
SEQUENCE: 82
atgtgtcagt cacgctatct tctcttcctt gctactctgg ccttgctcaa tcacttgtcc  60
cttgctcgtg tgattcctgt gtccggccca gctaggtgtc tctcccagtc acggaatctc  120
ctgaaaacca cggatgacat ggtaaagaca gctagggaga aactcaagca ctactcctgc  180
acagctgagg atatcgatca tgaggacatc accagggacc agacatccac tctgaaaact  240
tgcctgcctt tggaactcca caagaacgaa tcttgtctgg caacgcgtga aacgagttct  300
actacaagag ggtcctgtct tcccccctcaa aagacaagcc ttatgatgac cttgtgtctc  360
ggtagcattt atgaggacct aaagatgtat caaaccgagt ttcaggctat caatgcagcg  420
ctccagaatc ataaccatca gcagatcatt cttgacaaag gaatgctcgt ggccattgat  480
gaactaatgc agagcctaaa ccacaatggc gagactcttc gacagaaacc gcctgtgggc  540
gaggccgatc catatagagt caaaatgaaa ctgtgtattc tcctgcatgc atttagtact  600
cgtgtagtga ctattaacag agtgatgggt tacctttcct cagctggaag cggcgccacc  660
aacttctccc tgctgaagca ggccggcgac gtggaggaga accccggccc catgtgccca  720
cagaaactca caatttcttg gttcgcaatc gtcctgctgg tgtcacccct gatggcaatg  780
tgggagttgg aaaaggatgt atacgtcgtc gaggtcgact ggacacctga cgctccgggt  840
gaaactgtca acctcacttg cgatactcct gaagaggacg acatcacgtg gacgagcgac  900
cagcgacatg gagtgatagg gtctggcaag acgcttacta tcacggttaa ggaatttctc  960
gacgcagggc agtacacatg tcacaagggc ggcgagactc tgagccactc ccatttgctg  1020
ctgcacaaga aggagaatgg tatctggtct accgaaatcc tgaagaattt taagaacaag  1080
acttttctga aatgcgaggc cccaaattat tccggacgtt tcacttgcag ttggctcgtt  1140
caaagaaata tggacttgaa atttaacatt aaatccagct cttcatctcc tgacagcagg  1200
gccgtaactt gtggaatggc ttcattgtca gctgagaaag ttacgcttga ccaaagggat  1260
```

```
tatgagaaat acagcgtgag ttgccaggaa gatgtgacat gtccaacggc agaggaaacg  1320
ttgccaattg agctcgcttt ggaagctcgt caacaaaaca agtatgaaaa ctatagtact  1380
agcttcttca tacgggacat catcaaacca gatccaccta agaatttgca gatgaagcct  1440
ctgaagaatt cacaagtcga ggtatcctgg gaatacccag attcatggtc cactcctcat  1500
agttacttta gcctgaaatt ctttgtacgc atacagcgga agaaggagaa aatgaaggag  1560
acggaagaag gctgcaatca gaaaggcgct tttcttgttg aaaagacgag cactgaggtt  1620
caatgcaaag gcgggaatgt atgtgttcaa gcccaagata ggtattataa tagctcctgc  1680
tctaagtggg cttgcgtacc atgcagagtt agaagt                            1716

SEQ ID NO: 83          moltype = AA  length = 572
FEATURE                Location/Qualifiers
REGION                 1..572
                       note = Synthetic
source                 1..572
                       mol_type = protein
                       organism = synthetic construct
SEQUENCE: 83
MCQSRYLLFL ATLALLNHLS LARVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSAGSGAT NFSLLKQAGD VEENPGPMCP  240
QKLTISWFAI VLLVSPLMAM WELEKDVYVV EVDWTPDAPG ETVNLTCDTP EEDDITWTSD  300
QRHGVIGSGK TLTITVKEFL DAGQYTCHKG GETLSHSHLL LHKKENGIWS TEILKNFKNK  360
TFLKCEAPNY SGRFTCSWLV QRNMDLKFNI KSSSSSPDSR AVTCGMASLS AEKVTLDQRD  420
YEKYSVSCQE DVTCPTAEET LPIELALEAR QQNKYENYST SFFIRDIIKP DPPKNLQMKP  480
LKNSQVEVSW EYPDSWSTPH SYFSLKFFVR IQRKKEKMKE TEEGCNQKGA FLVEKTSTEV  540
QCKGGNVCVQ AQDRYYNSSC SKWACVPCRV RS                                572

SEQ ID NO: 84          moltype = DNA  length = 570
FEATURE                Location/Qualifiers
misc_feature           1..570
                       note = Synthetic
source                 1..570
                       mol_type = other DNA
                       organism = synthetic construct
SEQUENCE: 84
atggccaggc tttgcgcttt tctcgtcatg ctgatcgtca tgagttactg gtccatttgc  60
agcctcggat gtgatctgcc ccacacctac aacctgcgca acaaacgagc tctcaaagtg  120
ttggcccaaa tgaggcggtt gcccttcctt tcctgtctca aagacaggca agattttgga  180
tttccactag agaaagtaga caatcaacag atacagaaag ctcaagctat ccccgtgttg  240
agggacttga ctcaacagac gttgaatcta tttactagca aggccagctc tgctgcttgg  300
aatgccaccc ttcttgactc attttgcaat gacctacatc aacaactgaa tgatctccaa  360
acatgtttga tgcagcaggt aggtgtccaa gaacccccgc ttactcagga agacgccctt  420
ctggctgtcc gcaagtactt tcacagaatc acagtgtacc tgcgcgaaaa gaaacactcc  480
ccctgcgctt gggaagtggt cagggccgag gtttggcgag ccctgagtag ctccgtcaat  540
ctccttcctc ggttgtccga ggagaaagag                                   570

SEQ ID NO: 85          moltype = AA  length = 190
FEATURE                Location/Qualifiers
REGION                 1..190
                       note = Synthetic
source                 1..190
                       mol_type = protein
                       organism = synthetic construct
SEQUENCE: 85
MARLCAFLVM LIVMSYWSIC SLGCDLPHTY NLRNKRALKV LAQMRRLPFL SCLKDRQDFG  60
FPLEKVDNQQ IQKAQAIPVL RDLTQQTLNL FTSKASSAAW NATLLDSFCN DLHQQLNDLQ  120
TCLMQQVGVQ EPPLTQEDAL LAVRKYFHRI TVYLREKKHS PCAWEVVRAE VWRALSSSVN  180
LLPRLSEEKE                                                         190

SEQ ID NO: 86          moltype = DNA  length = 918
FEATURE                Location/Qualifiers
misc_feature           1..918
                       note = Synthetic
source                 1..918
                       mol_type = other DNA
                       organism = synthetic construct
SEQUENCE: 86
atggcttgca actgtcagct catgcaagat actcccctgc ttaagtttcc ctgccctaga  60
ctcattctcc tcttcgtcct tctcattcgc ctaagccagg tgagttccga tgtggatgaa  120
caactgagta aatctgtcaa ggataaagtt ctgctcccat gccgctacaa tagcccccat  180
gaggacgagt ccgaagatag gatttactgg cagaaacatg ataaggtggt gctatccgtc  240
attgccggta aattgaaggt gtggcccgaa tataagaata gaaccctgta tgacaacaca  300
acttatagcc taatcatcct cggtctcgta ctgagcgacc gaggtactta ctcatgcgtt  360
gtgcagaaga aggagcgcgg aacatacgaa gtcaagcacc ttgcattggt gaaattgtca  420
ataaaagctg acttttcaac tcctaatatt actgaatcag gtaacccttc cgcagacact  480
aaaagaatta catgcttcgc ctctggcggg tttcccaaac cacggttctc ttggctagag  540
aatgggagag aacttccagg tatcaataca accatctctc aagacccaga atcagaactg  600
tacaccatct ccagccaact cgatttcaat accacaagaa atcatacaat aaaatgtctg  660
```

```
ataaagtacg gagatgcaca tgtctctgaa gatttcacat gggagaaacc accagaggac  720
ccgccagaca gcaagaatac acttgtcctc tttggcgctg ggttcggcgc cgtcataacg  780
gttgttgtca tcgtggtaat aatcaagtgc ttttgcaagc acaggtcttg ttttcgcagg  840
aatgaagcct ctagagaaac aaataattca ctgacctttg gccccgaaga agctcttgca  900
gagcaaacgg tgtttctc                                                918

SEQ ID NO: 87          moltype = AA  length = 306
FEATURE                Location/Qualifiers
REGION                 1..306
                       note = Synthetic
source                 1..306
                       mol_type = protein
                       organism = synthetic construct
SEQUENCE: 87
MACNCQLMQD TPLLKFPCPR LILLFVLLIR LSQVSSDVDE QLSKSVKDKV LLPCRYNSPH  60
EDESEDRIYW QKHDKVVLSV IAGKLKVWPE YKNRTLYDNT TYSLIILGLV LSDRGTYSCV  120
VQKKERGTYE VKHLALVKLS IKADFSTPNI TESGNPSADT KRITCFASGG FPKPRFSWLE  180
NGRELPGINT TISQDPESEL YTISSQLDFN TTRNHTIKCL IKYGDAHVSE DFTWEKPPED  240
PPDSKNTLVL FGAGFGAVIT VVVIVVIIKC FCKHRSCFRR NEASRETNNS LTFGPEEALA  300
EQTVFL                                                             306

SEQ ID NO: 88          moltype = DNA  length = 780
FEATURE                Location/Qualifiers
misc_feature           1..780
                       note = Synthetic
source                 1..780
                       mol_type = other DNA
                       organism = synthetic construct
SEQUENCE: 88
atgatcgaaa cttattccca accctcaccg cgctcagtag caactggcct accagccagc  60
atgaagatat tcatgtacct cttgactgta ttcttgatca cgcaaatgat tggtagtgtt  120
ttgttcgccg tttatctcca caggcgcctg gataaagttg aagaagaggt taatctccat  180
gaagacttcg tgttcattaa gaaactcaaa agatgtaaca aaggtgaggg atctctgtct  240
cttctgaact gtgaggagat gcgacggcaa ttcgaggacc tcgtaaaaga cataactctc  300
aacaaagaag agaagaaaga aaactctttc gagatgcaac ggggcgacga ggaccctcaa  360
attgccgcac atgtcgtttc tgaagcgaat tccaatgccg cgtccgtgct ccagtgggcg  420
aagaagggat actacacgat gaagagcaac cttgtgatgc ttgaaaatgg caagcagctc  480
acagttaaac gcgagggact ctactatgta tacacccaag tgacctttg ttccaaccgg  540
gagccaagta gccaacgccc gttcatcgtt gggctgtggc tcaagccttc ttcagggagt  600
gaacgaatcc ttctcaaggc agccaacacg cattccagca gccaactgtg tgagcaacaa  660
tccgtgcatc ttggcggggt ctttgagctg caagcgggcg cctctgtgtt cgtgaatgtt  720
accgaagcca gccaggttat ccaccgcgtg ggtttcagta gttttggcct gctcaagctg  780

SEQ ID NO: 89          moltype = AA  length = 260
FEATURE                Location/Qualifiers
REGION                 1..260
                       note = Synthetic
source                 1..260
                       mol_type = protein
                       organism = synthetic construct
SEQUENCE: 89
MIETYSQPSP RSVATGLPAS MKIFMYLLTV FLITQMIGSV LFAVYLHRRL DKVEEEVNLH  60
EDFVFIKKLK RCNKGEGSLS LLNCEEMRRQ FEDLVKDITL NKEEKKENSF EMQRGDEDPQ  120
IAAHVVSEAN SNAASVLQWA KKGYYTMKSN LVMLENGKQL TVKREGLYYV YTQVTFCSNR  180
EPSSQRPFIV GLWLKPSSGS ERILLKAANT HSSSQLCEQQ SVHLGGVFEL QAGASVFVNV  240
TEASQVIHRV GFSSFGLLKL                                              260

SEQ ID NO: 90          moltype = DNA  length = 438
FEATURE                Location/Qualifiers
misc_feature           1..438
                       note = Synthetic
source                 1..438
                       mol_type = other DNA
                       organism = synthetic construct
SEQUENCE: 90
atggagcgta ctctggtctg ccttgttgtg atattcttgg ggacagttgc acacaaatca  60
tcaccccaag gaccggatag actcctcata cgcctgcgcc atctgattga cattgtcgag  120
cagttgaaga tttatgagaa cgacctggac cctgaactat tgagcgcgcc tcaagacgtc  180
aaagggcatt gcgagcatgc tgcatttgca tgttttcaga aagctaagct caaaccaagt  240
aatcccggta acaataaaac attcatcatc gacctggtgg cccaactaag acgccggttg  300
ccggcgcgcc ggggtggtaa gaaacagaaa catattgcta aatgcccctc ttgcgactct  360
tacgagaaaa ggacacctaa ggaattcctc gaacgattga aatggttgtt gcagaagatg  420
atccatcaac atctgagc                                                438

SEQ ID NO: 91          moltype = AA  length = 146
FEATURE                Location/Qualifiers
REGION                 1..146
                       note = Synthetic
source                 1..146
```

```
                        mol_type = protein
                        organism = synthetic construct
SEQUENCE: 91
MERTLVCLVV IFLGTVAHKS SPQGPDRLLI RLRHLIDIVE QLKIYENDLD PELLSAPQDV  60
KGHCEHAAFA CFQKAKLKPS NPGNNKTFII DLVAQLRRRL PARRGGKKQK HIAKCPSCDS  120
YEKRTPKEFL ERLKWLLQKM IHQHLS                                      146

SEQ ID NO: 92           moltype = DNA  length = 399
FEATURE                 Location/Qualifiers
misc_feature            1..399
                        note = Synthetic
source                  1..399
                        mol_type = other DNA
                        organism = synthetic construct
SEQUENCE: 92
atggcacaaa tgatgacact gtccctactt agtctagttc tagctttgtg tattccctgg  60
actcaaggca gtgacggagg aggacaagac tgctgcctca aatattctca aaagaaaatc  120
ccttattcta tagtccgagg ttaccgtaag caagaaccga gtctaggttg tcctatcccc  180
gcaatcctct ttctaccacg gaaacatagc aaaccagaat tgtgcgccaa cccagaagag  240
ggttgggtcc aaaatttgat gaggcgcctt gaccaaccac cggcccccggg taaacaatca  300
ccggggtgtc ggaagaatag gggtacatcc aaatccggga agaaagggaa ggggagtaag  360
ggctgtaaga gaacggaaca aactcaacct agcagaggt                        399

SEQ ID NO: 93           moltype = AA  length = 133
FEATURE                 Location/Qualifiers
REGION                  1..133
                        note = Synthetic
source                  1..133
                        mol_type = protein
                        organism = synthetic construct
SEQUENCE: 93
MAQMMTLSLL SLVLALCIPW TQGSDGGGQD CCLKYSQKKI PYSIVRGYRK QEPSLGCPIP  60
AILFLPRKHS KPELCANPEE GWVQNLMRRL DQPPAPGKQS PGCRKNRGTS KSGKKGKGSK  120
GCKRTEQTQP SRG                                                    133

SEQ ID NO: 94           moltype = DNA  length = 1224
FEATURE                 Location/Qualifiers
misc_feature            1..1224
                        note = Synthetic
source                  1..1224
                        mol_type = other DNA
                        organism = synthetic construct
SEQUENCE: 94
atggaaaccg acacattgct cctctgggtt ctccttctat gggtccccgg ttccaccgga  60
gatatccaaa tgacacaatc acccagcagc ctgcctgcct ctctgggcga ccgcgttacc  120
atcaattgtc aagcttccca agatataagt aattatctca actggtacca gcaaaagccc  180
ggtaaagcgc ctaaattgct gatttattat actaataaac tcgcagatgg agttcctagt  240
agattttctg gttcagggag tggacgggac tccagtttta ccatatcaag tctggaatcc  300
gaggatatcg gcagctacta ttgccagcaa tattataatt acccttggac ttttggaccc  360
gggactaaac ttgagatcaa aagaggcgga ggaggcagtg gtggtggtgg atcaggcggc  420
ggtggtagtg aggtacaact cgtggaatca ggcggcggac tggtccaacc cggcaagagc  480
cttaaactct cttgtgaggc cagtggattt acattcagcg gttatggaat gcactgggtg  540
agacaagctc ccggcagggg cctagaatca gtggcgtaca tcaccagctc atcaataaac  600
attaaatacg ctgatgcagt caagggccgg tttactgtat cccgcgacaa cgctaagaat  660
cttctctttc tgcaaatgaa catacttaag agcgaggata ctgccatgta ttattgtgcc  720
cgcttcgatt gggataagaa ttattgggga caaggcacca tggttaccgt tagtagtcca  780
aacatcacat caaataatag caaccccgtg gaaggggacg actctgtttc actcacctgt  840
gattcctata ccgatcctga taatatcaac tatctatggt ctcgtaacgg tgaaagtctc  900
agcgaaggcg accggttgaa actctccgaa ggtaacagaa cccttacgct tctgaacgtc  960
acccggaacg ataccgggcc ctatgtttgc gaaactagga accctgttag cgtgaatcgt  1020
agcgaccctt tctccctaaa taatactcta gtgctattcg gagcgggatt cggtgccgtc  1080
atcacagtag tcgttattgt agtcattatt aaatgctttt gtaaacatag gtcttgcttc  1140
agaagaaatg aggccagccg tgaaactaat aattccctga cctttgggcc cgaagaagct  1200
ttggctgaac agactgtgtt tctc                                        1224

SEQ ID NO: 95           moltype = AA  length = 408
FEATURE                 Location/Qualifiers
REGION                  1..408
                        note = Synthetic
source                  1..408
                        mol_type = protein
                        organism = synthetic construct
SEQUENCE: 95
METDTLLLWV LLLWVPGSTG DIQMTQSPSS LPASLGDRVT INCQASQDIS NYLNWYQQKP  60
GKAPKLLIYY TNKLADGVPS RFSGSGSGRD SSFTISSLES EDIGSYYCQQ YYNYPWTFGP  120
GTKLEIKRGG GGSGGGGSGG GGSEVQLVES GGGLVQPGKS LKLSCEASGF TFSGYGMHWV  180
RQAPGRGLES VAYITSSSIN IKYADAVKGR FTVSRDNAKN LLFLQMNILK SEDTAMYYCA  240
RFDWDKNYWG QGTMVTVSSP NITSNNSNPV EGDDSVSLTC DSYTDPDNIN YLWSRNGESL  300
SEGDRLKLSE GNRTLTLLNV TRNDTGPYVC ETRNPVSVNR SDPFSLNNTL VLFGAGFGAV  360
```

```
ITVVVIVVII KCFCKHRSCF RRNEASRETN NSLTFGPEEA LAEQTVFL            408

SEQ ID NO: 96           moltype = DNA  length = 420
FEATURE                 Location/Qualifiers
misc_feature            1..420
                        note = Synthetic
source                  1..420
                        mol_type = other DNA
                        organism = synthetic construct
SEQUENCE: 96
atggttcttc tcaggagcct cttcatcctg caagtactag tacggatggg gctaacttac  60
aacttttcta actgcaactt cacgtcaatt acgaaaatat attgtaacat aatttttcat  120
gacctgactg gagatttgaa aggggctaag ttcgagcaaa tcgaggactg tgagagcaag  180
ccagcttgtc tcctgaaaat cgagtactat actctcaatc ctatccctgg ctgcccttca  240
ctccccgaca aaacatttgc ccggagaaca agagaagccc tcaatgacca ctgcccaggc  300
taccctgaaa ctgagagaaa tgacggtact caggaaatgg cacaagaagt ccaaaacatc  360
tgcctgaatc aaacctcaca aattctaaga ttgtggtatt ccttcatgca atctccagaa  420

SEQ ID NO: 97           moltype = AA  length = 140
FEATURE                 Location/Qualifiers
REGION                  1..140
                        note = Synthetic
source                  1..140
                        mol_type = protein
                        organism = synthetic construct
SEQUENCE: 97
MVLLRSLFIL QVLVRMGLTY NFSNCNFTSI TKIYCNIIFH DLTGDLKGAK FEQIEDCESK  60
PACLLKIEYY TLNPIPGCPS LPDKTFARRT REALNDHCPG YPETERNDGT QEMAQEVQNI  120
CLNQTSQILR LWYSFMQSPE                                           140

SEQ ID NO: 98           moltype = DNA  length = 423
FEATURE                 Location/Qualifiers
misc_feature            1..423
                        note = Synthetic
source                  1..423
                        mol_type = other DNA
                        organism = synthetic construct
SEQUENCE: 98
atgtggctgc agaatttact tttcctgggc attgtggtct acagcctctc agcacccacc  60
cgctcaccca tcactgtcac ccggccttgg aagcatgtag aggccatcaa agaagccctg  120
aacctcctgg atgacatgcc tgtcacgttg aatgaagagg tagaagtcgt ctctaacgag  180
ttctccttca agaagctaac atgtgtgcag acccgcctga agatattcga gcagggtcta  240
cggggcaatt tcaccaaact caagggcgcc ttgaacatga cagccagcta ctaccagaca  300
tactgccccc caactccgga aacggactgt gaaacacaag ttaccaccta tgcggatttc  360
atagacagcc ttaaaacctt tctgactgat atcccctttg aatgcaaaaa accaggccaa  420
aaa                                                             423

SEQ ID NO: 99           moltype = AA  length = 141
FEATURE                 Location/Qualifiers
REGION                  1..141
                        note = Synthetic
source                  1..141
                        mol_type = protein
                        organism = synthetic construct
SEQUENCE: 99
MWLQNLLFLG IVVYSLSAPT RSPITVTRPW KHVEAIKEAL NLLDDMPVTL NEEVEVVSNE  60
FSFKKLTCVQ TRLKIFEQGL RGNFTKLKGA LNMTASYYQT YCPPTPETDC ETQVTTYADF  120
IDSLKTFLTD IPFECKKPGQ K                                         141

SEQ ID NO: 100          moltype = DNA  length = 465
FEATURE                 Location/Qualifiers
misc_feature            1..465
                        note = Synthetic
source                  1..465
                        mol_type = other DNA
                        organism = synthetic construct
SEQUENCE: 100
atgaacgcta cacactgcat cttggctttg cagctcttcc tcatggctgt ttctggctgt  60
tactgccacg gcacagtcat tgaaagccta gaaagtctga ataactattt taactcaagt  120
ggcatagatg tggaagaaaa gagtctcttc ttggatatct ggaggaactg gcaaaaggat  180
ggtgacatga aaatcctgca gagccagatt atctctttct acctcagact ctttgaagtc  240
ttgaaagaca atcaggccat cagcaacaac ataagcgtca ttgaatcaca cctgattact  300
accttcttca gcaacagcaa ggcgaaaaag gatgcattca tgagtattgc caagtttgag  360
gtcaacaacc cacaggtcca gcgccaagca ttcaatgagc tcatccgagt ggtccaccag  420
ctgttgccgg aatccagcct caggaagcgg aaaaggagtc gctgc               465

SEQ ID NO: 101          moltype = AA  length = 155
FEATURE                 Location/Qualifiers
REGION                  1..155
```

```
                        note = Synthetic
source                  1..155
                        mol_type = protein
                        organism = synthetic construct
SEQUENCE: 101
MNATHCILAL QLFLMAVSGC YCHGTVIESL ESLNNYFNSS GIDVEEKSLF LDIWRNWQKD  60
GDMKILQSQI ISFYLRLFEV LKDNQAISNN ISVIESHLIT TFFSNSKAKK DAFMSIAKFE  120
VNNPQVQRQA FNELIRVVHQ LLPESSLRKR KRSRC                            155

SEQ ID NO: 102          moltype = DNA  length = 462
FEATURE                 Location/Qualifiers
misc_feature            1..462
                        note = Synthetic
source                  1..462
                        mol_type = other DNA
                        organism = synthetic construct
SEQUENCE: 102
atgttccatg tttcttttag atatatcttt ggaattcctc cactgatcct tgttctgctg  60
cctgtcacat catctgagtg ccacattaaa gacaaagaag gtaaagcata tgagagtgta  120
ctgatgatca gcatcgatga attggacaaa atgacaggaa ctgatagtaa ttgcccgaat  180
aatgaaccaa actttttag aaaacatgta tgtgatgata caaaggaagc tgcttttcta  240
aatcgtgctg ctcgcaagtt gaagcaattt cttaaaatga atatcagtga agaattcaat  300
gtccacttac taacagtatc acaaggcaca caaacactgg tgaactgcac aagtaaggaa  360
gaaaaaaacg taaaggaaca gaaaaagaat gatgcatgtt tcctaaagag actactgaga  420
gaaataaaaa cttgttggaa taaaattttg aagggcagta ta                    462

SEQ ID NO: 103          moltype = AA  length = 154
FEATURE                 Location/Qualifiers
REGION                  1..154
                        note = Synthetic
source                  1..154
                        mol_type = protein
                        organism = synthetic construct
SEQUENCE: 103
MFHVSFRYIF GIPPLILVLL PVTSSECHIK DKEGKAYESV LMISIDELDK MTGTDSNCPN  60
NEPNFFRKHV CDDTKEAAFL NRAARKLKQF LKMNISEEFN VHLLTVSQGT QTLVNCTSKE  120
EKNVKEQKKN DACFLKRLLR EIKTCWNKIL KGSI                             154

SEQ ID NO: 104          moltype = DNA  length = 966
FEATURE                 Location/Qualifiers
misc_feature            1..966
                        note = Synthetic
source                  1..966
                        mol_type = other DNA
                        organism = synthetic construct
SEQUENCE: 104
atgcagctaa agtgtccctg ttttgtgtcc ttgggaacca ggcagcctgt ttggaagaag  60
ctccatgttt ctagcgggtt cttttctggt cttggtctgt tcttgctgct gttgagcagc  120
ctctgtgctg cctctgcaga gactgaagtc ggtgcaatgg tgggcagcaa tgtggtgctc  180
agctgcattg acccccacag acgccatttc aacttgagtg gtctgtatgt ctattggcaa  240
atcgaaaacc cagaagtttc ggtgacttac tacctgcctt acaagtctcc agggatcaat  300
gtggacagtt cctacaagaa caggggccat ctgtccctgg actccatgaa gcagggtaac  360
ttctctctgt acctgaagaa tgtcacccct caggataccc aggagttcac atgccgggta  420
tttatgaata cagccacaga gttagtcaag atcttggaag aggtggtcag gctgcgtgtg  480
gcagcaaact tcagtacacc tgtcatcagc acctctgata gctccaaccc gggccaggaa  540
cgtacctaca cctgcatgtc caagaatggc tacccagagc ccaacctgta ttggatcaac  600
acaacggaca atagcctaat agacacggct ctgcagaata acactgtcta cttgaacaag  660
ttgggcctgt atgatgtaat cagcacatta aggctccctt ggacatctcg tggggatgtt  720
ctgtgctgcg tagagaatgt ggctctccac cagaacatca ctagcattag ccaggcagaa  780
agtttcactg gaaataacac aaagaaccca caggaaaccc acaataatga gttaaaagtc  840
cttgtccccg tccttgctgt actggcggca gcggcattcg tttccttcat catatacaga  900
cgcacgcgtc cccaccgaag ctatacagga cccaagactg tacagcttga acttacagac  960
cacgcc                                                            966

SEQ ID NO: 105          moltype = AA  length = 322
FEATURE                 Location/Qualifiers
REGION                  1..322
                        note = Synthetic
source                  1..322
                        mol_type = protein
                        organism = synthetic construct
SEQUENCE: 105
MQLKCPCFVS LGTRQPVWKK LHVSSGFFSG LGLFLLLLSS LCAASAETEV GAMVGSNVVL  60
SCIDPHRRHF NLSGLYVYWQ IENPEVSVTY YLPYKSPGIN VDSSYKNRGH LSLDSMKQGN  120
FSLYLKNVTP QDTQEFTCRV FMNTATELVK ILEEVVRLRV AANFSTPVIS TSDSSNPGQE  180
RTYTCMSKNG YPEPNLYWIN TTDNSLIDTA LQNNTVYLNK LGLYDVISTL RLPWTSRGDV  240
LCCVENVALH QNITSISQAE SFTGNNTKNP QETHNNELKV LVPVLAVLAA AFVSFIIYR  300
RTRPHRSYTG PKTVQLELTD HA                                          322
```

```
SEQ ID NO: 106          moltype = DNA  length = 909
FEATURE                 Location/Qualifiers
misc_feature            1..909
                        note = Synthetic
source                  1..909
                        mol_type = other DNA
                        organism = synthetic construct
SEQUENCE: 106
atgtggccct tggcggcggc gctgttgctg ggctcctgct gctgcggttc agctcaacta  60
ctgtttagta acgtcaactc catagagttc acttcatgca atgaaactgt ggtcatccct  120
tgcatcgtcc gtaatgtgga ggcgcaaagc accgaagaaa tgtttgtgaa gtggaagttg  180
aacaaatcgt atattttcat ctatgatgga aataaaaata gcactactac agatcaaaac  240
tttaccagtg caaaaatctc agtctcagac ttaatcaatg gcattgcctc tttgaaaatg  300
gataagcgcg atgccatggt gggaaactac acttgcgaag tgacagagtt atccagagaa  360
ggcaaaacag ttatagagct gaaaaaccgc acggtttcgt ggttttctcc aaatgaaaag  420
atcctcattg ttattttccc aattttggct atactcctgt tctggggaaa gtttggtatt  480
ttaacactca aatataaatc cagccatacg aataagagaa tcattctgct gctcgttgcc  540
gggctggtgc tcacagtcat cgtggttgtt ggagccatcc ttctcatccc aggagaaaag  600
cccgtgaaga atgcttctgg acttggcctc attgtaatct ctacggggat attaatacta  660
cttcagtaca atgtgtttat gacagctttt ggaatgacct ctttcaccat tgccatattg  720
atcactcaag tgctgggcta cgtccttgct ttggtcgggc tgtgtctctg catcatggca  780
tgtgagccag tgcacggccc ccttttgatt tcaggtttgg ggatcatagc tctagcagaa  840
ctacttggat tagtttatat gaagtttgtc gcttccaacc agaggactat ccaacctcct  900
aggaatagg                                                          909

SEQ ID NO: 107          moltype = AA  length = 303
FEATURE                 Location/Qualifiers
REGION                  1..303
                        note = Synthetic
source                  1..303
                        mol_type = protein
                        organism = synthetic construct
SEQUENCE: 107
MWPLAAALLL GSCCCGSAQL LFSNVNSIEF TSCNETVVIP CIVRNVEAQS TEEMFVKWKL  60
NKSYIFIYDG NKNSTTTDQN FTSAKISVSD LINGIASLKM DKRDAMVGNY TCEVTELSRE  120
GKTVIELKNR TVSWFSPNEK ILIVIFPILA ILLFWGKFGI LTLKYKSSHT NKRIILLLVA  180
GLVLTVIVVV GAILLIPGEK PVKNASGLGL IVISTGILIL LQYNVFMTAF GMTSFTIAIL  240
ITQVLGYVLA LVGLCLCIMA CEPVHGPLLI SGLGIIALAE LLGLVYMKFV ASNQRTIQPP  300
RNR                                                                303

SEQ ID NO: 108          moltype = DNA  length = 1161
FEATURE                 Location/Qualifiers
misc_feature            1..1161
                        note = Synthetic
source                  1..1161
                        mol_type = other DNA
                        organism = synthetic construct
SEQUENCE: 108
atggcagcag cagtaacttg gatacctctc ctggcaggtc tcctggcagg actgagggac  60
accaaggccc agcagacaac tttacaccta cttgtgggtc gtgtgtttgt gcatcctttg  120
gaacatgcca ccttcctgcg ccttccagaa cacgttgcgg tgccacccac tgtccgactc  180
acctaccacg ctcacctcca gggacatcca gacctgccca ggtggctgca ctacacacag  240
cgcagtccct ataaccctgg cttcctctac ggctccccca ctccagaaga tcgtgggtac  300
caagtcatcg aggtcacagc ctacaatcga gacagtttttg acaccactag acagaggctg  360
ctgctgctga ttggggaccc cgaaggtccc cggttgccat accaagctga gttcctggtg  420
cgcagccatg atgtggagga ggtgctgccc accacacctg ccaaccgctt cctcaccgcc  480
ttgggggggac tgtgggagcc aggagagctt cagctgctca acatcacttc cgccttggac  540
cggggggaggcc gagtccctct tcctattgag ggacggaagg aaggggtata cattaaggta  600
ggctctgcca caccctctc cacctgcctg aagatggtgg cgtcgcccga cagctatgcc  660
cgttgtgccc agggacagcc tccactactg tcctgctacg acactttggc accccacttc  720
cgcgttgact ggtgcaatgt gtctctggta gacaagtcag tacccgagcc cctggatgag  780
gtacctactc caggcgatgg gatcttggag cacgacccgt tcttctgccc acccactgaa  840
gccacagacc gagacttcct gacagatgcc ttggtgaccc tcttggtgcc tttgttggtg  900
gctctgctgc ttactctgtt gctggcttac atcatgtgct ttcggcgtga aggacggctg  960
aagagagaca tggccacctc tgacatccag atgtttcacc actgttccat ccatgggaat  1020
acagaagagc ttcggcagat ggcagccagc cgagaggtgc cccggcctct ttccaccttg  1080
cccatgttta atgttcgtac aggagagcgg ttacctcccc gagtagacag cgcacagatg  1140
cctcttatcc tggaccagca c                                            1161

SEQ ID NO: 109          moltype = AA  length = 387
FEATURE                 Location/Qualifiers
REGION                  1..387
                        note = Synthetic
source                  1..387
                        mol_type = protein
                        organism = synthetic construct
SEQUENCE: 109
MAAAVTWIPL LAGLLAGLRD TKAQQTTLHL LVGRVFVHPL EHATFLRLPE HVAVPPTVRL  60
TYHAHLQGHP DLPRWLHYTQ RSPYNPGFLY GSPTPEDRGY QVIEVTAYNR DSFDTTRQRL  120
```

```
LLLIGDPEGP RLPYQAEFLV RSHDVEEVLP TTPANRFLTA LGGLWEPGEL QLLNITSALD  180
RGGRVPLPIE GRKEGVYIKV GSATPFSTCL KMVASPDSYA RCAQGQPPLL SCYDTLAPHF  240
RVDWCNVSLV DKSVPEPLDE VPTPGDGILE HDPFFCPPTE ATDRDFLTDA LVTLLVPLLV  300
ALLLTLLLAY IMCFRREGRL KRDMATSDIQ MFHHCSIHGN TEELRQMAAS REVPRPLSTL  360
PMFNVRTGER LPPRVDSAQM PLILDQH                                      387

SEQ ID NO: 110          moltype = DNA  length = 627
FEATURE                 Location/Qualifiers
misc_feature            1..627
                        note = Synthetic
source                  1..627
                        mol_type = other DNA
                        organism = synthetic construct
SEQUENCE: 110
atgtggaaat ggatactgac acattgtgcc tcagcctttc cccacctgcc gggctgctgt  60
tgctgcttct tgttgctctt tttggtgtct tcgttccctg tcacctgcca agctcttggt  120
caggacatgg tgtcacagga ggccaccaac tgctcttctt cctcctcgtc cttctcctct  180
ccttccagtg cgggaaggca tgtgcggagc tacaatcacc tccaaggaga tgtccgctgg  240
agaaggctgt tctccttcac caagtacttt ctcacgattg agaagaacgg caaggtcagc  300
gggaccaaga atgaagactg tccgtacagt gtcctggaga taacatcagt ggaaatcgga  360
gttgttgccg tcaaagccat caacagcaac tattacttag ccatgaacaa gaaggggaaa  420
ctctatggct caaaagagtt taacaacgac tgtaagctga aagagagaat agaggaaaat  480
ggatacaaca cctatgcatc ttttaactgg cagcacaatg gcaggcaaat gtatgtggca  540
ttgaatggaa aaggagctcc caggagagga caaaaaacaa gaaggaaaaa cacctctgct  600
cacttcctcc ccatgacgat ccaaaca                                      627

SEQ ID NO: 111          moltype = AA  length = 209
FEATURE                 Location/Qualifiers
REGION                  1..209
                        note = Synthetic
source                  1..209
                        mol_type = protein
                        organism = synthetic construct
SEQUENCE: 111
MWKWILTHCA SAFPHLPGCC CCFLLLFLVS SFPVTCQALG QDMVSQEATN CSSSSSSFSS  60
PSSAGRHVRS YNHLQGDVRW RRLFSFTKYF LTIEKNGKVS GTKNEDCPYS VLEITSVEIG  120
VVAVKAINSN YYLAMNKKGK LYGSKEFNND CKLKERIEEN GYNTYASFNW QHNGRQMYVA  180
LNGKGAPRRG QKTRRKNTSA HFLPMTIQT                                    209

SEQ ID NO: 112          moltype = DNA  length = 5853
FEATURE                 Location/Qualifiers
misc_feature            1..5853
                        note = Synthetic
source                  1..5853
                        mol_type = other DNA
                        organism = synthetic construct
SEQUENCE: 112
atgcctcctc tgccactgga acacagaccc aggcagcagc ctggtgcctc cgtgctggtt  60
cggtacttca tgatcccctg caacatctgc ttgatcctct tggctacttc tacgttgggc  120
tttgcggtgc tgcttttcct cagcaactac aaacctggga tccacttcac agcagcgcct  180
tctatgcctc ctgatgtgtg caggggaatg ttatgtggct ttggtgctgt gtgtgaacct  240
agtgttgagg atccaggccg ggcctcctgt gtgtgcaaga agaatgtctg ccctgctatg  300
gtagctcctg tgtgtggctc agatgcttcc acctatagca acgagtgtga gctacagcgt  360
gcacagtgca accagcaacg gcgcatccgc ctactccgcc aagggccatg tgggtcccgg  420
gacccctgtg ccaatgtgac ctgcagtttc ggtagtacct gtgtaccttc agccgatgga  480
cagaccgcct cgtgtctgtg tcctacaacc tgctttgggg cccctgatgg cacagtgtgt  540
ggcagtgatg gtgttgacta ccctagtgag tgccagctgc tccgtcatgc ctgtgccaac  600
caggagcaca tctttaagaa gttcgatggt ccttgtgacc cctgccaggg cagcatgtca  660
gacctgaatc atatttgccg ggtgaaccca cgtacacggc acccagaaat gcttctgcgg  720
cctgagaact gccccgccca acacacacct atctgtggag atgatggggt cacctatgaa  780
aacgactgtg tcatgagccg tataggtgca gcccgtggcc tgcttctcca gaaagtgcgc  840
tctggtcaat gccagactcg agaccagtgc ccggagacct gccagtttaa ctctgtatgc  900
ctgtcccgcc gcggccgtcc ccactgttcc tgcgatcgcg tcacctgtga tggggcttac  960
aggccagtgt gtgcccagga tgggcacacg tatgacaatg actgttggcg ccaacaggcc  1020
gagtgtcgac aacagcagac cattcccccc aagcaccagg gcccgtgtga ccagacccca  1080
tccccgtgcc gtggagcgca gtgtgcattt ggggcaacat gcacagtgaa gaatgggaaa  1140
gctgtgtgcg agtgccagcg ggtgtgctcg ggcggctacg atcctgtgtg cggcagtgat  1200
ggtgtcactt acggcagtgt gtgcgagctg gaatccatgg cctgtaccct tgggcgggaa  1260
atccgagtgg cccgcagagg accgtgtgac cgatgtgggc agtgccggtt tggatccttg  1320
tgcgaggtgg agactggacg ctgtgtgtgc ccctctgagt gtgtggagtc agcccagccc  1380
gtatgtggct ctgacggaca cacatatgct agtgaatgtg agctgcatgt ccacgcctgt  1440
acacaccaga tcagcctata cgtggcctca gccggacact gccagacctg tggagaaaca  1500
gtttgtacct ttggggctgt gtgctcagct ggacagtgtg tatgtccccg ttgtgagcac  1560
cccccacctg gccctgtgtg cggcagtgat ggcgtcacct acctcagtgc ctgtgagctc  1620
cgagaggctg cctgtcagca gcaggtacaa attgaggagg cccgtgcagg gccgtgtgag  1680
ccggctgagt gtggctcagg gggctctggg tctggggaag acaatgcgtg tgagcaggag  1740
ctgtgtcggc agcatggtgg tgtctgggat gaggactcag aagacgggcc gtgtgtctgt  1800
gactttagtt gccagagtgt ccttaaaagc ccagtgtgtg gctcagatgg agtcacctat  1860
agcacggagt gccatctgaa gaaggccaga tgtgaagcgc ggcaagagct gtacgtcgct  1920
```

-continued

```
gctcagggag cctgccgggg ccctaccttg gctccactgc tacctatggc ctccccacac  1980
tgtgcccaaa ccccctatgg ctgctgccag gacaatgtca ctgctgccca gggtgtgggc  2040
ttggctggct gtcccagcac ctgccattgc aacccacacg gctcctatag cggcacttgt  2100
gacccagtca cagggcagtg ctcctgccga ccaggtgtag gaggcctcag gtgtgatcgc  2160
tgtgagcctg gcttctggaa cttccgtggc attgtcaccg atggacatag tggttgcact  2220
ccctgcagct gtgaccctcg ggtgctgta agagatgact gtgagcagat gactggattg  2280
tgttcctgta gacctggtgt ggctggtccc aagtgtgggc agtgtccaga tggtcaagcc  2340
ctgggccatc ttggctgtga agcagatccc acaacaccag tgacttgtgt ggaaatgcac  2400
tgtgagtttg gcgcctcctg cgtagaggag gctggttttg cccagtgtgt ctgcccaact  2460
ctcacatgtc cagaggctaa ctctaccaag gtctgtggat cagatggtgt cacatacggc  2520
aatgaatgcc agctgaagac cattgcctgc cgccagcgtc tggacatctc cattcagagt  2580
cttggtccat gccgggagag tgttgctcct ggggtttccc ctacatctgc atctatgacc  2640
accccaaggc atatcctgag caggacactg gcgtctcccc acagcagcct tcctctgtct  2700
cccagcacta ctgcccatga ttggcccacc ccattaccca catcacctca gaccgtagtc  2760
ggcaccccca ggagcactgc agccacaccc tctgatgtgg ccagtcttgc tacagcgatc  2820
ttcagggaat ctggcagcac caacggcagt ggcgatgagg agctcagtgg cgatgaggag  2880
gccagtgggg gcgggtctgg gggacttgag cccccggtgg gcagcgttgt ggtgacccac  2940
gggccaccca tcgagagggc ttcctgttac aactcacctt tgggctgctg ctcagatggc  3000
aagacaccct cactggactc agaaggctcc aactgtccag ctaccaaggc attccagggc  3060
gtgctggagc ttgagggggt cgagggacag gaactgttct acacaccaga gatggctgac  3120
cccaagtcag agttgtttgg ggagactgca aggagcattg agagcacgct ggacgacctg  3180
ttccggaatt cggatgttaa gaaggacttc tggagcatcc gcctacggga actgggggcct  3240
ggcaaattag tccgtgccat tgtggatgtt cactttgacc ccaccacagc cttccaggca  3300
ccagatgtgg gtcaggcctt gctccaacag atccaggtat ccaggccgtg ggccctggca  3360
gtgaggaggc ctctgcggga gcatgtgcga ttcttggact ttgactggtt tcccactttt  3420
tttacgggag ctgcaacagg aaccacagct gctgtggcca cagccagagc caccactgtg  3480
agccgactgt ctgcctcttc tgtcacccca cgagtctacc ccagttacac cagccggcct  3540
gttggcagaa ctacggcacc gctaaccact cgccggccac caaccactac cgccagtatt  3600
gaccgacctc ggactccagg cccgcaacgg cccccaaagt cctgtgattc ccagccttgc  3660
ctccacggag gtacctgcca ggacctggat tctggcaagg gtttcagctg cagctgtact  3720
gcaggcaggg ctggcactgt ctgtgagaaa gtgcagctcc cctctgtgcc agcttttaag  3780
ggccactcct tcttggcctt ccccaccctc cgagcctacc acacgctgcg tctggcacta  3840
gaattccggg cgctggagac agagggactg ctgctctaca atggcaatgc acgtggcaaa  3900
gatttcctgg ctctggctct gttggatggt catgtacagt tcaggttcga cacgggctca  3960
gggccggcgg tgctaacaag cttagtgcca gtggaaccgg gacggtggca ccgcctcgag  4020
ttgtcacggc attggcggca gggcacactt tctgtggatg gcgaggctcc tgttgtaggt  4080
gaaagtccga gtggcactga tggcctcaac ttggacacga agctctatgt gggtggtctc  4140
ccagaagaac aagttgccac ggtgcttgat cggacctctg tgggcatcgg cctgaaagga  4200
tgcattcgta tgttggacat caacaaccag cagctggagc tgagcgattg gcagagggct  4260
gtggttcaaa gctctggtgt gggggaatgc ggagaccatc cctgctcacc taacccctgc  4320
catggcgggg ccctctgcca ggccctggag gctggcgtgt tcctctgtca gtgcccacct  4380
ggccgctttg gcccaacttg tgcagatgaa aagaacccct gccaaccgaa cccctgccac  4440
gggtcagccc cctgccatgt gctttccagg ggtggggcca agtgtgcgtg cccccctggga  4500
cgcagtggtt ccttctgtga gacagtcctg gagaatgctg gctcccggcc cttcctggct  4560
gactttaatg gcttctccta cctggaactg aaaggcttgc acaccttcga gagagaccta  4620
ggggagaaga tggcgctgga gatggtgttc ttggctcgtg ggcccagtgg cttactcctc  4680
tacaatgggc agaagacgga tggcaagggg gactttgtat ccctggccct gcataaccgg  4740
cacctagagt tccgctatga ccttggcaag gggggctgcaa tcatcaggag caaagagccc  4800
atagccctgg gcacctgggt tagggtattc ctggaacgaa atggccgcaa gggtgccctt  4860
caagtgggtg atgggccccg tgtgctaggg gaatctccga aatcccgcaa ggtcccgcac  4920
accatgctca acctcaagga gcccctctat gtggggggag ctcctgactt cagcaagctg  4980
gctcggggcg ctgcagtggc ctccggcttt gatggtgcca tccagctggt gtctctaaga  5040
ggccatcagc tgctgactca ggagcatgtg ttgcgggcag tagatgtagc gccttttgca  5100
ggccacccctt gtacccaggc cgtggacaac ccctgcctta atggggggctc ctgtatcccg  5160
agggaagcca cttatgagtg cctgtgtcct gggggcttct ctgggctgca ctgcgagaag  5220
gggatagttg agaagtcagt gggggaccta gaaacactgg cctttgatgg gcggacctac  5280
atcgagtacc tcaatgctgt gactgagagc gagctgacca atgagatccc agcccccgaa  5340
actctggatt cccgggccct tttcagtgag aaagcgctgc agagcaacca ctttgagctg  5400
agcttacgca ctgaggccac gcaggggctg gtgctgtgga ttggaaaggt tggagaacgt  5460
gcagactaca tggctctggc cattgtggat gggcacctac aactgagcta tgacctaggc  5520
tcccagccag ttgtgctgcg ctccactgtg aaggtcaaca ccaaccgctg gcttcgagtc  5580
agggctcaca gggagcacag ggaaggttcc cttcaggtgg gcaatgaagc cctgtgact  5640
ggctcttccc cgctgggtgc cacacaattg gacacagatg gagccctgtg gcttggaggc  5700
ctacagaagc ttcctgtggg gcaggctctc cccaaggcct atggcacggg ttttgtgggc  5760
tgtctgcggg acgtggtagt gggccatcgc cagctgcatc tgctggagga cgctgtcacc  5820
aaaccagagc taagaccctg ccccactctc tga                               5853
```

```
SEQ ID NO: 113          moltype = AA  length = 1949
FEATURE                 Location/Qualifiers
REGION                  1..1949
                        note = Synthetic
source                  1..1949
                        mol_type = protein
                        organism = synthetic construct
SEQUENCE: 113
MPPLPLEHRP RQQPGASVLV RYFMIPCNIC LILLATSTLG FAVLLFLSNY KPGIHFTAAP  60
SMPPDVCRGM LCGFGAVCEP SVEDPGRASC VCKKNVCPAM VAPVCGSDAS TYSNECELQR  120
AQCNQQRRIR LLRQGPCGSR DPCANVTCSF GSTCVPSADG QTASCLCPTT CFGAPDGTVC  180
GSDGVDYPSE CQLLRHACAN QEHIFKKFDG PCDPCQGSMS DLNHICRVNP RTRHPEMLLR  240
```

```
PENCPAQHTP ICGDDGVTYE NDCVMSRIGA ARGLLLQKVR SGQCQTRDQC PETCQFNSVC  300
LSRRGRPHCS CDRVTCDGAY RPVCAQDGHT YDNDCWRQQA ECRQQQTIPP KHQGPCDQTP  360
SPCRGAQCAF GATCTVKNGK AVCECQRVCS GGYDPVCGSD GVTYGSVCEL ESMACTLGRE  420
IRVARRGPCD RCGQCRFGSL CEVETGRCVC PSECVESAQP VCGSDGHTYA SECELHVHAC  480
THQISLYVAS AGHCQTCGET VCTFGAVCSA GQCVCPRCEH PPPGPVCGSD GVTYLSACEL  540
REAACQQQVQ IEEARAGPCE PAECGSGGSG SGEDNACEQE LCRQHGGVWD EDSEDGPCVC  600
DFSCQSVLKS PVCGSDGVTY STECHLKKAR CEARQELYVA AQGACRGPTL APLLPMASPH  660
CAQTPYGCCQ DNVTAAQGVG LAGCPSTCHC NPHGSYSGTC DPVTGQCSCR PGVGGLRCDR  720
CEPGFWNFRG IVTDGHSGCT PCSCDPRGAV RDDCEQMTGL CSCRPGVAGP KCGQCPDGQA  780
LGHLGCEADP TTPVTCVEMH CEFGASCVEE AGFAQCVCPT LTCPEANSTK VCGSDGVTYG  840
NECQLKTIAC RQRLDISIQS LGPCRESVAP GVSPTSASMT TPRHILSRTL ASPHSSLPLS  900
PSTTAHDWPT PLPTSPQTVV GTPRSTAATP SDVASLATAI FRESGSTNGS GDEELSGDEE  960
ASGGGSGGLE PPVGSVVVTH GPPIERASCY NSPLGCCSDG KTPSLDSEGS NCPATKAFQG  1020
VLELEGVEGQ ELFYTPEMAD PKSELFGETA RSIESTLDDL FRNSDVKKDF WSIRLRELGP  1080
GKLVRAIVDV HFDPTTAFQA PDVGQALLQQ IQVSRPWALA VRRPLREHVR FLDFDWFPTF  1140
FTGAATGTTA AVATARATTV SRLSASSVTP RVYPSYTSRP VGRTTAPLTT RRPPTTTASI  1200
DRPRTPGPQR PPKSCDSQPC LHGGTCQDLD SGKGFSCSCT AGRAGTVCEK VQLPSVPAFK  1260
GHSFLAFPTL RAYHTLRLAL EFRALETEGL LLYNGNARGK DFLALALLDG HVQFRFDTGS  1320
GPAVLTSLVP VEPGRWHRLE LSRHWRQGTL SVDGEAPVVG ESPSGTDGLN LDTKLYVGGL  1380
PEEQVATVLD RTSVGIGLKG CIRMLDINNQ QLELSDWQRA VVQSSGVGEC GDHPCSPNPC  1440
HGGALCQALE AGVFLCQCPP GRFGPTCADE KNPCQPNPCH GSAPCHVLSR GGAKCACPLG  1500
RSGSFCETVL ENAGSRPFAD FNGFSYLELK GLHTFERDLG EKMALEMVFL ARGPSGLLLY  1560
NGQKTDGKGD FVSLALHNRH LEFRYDLGKG AAIIRSKEPI ALGTWVRVFL ERNGRKGALQ  1620
VGDGPRVLGE SPKSRKVPHT MLNLKEPLYV GGAPDFSKLA RGAAVASGFD GAIQLVSLRG  1680
HQLLTQEHVL RAVDVAPFAG HPCTQAVDNP CLNGGSCIPR EATYECLCPG GFSGLHCEKG  1740
IVEKSVGDLE TLAFDGRTYI EYLNAVTESE LTNEIPAPET LDSRALFSEK ALQSNHFELS  1800
LRTEATQGLV LWIGKVGERA DYMALAIVDG HLQLSYDLGS QPVVLRSTVK VNTNRWLRVR  1860
AHREHREGSL QVGNEAPVTG SSPLGATQLD TDGALWLGGL QKLPVGQALP KAYGTGFVGC  1920
LRDVVVGHRQ LHLLEDAVTK PELRPCPTL                                    1949

SEQ ID NO: 114         moltype = DNA  length = 537
FEATURE                Location/Qualifiers
misc_feature           1..537
                       note = Synthetic
source                 1..537
                       mol_type = other DNA
                       organism = synthetic construct
SEQUENCE: 114
atgcctggct cagcactgct atgctgcctg ctcttactga ctggcatgag gatcagcagg  60
ggccagtaca gccgggaaga caataactgc acccacttcc cagtcggcca gagccacatg  120
ctcctagagc tgcggactgc cttcagccag gtgaagactt tctttcaaac aaaggaccag  180
ctggacaaca tactgctaac cgactcctta atgcaggact ttaagggtta cttgggttgc  240
caagccttat cggaaatgat ccagttttac ctggtagaag tgatgcccca ggcagagaag  300
catggcccag aaatcaagga gcatttgaat tccctgggtg agaagctgaa gaccctcagg  360
atgcggctga ggcgctgtca tcgatttctc ccctgtgaaa ataagagcaa ggcagtggag  420
caggtgaaga gtgattttaa taagctccaa gaccaaggtg tctacaaggc catgaatgaa  480
tttgacatct tcatcaactg catagaagca tacatgatga tcaaaatgaa aagctaa     537

SEQ ID NO: 115         moltype = AA  length = 178
FEATURE                Location/Qualifiers
REGION                 1..178
                       note = Synthetic
source                 1..178
                       mol_type = protein
                       organism = synthetic construct
SEQUENCE: 115
MPGSALLCCL LLLTGMRISR GQYSREDNNC THFPVGQSHM LLELRTAFSQ VKTFFQTKDQ  60
LDNILLTDSL MQDFKGYLGC QALSEMIQFY LVEVMPQAEK HGPEIKEHLN SLGEKLKTLR  120
MRLRRCHRFL PCENKSKAVE QVKSDFNKLQ DQGVYKAMNE FDIFINCIEA YMMIKMKS    178

SEQ ID NO: 116         moltype = DNA  length = 501
FEATURE                Location/Qualifiers
misc_feature           1..501
                       note = Synthetic
source                 1..501
                       mol_type = other DNA
                       organism = synthetic construct
SEQUENCE: 116
atggcagccc ccagcggagg cttctggact gcggtggtcc tggcggccgc agcgctgaaa  60
ttggccgccg ctgtgtccga gcccaccacc gtgccatttg acgtgaggcc cggaggggtc  120
gtgcattcgt tctcccagga cgtaggaccc gggaacaagt ttacatgtac attcacctac  180
gcttcccaag gagggaccaa cgagcaatgg cagatgagcc tggggacaag tgaagacagc  240
cagcacttta cctgtaccat ctggaggccc caggggaaat cctacctcta cttcacacag  300
ttcaaggctg agttgcgagg tgctgagatc gagtatgcca tggcctactc caaagccgca  360
tttgagagag agagtgatgt ccccctgaaa agtgaggagt ttgaagtgac caagacagca  420
gtgtctcaca ggcctggggc cttcaaagct gagctctcca agctggtgat cgtagccaag  480
gcggcacgct cggagctgtg a                                            501

SEQ ID NO: 117         moltype = AA  length = 166
```

```
FEATURE                Location/Qualifiers
REGION                 1..166
                       note = Synthetic
source                 1..166
                       mol_type = protein
                       organism = synthetic construct
SEQUENCE: 117
MAAPSGGFWT AVVLAAAALK LAAAVSEPTT VPFDVRPGGV VHSFSQDVGP GNKFTCTFTY  60
ASQGGTNEQW QMSLGTSEDS QHFTCTIWRP QGKSYLYFTQ FKAELRGAEI EYAMAYSKAA  120
FERESDVPLK SEEFEVTKTA VSHRPGAFKA ELSKLVIVAK AARSEL                 166

SEQ ID NO: 118         moltype = DNA  length = 2412
FEATURE                Location/Qualifiers
misc_feature           1..2412
                       note = Synthetic
source                 1..2412
                       mol_type = other DNA
                       organism = synthetic construct
SEQUENCE: 118
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggtcagccca aggccaaccc cactgtcact  360
ctgttcccgc cctcctctga ggagctccaa gccaacaagg ccacactagt gtgtctgatc  420
agtgacttct acccgggagc tgtgacagtg gcctggaagg cagatggcag ccccgtcaag  480
gcgggagtgg agaccaccaa accctccaaa cagagcaaca acaagtacgc ggccagcagc  540
tacctgagcc tgacgcccga gcagtggaag tcccacagaa gctacagctg ccaggtcacg  600
catgaaggga gcaccgtgga gaagacagtg gcccctacag aatgttcagg cgccggatct  660
ggtggaaact ggagtcatcc ccaattcgag aagggcggaa gcggtgggag tggcgggtcc  720
ggtggaagca actggtcaca cccacaattc gagaaaggcg gttctggcgg atctggtgga  780
tctggcggaa gtaactggtc tcatcctcaa ttcgaaaagg gcggaagcgg tggcggcagg  840
ctaggtggag gctcagtgca ggtgcagctg gtggagtctg gggggaggctt ggtacagcct  900
ggggggtccc tgagactctc ctgtgcagcc tctggattca cctttagcag ctatgccatg  960
agctgggtcc gccaggctcc agggaagggg ctggagtggg tctcagttat ttatagcggt  1020
ggtagtagca catactatgc agactccgtg aagggccggt tcaccatctc cagagataat  1080
tccaagaaca cgctgtatct gcaaatgaac agcctgagag ccgaggacac ggccgtatat  1140
tactgtgcgc gcacttctta cctgaaccat ggtgattact ggggtcaagg tactctggtg  1200
accgtgtcta gcgcctccac caagggccca tcggtcttcc ccctggcacc ctcctccaag  1260
agcacctctg gggcacagc ggccctgggc tgcctggtca aggactactt ccccgaaccg  1320
gtgacggtgt cgtggaactc aggcgccctg accagcggcg tgcacacctt cccggctgtc  1380
ctacagtcct caggactcta ctccctcagc agcgtggtga ccgtgccctc cagcagcttg  1440
ggcacccaga cctacatctg caacgtgaac cacaagccca gcaacaccaa ggtggacaag  1500
agagtggagc ccaagagctg cgacaagacc cacacctgcc cccctgccc agccccagag  1560
ctgctgggcg gaccctccgt gttcctgttc ccccccaagc ccaaggacac cctgatgatc  1620
agcaggaccc ccgaggtgac ctgcgtggtg gtggacgtga gccacgagga cccagaggtg  1680
aagttcaact ggtacgtgga cggcgtggag gtgcacaacg ccaagaccaa gcccagagag  1740
gagcagtaca acagcaccta cagggtggtg tccgtgctga ccgtgctgca ccaggactgg  1800
ctgaacggca aggaatacaa gtgcaaggtc tccaacaagg ccctgccagc ccccatcgaa  1860
aagaccatca gcaaggccaa gggccagcca cgggagcccc aggtgtacac cctgcccccc  1920
tcccgggagg agatgaccaa gaaccaggtg tccctgacct gtctggtgaa gggcttctac  1980
cccagcgaca tcgccgtgga gtgggagagc aacggccagc ccgagaacaa ctacaagacc  2040
acccccccag tgctggacag cgacggcagc ttcttcctgt acagcaagct gaccgtggac  2100
aagtccaggt ggcagcaggg caacgtgttc agctgcagcg tgatgcacga ggccctgcac  2160
aaccactaca cccagaagag cctgagcctg tcccccgagc tgcaactgga ggagagctgt  2220
gcggaggcgc aggacgggga gctggacggg ctgtggacga ccatcaccat cttcatcaca  2280
ctcttcctgt taagcgtgtg ctacagtgcc accgtcacct tcttcaaggt gaagtggatc  2340
ttctcctcgg tggtggacct gaagcagacc atcatccccg actacaggaa catgatcgga  2400
cagggggcct ga                                                    2412

SEQ ID NO: 119         moltype = AA  length = 803
FEATURE                Location/Qualifiers
REGION                 1..803
                       note = Synthetic
source                 1..803
                       mol_type = protein
                       organism = synthetic construct
SEQUENCE: 119
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECSGAGS GGNWSHPQFE KGGSGGSGGS  240
GGSNWSHPQF EKGGSGGSGG SGGSNWSHPQ FEKGGSGGGR LGGGSVQVQL VESGGGLVQP  300
GGSLRLSCAA SGFTFSSYAM SWVRQAPGKG LEWVSVIYSG GSSTYYADSV KGRFTISRDN  360
SKNTLYLQMN SLRAEDTAVY YCARTSYLNH GDYWGQGTLV TVSSASTKGP SVFPLAPSSK  420
STSGGTAALG CLVKDYFPEP VTVSWNSGAL TSGVHTFPAV LQSSGLYSLS SVVTVPSSSL  480
GTQTYICNVN HKPSNTKVDK RVEPKSCDKT HTCPPCPAPE LLGGPSVFLF PPKPKDTLMI  540
SRTPEVTCVV VDVSHEDPEV KFNWYVDGVE VHNAKTKPRE EQYNSTYRVV SVLTVLHQDW  600
```

```
LNGKEYKCKV SNKALPAPIE KTISKAKGQP REPQVYTLPP SREEMTKNQV SLTCLVKGFY  660
PSDIAVEWES NGQPENNYKT TPPVLDSDGS FFLYSKLTVD KSRWQQGNVF SCSVMHEALH  720
NHYTQKSLSL SPELQLEESC AEAQDGELDG LWTTITIFIT LFLLSVCYSA TVTFFKVKWI  780
FSSVVDLKQT IIPDYRNMIG QGA                                         803

SEQ ID NO: 120         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 120
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta tcttcagcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaaccacaag  600
cccagcaaca ccaaggtgga caagagagtg gagcccaaga gctgc                  645

SEQ ID NO: 121         moltype = AA  length = 215
FEATURE                Location/Qualifiers
REGION                 1..215
                       note = Synthetic
source                 1..215
                       mol_type = protein
                       organism = synthetic construct
SEQUENCE: 121
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKRV EPKSC                            215

SEQ ID NO: 122         moltype = DNA  length = 1566
FEATURE                Location/Qualifiers
misc_feature           1..1566
                       note = Synthetic
source                 1..1566
                       mol_type = other DNA
                       organism = synthetic construct
SEQUENCE: 122
caggtgcagc tggtggagtc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagtt atttatagcg gtggtagtag cacatactat  180
gcagactccg tgaagggccg gttcaccatc tccagagata attccaagaa cacgctgtat  240
ctgcaaatga acagcctgag agccgaggac acggccgtat attactgtgc gcgcacttct  300
tacctgaacc atggtgatta ctggggtcaa ggtactctgg tgaccgtgtc tagcgcctcc  360
gtggctgcac catctgtctt catcttcccg ccatctgatg agcagttgaa atctggaact  420
gcctctgttg tgtgcctgct gaataacttc tatcccagag aggccaaagt acagtggaag  480
gtggataacg ccctccaatc gggtaactcc caggagagtg tcacagagca ggacagcaag  540
gacagcacct acagcctcag cagcaccctg acgctgagca aagcagacta cgagaaacac  600
aaagtctacg cctgcgaagt cacccatcag ggcctgagct cgcccgtcac aaagagcttc  660
aacaggggag agtgtgacaa gacccacacc tgccccccct gcccagcccc agagctgctg  720
ggcggaccct ccgtgttcct gttccccccc aagcccaagg acaccctgat gatcagcagg  780
acccccgagg tgacctgcgt ggtggtggac gtgagccacg aggacccaga ggtgaagttc  840
aactggtacg tggacggcgt ggaggtgcac aacgccaaga ccaagcccag agaggagcag  900
tacaacagca cctacagggt ggtgtccgtg ctgaccgtgc tgcaccagga ctggctgaac  960
ggcaaggaat acaagtgcaa ggtctccaac aaggccctgc cagcccccat cgaaaagacc  1020
atcagcaagg ccaagggcca gccacgggag ccccaggtgt acaccctgcc cccctcccgg  1080
gaggagatga ccaagaacca ggtgtccctg acctgtctgg tgaagggctt ctaccccagc  1140
gacatcgccg tggagtggga gagcaacggc cagcccgaga acaactacaa gaccaccccc  1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga agagcctgag cctgtccccc gagctgcaac tggaggagag ctgtgcggag  1380
gcgcaggacg gggagctgga cgggctgtgg acgaccatca ccatcttcat cacactcttc  1440
ctgttaagcg tgtgctacag tgccaccgtc accttcttca aggtgaagtg gatcttctcc  1500
tcggtggtgg acctgaagca gaccatcatc cccgactaca ggaacatgat cggacagggg  1560
gcctga                                                             1566

SEQ ID NO: 123         moltype = AA  length = 521
FEATURE                Location/Qualifiers
REGION                 1..521
                       note = Synthetic
source                 1..521
```

```
                         mol_type = protein
                         organism = synthetic construct
SEQUENCE: 123
QVQLVESGGG LVQPGGSLRL SCAASGFTFS SYAMSWVRQA PGKGLEWVSV IYSGGSSTYY  60
ADSVKGRFTI SRDNSKNTLY LQMNSLRAED TAVYYCARTS YLNHGDYWGQ GTLVTVSSAS  120
VAAPSVFIFP PSDEQLKSGT ASVVCLLNNF YPREAKVQWK VDNALQSGNS QESVTEQDSK  180
DSTYSLSSTL TLSKADYEKH KVYACEVTHQ GLSSPVTKSF NRGECDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP ELQLEESCAE AQDGELDGLW TTITIFITLF  480
LLSVCYSATV TFFKVKWIFS SVVDLKQTII PDYRNMIGQG A                       521

SEQ ID NO: 124           moltype = DNA  length = 486
FEATURE                  Location/Qualifiers
misc_feature             1..486
                         note = Synthetic
source                   1..486
                         mol_type = other DNA
                         organism = synthetic construct
SEQUENCE: 124
atgaaaattt tgaaaccata tatgaggaat acatccatct cgtgctactt gtgtttcctt  60
ctaaacagtc actttttaac tgaggctggc attcatgtct tcattttggg ctgtgtcagt  120
gtaggtctcc ctaaaacaga ggccaactgg atagatgtaa gatatgacct ggagaaaatt  180
gaaagcctta ttcaatctat tcatattgac accactttat acactgacag tgactttcat  240
cccagttgca aagttactgc aatgaactgc tttctcctgg aattgcaggt tattttacat  300
gagtacagta acatgactct taatgaaaca gtaagaaacg tgctctacct tgcaaacagc  360
actctgtctt ctaacaagaa tgtagcagaa tctggctgca aggaatgtga ggagctggag  420
gagaaaacct tcacagagtt tttgcaaagc tttatacgca ttgtccaaat gttcatcaac  480
acgtcc                                                              486

SEQ ID NO: 125           moltype = AA  length = 162
FEATURE                  Location/Qualifiers
REGION                   1..162
                         note = Synthetic
source                   1..162
                         mol_type = protein
                         organism = synthetic construct
SEQUENCE: 125
MKILKPYMRN TSISCYLCFL LNSHFLTEAG IHVFILGCVS VGLPKTEANW IDVRYDLEKI  60
ESLIQSIHID TTLYTDSDFH PSCKVTAMNC FLLELQVILH EYSNMTLNET VRNVLYLANS  120
TLSSNKNVAE SGCKECEELE EKTFTEFLQS FIRIVQMFIN TS                      162

SEQ ID NO: 126           moltype = DNA  length = 1185
FEATURE                  Location/Qualifiers
misc_feature             1..1185
                         note = Synthetic
source                   1..1185
                         mol_type = other DNA
                         organism = synthetic construct
SEQUENCE: 126
cagtctgtgt tgacgcagcc gccctcagtg tctgcggccc caggacagag ggtcaccatc  60
tcctgctctg gaaccaggtc caacattggg agtgattatg tttcctggta ccaacacctc  120
ccaggaacag cccccaaact cctcgtttat ggcgataatc tgcgaccctc agggattcct  180
gaccgattct ctgcctccaa gtctggcacg tcagccaccc tgggcatcac cggactccag  240
actggggacg aggccgatta ttactgcggc acatgggatt acaccctgaa tggtgtggtg  300
ttcggcggag ggaccaagct gaccgtccta ggttctagag gtggtggtgg tagcggcggc  360
ggcggctctg gtggtggtgg atccctcgag atggcccagg tgcagctggt ggagtctggg  420
ggaggcttgg tacagcctgg ggggtccctg agactctcct gtgcagcctc tggattcacc  480
tttagcagct atgccatgag ctgggtccgc caggctccag ggaaggggct ggagtgggtc  540
tcagttattt atagcggtgg tagtagcaca tactatgcag actccgtgaa gggccggttc  600
accatctcca gagataattc caagaacacg ctgtatctgc aaatgaacag cctgagagcc  660
gaggacacgg ccgtatatta ctgtgcgcgc acttcttacc tgaaccatgg tgattactgg  720
ggtcaaggta ctctggtgac cgtgtctagc gccgctgcag tggtccccgt gctgcagaaa  780
gttaatagca ccaccactaa acctgtcctg aggactccta gtccagtgca cccaacaggg  840
accagtcagc cacagagacc ggaagactgc agaccaagag gttcagtgaa gggaaccggc  900
ctggatttcg cctgcgattt ttgggccctg gtcgtcgtcg caggagtttt gttttgctat  960
ggactgctcg tcacagttgc tttgtgtgtt atctggacaa ggaaacggtg gcaaaatgag  1020
aagtttgggg tggacatgcc agatgactat gaagatgaaa atctctatga gggcctgaac  1080
cttgatgact gttctatgta tgaggacatc tccaggggac tccagggcac ctaccaggat  1140
gtgggcaacc tccacattgg agatgcccag ctggaaaagc catga                   1185

SEQ ID NO: 127           moltype = AA  length = 394
FEATURE                  Location/Qualifiers
REGION                   1..394
                         note = Synthetic
source                   1..394
                         mol_type = protein
                         organism = synthetic construct
```

```
SEQUENCE: 127
QSVLTQPPSV SAAPGQRVTI SCSGTRSNIG SDYVSWYQHL PGTAPKLLVY GDNLRPSGIP  60
DRFSASKSGT SATLGITGLQ TGDEADYYCG TWDYTLNGVV FGGGTKLTVL GSRGGGGSGG  120
GGSGGGGSLE MAQVQLVESG GGLVQPGGSL RLSCAASGFT FSSYAMSWVR QAPGKGLEWV  180
SVIYSGGSST YYADSVKGRF TISRDNSKNT LYLQMNSLRA EDTAVYYCAR TSYLNHGDYW  240
GQGTLVTVSS AAAVVPVLQK VNSTTTKPVL RTPSPVHPTG TSQPQRPEDC RPRGSVKGTG  300
LDFACDFWAL VVVAGVLFCY GLLVTVALCV IWTRKRWQNE KFGVDMPDDY EDENLYEGLN  360
LDDCSMYEDI SRGLQGTYQD VGNLHIGDAQ LEKP                              394

SEQ ID NO: 128         moltype = DNA  length = 1152
FEATURE                Location/Qualifiers
misc_feature           1..1152
                       note = Synthetic
source                 1..1152
                       mol_type = other DNA
                       organism = synthetic construct
SEQUENCE: 128
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaagtgg tccccgtgct gcagaaagtt aatagcacca ccactaaacc tgtcctgagg  780
actcctagtc cagtgcaccc aacagggacc agtcagccac agagaccgga agactgcaga  840
ccaagaggtt cagtgaaggg aaccggcctg gatttcgcct gcgatttttg ggccctggtc  900
gtcgtcgcag gagttttgtt ttgctatgga ctgctcgtca cagttgcttt gtgtgttatc  960
tggacaagga aacggtggca aaatgagaag tttggggtgg acatgccaga tgactatgaa  1020
gatgaaaatc tctatgaggg cctgaacctt gatgactgtt ctatgtatga ggacatctcc  1080
aggggactcc agggcaccta ccaggatgtg ggcaacctcc acattggaga tgcccagctg  1140
gaaaagccat ga                                                      1152

SEQ ID NO: 129         moltype = AA  length = 383
FEATURE                Location/Qualifiers
REGION                 1..383
                       note = Synthetic
source                 1..383
                       mol_type = protein
                       organism = synthetic construct
SEQUENCE: 129
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSGKPGS  120
GKPGSGKPGS GKPGSDIVMT QSPDSLAVSL GERATLSCRA SQDVGTAVDW YQQKPDQSPK  180
LLIYWASTRH TGVPDRFTGS GSGTDFTLTI SSLQAEDVAV YFCQQYNSYP LTFGAGTKVE  240
IKVVPVLQKV NSTTTKPVLR TPSPVHPTGT SQPQRPEDCR PRGSVKGTGL DFACDFWALV  300
VVAGVLFCYG LLVTVALCVI WTRKRWQNEK FGVDMPDDYE DENLYEGLNL DDCSMYEDIS  360
RGLQGTYQDV GNLHIGDAQL EKP                                          383

SEQ ID NO: 130         moltype = DNA  length = 1344
FEATURE                Location/Qualifiers
source                 1..1344
                       mol_type = unassigned DNA
                       organism = Mus musculus
SEQUENCE: 130
atgtgtcagt cacgctatct tctcttcctt gctactctgg ccttgctcaa tcacttgtcc  60
cttgctcgtg tgattcctgt gtccggccca gctaggtgtc tctcccagtc acggaatctc  120
ctgaaaacca cggatgacat ggtaaagaca gctagggaga aactcaagca ctactcctgc  180
acagctgagg atatcgatca tgaggacatc accagggacc agacatccac tctgaaaact  240
tgcctgcctt tggaactcca caagaacgaa tcttgtctgg caacgcgtga aacgagttct  300
actacaagag ggtcctgtct tccccctcaa aagacaagcc ttatgatgac cttgtgtctc  360
ggtagcattt atgaggacct aaagatgtat caaaccgagt ttcaggctat caatgcagcg  420
ctccagaatc ataaccatca gcagatcatt cttgacaaag gaatgctcgt ggccattgat  480
gaactaatgc agagcctaaa ccacaatggc gagactcttc gacagaaacc gcctgtgggc  540
gaggccgatc catatagagt caaaatgaaa ctgtgtattc tcctgcatgc atttagtact  600
cgtgtagtga ctattaacag agtgatgggt tacctttcct cagctcccag agggcccaca  660
atcaagccct gtcctccatg caaatgccca gcacctaacc tcttgggtgg accatccgtc  720
ttcatcttcc ctccaaagat caaggatgta ctcatgatct ccctgagccc catagtcaca  780
tgtgtggtgg tggatgtgag cgaggatgac ccagatgtcc agatcagctg gtttgtgaac  840
aacgtggaag tacacacagc tcagacacaa acccatagag aggattacaa cagtactctc  900
cgggtggtca gtgccctccc catccagcac caggactgga tgagtggcaa ggagttcaaa  960
tgcaaggtca acaacaaaga cctcccagcg cccatcgaga gaaccatctc aaaacccaaa  1020
gggtcagtaa gagctccaca ggtatatgtc ttgcctccac cagaagaaga gatgactaag  1080
aaacaggtca ctctgacctg catggtcaca gacttcatgc ctgaagacat ttacgtggag  1140
```

```
tggaccaaca acgggaaaac agagctaaac tacaagaaca ctgaaccagt cctggactct  1200
gatggttctt acttcatgta cagcaagctg agagtggaaa agaagaactg ggtggaaaga  1260
aatagctact cctgttcagt ggtccacgag ggtctgcaca atcaccacac gactaagagc  1320
ttctcccgga ctccgggtaa atag                                          1344

SEQ ID NO: 131          moltype = AA  length = 447
FEATURE                 Location/Qualifiers
source                  1..447
                        mol_type = protein
                        organism = Mus musculus
SEQUENCE: 131
MCQSRYLLFL ATLALLNHLS LARVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSAPRGPT IKPCPPCKCP APNLLGGPSV  240
FIFPPKIKDV LMISLSPIVT CVVVDVSEDD PDVQISWFVN NVEVHTAQTQ THREDYNSTL  300
RVVSALPIQH QDWMSGKEFK CKVNNKDLPA PIERTISKPK GSVRAPQVYV LPPPEEEMTK  360
KQVTLTCMVT DFMPEDIYVE WTNNGKTELN YKNTEPVLDS DGSYFMYSKL RVEKKNWVER  420
NSYSCSVVHE GLHNHHTTKS FSRTPGK                                       447

SEQ ID NO: 132          moltype = DNA  length = 1704
FEATURE                 Location/Qualifiers
source                  1..1704
                        mol_type = unassigned DNA
                        organism = Mus musculus
SEQUENCE: 132
atgtgcccac agaaactcac aatttcttgg ttcgcaatcg tcctgctggt gtcacccctg  60
atggcaatgt gggagttgga aaaggatgta tacgtcgtcg aggtcgactg gacacctgac  120
gctccgggtg aaactgtcaa cctcacttgc gatactcctg aagaggacga catcacgtgg  180
acgagcgacc agcgacatgg agtgataggg tctggcaaga cgcttactat cacggttaag  240
gaatttctcg acgcagggca gtacacatgt cacaagggcg gcgagactct gagccactcc  300
catttgctgc tgcacaagaa ggagaatggt atctggtcta ccgaaatcct gaagaatttt  360
aagaacaaga cttttctgaa atgcgaggcc ccaaattatt ccggacgttt cacttgcagt  420
tggctcgttc aaagaaatat ggacttgaaa tttaacatta aatccagctc ttcatctcct  480
gacagcaggg ccgtaacttg tggaatggct tcattgtcag ctgagaaagt tacgcttgac  540
caaagggatt atgagaaata cagcgtgagt tgccaggaag atgtgacatg tccaacggca  600
gaggaaacgt tgccaattga gctcgctttg gaagctcgtc aacaaaacaa gtatgaaaac  660
tatagtacta gcttcttcat acgggacatc atcaaaccag atccacctaa gaatttgcag  720
atgaagcctc tgaagaattc acaagtcgag gtatcctggg aataccaga ttcatggtcc   780
actcctcata gttactttag cctgaaattc tttgtacgca tacagcggaa gaaggagaaa  840
atgaaggaga cggaagaagg ctgcaatcag aaaggcgctt ttcttgttga aaagacgagc  900
actgaggttc aatgcaaagg cggaatgta tgtgttcaag cccaagatag gtattataat   960
agctcctgct ctaagtgggc ttgcgtacca tgcagagtta gaagtcccag agggcccaca  1020
atcaagccct gtcctccatg caaatgccca gcacctaacc tcttgggtgg accatccgtc  1080
ttcatcttcc ctccaaagat caaggatgta ctcatgatct ccctgagccc catagtcaca  1140
tgtgtggtgg tggatgtgag cgaggatgac ccagatgtcc agatcagctg gtttgtgaac  1200
aacgtggaag tacacacagc tcagacacaa acccatagag aggattacaa cagtactctc  1260
cgggtggtca gtgccctccc catccagcac caggactgga tgagtggcaa ggagttcaaa  1320
tgcaaggtca acaacaaaga cctcccagcg cccatcgaga gaaccatctc aaaacccaaa  1380
gggtcagtaa gagctccaca ggtatatgtc ttgcctccac cagaagaaga gatgactaag  1440
aaacaggtca ctctgacctg catggtcaca gacttcatgc ctgaagacat ttacgtggag  1500
tggaccaaca acgggaaaac agagctaaac tacaagaaca ctgaaccagt cctggactct  1560
gatggttctt acttcatgta cagcaagctg agagtggaaa agaagaactg ggtggaaaga  1620
aatagctact cctgttcagt ggtccacgag ggtctgcaca atcaccacac gactaagagc  1680
ttctcccgga ctccgggtaa atag                                          1704

SEQ ID NO: 133          moltype = AA  length = 567
FEATURE                 Location/Qualifiers
source                  1..567
                        mol_type = protein
                        organism = Mus musculus
SEQUENCE: 133
MCPQKLTISW FAIVLLVSPL MAMWELEKDV YVVEVDWTPD APGETVNLTC DTPEEDDITW  60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRSPRGPT IKPCPPCKCP APNLLGGPSV  360
FIFPPKIKDV LMISLSPIVT CVVVDVSEDD PDVQISWFVN NVEVHTAQTQ THREDYNSTL  420
RVVSALPIQH QDWMSGKEFK CKVNNKDLPA PIERTISKPK GSVRAPQVYV LPPPEEEMTK  480
KQVTLTCMVT DFMPEDIYVE WTNNGKTELN YKNTEPVLDS DGSYFMYSKL RVEKKNWVER  540
NSYSCSVVHE GLHNHHTTKS FSRTPGK                                       567

SEQ ID NO: 134          moltype = DNA  length = 1344
FEATURE                 Location/Qualifiers
source                  1..1344
                        mol_type = unassigned DNA
                        organism = Mus musculus
SEQUENCE: 134
```

```
atgtgtcagt cacgctatct tctcttcctt gctactctgg ccttgctcaa tcacttgtcc  60
cttgctcgtg tgattcctgt gtccggccca gctaggtgtc tctcccagtc acggaatctc  120
ctgaaaacca cggatgacat ggtaaagaca gctagggaga aactcaagca ctactcctgc  180
acagctgagg atatcgatca tgaggacatc accagggacc agacatccac tctgaaaact  240
tgcctgcctt tggaactcca caagaacgaa tcttgtctgg caacgcgtga aacgagttct  300
actacaagag ggtcctgtct tccccctcaa aagacaagcc ttatgatgac cttgtgtctc  360
ggtagcattt atgaggacct aaagatgtat caaaccgagt ttcaggctat caatgcagcg  420
ctccagaatc ataaccatca gcagatcatt cttgacaaag gaatgctcgt ggccattgat  480
gaactaatgc agagcctaaa ccacaatggc gagactcttc gacagaaacc gcctgtgggc  540
gaggccgatc catatagagt caaaatgaaa ctgtgtattc tcctgcatgc atttagtact  600
cgtgtagtga ctattaacag agtgatgggt tacctttcct cagctcccag agggcccaca  660
atcaagccct gtcctccatg caaatgccca gcacctaacg ctgccggtgg accatccgtc  720
ttcatcttcc ctccaaagat caaggatgta ctcatgatct ccctgagccc catagtcaca  780
tgtgtggtgg tggatgtgag cgaggatgac ccagatgtcc agatcagctg gtttgtgaac  840
aacgtggaag tacacacagc tcagacacaa acccatagag aggattacaa cagtactctc  900
cgggtggtca gtgccctccc catccagcac caggactgga tgagtggcaa ggagttcaaa  960
tgcaaggtca acaacaaaga cctcggagcg cccatcgaga gaaccatctc aaaacccaaa  1020
gggtcagtaa gagctccaca ggtatatgtc ttgcctccac cagaagaaga gatgactaag  1080
aaacaggtca ctctgacctg catggtcaca gacttcatgc ctgaagacat ttacgtggag  1140
tggaccaaca acgggaaaac agagctaaac tacaagaaca ctgaaccagt cctggactct  1200
gatggttctt acttcatgta cagcaagctg agagtggaaa agaagaactg ggtggaaaga  1260
aatagctact cctgttcagt ggtccacgag ggtctgcaca atcaccacac gactaagagc  1320
ttctcccgga ctccgggtaa atga                                        1344

SEQ ID NO: 135         moltype = AA  length = 447
FEATURE                Location/Qualifiers
source                 1..447
                       mol_type = protein
                       organism = Mus musculus
SEQUENCE: 135
MCQSRYLLFL ATLALLNHLS LARVIPVSGP ARCLSQSRNL LKTTDDMVKT AREKLKHYSC  60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSAPRGPT IKPCPPCKCP APNAAGGPSV  240
FIFPPKIKDV LMISLSPIVT CVVVDVSEDD PDVQISWFVN NVEVHTAQTQ THREDYNSTL  300
RVVSALPIQH QDWMSGKEFK CKVNNKDLGA PIERTISKPK GSVRAPQVYV LPPPEEEMTK  360
KQVTLTCMVT DFMPEDIYVE WTNNGKTELN YKNTEPVLDS DGSYFMYSKL RVEKKNWVER  420
NSYSCSVVHE GLHNHHTTKS FSRTPGK                                     447

SEQ ID NO: 136         moltype = DNA  length = 1704
FEATURE                Location/Qualifiers
source                 1..1704
                       mol_type = unassigned DNA
                       organism = Mus musculus
SEQUENCE: 136
atgtgcccac agaaactcac aatttcttgg ttcgcaatcg tcctgctggt gtcacccctg  60
atggcaatgt gggagttgga aaaggatgta tacgtcgtcg aggtcgactg gacacctgac  120
gctccgggtg aaactgtcaa cctcacttgc gatactcctg aagaggacga catcacgtgg  180
acgagcgacc agcgacatgg agtgataggg tctggcaaga cgcttactat cacggttaag  240
gaatttctcg acgcagggca gtacacatgt cacaagggcg gcgagactct gagccactcc  300
catttgctgc tgcacaagaa ggagaatggt atctggtcta ccgaaatcct gaagaatttt  360
aagaacaaga cttttctgaa atgcgaggcc ccaaattatt ccggacgttt cacttgcagt  420
tggctcgttc aaagaaatat ggacttgaaa tttaacatta aatccagctc ttcatctcct  480
gacagcaggg ccgtaacttg tggaatggct tcattgtcag ctgagaaagt tacgcttgac  540
caaagggatt atgagaaata cagcgtgagt tgccaggaag atgtgacatg tccaacggca  600
gaggaaacgt tgccaattga gctcgctttg gaagctcgtc aacaaaacaa gtatgaaaac  660
tatagtacta gcttcttcat acgggacatc atcaaaccag atccacctaa gaatttgcag  720
atgaagcctc tgaagaattc acaagtcgag gtatcctggg aatacccaga ttcatggtcc  780
actcctcata gttactttag cctgaaattc tttgtacgca tacagcggaa gaaggagaaa  840
atgaaggaga cggaagaagg ctgcaatcag aaaggcgctt ttcttgttga aaagacgagc  900
actgaggttc aatgcaaagg cggaatgta tgtgttcaag cccaagatag gtattataat  960
agctcctgct ctaagtgggc ttgcgtacca tgcagagtta gaagtcccag agggcccaca  1020
atcaagccct gtcctccatg caaatgccca gcacctaacg ctgccggtgg accatccgtc  1080
ttcatcttcc ctccaaagat caaggatgta ctcatgatct ccctgagccc catagtcaca  1140
tgtgtggtgg tggatgtgag cgaggatgac ccagatgtcc agatcagctg gtttgtgaac  1200
aacgtggaag tacacacagc tcagacacaa acccatagag aggattacaa cagtactctc  1260
cgggtggtca gtgccctccc catccagcac caggactgga tgagtggcaa ggagttcaaa  1320
tgcaaggtca acaacaaaga cctcggagcg cccatcgaga gaaccatctc aaaacccaaa  1380
gggtcagtaa gagctccaca ggtatatgtc ttgcctccac cagaagaaga gatgactaag  1440
aaacaggtca ctctgacctg catggtcaca gacttcatgc ctgaagacat ttacgtggag  1500
tggaccaaca acgggaaaac agagctaaac tacaagaaca ctgaaccagt cctggactct  1560
gatggttctt acttcatgta cagcaagctg agagtggaaa agaagaactg ggtggaaaga  1620
aatagctact cctgttcagt ggtccacgag ggtctgcaca atcaccacac gactaagagc  1680
ttctcccgga ctccgggtaa atga                                        1704

SEQ ID NO: 137         moltype = AA  length = 567
FEATURE                Location/Qualifiers
source                 1..567
                       mol_type = protein
```

```
                         organism = Mus musculus
SEQUENCE: 137
MCPQKLTISW FAIVLLVSPL MAMWELEKDV YVVEVDWTPD APGETVNLTC DTPEEDDITW  60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRSPRGPT IKPCPPCKCP APNAAGGPSV  360
FIFPPKIKDV LMISLSPIVT CVVVDVSEDD PDVQISWFVN NVEVHTAQTQ THREDYNSTL  420
RVVSALPIQH QDWMSGKEFK CKVNNKDLGA PIERTISKPK GSVRAPQVYV LPPPEEEMTK  480
KQVTLTCMVT DFMPEDIYVE WTNNGKTELN YKNTEPVLDS DGSYFMYSKL RVEKKNWVER  540
NSYSCSVVHE GLHNHHTTKS FSRTPGK                                     567

SEQ ID NO: 138           moltype = AA  length = 113
FEATURE                  Location/Qualifiers
source                   1..113
                         mol_type = protein
                         organism = Homo sapiens
SEQUENCE: 138
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR         113

SEQ ID NO: 139           moltype = DNA  length = 342
FEATURE                  Location/Qualifiers
source                   1..342
                         mol_type = genomic DNA
                         organism = Homo sapiens
SEQUENCE: 139
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgcag agaaggaaga accctcagga aggcctgtac  180
aatgaactgc agaaagataa gatggcggag gcctacagtg agattgggat gaaaggcgag  240
cgccggaggg gcaaggggca cgatggcctt taccagggtc tcagtacagc caccaaggac  300
acctacgacg cccttcacat gcaggccctg ccccctcgct aa                    342

SEQ ID NO: 140           moltype = AA  length = 570
FEATURE                  Location/Qualifiers
REGION                   1..570
                         note = Synthetic
source                   1..570
                         mol_type = protein
                         organism = synthetic construct
SEQUENCE: 140
METDTLLLWV LLLWVPGSTG QSVLTQPPSV SAAPGQRVTI SCSGTRSNIG SDYVSWYQHL  60
PGTAPKLLVY GDNLRPSGIP DRFSASKSGT SATLGITGLQ TGDEADYYCG TWDYTLNGVV  120
FGGGTKLTVL GSRGGGGSGG GGSGGGGSLE MAQVQLVESG GGLVQPGGSL RLSCAASGFT  180
FSSYAMSWVR QAPGKGLEWV SVIYSGGSST YYADSVKGRF TISRDNSKNT LYLQMNSLRA  240
EDTAVYYCAR TSYLNHGDYW GQGTLVTVSS PKSCDKTHTC PPCPAPELLG GPSVFLFPPK  300
PKDTLMISRT PEVTCVVVDV SHEDPEVKFN WYVDGVEVHN AKTKPREEQY NSTYRVVSVL  360
TVLHQDWLNG KEYKCKVSNK ALPAPIEKTI SKAKGQPREP QVYTLPPSRE EMTKNQVSLT  420
CLVKGFYPSD IAVEWESNGQ PENNYKTTPP VLDSDGSFFL YSKLTVDKSR WQQGNVFSCS  480
VMHEALHNHY TQKSLSLSPE LQLEESCAEA QDGELDGLWT TITIFITLFL LSVCYSATVT  540
FFKVKWIFSS VVDLKQTIIP DYRNMIGQGA                                  570

SEQ ID NO: 141           moltype = DNA  length = 1713
FEATURE                  Location/Qualifiers
misc_feature             1..1713
                         note = Synthetic
source                   1..1713
                         mol_type = other DNA
                         organism = synthetic construct
SEQUENCE: 141
atggaaaccg atacactgct gctgtgggtg ctgctgctgt gggtgccagg atctaccggt  60
cagtctgtgt tgacgcagcc gccctcagtg tctgcggccc caggacagag ggtcaccatc  120
tcctgctctg gaaccaggtc caacattggg agtgattatg tttcctggta ccaacacctc  180
ccaggaacag cccccaaact cctcgtttat ggcgataatc tgcgaccctc agggattcct  240
gaccgattct ctgcctccaa gtctggcacg tcagccaccc tgggcatcac cggactccag  300
actggggacg aggccgatta ttactgcggc acatgggatt acaccctgaa tggtgtggtg  360
ttcggcggag ggaccaagct gaccgtccta ggttctagag gtggtggtgg tagcggcggc  420
ggcggctctg gtggtggtgg atccctcgag atggcccagg tgcagctggt ggagtctggg  480
ggaggcttgg tacagcctgg ggggtccctg agactctcct gtgcagcctc tggattcacc  540
tttagcagct atgccatgag ctgggtccgc caggctccag ggaaggggct ggagtgggtc  600
tcagttattt atagcggtgg tagtagcaca tactatgcag actccgtgaa gggccggttc  660
accatctcca gagataattc caagaacacg ctgtatctgc aaatgaacag cctgagagcc  720
gaggacacgg ccgtatatta ctgtgcgcgc acttcttacc tgaaccatgg tgattactgg  780
ggtcaaggta ctctggtgac cgtgtctagc cccaagagct gcgacaagac ccacacctgc  840
ccccccctgcc cagccccaga gctgctgggc ggaccctccg tgttcctgtt cccccccaag  900
cccaaggaca ccctgatgat cagcaggacc cccgaggtga cctgcgtggt ggtggacgtg  960
agccacgagg acccagaggt gaagttcaac tggtacgtgg acggcgtgga ggtgcacaac  1020
```

```
gccaagacca agcccagaga ggagcagtac aacagcacct acagggtggt gtccgtgctg  1080
accgtgctgc accaggactg gctgaacggc aaggaataca agtgcaaggt ctccaacaag  1140
gccctgccag cccccatcga aaagaccatc agcaaggcca agggccagcc acgggagccc  1200
caggtgtaca ccctgccccc ctcccgggag gagatgacca agaaccaggt gtccctgacc  1260
tgtctggtga agggcttcta ccccagcgac atcgccgtgg agtgggagag caacggccag  1320
cccgagaaca actacaagac caccccccca gtgctggaca gcgacggcag cttcttcctg  1380
tacagcaagc tgaccgtgga caagtccagg tggcagcagg gcaacgtgtt cagctgcagc  1440
gtgatgcacg aggccctgca caaccactac acccagaaga gcctgagcct gtcccccgag  1500
ctgcaactgg aggagagctg tgcggaggcg caggacgggg agctggacgg gctgtggacg  1560
accatcacca tcttcatcac actcttcctg ttaagcgtgt gctacagtgc caccgtcacc  1620
ttcttcaagg tgaagtggat cttctcctcg gtggtggacc tgaagcagac catcatcccc  1680
gactacagga acatgatcgg acagggggcc tga                                1713

SEQ ID NO: 142          moltype = AA  length = 236
FEATURE                 Location/Qualifiers
REGION                  1..236
                        note = Synthetic
source                  1..236
                        mol_type = protein
                        organism = synthetic construct
SEQUENCE: 142
METDTLLLWV LLLWVPGSTG QSVLTQPPSV SAAPGQRVTI SCSGTRSNIG SDYVSWYQHL  60
PGTAPKLLVY GDNLRPSGIP DRFSASKSGT SATLGITGLQ TGDEADYYCG TWDYTLNGVV  120
FGGGTKLTVL GQPKANPTVT LFPPSSEELQ ANKATLVCLI SDFYPGAVTV AWKADGSPVK  180
AGVETTKPSK QSNNKYAASS YLSLTPEQWK SHRSYSCQVT HEGSTVEKTV APTECS      236

SEQ ID NO: 143          moltype = DNA  length = 711
FEATURE                 Location/Qualifiers
misc_feature            1..711
                        note = Synthetic
source                  1..711
                        mol_type = other DNA
                        organism = synthetic construct
SEQUENCE: 143
atggaaaccg atacactgct gctgtgggtg ctgctgctgt gggtgccagg atctaccggt  60
cagtctgtgt tgacgcagcc gccctcagtg tctgcggccc caggacagag ggtcaccatc  120
tcctgctctg gaaccaggtc caacattggg agtgattatg tttcctggta ccaacacctc  180
ccaggaacag cccccaaact cctcgtttat ggcgataatc tgcgaccctc agggattcct  240
gaccgattct ctgcctccaa gtctggcacg tcagccaccc tgggcatcac cggactccag  300
actggggacg aggccgatta ttactgcggc acatgggatt acaccctgaa tggtgtggtg  360
ttcggcggag ggaccaagct gaccgtccta ggtcagccca aggccaaccc cactgtcact  420
ctgttcccgc cctcctctga ggagctccaa gccaacaagg ccacactagt gtgtctgatc  480
agtgacttct acccgggagc tgtgacagtg gcctggaagg cagatggcag ccccgtcaag  540
gcgggagtgg agaccaccaa accctccaaa cagagcaaca acaagtacgc ggccagcagc  600
tacctgagcc tgacgcccga gcagtggaag tcccacagaa gctacagctg ccaggtcacg  660
catgaaggga gcaccgtgga gaagacagtg gcccctacag aatgttcata g            711

SEQ ID NO: 144          moltype = AA  length = 537
FEATURE                 Location/Qualifiers
REGION                  1..537
                        note = Synthetic
source                  1..537
                        mol_type = protein
                        organism = synthetic construct
SEQUENCE: 144
MVFTPQILGL MLFWISASRG QVQLVESGGG LVQPGGSLRL SCAASGFTFS SYAMSWVRQA  60
PGKGLEWVSV IYSGGSSTYY ADSVKGRFTI SRDNSKNTLY LQMNSLRAED TAVYYCARTS  120
YLNHGDYWGQ GTLVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKRVEPKS  240
CDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSREEMT KNQVSLTCLV KGFYPSDIAV EWESNGQPEN NYKTTPPVLD  420
SDGSFFLYSK LTVDKSRWQQ GNVFSCSVMH EALHNHYTQK SLSLSPELQL EESCAEAQDG  480
ELDGLWTTIT IFITLFLLSV CYSATVTFFK VKWIFSSVVD LKQTIIPDYR NMIGQGA      537

SEQ ID NO: 145          moltype = DNA  length = 1614
FEATURE                 Location/Qualifiers
misc_feature            1..1614
                        note = Synthetic
source                  1..1614
                        mol_type = other DNA
                        organism = synthetic construct
SEQUENCE: 145
atggtgttta caccgcaaat attggggctc atgcttttct ggatcagtgc aagcagggga  60
caggtgcagc tggtggagtc tgggggaggc ttggtacagc ctggggggtc cctgagactc  120
tcctgtgcag cctctggatt cacctttagc agctatgcca tgagctgggt ccgccaggct  180
ccagggaagg ggctggagtg ggtctcagtt atttatagcg gtggtagtag cacatactat  240
gcagactccg tgaagggccg gttcaccatc tccagagata attccaagaa cacgctgtat  300
ctgcaaatga acagcctgag agccgaggac acggccgtat attactgtgc gcgcacttct  360
```

```
tacctgaacc atggtgatta ctggggtcaa ggtactctgg tgaccgtgtc tagcgcctcc  420
accaagggcc catcggtctt ccccctggca ccctcctcca agagcacctc tgggggcaca  480
gcggccctgg gctgcctggt caaggactac ttccccgaac cggtgacggt gtcgtggaac  540
tcaggcgccc tgaccagcgg cgtgcacacc ttcccggctg tcctacagtc ctcaggactc  600
tactccctca gcagcgtggt gaccgtgccc tccagcagct tgggcaccca gacctacatc  660
tgcaacgtga accacaagcc cagcaacacc aaggtggaca agagagtgga gcccaagagc  720
tgcgacaaga cccacacctg ccccccctgc ccagccccag agctgctggg cggaccctcc  780
gtgttcctgt tccccccaa gcccaaggac accctgatga tcagcaggac ccccgaggtg  840
acctgcgtgg tggtggacgt gagccacgag gacccagagg tgaagttcaa ctggtacgtg  900
gacggcgtgg aggtgcacaa cgccaagacc aagcccagag aggagcagta caacagcacc  960
tacagggtgg tgtccgtgct gaccgtgctg caccaggact ggctgaacgg caaggaatac  1020
aagtgcaagg tctccaacaa ggccctgcca gcccccatcg aaaagaccat cagcaaggcc  1080
aagggccagc cacgggagcc ccaggtgtac accctgcccc cctcccggga ggagatgacc  1140
aagaaccagg tgtccctgac ctgtctggtg aagggcttct accccagcga catcgccgtg  1200
gagtgggaga gcaacggcca gcccgagaac aactacaaga ccaccccccc agtgctggac  1260
agcgacggca gcttcttcct gtacagcaag ctgaccgtgg acaagtccag gtggcagcag  1320
ggcaacgtgt tcagctgcag cgtgatgcac gaggccctgc acaaccacta cacccagaag  1380
agcctgagcc tgtcccccga gctgcaactg gaggagagct gtgcggaggc gcaggacggg  1440
gagctggacg ggctgtggac gaccatcacc atcttcatca cactcttcct gttaagcgtg  1500
tgctacagtg ccaccgtcac cttcttcaag gtgaagtgga tcttctcctc ggtggtggac  1560
ctgaagcaga ccatcatccc cgactacagg aacatgatcg gacagggggc ctga       1614

SEQ ID NO: 146         moltype = AA  length = 404
FEATURE                Location/Qualifiers
REGION                 1..404
                       note = Synthetic
source                 1..404
                       mol_type = protein
                       organism = synthetic construct
SEQUENCE: 146
METDTLLLWV LLLWVPGSTG QSVLTQPPSV SAAPGQRVTI SCSGTRSNIG SDYVSWYQHL  60
PGTAPKLLVY GDNLRPSGIP DRFSASKSGT SATLGITGLQ TGDEADYYCG TWDYTLNGVV  120
FGGGTKLTVL GSRGGGGSGG GGSGGGGSLE MAQVQLVESG GGLVQPGGSL RLSCAASGFT  180
FSSYAMSWVR QAPGKGLEWV SVIYSGGSST YYADSVKGRF TISRDNSKNT LYLQMNSLRA  240
EDTAVYYCAR TSYLNHGDYW GQGTLVTVSS AAAFVPVFLP AKPTTTPAPR PPTPAPTIAS  300
QPLSLRPEAC RPAAGGAVHT RGLDFACDFW VLVVVGGVLA CYSLLVTVAF IIFWVLDKDD  360
SKAGMEEDHT YEGLDIDQTA TYEDIVTLRT GEVKWSVGEH PGQE                  404

SEQ ID NO: 147         moltype = DNA  length = 1215
FEATURE                Location/Qualifiers
misc_feature           1..1215
                       note = Synthetic
source                 1..1215
                       mol_type = other DNA
                       organism = synthetic construct
SEQUENCE: 147
atggaaaccg atacactgct gctgtgggtg ctgctgctgt gggtgccagg atctaccggt  60
cagtctgtgt tgacgcagcc gccctcagtg tctgcggccc caggacagag ggtcaccatc  120
tcctgctctg gaaccaggtc caacattggg agtgattatg tttcctggta ccaacacctc  180
ccaggaacag cccccaaact cctcgtttat ggcgataatc tgcgaccctc agggattcct  240
gaccgattct ctgcctccaa gtctggcacg tcagccaccc tgggcatcac cggactccag  300
actggggacg aggccgatta ttactgcggc acatgggatt acaccctgaa tggtgtggtg  360
ttcggcggag ggaccaagct gaccgtccta ggttctagag gtggtggtgg tagcggcggc  420
ggcggctctg gtggtggtgg atccctcgag atggcccagg tgcagctggt ggagtctggg  480
ggaggcttgg tacagcctgg ggggtccctg agactctcct gtgcagcctc tggattcacc  540
tttagcagct atgccatgag ctgggtccgc caggctccag ggaaggggct ggagtgggtc  600
tcagttattt atagcggtgg tagtagcaca tactatgcag actccgtgaa gggccggttc  660
accatctcca gagataattc caagaacacg ctgtatctgc aaatgaacag cctgagagcc  720
gaggacacgg ccgtatatta ctgtgcgcgc acttcttacc tgaaccatgg tgattactgg  780
ggtcaaggta ctctggtgac cgtgtctagc gccgctgcat tcgtgcctgt gttcctccca  840
gctaagccca ctaccacccc cgctccaagg ccgcccacgc ccgctcctac tattgctagt  900
cagcctttaa gtttacgacc cgaagcttgc aggcccgccg ccggcggcgc tgtgcacacc  960
agggggcttg attttgcctg cgacttttgg gtattggtag tggtgggcgg agttttagcc  1020
tgctacagcc tcctggtaac agtggctttt atcatctttt gggtgctgga caaggatgac  1080
agcaaggctg gcatggagga agatcacacc tacgagggcc tggacattga ccagacagcc  1140
acctatgagg acatagtgac gctgcggaca ggggaagtga agtggtctgt aggtgagcac  1200
ccaggccagg agtga                                                  1215

SEQ ID NO: 148         moltype = AA  length = 416
FEATURE                Location/Qualifiers
REGION                 1..416
                       note = Synthetic
source                 1..416
                       mol_type = protein
                       organism = synthetic construct
SEQUENCE: 148
METDTLLLWV LLLWVPGSTG QSVLTQPPSV SAAPGQRVTI SCSGTRSNIG SDYVSWYQHL  60
PGTAPKLLVY GDNLRPSGIP DRFSASKSGT SATLGITGLQ TGDEADYYCG TWDYTLNGVV  120
FGGGTKLTVL GSRGGGGSGG GGSGGGGSLE MAQVQLVESG GGLVQPGGSL RLSCAASGFT  180
```

-continued

```
FSSYAMSWVR QAPGKGLEWV SVIYSGGSST YYADSVKGRF TISRDNSKNT LYLQMNSLRA  240
EDTAVYYCAR TSYLNHGDYW GQGTLVTVSS AAAFVPVFLP AKPTTTPAPR PPTPAPTIAS  300
QPLSLRPEAC RPAAGGAVHT RGLDFACDFW VLVVVGGVLA CYSLLVTVAF IIFWVRKRWQ  360
NEKLGLDAGD EYEDENLYEG LNLDDCSMYE DISRGLQGTY QDVGSLNIGD VQLEKP      416

SEQ ID NO: 149          moltype = DNA  length = 1251
FEATURE                 Location/Qualifiers
misc_feature            1..1251
                        note = Synthetic
source                  1..1251
                        mol_type = other DNA
                        organism = synthetic construct
SEQUENCE: 149
atggaaaccg atacactgct gctgtgggtg ctgctgctgt gggtgccagg atctaccggt  60
cagtctgtgt tgacgcagcc gccctcagtg tctgcggccc caggacagag ggtcaccatc  120
tcctgctctg gaaccaggtc caacattggg agtgattatg tttcctggta ccaacacctc  180
ccaggaacag cccccaaact cctcgtttat ggcgataatc tgcgaccctc agggattcct  240
gaccgattct ctgcctccaa gtctggcacg tcagccaccc tgggcatcac cggactccag  300
actggggacg aggccgatta ttactgcggc acatgggatt acaccctgaa tggtgtggtg  360
ttcggcggag ggaccaagct gaccgtccta ggttctagag gtggtggtgg tagcggcggc  420
ggcggctctg gtggtggtgg atccctcgag atggcccagg tgcagctggt ggagtctggg  480
ggaggcttgg tacagcctgg ggggtccctg agactctcct gtgcagcctc tggattcacc  540
tttagcagct atgccatgag ctgggtccgc caggctccag ggaaggggct ggagtgggtc  600
tcagttattt atagcggtgg tagtagcaca tactatgcag actccgtgaa gggccggttc  660
accatctcca gagataattc caagaacacg ctgtatctgc aaatgaacag cctgagagcc  720
gaggacacgg ccgtatatta ctgtgcgcgc acttcttacc tgaaccatgg tgattactgg  780
ggtcaaggta ctctggtgac cgtgtctagc gccgctgcat tcgtgcctgt gttcctccca  840
gctaagccca ctaccacccc cgctccaagg ccgcccacgc ccgctcctac tattgctagt  900
cagcctttaa gtttacgacc cgaagcttgc aggcccgccg ccggcggcgc tgtgcacacc  960
agggggcttg attttgcctg cgacttttgg gtattggtag tggtgggcgg agttttagcc  1020
tgctacagcc tcctggtaac agtggctttt atcatctttt gggtgaggaa acgatggcag  1080
aacgagaagc tcgggttgga tgccggggat gaatatgaag atgaaaacct ttatgaaggc  1140
ctgaacctgg acgactgctc catgtatgag gacatctccc ggggcctcca gggcacctac  1200
caggatgtgg gcagcctcaa cataggagat gtccagctgg agaagccgtg a           1251

SEQ ID NO: 150          moltype = DNA  length = 1389
FEATURE                 Location/Qualifiers
misc_feature            1..1389
                        note = Synthetic
source                  1..1389
                        mol_type = other DNA
                        organism = synthetic construct
SEQUENCE: 150
gaggttcaac ttgttcaatc tggggcagaa gtgaagaagc ccggggcatc tgtgaaagta  60
tcatgcaaaa catccggcta tacgtttacc gaatacacca ttcactgggt cagacaggct  120
cccggtcaaa gcctcgaatg gatgggaaat attaacccta acaatggcgg aaccacatat  180
aatcagaaat tccaaggccg agtgacgata actgtcgata agagtacgtc cacagcttac  240
atggaactca gctctttgag atccgaagac actgcagttt attattgtgc agctggatgg  300
aacttcgact attggggaca agggactctt gttacggtgt ccagtggcaa accaggtagt  360
ggtaaacccg gaagcggcaa gcccgggagc ggtaaacctg gtagcgacat cgtcatgact  420
caaagccctg actcactcgc cgtgagcctg ggagagcgtg caacgctatc ttgtcgggcc  480
tctcaggatg tcggaactgc tgtagactgg tatcaacaga aacctgacca atcaccaaaa  540
ctcctgattt attgggcctc aacacgtcac acaggagtgc cagataggtt cacaggtagt  600
ggcagtggaa ctgattttac tttgacaatt agcagcctgc aagccgaaga tgtagccgtt  660
tacttctgtc aacaatataa ctcataccca ctaacgttcg gtgccgggac gaaggtagag  720
attaaattcg tgcctgtgtt cctcccagct aagcccacta ccacccccgc tccaaggccg  780
cccacgcccg ctcctactat tgctagtcag cctttaagtt tacgacccga agcttgcagg  840
cccgccgccg gcggcgctgt gcacaccagg gggcttgatt ttgcctgcga cttttgggta  900
ttggtagtgg tgggcggagt tttagcctgc tacagcctcc tggtaacagt ggcttttatc  960
atcttttggg tgaagaaggt tgcaaaaaaa cctactaata aggctcccca tcctaagcaa  1020
gagccccaag aaattaactt tcccgatgat cttccgggtt ctaacacggc agccccggtg  1080
caggagaccc tgcatggttg tcaacccgtc actcaggagg acgggaaaga gtctcgtatc  1140
tccgtccagg agagacagcg caaaaaacgt ataagcgcaa actctacaga tccagtaaaa  1200
gccgcgcaat tcgagcctcc cggccgccag atgattgcaa tacggaaacg tcaactggag  1260
gaaactaata atgactatga gacggccgac ggtggataca tgacccttaa tccccgcgcg  1320
ccaaccgacg atgataagaa catatatctg acgctccccc ctaacgatca cgttaacagt  1380
aataattaa                                                          1389
```

MODIFIED B CELLS AND METHODS OF USE THEREOF

RELATED APPLICATIONS

The present application is a continuation of U.S. application Ser. No. 17/465,759, filed Sep. 2, 2021 (now allowed), which is a continuation of International Patent Application No. PCT/US2021/025273, filed Mar. 31, 2021, which claims the benefit of priority to U.S. Provisional Patent Application No. 63/003,120, filed Mar. 31, 2020, and the present application also claims priority to U.S. Provisional Patent Application No. 63/073,799, filed Sep. 2, 2020.

SEQUENCE LISTING

The instant application contains a Sequence Listing, which has been submitted electronically in XML format and is hereby incorporated by reference in its entirety. Said XML copy, created on May 11, 2023, is named "109036-0097 Sequence-Listing.xml" and is 266,706 bytes in size.

BACKGROUND OF THE INVENTION

Most cellular immunotherapies to date have focused in T cells. For example, cancer immunotherapies are primarily focused on modification and administration of T cells—enhancing the killer T cell response to a tumor. Modifying B cells for the treatment of various disease, however, is a technique that has not been extensively studied, despite the critical role of B cells in immune responses.

B cells, also known as B lymphocytes, are a type of white blood cell responsible for, among other things, helping the body resist infection and diseases. They are part of our adaptive immune system, and are capable of various immune responses, for example, secreting antibodies in response to a recognized antigen. Additionally, B cells are capable of presenting antigens, and can also secret cytokines.

Many B cells mature into plasma cells that produce antibodies (proteins) capable of fighting off infections. Other B cells mature into memory B cells. All plasma cells descended from a single B cell produce the same antibody that is directed against the antigen that stimulated it to mature. The same principle holds with memory B cells. Thus, all plasma cells and memory cells "remember" the stimulus that led to their formation. The B cell, or B lymphocyte, is not thymus-dependent, has a short lifespan, and is responsible for the production of immunoglobulins. See e.g., https://www.medicinenet.com/script/main/art.asp?articlekey=2413. The B cell is thus an immunologically important cell.

B cells appear to be associated with patient outcomes in the treatment of cancer. For example, the presence of tertiary lymphoid structures (TLSs) is associated with better patient outcomes. See, e.g., Helmink, B. A., et al., Nature, 2020, 577(7791), 549-555; Petitprez F et al., Nature, 2020, 577 (7791), 556-560. TLSs are aggregates of immune cells (mostly T and B cells) that arise in response to immunological stimuli. While TLSs that surround tumor cells include B cells, the role of B cells in antitumor responses have been unclear. B cells found in tumors can produce inhibitory factors that hinder the function of immune cells. See, e.g., Kessel, A., et al., Autoimmun Rev., 2012, 11(9), 670-677; Khan, A. R., et al., Nature Commun., 2015, 6, 5997. Further, current evidence indicates that B cells impede antitumor responses in most mouse models of cancer. Affara, N. I., et al. Cancer Cell, 2014, 25(6), 809-821; Shalapour, S., et al., Nature, 2017, 551, 340-345; Ammirante, M. et al., Nature, 2010, 464, 302-305. Yet, the presence of B cells in TLS structures is correlated with positive clinical outcomes to cancer immunotherapy. Petitprez 2020. Intratumoral injection of LPS-activated spleen cells, which include B cells, in combination with checkpoint inhibitors has been shown to produce anti-tumor responses. Soldevilla et al., Oncoimmunology, 2018, 7:8, e1450711.

CD79 (also termed "Cluster of Differentiation 79") is a transmembrane protein that forms a complex with the B-cell receptor and is capable of generating a signal following recognition of an antigen by the B-cell receptor.[1] CD79 is comprised of two different chains known as CD79A and CD79B (also termed Igα and Igβ). CD79a and CD79b are both members of the immunoglobulin superfamily. These form a heterodimer on the surface of B cells stabilized by disulfide bonding. Both CD79 chains contain an immunoreceptor tyrosine-based activation motif ("ITAM") in their intracellular tail regions that propagate a signal in a B cell.[2]

[1] See Chu P G, Arber D A (June 2001); CD79: a review; Applied Immunohistochemistry & Molecular Morphology. 9 (2): 97-106. doi:10.1097/00022744-200106000-00001. PMID 11396639. See also https://en.wikipedia.org/wild/CD79.

[2] See Müller B, Cooper L, Terhorst C (January 1995), Interplay between the human TCR/CD3 epsilon and the B-cell antigen receptor associated Ig-beta (B29); Immunology Letters. 44 (2-3): 97-103. doi:10.1016/0165-2478(94)00199-2. PMID 7541024.

Given the natural ability of B cells to present antigens and secrete proteins, there is great potential as a cellular therapy for targeting certain diseased cell types and secreting therapeutic payloads. There thus exists a need for alternative treatments beyond T cell therapies, such as engineered B cells, for the treatment of a variety of diseases and disorders, including cancer, heart disease, inflammatory disease, muscle wasting disease, neurological disease, and the like.

SUMMARY OF THE INVENTION

It has now been found that engineered B cells can be efficacious in the treatment of various diseases and disorders as recited herein. The invention therefore relates to modified B cells.

It has also been found that CD79a (Immunoglobulin α) when incorporated into the intracellular signaling domain of the CAR-B constructs of the invention exhibits superior qualities over CD79b (Immunoglobulin β). Further, it has further been found that when used in the CAR-B constructs described herein, intracellular CD79b (Immunoglobulin β) displays no (or even a negative effect) on efficacy. The invention thus relates to, inter alia, CAR-B constructs comprising the CD79a intracellular signaling domain.

In certain embodiments, the invention relates to an isolated modified B cell ("CAR-B cell), capable of expressing a chimeric receptor ("CAR-B receptor"), wherein said chimeric receptor comprises (a) an extracellular domain; (b) a transmembrane domain; and (c) a cytoplasmic domain that comprises at least one signaling domain. The cytoplasmic domain preferably comprises CD79a. In various embodiments, the extracellular domain comprises an extracellular binding domain and a hinge domain. In various embodiments, the extracellular binding domain(s) recognizes at least one antigen or protein expressed on the surface of a target cell. In various embodiments, the target cell is selected from the group consisting of a tumor cell, cardiac muscle cell, a skeletal muscle cell, a bone cell, a blood cell, a nerve cell, a fat cell, a skin cell, and an endothelial cell. In various embodiments, the B cell expresses more than one CAR-B receptor construct. In various embodiments, the CAR-B receptor comprises more than one extracellular binding domain. In various embodiments, the extracellular binding domain is a single chain variable fragment (scFv), or a full-length antibody, or the extracellular domain of a receptor or ligand. In various embodiments, the extracellular binding domain is capable of binding to an antigen or protein selected from the group consisting of: PSMA, GPC3, ASGR1, ASGR2, Sarcoglycan, Corin, FAP (fibroblast activation protein) and Her2. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, 31. In various embodiments, the cytoplasmic domain comprises at least one signaling domain native to B cell receptors. In various embodiments, the cytoplasmic domain comprises a domain that is selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain.

In various embodiments, the invention comprises an isolated modified B cell, wherein said B cell is capable of expressing and secreting a payload, wherein the payload is not naturally expressed in a B cell or is expressed at higher levels than is naturally expressed in a B cell. In various embodiments, the payload is an antibody or fragment thereof. In various embodiments, the antibody is a secreted antibody and can include blocking antibodies (eg anti-PD-1) or agonist antibodies (anti-CD137, GITR, OX40) engineered to contain native or engineered Fc regions and can be soluble or membrane-bound In various embodiments, the payload(s) can be immune modifiers such as chemokines or cytokines. In various embodiments, the payload is selected from the group consisting of: IL-1, IL-7, IL-8, IL-10, IL-12, IL-13, IL-17, IL18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-β trap, decoy or other inhibitory molecule; an anti-BMP antibody; a BMP trap, decoy or other inhibitory molecule. In various embodiments, the B cell is capable of expressing more than one payload. In various embodiments, the B cell is capable of expressing more than 1, 2, 3, 4, 5, 6, 7, 8, 9, 10, 11, or 12 payloads.

In various embodiments, the invention relates to a method of treating a patient comprising administering the modified B cell of the present invention. In various embodiments, the modified B cell is administered intra-tumorally, intravenously, subcutaneously, or intradermally. In various embodiments, the method further comprises administering a checkpoint inhibitor. In various embodiments, the checkpoint inhibitor to a checkpoint molecule that is selected from the group consisting of PD-1, PD-L1, CTLA-4, LAGS, TIM-3 and NKG2A proteins. In various embodiments, the checkpoint inhibitor is a monoclonal antibody.

In various embodiments, the invention relates to an isolated modified B cell, capable of expressing a chimeric receptor, wherein said chimeric receptor comprises (a) an extracellular domain, wherein the extracellular domain comprises an extracellular binding domain and a hinge domain; (b) a transmembrane domain; and (c) a cytoplasmic domain that comprises at least one signaling domain, wherein said modified B cell is further capable of expressing a payload, wherein the payload is not naturally expressed on the surface of a cell. In various embodiments, the extracellular binding domain recognizes an antigen or protein expressed on the surface of a target cell. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the B cell expresses more than one CAR-B receptor construct. In various embodiments, the CAR-B receptor comprises more than one extracellular binding domain. In various embodiments, the extracellular binding domain is a single chain variable fragment (scFv), an antibody, or the extracellular domain of a receptor or ligand. In various embodiments, the extracellular binding domain is capable of binding to an antigen or protein selected from the group consisting of PSMA, GP3, ASGR1, ASGR2, Sarcoglycan, Corin, FAP and Her2. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cells. In various embodiments, the cytoplasmic domain comprises a domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain. In various embodiments, the payload is a secreted or membrane bound antibody or fragment thereof. In various embodiments, the payload is selected from the group consisting of: IL-1, IL-7, IL-8, IL-10, IL-12, IL-13, IL-17, IL-18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-β trap, decoy or other inhibitory molecule; an anti-BMP antibody; a BMP trap, decoy or other inhibitory molecule. In various embodiments, the B cell is capable of expressing more than one payload. In various embodiments, the B cell is capable of expressing more than 1, 2, 3, 4, 5, 6, 7, 8, 9, 10, 11, or 12 payloads. In various embodiments, the modified B cell further encodes at least one protein selected from the group consisting of: the cytoplasmic domains of CD79a, CD79b, CD40, CD19, CD137, Fcγr2a, CD3ζ and MyD88. In various embodiments, the intention relates to a method of treating a patient comprising administering the modified B cell. In various embodiments, the method further comprises administering a checkpoint inhibitor. In various embodiments, the checkpoint inhibitor is selected from inhibitors to one or more checkpoint molecules from the group consisting of: PD-1, PD-L1, CTLA-4, LAGS, TIM-3 and NKG2A. In various embodiments, the checkpoint inhibitor is a monoclonal antibody. In various embodiments, the present invention relates to an isolated modified B cell, capable of expressing a chimeric receptor, wherein said chimeric receptor comprises an extracellular domain, wherein said extracellular domain comprises a hinge domain and an extracellular binding domain, wherein said extracellular binding domain is not naturally expressed on a B cell; and wherein said extracellular binding domain is capable of recognizing a target of interest. In various embodiments, the binding domain is a single chain variable fragment (scFv), antibody, ligand or receptor. In various embodiments, the binding domain is an scFv. In various embodiments, the binding domain is a receptor, a ligand, or a fragment thereof. In various embodiments, the B cell is further capable of expressing a payload. In various embodiments, the invention comprises a method of treating a patient comprising administering the modified B cell to a patient.

In various embodiments, the present invention comprises a nucleic acid capable of expressing a chimeric B cell receptor, wherein said chimeric receptor comprises: (a) an extracellular domain, wherein said extracellular domain comprises an extracellular binding domain and a hinge domain; (b) a transmembrane domain; and (c) a cytoplasmic domain that comprises at least one signaling domain. In various embodiments, the extracellular binding domain, recognizes an antigen or protein expressed on the surface of a target cell. In various embodiments, the extracellular binding domain is a single chain variable fragment (scFv), antibody, receptor or ligand. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the vector expresses more than one CAR-B receptor. In various embodiments, the CAR-B receptor expresses more than one extracellular binding domain. In various embodiments, the extracellular binding domain is capable of binding to an antigen or protein selected from the group consisting of: PSMA, GP3, ASGR1, ASGR2, Sarcoglycan, Corin, Her2, FAP, MUC1, CEA153, JAM-1, and LFA-1. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cell receptors. In various embodiments, the cytoplasmic domain comprises a domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain.

In various embodiments, the invention relates to a vector comprising a nucleic acid capable of expressing a chimeric B cell receptor, wherein said chimeric receptor comprises: (a) an extracellular domain, wherein said extracellular domain comprises an extracellular binding domain and a hinge domain; (b) a transmembrane domain; and (c) a cytoplasmic domain that comprises at least one signaling domain. In various embodiments, the extracellular binding domain recognizes an antigen or protein. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the vector expresses more than one CAR-B receptor. In various embodiments, the CAR-B expresses more than one extracellular binding domain. In various embodiments, the extracellular binding domain is a single chain variable fragment (scFv), antibody, receptor or ligand. In various embodiments, the extracellular binding domain is capable of binding to an antigen or protein selected from the group consisting of: PSMA, GPC3, ASGR1, AGSR2, Sarcoglycan, Corin, Her2, FAP, MUC1, CEA153, JAM-1, and LFA-1. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cells. In various embodiments, the cytoplasmic domain comprises a signaling domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain. The various embodiments, the cytoplasmic region is comprised of multiple, 2 or more, domains, being either identical or unique.

In various embodiments, the invention relates to an isolated modified B cell, capable of expressing an integrin, a homing antibody, protein, a receptor, or combinations thereof, wherein said integrin, homing antibody, protein, or receptor is not naturally expressed in a B cell or is expressed at higher levels than is naturally expressed in a B cell; and wherein said integrin, homing antibody, protein, receptor, or combinations thereof is attracted to a site or target of interest. In various embodiments, the integrin, homing antibody, protein, and receptor is selected from CLA (PSGL-1 glycoform), CLA (PSGL-1 glycoform), CCR10, CCR3, CCR4, CCR5, CCR6, CCR9, CD43E, CD44, c-Met, CXCR3, CXCR4, LFA-1, LFA-1 (αLβ2), selectin ligands, VLA-4, VLA-4 (α4β1), and α4β7, or combinations thereof. In various embodiments, the site of interest is a homing or target tissue, an inflammatory site in a specific location or tissue, or a tumor or tumor microenvironment, where delivery of payloads is desirable. In various embodiments, the homing or target tissue is selected from skin, gut (intestine, colon, mesenteric lymph nodes (mLN), Peyer's Patch (PP), small intestine), liver, lung, bone marrow, heart, peripheral lymph node (LN), CNS, thymus, and bone marrow. In various embodiments, the target of interest is selected from CXCL16, CCL17, CCL17(22), CCL20 (MIP-3a), CCL21, CCL25, CCL27, CCL28, CCL4, CCL5, CD62E, CD62P, CXCL10, CXCL12, CXCL13, CXCL16, CXCL9/CXCL10, CXCR3, E/P-selectin, E-selectin, GPR15L, HGF, Hyaluronate, ICAM-1, ligands for CCR1, 2, 5, MAdCAM, MAdCAM-1, PNAd, VAP-1, VCAM, and VCAM-1, or combinations thereof. In various embodiments, the method comprises treating a patient by administering the isolated modified B cell. In various embodiments, the method involves further administering a compound or a derivative thereof, wherein the compound or derivative thereof is capable of increasing the expression of the integrin, homing antibody, protein, and receptor, or combinations thereof. In various embodiments, the compound or a derivative thereof is capable of altering trafficking of B cells to a site or target of interest in the patient. In various embodiments, the compound is all-trans-retinoic acid (ATRA) or a derivative thereof.

In various embodiments, the invention relates to an isolated modified B cell, capable of expressing an immune inhibitory molecule, wherein said immune inhibitory molecule is not naturally expressed in a B cell or is expressed at higher levels than is naturally expressed in a B cell. In various embodiments, said immune inhibitory molecule is selected from IL-10, TGF-β, PD-L1, PD-L2, LAG-3, and TIM-3, or combinations thereof. In various embodiments, said immune inhibitory molecule is capable of decreasing inflammation and autoimmune activity of B cells at a site or target of interest in a patient. In various embodiments, the invention relates to a method of treating a patient comprising administering said isolated modified B cell. In various embodiments, said immune inhibitory molecule is selected from IL-10, TGF-β, PD-L1, PD-L2, LAG-3, and TIM-3, or combinations thereof. In various embodiments, said immune inhibitory molecule is capable of decreasing inflammation and autoimmune activity of B cells at a site or target of interest in the patient. In various embodiments, the invention relates to further administering a compound or a derivative thereof capable of increasing the expression of an integrin, a homing antibody, a protein, a receptor, or combinations thereof in the B cell. In various embodiments, said compound or derivative thereof is capable of altering trafficking of B cells to a site or target of interest in the patient. In various embodiments, said compound is all-trans-retinoic acid (ATRA) or a derivative thereof. In various embodiments, the invention relates to an isolated modified B cell, wherein the isolated modified B cell is treated with a compound or a derivative thereof, wherein said compound or derivative thereof is capable of increasing the expression of an integrin, a homing antibody, a protein, a receptor, or combinations thereof in B cells. In various embodiments, said compound or derivative thereof is capable of altering trafficking of B cells to a site or target of interest in the patient. In various embodiments, said compound is all-trans-retinoic acid (ATRA) or a derivative thereof. In various embodiments, said compound or derivative thereof is capable of (i) increasing the expression of an integrin, a homing antibody, a protein, a receptor, or combinations thereof in B cells, and (ii) altering trafficking of B cells to a site or target of interest in the patient. In various embodiments, said compound is all-trans-retinoic acid (ATRA) or a derivative thereof.

In various embodiments, the invention relates to an isolated modified B cell, capable of expressing at least one or more of a constitutively active Toll-like receptor (TLR), wherein said TLR is not naturally expressed in a B cell or is expressed at higher levels than is naturally expressed in a B cell. In various embodiments, said TLR is selected from TLR1, TLR2, TLR3, TLR4, TLR5, TLR6, TLR7, TLR8, TLR9, TLR10, TLR11, TLR12, and TLR13, or combinations thereof. In various embodiments, said TLR is capable of potentiating B cells for increasing immune responses in a patient. In various embodiments, said TLR is capable of producing potent effector B cells for increasing immune responses in a patient. In various embodiments, said immune inhibitory molecule is capable of decreasing inflammation and autoimmune activity of B cells at a site or target of interest in a patient. In various embodiments, said TLR is selected from TLR1, TLR2, TLR3, TLR4, TLR5, TLR6, TLR7, TLR8, TLR9, TLR10, TLR11, TLR12, and TLR13, or combinations thereof. In various embodiments, said TLR is capable of (i) potentiating B cells, and (ii) producing potent effector B cells, for increasing immune responses in a patient. In various embodiments, at least one or more of a TLR agonist is administered to the patient. In various embodiments, the isolated modified B cell is treated with at least one or more of a TLR agonist. In various embodiments, said TLR agonist is capable of (i) potentiating B cells, and (ii) producing potent effector B cells, for increasing immune responses in a patient. In various embodiments, said TLR agonist binds to one or more TLRs selected from TLR1, TLR2, TLR3, TLR4, TLR5, TLR6, TLR7, TLR8, TLR9, TLR10, TLR11, TLR12, and TLR13, or combinations thereof. In various embodiments, said TLR agonist is selected from CpG-rich oligonucleotides, double-stranded RNA mimic, polyinosinic acid:polycytidylic acid (poly-I:C). In various embodiments, said TLR agonist comprises CpG oligonucleotides. In various embodiments, said TLR agonist is capable of is capable of (i) potentiating B cells, and (ii) producing potent effector B cells, for increasing immune responses in the patient. In various embodiments, said TLR agonist binds to one or more TLRs selected from TLR1, TLR2, TLR3, TLR4, TLR5, TLR6, TLR7, TLR8, TLR9, TLR10, TLR11, TLR12, and TLR13, or combinations thereof. In various embodiments, said TLR agonist is selected from CpG-rich oligonucleotides, double-stranded RNA mimic, polyinosinic acid:polycytidylic acid (poly-I:C). In various embodiments, said TLR agonist comprises CpG oligonucleotides.

In various embodiments, the invention relates to an isolated modified B cell, wherein said B cell is electroporated with an mRNA encoding at least one or more of an antigen fused to a targeting signal. In various embodiments, said antigen is (i) not naturally presented by a B cell, (ii) not presented by a B cell simultaneously in both HLA class I and class II molecules naturally, or (iii) not presented by a B cell with high efficiencies in both HLA class I and class II molecules naturally. In various embodiments, said targeting signal is targeting signal of a lysosomal protein. In various embodiments, said targeting signal is a targeting signal of lysosome-associated membrane protein-1 (LAMP1). In various embodiments, said antigen is capable of being targeted to the lysosomes and presented simultaneously and efficiently in both HLA class I and class II molecules. In various embodiments, said B cells is capable of increasing antigen-specific immune responses in a patient. In various embodiments, said antigen is (i) not naturally presented by a B cell, (ii) not presented by a B cell simultaneously in both HLA class I and class II molecules naturally, or (iii) not presented by a B cell with high efficiencies in both HLA class I and class II molecules naturally. In various embodiments, said targeting signal is targeting signal of a lysosomal protein. In various embodiments, said targeting signal is a targeting signal of lysosome-associated membrane protein-1 (LAMP1). In various embodiments, said antigen is capable of being targeted to the lysosomes and presented simultaneously and efficiently in both HLA class I and class II molecules. In various embodiments, said B cells is capable of increasing antigen-specific immune responses in the patient.

BRIEF DESCRIPTION OF THE FIGURES

FIG. 3 shows examples of certain CAR-B constructs of the present invention. (A) CAR-B that binds GPC3. (B) CAR-B that binds PSMA.

DETAILED DESCRIPTION

Figure 1:
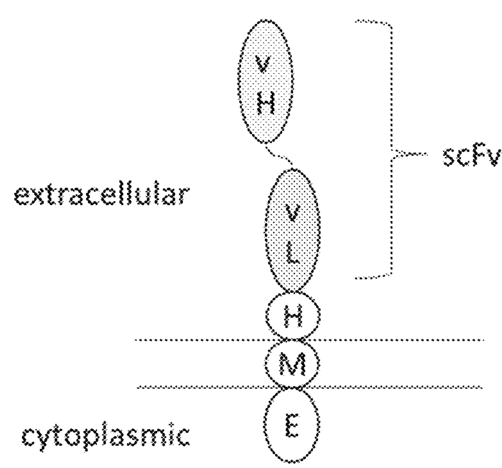
FIG. 1 sets forth an example of a chimeric B Cell Receptor (CAR-B) of the present invention. In certain embodiments, the CAR-B construct will comprise an extracellular domain, a transmembrane domain, and a cytoplasmic domain. As depicted in FIG. 1, the extracellular domain may in certain embodiments comprise a binding domain and a hinge region. In certain embodiments, the binding region may be an scFv. CAR-B constructs are cloned into a vector for expression.

The invention disclosed herein relates to several embodiments of engineered or modified B cells:

1. B cells that have been modified to home to a site/target of interest, using, e.g., a binding domain such as an scFv, antibody, ligand, receptor, or fragments thereof;
2. B cells that have been modified with a homing domain, further comprising an activation, and optionally a costimulatory domain, such that the B cells can home and activate upon interaction with a desired target;
3. B cells engineered to be capable of making a desired protein payload, such as an antibody, therapeutic protein, polypeptide, nucleic acid sequence (such as RNAi) or the like;
4. Engineered B cells comprising a homing/binding domain, an activating domain, an optional costimulatory domain, and further engineered to express a desire protein payload, such as an antibody, therapeutic protein, polypeptide, nucleic acid sequence (such as RNAi) or the like;
5. B cells that have been modified to express an integrin, a homing antibody, protein, or a receptor, such that the B cells are attracted to specific ligands, chemokines, or attractants at a specific site/target of interest (e.g., a homing tissue) and can thereby home to the site/target of interest, for example, to deliver a desired payload;
6. B cells that have been modified to express an immune inhibitory molecule, such that the inflammation and autoimmune activity of B cells localized to a site/target of interest is decreased, thereby leading to a positive therapeutic response;
7. B cells that have been treated with a compound or derivatives thereof, such that trafficking of the B cells is altered by expression of specific B cell integrins and/or homing receptors;
8. B cells that have been (i) treated with a Toll-like receptor (TLR) agonist, and/or (ii) engineered to express a constitutively active TLR, for potentiating B cells and/or producing potent effector B cells for increasing immune responses in a subject;
9. B cells that have been electroporated with an mRNA encoding specific antigens of interest fused to a targeting signal of a lysosomal protein, such that the B cells can simultaneously and efficiently present the specific antigens and/or antigen-derived epitopes of interest in both HLA class I and class II molecules.
10. B cells that have been electroporated with a self-amplifying RNA that encodes any items noted heretofore in 1-9.

It is understood that the various embodiments of engineered or modified B cells of the present application are not mutually exclusive and can be combined with each other in any way and without any restriction unless explicitly indicated, for achieving of facilitating any of the results and/or therapeutic responses contemplated herein.

Tumor Antigen. In certain embodiments, the site/target of interest is a tumor antigen. The selection of the antigen-binding domain (moiety) of the invention will depend on the particular type of cancer to be treated. Some tumor antigens may be membrane bound, whereas other may be secreted. For example, a tumor antigen may be secreted and accumulate in the extracellular matrix, or the tumor antigen may be expressed as part of the MHC complex. Tumor antigens are well known in the art and may include, for example, CD19, KRAS, HGF, CLL, a glioma-associated antigen, carcinoembryonic antigen (CEA); (3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, protein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, EGFR, BCMA, KIT and IL-13.

Infectious Disease Antigen. In certain embodiments, the site/target of interest is an infectious disease antigen against which an immune response may be desired. Infectious disease antigens are well known in the art and may include, but are not limited to, viruses, bacteria, protists, and parasitic antigens, such as parasites, fungi, yeasts, mycoplasma, viral proteins, bacterial proteins and carbohydrates, and fungal proteins and carbohydrates. In addition, the type of infectious disease of the infectious disease antigen is not particularly limited, and may include, but are not limited to, intractable diseases among viral infectious diseases such as AIDS, hepatitis B, Epstein Barr Virus (EBV) infection, HPV infection, HCV infection, SARS, SARS-CoV2, etc. Parasitic antigens may include, but are not limited to, the malaria parasite sporozoide protein.

In certain embodiments the modified B cells express an engineered B cell receptor (CAR-B) comprising an extracellular domain, a transmembrane domain and an intracellular domain. In certain embodiments, the extracellular domain comprises a binding domain and a hinge domain. In certain embodiments, the extracellular domain comprises a binding domain, such as an scFv, ligand, antibody, receptor, or fragment thereof which allows the modified B cell to target specific target cells by binding to proteins expressed on the surface of those cells. In certain embodiments, the modified tumor cells target and bind to proteins/antigens expressed on the surface of tumor cells. In certain embodiments, the modified B cell further expresses a payload. In certain embodiments, the payload is capable of increasing the number of cross-presenting antigen or antigenic fragments to dendritic cells (DC) in tumors or in lymph nodes. In certain embodiments, the payload is capable of activating and attracting T cells into tumors. In certain embodiments, the payload is capable of fomenting the formation of tertiary lymphoid structures (TLS) in tumors. In certain embodiments of the invention, the modified B cell expresses both a CAR-B and a payload. In certain embodiments, the CAR-B comprises stimulatory domains that activate expression of the payload when bound to an antigen or protein expressed on the surface of a tumor cell.

1. Design and Domain Orientation of Chimeric Antigen Receptors in B Cells (CAR-Bs)

In various embodiments, the invention provides a chimeric B Cell Receptor (CAR-B). It will be appreciated that chimeric B cell receptors (CAR-Bs) are genetically engineered receptors. These engineered receptors can be readily inserted into and expressed by B cells in accordance with techniques known in the art. With a CAR-B, a single receptor can be programmed to both recognize a specific protein or antigen expressed on a tumor cell, and when bound to said protein or antigen elicit an anti-tumor response. In various embodiments, the CAR-Bs serve in part as a homing mechanism to deliver B cells to target tissue.

It will be appreciated that relative to the cell bearing the receptor, the chimeric B cell receptor of the invention will comprise an extracellular domain (which will comprise an antigen-binding domain and may comprise an extracellular signaling domain and/or a hinge domain), a transmembrane domain, and an intracellular domain. The intracellular domain comprises at least an activating domain, preferably comprised of CD79a (Immunoglobulin α), CD79b (Immunoglobulin β), CD40, CD19, CD137, CD3ζ, Fcγr2a and/or MyD88. It will further be appreciated that the antigen-binding domain is engineered such that it is located in the extracellular portion of the molecule/construct, such that it is capable of recognizing and binding to its target or targets.

Structurally it will be appreciated that these domains correspond to locations relative to the immune cell. Exemplary CAR-B constructs in accordance with the invention are set forth in Table 1:

TABLE 1

| Construct Name | Extracellular Domain | Hinge | TM | Signal 1 | Signal 2 |
|---|---|---|---|---|---|
| pWF-82 | anti-PSMA | CD8 | CD28 | hCD19 | |
| pWF-83 | anti-PSMA | CD8 | CD28 | hCD40 | |
| pWF-84 | anti-PSMA | CD8 | CD28 | hCD40 | CD79b |
| pWF-85 | anti-PSMA | CD8 | CD28 | hCD40 | CD137 |
| pWF-86 | anti-PSMA | CD8 | CD28 | hCD40 | Fcγr2a |
| pWF-87 | anti-PSMA | CD8 | CD28 | hMyd88 | hCD40 |
| pWF-88 | anti-PSMA | CD8 | CD28 | CD79a | |
| pWF-89 | anti-PSMA | CD8 | CD28 | CD79b | |
| pWF-391 | anti-PSMA | 3x strep II tag | CD28 | CD79b | |
| pWF-394 | anti-Sarcoglycan | 3x strep II tag | CD28 | CD79b | |
| pWF-396 | anti-GPC-3 | CD8 | CD28 | CD79a | |
| pWF-397 | anti-GPC-3 | CD8 | CD28 | CD79b | |
| pWF-460 | anti-GPC-3 | Human IgG1 Fc | CD28 | CD79a | |
| pWF428 | anti-GPC-3 | Human Lambda Constant region | Human Lambda Constant region | | |
| pWF429 | anti-GPC-3 | Human IgG1 Fc | Human IgG1 Fc | | |
| pWF-521 | Anti-GPC3 vL-hclambda constant region-linker-vH-hcH1-cH2-cH3 | Human IgG1 Fc | Human IgG1 | Endogenous BCR complex | |

TABLE 1-continued

| Construct Name | Extracellular Domain | Hinge | TM | Signal 1 | Signal 2 |
|---|---|---|---|---|---|
| pWF-533 | Anti-GPC3-vL-hcH1 | | Human IgG1 (complex with pWF534) | Endogenous BCR complex | |
| pWF-534 | Anti-GPC3-vH-hcKappa-hcH2-cH3 | Human IgG1 Fc | Human IgG1 | Endogenous BCR complex | |

In various embodiments, chimeric B cell receptors are comprised of an extracellular domain, a transmembrane domain and a cytoplasmic domain. In various embodiments, the cytoplasmic domain comprises an activating domain. In various embodiments, the cytoplasmic domain may also comprise a co-stimulatory domain. In various embodiments, the extracellular domain comprises an antigen-binding domain. In various embodiments, the extracellular domain further comprises a hinge region between the antigen-binding domain and the transmembrane domain. FIG. 1 provides a schematic representation of a chimeric B cell receptor of various embodiments of the present invention.

Extracellular Domain. A number of extracellular domains may be used with the present invention. In various embodiments, the extracellular domain comprises an antigen-binding domain. In various embodiments, the extracellular domain may also comprise a hinge region and/or a signaling domain. In various embodiments, the extracellular domains containing IgG1 constant domain may also comprise either IgG1 (hole) or IgG1 (knob) to facilitate directed CAR-B formation.

Antigen-Binding Domain and Binding Domain. As used herein, an "antigen binding domain," "antigen-binding domain" or "binding domain" refers to a portion of the CAR-B capable of binding an antigen or protein expressed on the surface of a cell. In some embodiments, the antigen-binding domain binds to an antigen or protein on a cell involved in a hyperproliferative disease. In preferred embodiments, the antigen-binding domain binds to an antigen or protein expressed on the surface of a tumor cell. The antigen-binding molecules will be further understood in view of the definitions and descriptions below.

An antigen-binding domain is said to "specifically bind" its target antigen or protein when the dissociation constant ($K_d$) is $1\times10^{-7}$ M. The antigen-binding domain specifically binds antigen with "high affinity" when the $K_d$ is $1\text{-}5\times10^{-9}$ M, and with "very high affinity" when the $K_d$ is $1\text{-}5\times10^{-10}$ M. In one embodiment, the antigen-binding domain has a $K_d$ of $10^{-9}$ M. In one embodiment, the off-rate is $<1\times10^{-5}$. In other embodiments, the antigen-binding domain will bind to antigen or protein with a $K_d$ of between about $10^{-7}$ M and $10^{-13}$ M, and in yet another embodiment the antigen-binding domain will bind with a $K_d$ $1.0\text{-}5.0\times^{10}$.

An antigen-binding domain is said to be "selective" when it binds to one target more tightly than it binds to a second target.

The term "neutralizing" refers to an antigen-binding domain that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen-binding domain that prevents the protein to which it is bound from performing a biological function.

The term "target" or "antigen" refers to a molecule or a portion of a molecule capable of being bound by an antigen-binding molecule. In certain embodiments, a target can have one or more epitopes.

The term "antibody" refers to what are known as immunoglobulins, Y-shaped proteins that are produced by the immune system to recognize a particular antigen. The term "antibody fragment" refers to antigen-binding fragments and Fc fragments of antibodies. Types of antigen-binding fragments include: F(ab')2, Fab, Fab' and scFv molecules. Fc fragments are generated entirely from the heavy chain constant region of an immunoglobulin.

Extracellular Signaling Domains. The extracellular domain is beneficial for signaling and for an efficient response of lymphocytes to an antigen. Extracellular domains of particular use in this invention may be derived from (i.e., comprise) CD28, CD28T (See e.g., U.S. Patent Application US2017/0283500A1), OX40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, CD79a (Immunoglobulin α), CD79b (Immunoglobulin β), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The extracellular domain may be derived either from a natural or from a synthetic source.

Hinge Domains. As described herein, extracellular domains often comprise a hinge portion. This is a portion of the extracellular domain proximal to the cell membrane. The extracellular domain may further comprise a spacer region. A variety of hinges can be employed in accordance with the invention, including costimulatory molecules as discussed above, as well as immunoglobulin (Ig) sequences a 3× strep II spacer or other suitable molecules to achieve the desired special distance from the target cell. In some embodiments, the hinge region comprises the extracellular domain of CD28, or CD8 or a portion thereof as described herein.

Transmembrane Domains. The CAR-B can be designed to comprise a transmembrane domain that is fused or otherwise linked to the extracellular domain of the CAR-B-B. It can similarly be fused to the intracellular domain of the CAR-B. In one embodiment, the transmembrane domain that naturally is associated with one of the domains in a CAR-B is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (i.e. comprise) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, CD79a (Immunoglobulin α), CD79b (Immunoglobulin β), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

Optionally, short linkers may form linkages between any or some of the extracellular, transmembrane, and intracellular domains of the CAR-B.

In certain embodiments, the transmembrane domain in the CAR-B of the invention is the CD28 transmembrane domain. In one embodiment, the CD28 transmembrane domain comprises the nucleic acid sequence of SEQ ID NO: 1. In one embodiment, the CD28 transmembrane domain comprises the nucleic acid sequence that encodes the amino acid sequence of SEQ ID NO: 2. In one embodiment, the CD28 transmembrane domain comprises the nucleic acid sequence of SEQ ID NO: 3. In another embodiment, the CD28 transmembrane domain comprises the amino acid sequence of SEQ ID NO: 4.

In one embodiment, the transmembrane domain in the CAR-B of the invention is a CD8 transmembrane domain.

Intracellular (Cytoplasmic) Domains. The intracellular (IC, or cytoplasmic) domain of the CAR-B receptors of the invention can provide activation of at least one of the normal effector functions of the immune cell.

It will be appreciated that suitable intracellular molecules, include, but are not limited to CD79a (Immunoglobulin α), CD79b (Immunoglobulin β), CD40, CD19, CD137, Fcγr2a CD3ζ and MyD88. Intraceullar molecules may further include CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The cytoplasmic signaling sequences within the cytoplasmic signaling portion of the CAR-B of the invention may be linked to each other in a random or specified order.

The term "co-stimulatory" domain or molecule as used herein refers to a heterogenous group of cell surface molecules that act to amplify or counteract initial activating signals of the cell.

In one preferred embodiment, the cytoplasmic domain is designed to comprise the signaling domain of hCD19, wherein the hCD19 domain comprises the nucleic acid sequence set forth in SEQ ID NO. 5. In another embodiment, the cytoplasmic domain is designed to comprise the signaling domain of hCD40, wherein the hCD40 domain comprises the nucleic acid sequence set forth in SEQ ID NO. 7. In another embodiment, the cytoplasmic domain is designed to comprise the signaling domain of hCD40 and hCD79b, wherein the hCD40 domain comprises the nucleic acid sequence set forth in SEQ ID NO. 7 and the hCD79b domain comprises the nucleic acid sequence set forth in SEQ ID NO. 25. In another embodiment, the cytoplasmic domain is designed to comprise the signaling domain of hCD40 and hCD137, wherein the hCD40 domain comprises the nucleic acid sequence set forth in SEQ ID NO. 7 and the hCD137 domain comprises the nucleic acid sequence set forth in SEQ ID NO. 13. In another embodiment, the cytoplasmic domain is designed to comprise the signaling domain of hCD40 and hFcγr2a, wherein the hCD40 domain comprises the nucleic acid sequence set forth in SEQ ID NO. 7 and the hFcγr2a domain comprises the nucleic acid sequence set forth in SEQ ID NO. 17. In another embodiment, the cytoplasmic domain is designed to comprise the signaling domain of hCD40 and hMyd88, wherein the hCD40 domain comprises the nucleic acid sequence set forth in SEQ ID NO. 7 and the hMyd88 domain comprises the nucleic acid sequence set forth in SEQ ID NO. 21. In another embodiment, the cytoplasmic domain is designed to comprise the signaling domain of hCD79a, wherein the hCD79a domain comprises the nucleic acid sequence set forth in SEQ ID NO. 23. In another embodiment, the cytoplasmic domain is designed to comprise the signaling domain of hCD79b, wherein the hCD79b domain comprises the nucleic acid sequence set forth in SEQ ID NO. 25. These embodiments are preferably of human origin but may be derived from other species. In various embodiments the signaling domain comprises both hCD79a in tandem with hCD79b or another hCD79a domain. In various embodiments the signaling domain comprises both hCD79b in tandem with hCD79a or another hCD79b domain.

2. Modified B Cells

Modified B Cells that Express Payloads. In various embodiments of the present invention a modified B cell is provided that is capable of expressing a payload. As used herein the term "payload" refers to an amino acid sequence, a nucleic acid sequence encoding a peptide or protein, or an RNA molecule, for use as a therapeutic agent. In certain embodiments the payload is for delivery to the tumor or tumor microenvironment or the draining lymph node. In certain embodiments, it is desirable that the B cell deliver to the tumor or tumor microenvironment or draining lymph node a payload capable of, for example, increasing the number of cross-presenting dendritic cells (DCs) in tumors. Cross-presenting DCs will allow for improved presentation of tumor antigens. In various embodiments, the payload may be capable of activating and attracting T cells into tumors. Activating more T cells in tumors will complement the cross-presenting DCs to remold the tumor environment to have more potent antitumor immune capabilities. Payloads may also foment the formation of tertiary lymphoid structures (TLS) in tumors. Clinical studies have demonstrated that there is a relationship between B cells, TLS and responses to immune checkpoint blockade.

Nonexclusive examples of payloads of the present invention include: IL-1, IL-7, IL-8, IL-10, IL-12, IL-13, IL-17, IL-18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-β trap, decoy or other inhibitory molecule; an anti-BMP antibody; a BMP trap, decoy or other inhibitory molecule.

Signaling for Payload Expression. In various embodiments of the present invention, the payload is expressed in the modified B cell as a DNA construct under the control of an activated transcriptional pathway. In certain embodiments, the expression of the payload is controlled of the Nuclear Factor of Activated T cell ("NFAT") pathway. The NFAT pathway is a transcription factor pathway activated during an immune response and is activated by the NFκB. In various embodiments, the modified B cell expresses both a payload and a CAR-B. In various embodiments, where the modified B cell expresses both a payload and a CAR-B, the CAR-B may further encode signaling molecules that induce activation of the NFκB pathway. Such molecules include but are not limited to: CD79a (Immunoglobulin α), CD79b (Immunoglobulin β), CD40, CD19, CD137, Fcγr2a, CD3ζ and MyD88.

In various embodiments, the invention relates to isolated B cells that express at least one payload. In various embodiments, the invention relates to isolated B cells that express more than one payload. In various embodiments, the invention relates to isolated B cells that express 1, 2, 3, 4, 5, 6, 7, 8, 9, 10, 11 or 12 different payloads.

Figures 2A, 2B, 2C:
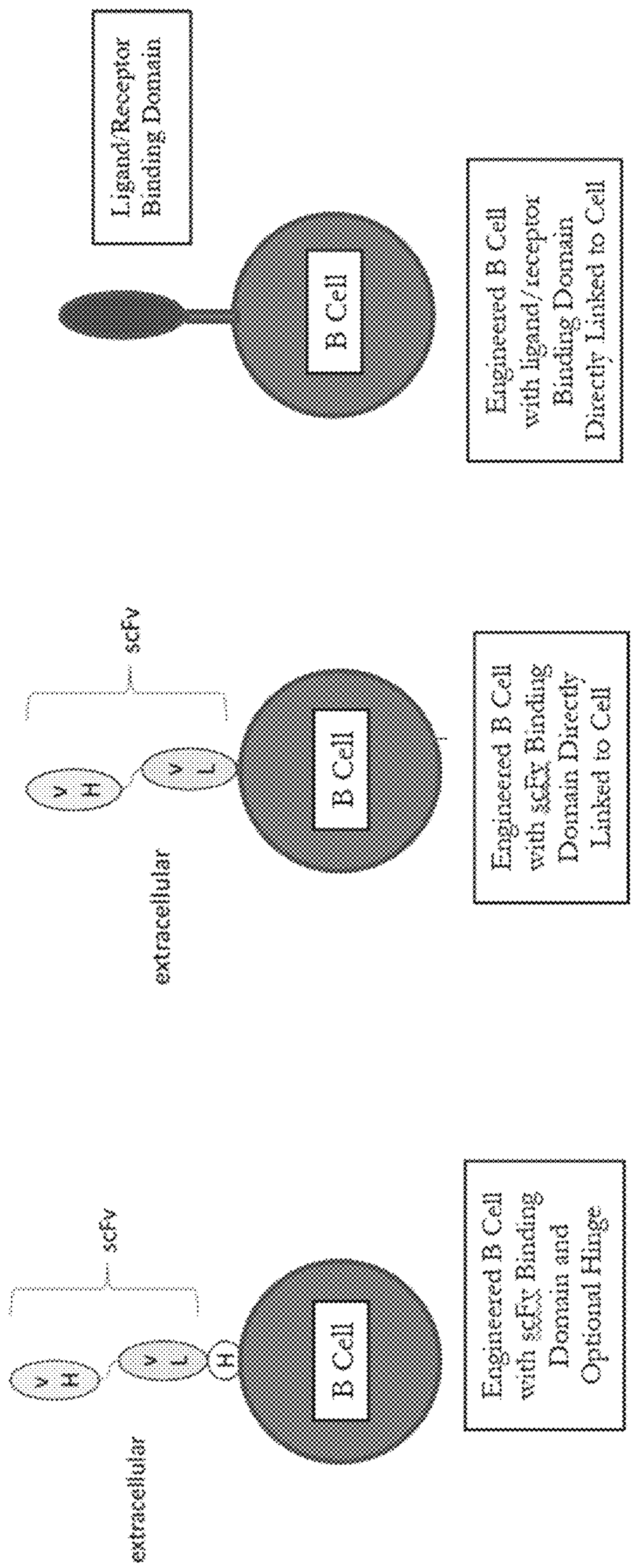
FIGS. 2A-2C show examples of engineered B cells with homing domains. In various embodiments, the engineered B cells may comprise (a) an scFv binding domain and optional hinge region; (b) an scFv binding domain directly linked to the cell through a transmembrane domain, or (c) a ligand/receptor binding domain directly linked to a cell through a transmembrane domain.
Figure 4:
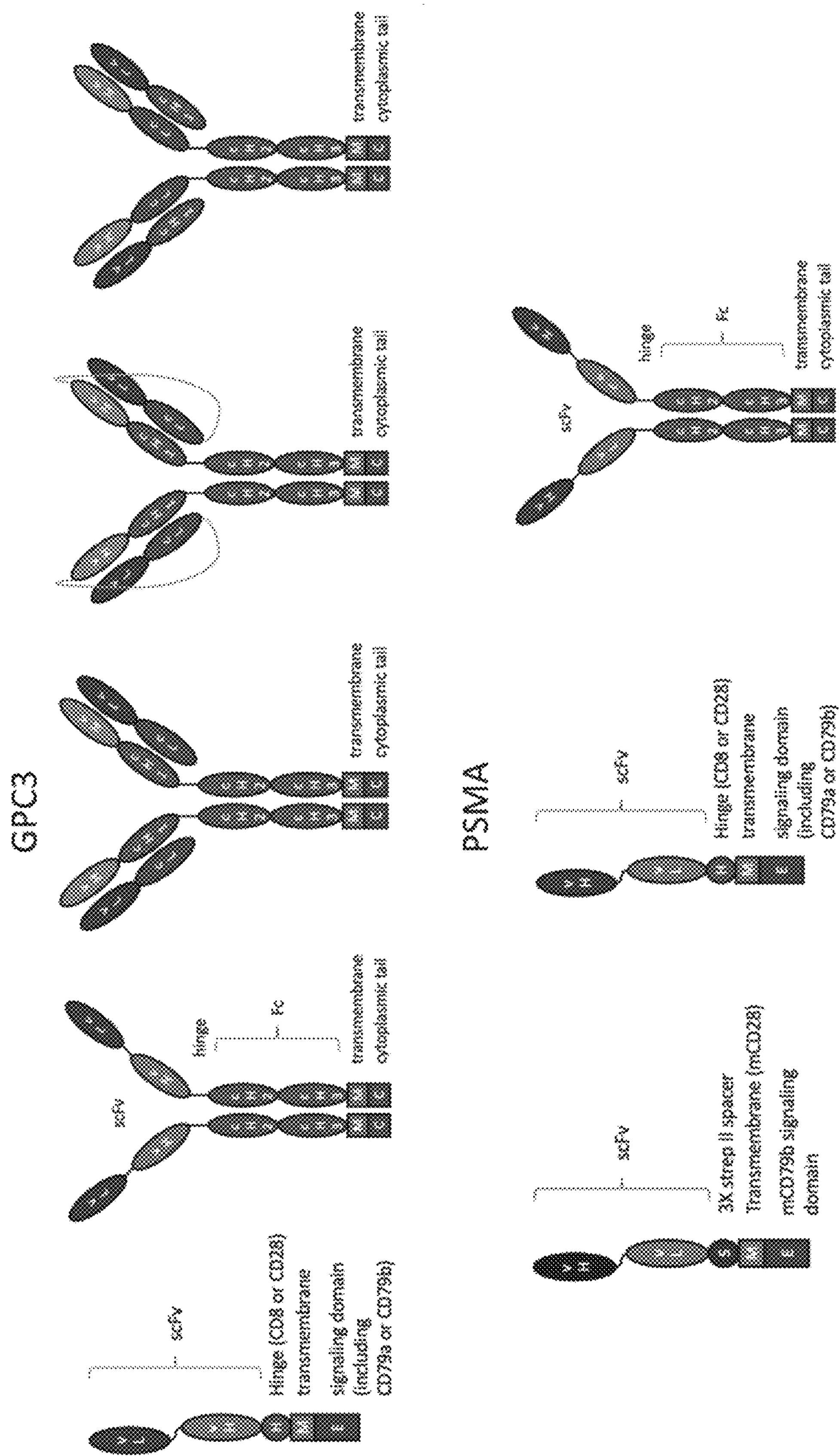
FIG. 4 shows examples of CAR-B receptors of the present invention capable of binding (A) GPC3 and (B) PSMA. The "C" domain corresponds to the native BCR C-terminus.

Modification of B Cells for homing. In various embodiments of the present invention, the engineered B cells can be modified with homing domains (e.g., as illustrated in FIG. 2) such that the B cells can home to a site/target of interest and activate upon interaction with the target. Additionally, B cell homing receptors expressed on B cell membranes that recognize addressins and ligands on target tissues, compound or derivatives thereof that alter the trafficking of B cells to a particular site, and inhibitory molecules inflammation and autoimmune activity of the B cells, can play a role in B cell homing and development of specialized immune responses.

Modified B cells that Express Integrin of Interest. The major homing receptors expressed by lymphocytes are the integrins, which are a large class of molecules characterized by a heterodimeric structure of α and β chains. In general, the pairing of specific α and β chains of the integrin determines the type of the homing receptor. For example, pairing of the α4 chain with β7 chain characterizes the major integrin molecule (α4β7) responsible for lymphocyte binding to Mucosal addressin cell adhesion molecule 1 (MAdCAM-1) expressed on high endothelial venules (HEVs) in Peyer's patches (PP) and gastrointestinal (GI) tract lamina propria endothelial venules (LPVs). Similarly, pairing of the α4 chain with β1 chain characterizes the homing receptor (α4β1) for the skin.

In various embodiments of the present inventions, a B cell to be modified can be selected for in advance, with specific traits that mediate preferred localizations. For example, memory B cells expressing CXCR3 may be enriched for and then subjected to engineering. CXCR3 cells may be attracted to ligands expressed at sites of inflammation. As such, modified B cells can preferentially localize to such sites.

In various embodiments of the present invention, a modified B cell is provided that expresses the α4 and β7 chains of an integrin. It is desirable that expression of the α4β7 integrin will promote homing of the modified B cell to the colon. In various embodiments, a modified B cell is provided that expresses the α4 and β1 chains of an integrin. It is desirable that expression of the α4β1 integrin will promote homing of the modified B cell to the skin. In various embodiments, a modified B cell is provided that expresses a desired pairing of an α and a β chain of an integrin, such that the expressed integrin promotes homing of the modified B cell to a desired site/target of interest. Accordingly, in various embodiments, any desired combination of the α and β chains of an integrin is contemplated for expression in the B cells, such that the modified B cells expressing the specific integrin is targeted to a desired site/target of interest.

Modified B cells that Express Homing Receptors of Interest. B cells have an ability to home to inflammatory tissues and altering their homing receptor expression can complement their native homing tendencies. B cell localization is also driven by expression of attractant molecules (e.g., targets such as ligands and chemokines) at inflammatory sites in specific locations or tissues. Such molecules can also include antibodies, such as the MECA79 antibody that targets cells to peripheral node addressin (PNAd). Bahmani et al., J Clin Invest. 2018; 128(11):4770-4786; Azzi et al., Cell Rep. 2016; 15(6):1202-13. Accordingly, B cells can be engineered to express certain antibodies, proteins, and receptors that facilitate B cell homing to a site/target of interest and interactions of such B cells with the desired target. In certain instances, expression of such receptors redirects the B cells to the tissue of interest.

In various embodiments of the present invention, a modified B cell is provided that is capable of expressing a homing antibody, protein, or a receptor, expression of which is capable of directing the B cell to a specific site/target of interest. Exemplary homing of T cells to specific homing tissues (target tissues) using specific homing receptor/ligand pairs are set forth in Table 2. The same specific homing receptor/ligand pairs are also capable of facilitating homing of B cells to a specific homing tissue (target tissue). Accordingly, in various embodiments of the present invention, homing of the modified B cells to an exemplary homing tissue (target tissue) is facilitated using the corresponding homing receptor/ligand pairs as set forth in Table 2.

TABLE 2

$T_{eff}$ cell homing receptors and their cognate ligands mediating organotropic targeting

| Homing Tissue Type | $T_{eff}$ Cell Homing Receptor | Cognate Ligand |
|---|---|---|
| Skin | CLA (PSGL-1 glycoform) | E/P-selectin |
| | CD43E | E-selectin |
| | VLA-4 ($\alpha_4\beta_1$) | VCAM-1 |
| | LFA-1 ($\alpha_L\beta_2$) | ICAM-1 |
| | CCR4 | CCL17 |
| | CCR10 | CCL27 |
| Gut (intestine, colon, mLN, PP) | $\alpha_4\beta_7$ | MAdCAM-1 |
| | CCR9[a] | CCL25[a] |
| | CXCR4 | CXCL12 |
| | Selectin ligands[b] | E/P-selectin[b] |
| | VLA-4[b] | VCAM-1[b] |
| | LFA-1[b] | ICAM-1[b] |
| | CCR6[b] | CCL20 (MIP-3α)[b] |
| Liver | CD44 | Hyaluronate |
| | VLA-4 | VCAM-1 |
| | CCR5 | CCL5 |
| | | VAP-1 |
| | Selectin ligands[b] | E/P-selectin |
| | $\alpha_4\beta_7$[b] | MAdCAM-1[b] |
| Lung | LFA-1 | ICAM-1 |
| | CCR3 | CCL28 |
| | CCR4 | CCL17 |
| | CXCR4 | CXCL12 |
| | Selectin ligands[b] | E/P-selectin[b] |
| | VLA-4[b] | VCAM-1[b] |
| | LFA-1[b] | ICAM-1[b] |
| Bone Marrow | CLA (PSGL-1 glycoform) | E/P-selectin |
| | CD43E | E-selectin |
| | VLA-4 | VCAM-1 |
| | LFA-1 | ICAM-1 |
| | CXCR4 | CXCL12 |
| | $\alpha_4\beta_7$[b] | MAdCAM-1[b] |
| Heart | CCR5 | CCL4, CCL5 |
| | CCR4 | ? |
| | CXCR3 | CXCL10 |
| | c-Met | HGF |
| Brain | VLA-4[b] | VCAM-1[b] |
| | LFA-1[b] | ICAM-1[b] |
| | CXCR3[b] | CXCL9/CXCL10[b] |
| Peripheral LN[c] | Selectin ligands[b] | E/P-selectin[b] |
| | LFA-1[b] | ICAM-1[b] |
| | CXCR3[b] | CXCL9/CXCL10[b] |

[a]Involved in $T_{eff}$ cell homing to the intestine but not colon.

[b]Inflammatory reactions, tissue injury.

[c]Under non-inflamed, steady-state conditions, $T_{eff}$ cells typically lose L-selectin and CCR7 expression and are largely restricted from LN access though may enter during inflammatory reactions (b) as shown. In contrast, both naïve T cells and $T_{cm}$ cells express L-selectin, CCR7, and CXCR4 and engage PNAd, CCL19/CCL21, and CXCL12, respectively, to undergo T-cell rolling and LFA-1/ICAM-1/2- mediated adhesion and transmigration into LNs.

Exemplary homing tissue (target tissue) type and ligand or chemokine that enables tissue-restricted B cell homing in accordance with the invention are set forth in Table 3.

TABLE 3

| Homing Tissue Type | Ligand/Chemokines |
|---|---|
| CNS | VCAM-1, CD62P, ligands for CCR1, 2, 5, CXCR3 |
| Liver | CD62P, VAP-1, CXCL16 |
| Small Intestine | MAdCAM, CD62P, CCL25 |
| Colon | MAdCAM, CD62P, CCL20, GPR15L |
| Skin | CD62E, CD62P, CCL17(22), ICAM-1 |

TABLE 3-continued

| Homing Tissue Type | Ligand/Chemokines |
|---|---|
| Thymus | VCAM, CD62P, CCL25 |
| Peripheral Lymph Node | PNAd, CCL21, ICAM-1 |
| Peyer's Patch | MAdCAM, CCL21, CXCL13 |
| Bone Marrow | VCAM, CD62P, CXCL12, ICAM-1 |

In various embodiments of the present invention, a modified B cell is provided that expresses one or more of an antibody, a protein, or a receptor that facilitate homing of the modified B cell to the exemplary target/homing tissues using the specific homing receptor/ligand pairs as set forth in Table 2. In various embodiments of the present invention, a modified B cell is provided that expresses one or more of a homing receptor that facilitate homing of the modified B cell to the exemplary target/homing tissue using the ligand or chemokines are set forth in Tables 2 and/or 3. As used herein, the term "B cell homing" refers to localizing, targeting, trafficking, directing, or redirecting of the B cell of the present application to a site/target of interest, for example, a homing or target tissue, an inflammatory site in a specific location or tissue, or a tumor or tumor microenvironment, where delivery of therapeutic payloads is desirable. As used in the context of B cell homing, the term "antibody", "protein" or a "receptor" refers to an amino acid sequence, a nucleic acid sequence encoding a peptide or protein, or an RNA molecule, for use as a therapeutic agent, which when expressed in a modified B cell of the present invention will direct the B cell to a site/target of interest.

In certain embodiments, the homing antibody, protein, or receptor molecule is for homing/targeting the modified B cell expressing such a molecule to a site/target of interest. In certain embodiments, the homing antibody, protein, or receptor molecule is for homing/targeting the modified B cell expressing such a molecule to inflammatory sites in specific locations or tissues. In certain embodiments, the homing antibody, protein or receptor is for targeting the B cell to a tumor or tumor microenvironment and to the tumor draining lymph node In certain embodiments, targeting B cells to particular locations is desirable so that the engineered or modified B cells of the present invention can deliver therapeutic payloads to desired locations of interest, for example, a homing or target tissue, an inflammatory site in a specific location or tissue, or a tumor or tumor microenvironment. Accordingly, in certain embodiments, it is desirable that the B cells home to a site/target of interest, for example, a tumor or tumor microenvironment and tumor-draining lymph node and deliver to the site/target of interest a payload capable of, for example, increasing the number of cross-presenting dendritic cells (DCs) at the site/target of interest (e.g., in tumors).

In various embodiments, the homing antibody, protein, or receptor is expressed in the modified or engineered B cell as a DNA construct. In various embodiments, the homing antibody, protein, or receptor is expressed in the modified B cell as a DNA construct under the control of a constitutively activated transcriptional pathway. In various embodiments, the homing antibody, protein, or receptor involved in the B cell homing/targeting is either not naturally expressed in a B cell or is expressed at higher levels than is naturally expressed in a B cell. Exemplary homing of the modified B cells to specific homing/target tissues using specific homing receptor/ligand pairs in accordance with the present invention is set forth in Table 4. It should be understood that, notwithstanding the exemplary homing tissues, homing receptor, and ligand pairs set forth in Table 4, a modified B cell of the present invention may be engineered to express any homing antibody, protein, or a receptor (e.g., any homing receptor set for in Table 2), such that the modified B cell can be directed to a specific site/target of interest.

TABLE 4

| Homing Tissue Type | Homing Receptor | Ligand/Chemokine |
|---|---|---|
| Liver | CXCR6 | CXCL16 |
| Small Intestine | CCR9 | CCL25 |
| Large Intestine (Colon) | CCR6 | CCL20 |
| Lymph Node | CCR7 | CCL21 |
| Bone Marrow | CXCR4 | CXCL12 |
| Peyer's Patch | CCR7 and CXCR5 | CCL21 and CXCL13, respectively |
| Skin | CCR4 | CCL17(22) |

Nonexclusive examples of homing (target) tissue types for the specific homing receptor/ligand pairs of the present invention include: skin, gut (intestine, colon, mesenteric lymph nodes (mLN), Peyer's Patch (PP), small intestine), liver, lung, bone marrow, heart, peripheral lymph node (LN), CNS, thymus, and bone marrow.

Nonexclusive examples of homing receptors that can be paired with specific or corresponding attractants/ligands/chemokines of the present invention include: CLA (PSGL-1 glycoform), CLA (PSGL-1 glycoform), CCR10, CCR3, CCR4, CCR5, CCR6, CCR9, CD43E, CD44, c-Met, CXCR3, CXCR4, LFA-1, LFA-1 ($\alpha L\beta 2$), Selectin ligands, VLA-4, VLA-4 ($\alpha 4\beta 1$), and $\alpha 4\beta 7$.

Nonexclusive examples of ligands/chemokines that can be paired with specific or corresponding homing receptors of the present invention include: CXCL16, CCL17, CCL17 (22), CCL20 (MIP-3$\alpha$), CCL21, CCL25, CCL27, CCL28, CCL4, CCL5, CD62E, CD62P, CXCL10, CXCL12, CXCL13, CXCL16, CXCL9/CXCL10, CXCR3, E/P-selectin, E-selectin, GPR15L, HGF, Hyaluronate, ICAM-1, ligands for CCR1, 2, 5, MAdCAM, MAdCAM-1, PNAd, VAP-1, VCAM, and VCAM-1.

In certain embodiments of the present invention, a modified B cell is provided that express or have increased expression of the exemplary B cell homing receptors (e.g., as set forth in Table 2), such that the modified B cell is targeted to the corresponding homing tissue of interest that expresses the corresponding ligand/chemokines (e.g., as set forth in Tables 2 and/or 3). In certain embodiments of the present invention, a modified B cell is provided that co-expresses an integrin with a specific $\alpha$ and $\beta$ chain pairing and a specific B cell homing receptor (e.g., as set forth in Tables 2 and/or 3), expression of which integrin and/or homing receptor promote or facilitate homing/targeting of the modified B cell to a site/target of interest. In some embodiments, a modified B cell is provided that co-expresses an $\alpha 4\beta 7$ integrin and CCR9. It is desirable that co-expression of $\alpha 4\beta 7$ and CCR9 will promote small intestine homing of the modified B cells of the present invention. In some embodiments, a modified B cell is provided that co-expresses an $\alpha 4\beta 1$ integrin and CCR4. It is desirable that co-expression of $\alpha 4\beta 1$ and CCR4 will promote small intestine homing of the modified B cells of the present invention.

Modified B cells that Express Immune Inhibitory Molecules. B cells are key contributors to many autoimmune diseases. However, B cells can be used therapeutically to antagonize autoimmunity. Specifically, B cells can be engineered to express at least one or more immune inhibitory molecules, which may decrease the autoimmune activity of the B cells, leading to decrease in an autoimmune disease. Immune inhibitory molecules are well known in the art. Such inhibitory molecules may include, but are not limited to, IL-10, TGF-$\beta$, PD-L1, PD-L2, LAG-3, and TIM-3. In certain embodiments of the present invention, a modified B cell is provided that is engineered to express at least one or more of an inhibitory molecule selected from IL-10, TGF-$\beta$, PD-L1, PD-L2, LAG-3, and TIM-3, or any combinations thereof, such that the inflammation at the site and autoimmune activity of the B cells localized to the site are decreased, thereby leading to a positive therapeutic response.

Compounds that alter B cell Trafficking. In certain embodiments of the present invention, a modified B cell is provided that is treated with at least one or more compound or derivatives thereof that alter the trafficking of B cells by inducing expression of a specific B cell integrin and/or a homing receptor. Compounds or derivatives thereof that alter the trafficking of B cells are well known in the art. In certain embodiments, a modified B cell is provided that is treated with all-trans-retinoic acid (ATRA) or derivatives thereof that promote homing of the B cells to gut (small intestine) due to the increased expression of $\alpha 4\beta 7$ integrin and CCR9 homing receptor. As used herein, the term "compound" refers to a chemical, drug, a therapeutic agent, or derivatives thereof, that alter the trafficking of B cells in a desired manner.

In various embodiments of the present invention, a modified B cell engineered to co-express a specific integrin (e.g., with a specific $\alpha$ and $\beta$ chain pairing) and a specific B cell homing receptor of interest is treated with at least one or more compounds or derivatives thereof that alter the trafficking of the modified B cells and promote homing of the cells to a specific site/target of interest due to the increased expression of the specific integrin and/or the homing receptor. In various embodiments, a B cell modified to co-express an integrin with a specific $\alpha$ and $\beta$ chain pairings and a specific B cell homing receptor further expresses at least one or more immune inhibitory molecules, such that the autoimmune activity of the modified B cells targeted to a specific site of inflammation is decreased, leading to a decrease in the autoimmune disease. In some embodiments, a modified B cell engineered to express one or more immune inhibitory molecules, for example IL-10, TGF-$\beta$, PD-L1, PD-L2, LAG-3, and TIM-3, or combinations thereof, is treated with ATRA or derivatives thereof for a specified period of time, such that expression of the $\alpha 4\beta 7$ integrin and CCR9 homing receptor is induced to promote B cell homing to a specific site/target of interest (e.g., the gut), but the inflammation at the site and autoimmune activity of B cells localized to the site are decreased, leading to a positive therapeutic response. In one embodiment, a modified B cell engineered to express one or more immune inhibitory molecules, for example IL-10, TGF-$\beta$, or combinations thereof, is treated with ATRA or derivatives thereof for a specified period of time, such that expression of the $\alpha 4\beta 7$ integrin and CCR9 homing receptor is induced to promote B cell homing to a specific site/target of interest (e.g., the gut), but the inflammation at the site and autoimmune activity of B cells localized to the site are decreased, leading to a positive therapeutic response.

It is understood that, any B cell of the present invention modified to co-express a specific B cell integrin and homing receptor that targets the B cell to a particular homing/target tissue of interest, may be further engineered to express one or more immune inhibitory molecules for reducing inflammation and autoimmune activity of the B cells localized to the site, and/or treated with a compound that alter the homing/targeting of the modified B cells by inducing expression of the specific B cell integrin and/or the homing receptor.

Activation of B cells with TLR agonists and TLRs. B cells have a natural ability to uptake and present antigens recognized by their specific B cell receptors (BCRs). B cells activated by Toll-like receptors (TLRs) result in potent effector B cells in defending the body in an immune response. Expression of or increasing the expression of TLRs in B cells can provide a mechanism for potentiating B cells for innate signals regulating adaptive immune responses.

Activation of B cells with TLR agonists. In various embodiments of the present invention, a B cell is provided, where the B cell is treated in vitro with at least one TLR agonist. In various embodiments, the TLR can be a TLR1, TLR2, TLR3, TLR4, TLR5, TLR6, TLR7, TLR8, TLR9, TLR10, TLR11, TLR12, and/or a TLR13. In various embodiments, the TLR agonist preferentially binds to one or more TLR selected from the group consisting of TLR1, TLR2, TLR3, TLR4, TLR5, TLR6, TLR7, TLR8, TLR9, TLR10, TLR11, TLR12, and TLR13. TLR agonists are well known in the art and may include, but are not limited to, CpG-rich oligonucleotides and the double-stranded RNA mimic, polyinosinic acid:polycytidylic acid (poly-I:C). In various embodiments, the TLR agonist can be CpG oligonucleotides.

In various embodiments, each B cell may be treated with one TLR agonist. In various embodiments, each B cell may be treated with more than one TLR agonist. For example, each B cell may be treated 1, 2, 3, 4, 5, 6, 7, 8, 9, 10, 11, or 12 different TLR agonists. Alternatively, the patient may be administered a heterogeneous population of B cells, each B cell treated with a unique TLR agonist or a combination of TLR agonists. In some embodiments, the B cells for use a therapeutic agent is treated with one or more TLR agonists at the same time or in advance of the administration of the B cells to a subject or patient in need thereof. In certain embodiments, treatment with one or more TLR agonist is capable of producing more potent effector B cells for defending the body in an immune response. In certain embodiments, treatment with one or more TLR agonist is capable of potentiating B cells for immune responses. In some embodiments, treating a B cell of the present invention with at least one or more TLR agonists induces expression or activation of one or more TLRs.

Activation of B cells with TLR Expression. In various embodiments of the present invention, a modified B cell is provided that is capable of expressing a constitutively active TLR. In various embodiments, the TLR is expressed in the modified or engineered B cell as a DNA construct under the control of a constitutively activated transcriptional pathway. In various embodiments, the TLR is either not naturally expressed in a B cell or is expressed at higher levels than is naturally expressed in a B cell. In various embodiments, the TLR can be a TLR1, TLR2, TLR3, TLR4, TLR5, TLR6, TLR7, TLR8, TLR9, TLR10, TLR11, TLR12, and/or a TLR13.

In various embodiments, each B cell may express more than one constitutively active TLR. For example, each B cell may express 1, 2, 3, 4, 5, 6, 7, 8, 9, 10, 11, 12 or 13 different constitutively active TLRs. Alternatively, the patient may be administered a heterogeneous population of B cells, each B cell capable of expressing and/or secreting a unique TLR or combination of TLRs, which are constitutively active. In various embodiments, 1, 2, 3, 4, 5, 6, 7, 8, 9, 10, 11, 12 or 13 different constitutively active TLRs may be administered to the subject or patient through a heterogeneous population of B cells.

In certain embodiments of the present invention, the B cell is a modified B cell that expresses at least one constitutively active TLR. In certain embodiments, the modified B cell that expresses at least one constitutively active TLR is treated with one or more TLR agonist. In certain embodiments, the expression of the constitutively active TLR is capable of producing more potent effector B cells for defending the body in an immune response. In certain embodiments, the expression of the constitutively active TLR is capable of potentiating B cells for immune responses. In certain embodiments, the modified B cell expresses both a TLR that is constitutively active and any CAR-B of the present application. In various embodiments, the modified B cell expressing a TLR that is constitutively active and/or a CAR-B is further treated with one or more TLR agonist at the same time or in advance of the administration of the modified B cells to a subject or patient in need thereof. In certain embodiments, B cells may be engineered to express payloads and modifiers, such as TLRs, in the absence of CAR-B, for intratumoral administration.

Modified B Cells that Present Antigens Simultaneously in HLA Class I and Class II Molecules. B cells, in addition to their function in antibody production, also express high level of Human Leukocyte Antigen (HLA) class II molecules and can present antigens to CD4+ T cells (Hong et al., 2018, Immunity 49, 695-708). In various embodiments of the present invention, a modified B cell is provided that is capable of presenting specific antigens and/or antigen-derived epitopes of interest, such as tumor antigens or infectious disease antigens, simultaneously in both HLA class I and class II molecules. Tumor antigens and infectious disease antigens are well known in the art and are described in the foregoing sections. In certain embodiments, a specific antigen of interest, e.g., a tumor antigen or an infectious disease antigen, is fused to a targeting signal of a lysosomal protein that targets the antigen to the lysosomes and presents the antigen simultaneously and efficiently in both HLA class I and class II molecules. In some embodiments, the targeting signal is the targeting signal of lysosome-associated membrane protein-1 (LAMP1). In some embodiments, the targeting signal is capable of entering endosomal recycling compartments. The c-terminal sequence of Clec9A is such a targeting moiety. As used herein, a specific tumor antigen or an infectious disease antigen fused to a targeting signal refers to an amino acid sequence, a nucleic acid sequence encoding a peptide or protein, or an RNA molecule (e.g., an mRNA molecule), for use as a therapeutic agent. In one embodiment, a specific tumor antigen or an infectious disease antigen fused to a targeting signal refers to an mRNA molecule for use as a therapeutic agent. In certain embodiments, it is desirable that the specific tumor antigens and/or infectious disease antigens fused to a targeting signal, such as the targeting signal of LAMP1 or Clec9A, be targeted to the lysosomes or endosomes and presented simultaneously and efficiently in both HLA class I and class II molecules. In certain embodiments, it is desirable that electroporation of B cells (e.g., human B cells), before or after maturation, with an mRNA encoding specific tumor antigens and/or infectious disease antigens of interest fused to a targeting signal, such as the targeting signal of LAMP1 or Clec9A, be capable of simultaneously and efficiently presenting the specific antigens and/or antigen-derived epitopes in both HLA class I and class II molecules. In various embodiments, the specific tumor antigens and/or infectious disease antigens of interest is either not naturally presented by a B cell, is not presented by a B cell simultaneously in both HLA class I and class II molecules naturally, or is not presented by a B cell with high efficiencies in both HLA class I and class II molecules naturally. It is contemplated that, introduction of such electroporated B cells into a subject, e.g., a human host, will promote development of or potentiate antigen-specific immune responses by presenting specific antigens and/or antigen-derived epitopes of interest simultaneously and efficiently in both HLA class I and class II molecules.

In various embodiments, the invention relates to a nucleic acid sequence, e.g., an mRNA sequence, encoding at least one specific antigen of interest, e.g., a tumor antigen or an infectious disease antigen, fused to a targeting signal, such as the targeting signal of LAMP1, for use as a therapeutic agent in electroporation of B cells for simultaneously and efficiently presenting the specific antigen and/or antigen-derived epitopes in both HLA class I and class II molecules. In various embodiments, the invention relates to nucleic acid sequence, e.g., an mRNA sequence, encoding more than one (e.g., 1, 2, 3, 4, 5, or more) specific tumor antigen and/or an infectious disease antigen of interest fused to a targeting signal. In various embodiments, the invention relates to pools of different nucleic acid sequences, e.g., pools of different mRNA sequences, for use as a therapeutic agent in electroporation of B cells as described above, where each pool encodes at least one specific antigen of interest, e.g., a tumor antigen or an infectious disease antigen, fused to a targeting signal that is different from the other pools of the mRNA sequences. Accordingly, in some embodiments, the subject may be administered a homogeneous population of B cells, where each B cell is electroporated with an mRNA encoding at least one specific antigen of interest fused to a targeting signal. In some embodiments, the subject may be administered a homogeneous a population of B cells, where each B cell is electroporated with an mRNA encoding more than one specific antigen of interest fused to targeting signal. In some embodiments, the subject may be administered a heterogeneous population of B cells, where each B cell is electroporated with a combination of mRNAs each encoding at least one specific antigen of interest fused to a different targeting signal.

In some embodiments, the B cells for use in electroporation as described above may be any of the modified B cells of the present application. In some embodiments, the modified B cell comprises a chimeric antigen receptor for B cells (CAR-B). In various embodiments, the modified B cell can express a CAR-B and simultaneously and efficiently present specific antigen and/or antigen-derived epitopes of interest in both HLA class I and class II molecules.

In various embodiments, the invention relates to a method of administering an isolated B cell to a patient in need thereof. In various embodiments, a population of B cells may be administered to the patient. In various embodiments, each B cell may express more than one payload peptide or protein. For example, each B cell may express 1, 2, 3, 4, 5, 6, 7, 8, 9, 10, 11 or 12 different payloads. Alternatively, the patient may be administered a heterogeneous population of B cells, each B cell capable of expressing and/or secreting a unique payload or combination of payloads. In various embodiments, 1, 2, 3, 4, 5, 6, 7, 8, 9, 10, 11 or 12 different payloads may be administered to the patient through a heterogeneous population of B cells.

3. Methods of Treatment

In some aspects, the invention therefore comprises a method for treating or preventing a tumor or cancerous tissue, comprising administering to a patient in need thereof an effective amount of at least one CAR-B disclosed herein.

Methods are provided for treating diseases or disorders, including cancer. In some embodiments, the invention relates to creating a B cell-mediated immune response in a subject, comprising administering an effective amount of the engineered immune cells of the present application to the subject. In some embodiments, the B cell-mediated immune response is directed against a target cell or cells. In some embodiments, the engineered immune cell comprises a chimeric antigen receptor for B cells (CAR-B). In some embodiments, the target cell is a tumor cell. In some aspects, the invention comprises a method for treating or preventing a malignancy, said method comprising administering to a subject in need thereof an effective amount of at least one isolated antigen-binding molecule described herein. In some aspects, the invention comprises a method for treating or preventing a malignancy, said method comprising administering to a subject in need thereof an effective amount of at least one immune cell, wherein the immune cell comprises at least one chimeric antigen receptor.

In some aspects, the invention comprises a pharmaceutical composition comprising at least one antigen-binding molecule as described herein and a pharmaceutically acceptable excipient. In some embodiments, the pharmaceutical composition further comprises an additional active agent.

In some embodiments, the subject is diagnosed with a metastatic disease localized to the liver. In other embodiments, the metastatic disease is a cancer. In still other embodiments, the cancer metastasized from a primary tumor in the breast, colon, rectum, esophagus, lung, pancreas and/or stomach. In still other embodiments, the subject is diagnosed with unresectable metastatic liver tumors. In yet other embodiments, the subject is diagnosed with unresectable metastatic liver tumors from primary colorectal cancer. In some embodiments, the subject is diagnosed with hepatocellular carcinoma.

It will be appreciated that target doses for modified B cells can range from $1\times10^6$-$2\times10^{10}$ cells/kg, preferably $2\times10^6$ cells/kg, more preferably. It will be appreciated that doses above and below this range may be appropriate for certain subjects, and appropriate dose levels can be determined by the healthcare provider as needed. Additionally, multiple doses of cells can be provided in accordance with the invention.

Also provided are methods for reducing the size of a tumor in a subject, comprising administering to the subject a modified B cell of the present invention, wherein the cell comprises a CAR-B receptor comprising an antigen-binding domain that binds to an antigen on a tumor, a payload or both a CAR-B and a payload. In some embodiments, the subject has a solid tumor, or a blood malignancy such as lymphoma or leukemia. In some embodiments, the modified B cell is delivered to a tumor bed. In some embodiments, the cancer is present in the bone marrow of the subject.

Also provided are methods for homing B cells to a site/target of interest in a subject, comprising administering to the subject a modified B cell of the present invention, wherein the cell comprises an integrin, a homing antibody, protein, or a receptor that is attracted to a ligand, chemokine, or an attractant at the site/target of interest. In some embodiments, the site/target of interest is, for example, a homing or target tissue, an inflammatory site in a specific location or tissue, or a tumor or tumor microenvironment, where delivery of therapeutic payloads is desirable.

Also provided are methods for decreasing inflammation and autoimmune activity of B cells at a site/target of interest in a subject, comprising administering to the subject a modified B cell of the present invention, wherein the cell comprises an immune inhibitory molecule. In some embodiments, the site/target of interest is, for example, a homing or target tissue, an inflammatory site in a specific location or tissue, or a tumor or tumor microenvironment, where delivery of therapeutic payloads is desirable.

Also provided are methods for altering trafficking of B cells to a site/target of interest in a subject, comprising treating a B cell of the present invention with a compound or derivatives thereof suitable for altering B cell trafficking, and administering the treated B cell to the subject in need thereof. In some instances, the compound or derivatives thereof alters B cell trafficking by increasing the expression of an integrin, homing antibody, protein, receptor, or combinations thereof, expressed by the B cells.

Also provided are methods for potentiating B cells and/or producing potent effector B cells for increasing immune responses in a subject, comprising treating a B cell of the present invention with at least one or more TLR agonists, and administering the treated B cell to the subject in need thereof. In some embodiments, treating a B cell of the present invention with at least one or more TLR agonists induces expression or activation of one or more TLRs. In some embodiments, the method for potentiating B cells and/or producing potent effector B cells for increasing immune responses in a subject, further comprises administering to the subject a modified B cell of the present invention that expresses at least one or more constitutively active TLRs. Also provided are methods for potentiating B cells and/or producing potent effector B cells for increasing immune responses in a subject, comprising administering to the subject a modified B cell of the present invention, wherein the cell expresses a CAR-B receptor comprising an antigen-binding domain that binds to an antigen on a tumor, a constitutively active TLR or both a CAR-B and a constitutively active TLR, where the cell is treated with at least one or more TLR agonists at the same time or in advance of the administration of the cells to the subject.

Also provided are methods for increasing antigen-specific immune responses in a subject, comprising administering to the subject a modified B cell of the present invention, wherein the cell is electroporated with a nucleic acid sequence, e.g., an mRNA, encoding specific tumor antigens and/or infectious disease antigens fused to a targeting signal, such as the targeting signal of LAMP1 or Clec9A, for simultaneously and efficiently presenting the specific antigens and/or antigen-derived epitopes in both HLA class I and class II molecules. In some embodiments, the subject has a solid tumor, or a blood malignancy such as lymphoma or leukemia.

It is understood that the various embodiments of the methods of treatment using the engineered or modified B cells of the present application are not mutually exclusive and can be combined with each other in any way and without any restriction unless explicitly indicated, for achieving of facilitating any of the results and/or therapeutic responses contemplated herein.

In some embodiments, the modified B cells are autologous B cells. In some embodiments, the modified B cells are allogeneic B cells. In some embodiments, the modified B cells are heterologous B cells. In some embodiments, the modified B cells of the present application are transfected or transduced in vivo. In other embodiments, the engineered cells are transfected or transduced ex vivo.

As used herein, the term "subject" or "patient" means an individual. In some aspect, a subject is a mammal such as a human. In some aspect, a subject can be a non-human primate. Non-human primates include marmosets, monkeys, chimpanzees, gorillas, orangutans, and gibbons, to name a few. The term "subject" also includes domesticated animals, such as cats, dogs, etc., livestock (e.g., llama, horses, cows), wild animals (e.g., deer, elk, moose, etc.), laboratory animals (e.g., mouse, rabbit, rat, gerbil, guinea pig, etc.) and avian species (e.g., chickens, turkeys, ducks, etc.). Preferably, the subject is a human subject. More preferably, the subject is a human patient.

The methods can further comprise administering one or more chemotherapeutic agents. In certain embodiments, the chemotherapeutic agent is a lymphodepleting (preconditioning) chemotherapeutic. Beneficial preconditioning treatment regimens, along with correlative beneficial biomarkers are described in U.S. Provisional Patent Applications 62/262,143 and 62/167,750, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). A preferred dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered B cells to the patient.

In other embodiments, the antigen-binding molecule, transduced (or otherwise engineered) cells (such as CARs), and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (Taxol®, Bristol-Myers Squibb) and doxetaxel (Taxotere®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); Ontak™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®) Doxorubicin (hydroxydoxorubicin), Fludarabine, Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In other embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 (or PD-L1) inhibitors such as nivolumab (Opdivo®), pembrolizumab (Keytruda®), pembrolizumab, pidilizumab, and atezolizumab (Tecentriq®). Other additional therapeutics include anti-CTLA-4 antibodies (e.g., Ipilimumab®), anti-LAG-3 antibodies (e.g., Relatlimab, BMS), alone or in combination with PD-1 and/or PD-L1 inhibitors.

Additional therapeutic agents suitable for use in combination with the invention include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR-containing B cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAID s include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

4. Methods of Making

A variety of known techniques can be utilized in making the polynucleotides, polypeptides, vectors, antigen-binding molecules, immune cells, compositions, and the like according to the invention.

Prior to the in vitro manipulation or genetic modification of the immune cells described herein, the cells may be obtained from a subject. In some embodiments, the immune cells comprise B cells. B cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, B cells can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing. The cells may be washed with PBS. As will be appreciated, a washing step may be used, such as by using a semiautomated flowthrough centrifuge for example, the Cobe™ 2991 cell processor, the Baxter CytoMate™, or the like. After washing, the cells may be resuspended in a variety of biocompatible buffers, or other saline solution with or without buffer. In certain embodiments, the undesired components of the apheresis sample may be removed.

The immune cells, such as B cells, can be genetically modified following isolation using known methods, or the immune cells can be activated and expanded (or differentiated in the case of progenitors) in vitro prior to being genetically modified. In another embodiment, the immune cells, such as B cells, are genetically modified with the chimeric B cell receptors described herein (e.g., transduced with a viral vector comprising one or more nucleotide sequences encoding a CAR-B) and then are activated and/or expanded in vitro. Methods for activating and expanding B cells are known in the art and are described, for example, in U.S. Pat. Nos. 6,905,874; 6,867,041; 6,797,514; and PCT WO 2012/079000, the contents of which are hereby incorporated by reference in their entirety. Generally, such methods include contacting PBMC or isolated B cells with a stimulatory agent and costimulatory agent generally attached to a bead or other surface, in a culture medium with appropriate cytokines, such as IL-2.

In other embodiments, the B cells may be activated and stimulated to proliferate with feeder cells and appropriate antibodies and cytokines using methods such as those described in U.S. Pat. Nos. 6,040,177; 5,827,642; and WO/2012129514, the contents of which are hereby incorporated by reference in their entirety.

Certain methods for making the constructs and engineered immune cells of the invention are described in PCT application PCT/US2015/14520, the contents of which are hereby incorporated by reference in their entirety. Additional methods of making the constructs and cells can be found in U.S. provisional patent application No. 62/244,036 the contents of which are hereby incorporated by reference in their entirety.

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR-Bs as disclosed herein. The resulting transduced immune effector cells form a mixed population of engineered cells, with a proportion of the engineered cells expressing more than one different CAR-Bs.

In one embodiment, the invention provides a method of storing genetically engineered cells expressing CAR-Bs that target a protein. This involves cryopreserving the immune cells such that the cells remain viable upon thawing. A fraction of the immune cells expressing the CAR-Bs can be cryopreserved by methods known in the art to provide a permanent source of such cells for the future treatment of patients afflicted with a malignancy. When needed, the cryopreserved transformed immune cells can be thawed, grown and expanded for more such cells.

As used herein, "cryopreserve" refers to the preservation of cells by cooling to sub-zero temperatures, such as (typically) 77 Kelvin or 196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used in accordance with the invention include but are not limited to: dimethyl sulfoxide (DMSO) (Lovelock & Bishop, Nature, 1959, 183, 1394-1395; Ashwood-Smith, Nature, 1961, 190, 1204-1205), glycerol, polyvinylpyrrolidine (Rinfret, Ann. N.Y. Acad. Sci., 1960, 85, 576), and polyethylene glycol (Sloviter & Ravdin, Nature, 1962, 196, 48). The preferred cooling rate is 1°-3° C./minute.

The term, "substantially pure," is used to indicate that a given component is present at a high level. The component is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration. At very high levels (e.g. at levels of more than 90%, of more than 95% or of more than 99%) the component can be regarded as being in "pure form." Biologically active substances of the present invention (including polypeptides, nucleic acid molecules, antigen-binding molecules, moieties) can be provided in a form that is substantially free of one or more contaminants with which the substance might otherwise be associated. When a composition is substantially free of a given contaminant, the contaminant will be at a low level (e.g., at a level of less than 10%, less than 5%, or less than 1% on the dry weight/dry weight basis set out above).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR-B treatments may be administered multiple times at dosages within these ranges. The cells may be autologous, allogeneic, or heterologous to the patient undergoing therapy. In some aspects, different CAR-B cells are found in a single product. The composition can be as few as 2, 3, 4, 5, 6, 7, 8, 9 or up to 10 different CAR-B cells. These can consist of cells expressing a chimeric CAR protein and B cells expressing other CARs and/or payloads.

The B cells of the present invention may be administered either alone, or as a pharmaceutical composition in combination with diluents and/or with other components such as IL-2 or other cytokines or cell populations. Pharmaceutical compositions of the present invention may comprise a CAR-B expressing cell population, such as B cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration. Treatment may also include one or more corticosteroid treatment, such as dexamethasone and/or methylprednisolone.

The compositions of the present application can comprise, consist essentially of, or consist of, the components disclosed.

The pharmaceutical compositions of the invention (solutions, suspensions or the like), may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylene-diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

It will be appreciated that adverse events may be minimized by transducing the immune cells (containing one or more CAR-B) with a suicide gene. It may also be desired to incorporate an inducible "on" or "accelerator" switch into the immune cells. These techniques may employ the use of dimerization domains and optional activators of such domain dimerization. These techniques include, e.g., those described by Wu et al., Science 2014, 350(6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

Suitable techniques include use of inducible caspase-9 (U.S. Appl. Pub. No. 2011/0286980) or a thymidine kinase, before, after or at the same time, as the cells are transduced with the CAR-B construct of the present invention. Additional methods for introducing suicide genes and/or "on" switches include CRISPR, TALENS, MEGATALEN, zinc fingers, RNAi, siRNA, shRNA, antisense technology, and other techniques known in the art.

Anti-CD20 or anti-CD19 represent additional means to reduce or eliminate engineered B cells if such cells are responsible for adverse events or pathologies.

It will be understood that descriptions herein are exemplary and explanatory only and are not restrictive of the invention as claimed. In this application, the use of the singular includes the plural unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The term "polynucleotide", "nucleotide", or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphoro-diselenoate, phosphoro-anilothioate, phoshoraniladate and phosphoroamidate.

The term "oligonucleotide" refers to a polynucleotide comprising 200 or fewer nucleotides. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences (signal peptides) and/or fusion partner sequences.

As used herein, "operably linked" means that the components to which the term is applied are in a relationship that allows them to carry out their inherent functions under suitable conditions.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" refers to a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous DNA by a cell. A number of transfection techniques are well known in the art and are disclosed herein. See, e.g., Graham et al., Virology, 1973, 52:456; Sambrook et al., Molecular Cloning: A Laboratory Manual, 2001, supra; Davis et al., Basic Methods in Molecular Biology, 1986, Elsevier; Chu et al., Gene, 1981, 13:197.

The term "transduction" refers to the process whereby foreign DNA is introduced into a cell via viral vector. See, e.g., Jones et al., Genetics: principles and analysis, 1998, Boston: Jones & Bartlett Publ.

The terms "polypeptide" or "protein" refer to a macromolecule having the amino acid sequence of a protein, including deletions from, additions to, and/or substitutions of one or more amino acids of the native sequence. The terms "polypeptide" and "protein" specifically encompass antigen-binding molecules, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. Useful polypeptide fragments include immunologically functional fragments of antigen-binding molecules.

The term "isolated" means (i) free of at least some other proteins with which it would normally be found, (ii) is essentially free of other proteins from the same source, e.g., from the same species, (iii) separated from at least about 50 percent of polynucleotides, lipids, carbohydrates, or other materials with which it is associated in nature, (iv) operably associated (by covalent or noncovalent interaction) with a polypeptide with which it is not associated in nature, or (v) does not occur in nature.

A "variant" of a polypeptide (e.g., an antigen-binding molecule) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm").

To calculate percent identity, the sequences being compared are typically aligned in a way that gives the largest match between the sequences. One example of a computer program that can be used to determine percent identity is the GCG program package, which includes GAP (Devereux et al., Nucl. Acid Res., 1984, 12, 387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, e.g., Dayhoff et al., 1978, Atlas of Protein Sequence and Structure, 1978, 5:345-352 for the PAM 250 comparison matrix; Henikoff et al., Proc. Natl. Acad. Sci. U.S.A. 1992, 89, 10915-10919 for the BLO-SUM 62 comparison matrix) is also used by the algorithm.

As used herein, the twenty conventional (e.g., naturally occurring) amino acids and their abbreviations follow conventional usage. See, e.g., Immunology A Synthesis (2nd Edition, Golub and Green, Eds., Sinauer Assoc., Sunderland, Mass. (1991)), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, .gamma.-carboxy-glutamate, epsilon-N,N,N-trimethyllysine, e-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:

a) hydrophobic: norleucine, Met, Ala, Val, Leu, Ile;

b) neutral hydrophilic: Cys, Ser, Thr, Asn, Gln;

c) acidic: Asp, Glu;

d) basic: His, Lys, Arg;

e) residues that influence chain orientation: Gly, Pro; and f) aromatic: Trp, Tyr, Phe.

For example, non-conservative substitutions can involve the exchange of a member of one of these classes for a member from another class.

In making changes to the antigen-binding molecule, the costimulatory or activating domains of the engineered T cell, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). See, e.g., Kyte et al., J. Mol. Biol., 1982, 157, 105-131. It is known that certain amino acids can be substituted for other amino acids having a similar hydropathic index or score and still retain a similar biological activity. It is also understood in the art that the substitution of like amino acids can be made effectively on the basis of hydrophilicity, particularly where the biologically functional protein or peptide thereby created is intended for use in immunological embodiments, as in the present case. Exemplary amino acid substitutions are set forth in Table 5.

TABLE 5

| Original Residues | Exemplary Substitutions | Preferred Substitutions |
|---|---|---|
| Ala | Val, Leu, Ile | Val |
| Arg | Lys, Gin, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Va, Met, Ala, Phe | Ile |
| Lys | Arg, 1,4 Diamino-butyric Acid, Gin, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding molecule can have a greater circulating half-life than an antigen-binding molecule that is not chemically modified. In some embodiments, a derivative antigen-binding molecule is covalently modified to include one or more water soluble polymer attachments, including, but not limited to, polyethylene glycol, polyoxyethylene glycol, or polypropylene glycol.

Peptide analogs are commonly used in the pharmaceutical industry as non-peptide drugs with properties analogous to those of the template peptide. These types of non-peptide compound are termed "peptide mimetics" or "peptidomimetics." Fauchere, J. L., Adv. Drug Res., 1986, 15, 29; Veber, D. F. & Freidinger, R. M., Trends in Neuroscience, 1985, 8, 392-396; and Evans, B. E., et al., J. Med. Chem., 1987, 30, 1229-1239, which are incorporated herein by reference for any purpose.

The term "therapeutically effective amount" refers to the amount of CAR-B cells determined to produce a therapeutic response in a mammal. Such therapeutically effective amounts are readily ascertained by one of ordinary skill in the art.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

5. Sequences

The following sequences will further exemplify the invention:

```
CD28 transmembrane domain - mouse
                                                  (SEQ ID NO: 1)
TTCTGGGCCCTTGTGGTGGTTGCCGGAGTGCTGTTTTGCTATGGGCTCCTGGTTACCGT
TGCCCTTTGTGTGATTTGGACC

CD28 transmembrane domain - mouse
                                                  (SEQ ID NO: 2)
FWALVVVAGVLFCYGLLVTVALCVIWT

CD28 transmembrane domain - human
                                                  (SEQ ID NO: 3)
TTTTGGGTATTGGTAGTGGTGGGCGGAGTTTTAGCCTGCTACAGCCTCCTGGTAACAGT
GGCTTTTATCATCTTTTGGGTG

CD28 transmembrane domain - human
                                                  (SEQ ID NO: 4)
FWVLVVVGGVLACYSLLVTVAFIIFWV

CD19 cytoplasmic domain - human
                                                  (SEQ ID NO: 5)
CAGCGGGCTTTAGTCTTGCGGCGTAAACGTAAAAGAATGACAGATCCAACTCGCAGGT
TCTTCAAAGTGACCCCCCCACCTGGGTCCGGACCGCAGAACCAATATGGGAATGTCCT
GTCTCTGCCTACGCCTACAAGTGGACTGGGTAGGGCTCAGAGGTGGGCTGCCGGTCTC
GGCGGAACTGCGCCATCTTACGGAAATCCCTCCTCCGACGTTCAGGCAGACGGGGCCC
TGGGGTCTCGATCCCCGCCTGGTGTTGGACCAGAAGAGGAAGAGGGCGAGGGCTACG
AAGAGCCCGACTCCGAAGAGGACAGTGAGTTTTACGAGAACGACAGCAACCTGGGGC
AGGATCAGCTGTCACAGGATGGCTCAGGATATGAAAACCCTGAGGACGAGCCTTTGGG
GCCTGAAGATGAGGACTCCTTTTCTAATGCAGAGTCATATGAGAATGAGGACGAAGAA
TTGACTCAACCCGTGGCAAGAACAATGGATTTCCTCAGTCCACACGGGAGTGCATGGG
ACCCCTCCAGAGAGGCTACTAGCCTCGGTTCTCAAAGCTATGAGGACATGAGGGGTAT
TCTGTACGCAGCGCCTCAGTTGAGGTCCATCCGCGGCCAGCCAGGCCCAAACCATGAG
GAAGATGCCGATTCTTACGAAAACATGGACAACCCCGATGGTCCTGACCCCGCATGGG
GGGGCGGCGGGAGGATGGGCACCTGGTCTACTCGC

CD19 cytoplasmic domain - human
                                                  (SEQ ID NO: 6)
QRALVLRRKRKRMTDPTRRFFKVTPPPGSGPQNQYGNVLSLPTPTSGLGRAQRWAAGLGG
TAPSYGNPSSDVQADGALGSRSPPGVGPEEEEGEGYEEPDSEEDSEFYENDSNLGQDQLSQ
DGSGYENPEDEPLGPEDEDSFSNAESYENEDEELTQPVARTMDFLSPHGSAWDPSREATSL
GSQSYEDMRGILYAAPQLRSIRGQPGPNHEEDADSYENMDNPDGPDPAWGGGGRMGTWS
TR

CD40 cytoplasmic domain - human
                                                  (SEQ ID NO: 7)
AAGAAGGTTGCAAAAAAACCTACTAATAAGGCTCCCCATCCTAAGCAAGAGCCCCAA
GAAATTAACTTTCCCGATGATCTTCCGGGTTCTAACACGGCAGCCCCGGTGCAGGAGA
CCCTGCATGGTTGTCAACCCGTCACTCAGGAGGACGGGAAAGAGTCTCGTATCTCCGT
CCAGGAGAGACAG

CD40 cytoplasmic domain - human
                                                  (SEQ ID NO: 8)
KKVAKKPTNKAPHPKQEPQEINFPDDLPGSNTAAPVQETLHGCQPVTQEDGKESRISVQER
Q

CD40 + CD79b cytoplasmic domain - human
                                                  (SEQ ID NO: 9)
AAGAAGGTTGCAAAAAAACCTACTAATAAGGCTCCCCATCCTAAGCAAGAGCCCCAA
```

-continued

GAAATTAACTTTCCCGATGATCTTCCGGGTTCTAACACGGCAGCCCCGGTGCAGGAGA
CCCTGCATGGTTGTCAACCCGTCACTCAGGAGGACGGGAAAGAGTCTCGTATCTCCGT
CCAGGAGAGACAGGACAAGGACGATAGTAAAGCAGGGATGGAGGAGGACCATACAT
ACGAGGGACTGGATATCGATCAGACAGCCACGTACGAAGACATTGTGACACTGAGAA
CTGGCGAGGTGAAGTGGTCAGTGGGAGAACATCCGGGGCAGGAA

CD40 + CD79b cytoplasmic domain - human
(SEQ ID NO: 10)
KKVAKKPTNK APHPKQEPQE INFPDDLPGS NTAAPVQETL HGCQPVTQED
GKESRISVQE RQDKDDSKAG MEEDHTYEGL DIDQTATYED IVTLRTGEVK
WSVGEHPGQE CD40 + CD137 cytoplasmic domain - human
(SEQ ID NO: 11)
AAGAAGGTTGCAAAAAAACCTACTAATAAGGCTCCCCATCCTAAGCAAGAGCCCCAA
GAAATTAACTTTCCCGATGATCTTCCGGGTTCTAACACGGCAGCCCCGGTGCAGGAGA
CCCTGCATGGTTGTCAACCCGTCACTCAGGAGGACGGGAAAGAGTCTCGTATCTCCGT
CCAGGAGAGACAGAAAAGAGGCCGAAAAAAGCTGCTGTACATCTTCAAACAACCCTT
CATGCGACCTGTTCAGACGACACAGGAGGAGGACGGCTGCAGCTGTAGGTTTCCCGAA
GAAGAGGAGGGAGGATGCGAACTT CD40 + CD137 cytoplasmic domain - human
(SEQ ID NO: 12)
KKVAKKPTNKAPHPKQEPQEINFPDDLPGSNTAAPVQETLHGCQPVTQEDGKESRISVQER
QKRGRKKLLYIFKQPFMRPVQTTQEEDGCSCRFPEEEEGGCEL CD137 cytoplasmic domain - human
(SEQ ID NO: 13)
AAAAGAGGCCGAAAAAAGCTGCTGTACATCTTCAAACAACCCTTCATGCGACCTGTTC
AGACGACACAGGAGGAGGACGGCTGCAGCTGTAGGTTTCCCGAAGAAGAGGAGGGAG
GATGCGAACTT CD137 cytoplasmic domain - human
(SEQ ID NO: 14)
KRGRKKLLYIFKQPFMRPVQTTQEEDGCSCRFPEEEEGGCEL CD40 and Fc gamma receptor 2a cytoplasmic domain - human
(SEQ ID NO: 15)
AAGAAGGTTGCAAAAAAACCTACTAATAAGGCTCCCCATCCTAAGCAAGAGCCCCAA
GAAATTAACTTTCCCGATGATCTTCCGGGTTCTAACACGGCAGCCCCGGTGCAGGAGA
CCCTGCATGGTTGTCAACCCGTCACTCAGGAGGACGGGAAAGAGTCTCGTATCTCCGT
CCAGGAGAGACAGCGCAAAAAACGTATAAGCGCAAACTCTACAGATCCAGTAAAAGC
CGCGCAATTCGAGCCTCCCGGCCGCCAGATGATTGCAATACGGAAACGTCAACTGGAG
GAAACTAATAATGACTATGAGACGGCCGACGGTGGATACATGACCCTTAATCCCCGCG
CGCCAACCGACGATGATAAGAACATATATCTGACGCTCCCCCCTAACGATCACGTTAA
CAGTAATAAT CD40 and Fc gamma receptor 2a cytoplasmic domain - human
(SEQ ID NO: 16)
KKVAKKPTNKAPHPKQEPQEINFPDDLPGSNTAAPVQETLHGCQPVTQEDGKESRISVQER
QRKKRISANSTDPVKAAQFEPPGRQMIAIRKRQLEETNNDYETADGGYMTLNPRAPTDDD
KNIYLTLPPNDHVNSNN Fc gamma receptor 2a cytoplasmic domain - human
(SEQ ID NO: 17)
CGCAAAAAACGTATAAGCGCAAACTCTACAGATCCAGTAAAAGCCGCGCAATTCGAG
CCTCCCGGCCGCCAGATGATTGCAATACGGAAACGTCAACTGGAGGAAACTAATAATG
ACTATGAGACGGCCGACGGTGGATACATGACCCTTAATCCCCGCGCGCCAACCGACGA
TGATAAGAACATATATCTGACGCTCCCCCCTAACGATCACGTTAACAGTAATAAT Fc gamma receptor 2a cytoplasmic domain - human
(SEQ ID NO: 18)
RKKRISANSTDPVKAAQFEPPGRQMIAIRKRQLEETNNDYETADGGYMTLNPRAPTDDDK
NIYLTLPPNDHVNSNN Myd88 + CD40 cytoplasmic domain - human
(SEQ ID NO: 19)
ATGGCGGCGGGCGGCCCGGCGCCGGAAGCGCCGCGCCAGTCTCATCTACGTCCAGTC
TGCCACTGGCTGCCCTGAACATGAGAGTGAGACGCCGTTTATCCCTCTTCCTGAATGTG
CGGACCCAGGTCGCCGCTGATTGGACCGCCCTGGCCGAAGAGATGGACTTTGAATACT
TGGAAATCAGACAGCTGGAAACACAGGCAGACCCAACCGGGAGACTGCTTGACGCCT
GGCAGGGACGCCCAGGGGCAAGTGTTGGTCGGTTACTGGAGCTTTTAACTAAGTTGGG
CCGCGATGACGTGCTGTTGGAGTTAGGACCCAGTATCGAGGAGGATTGTCAGAAATAC
ATCTTGAAACAGCAGCAGGAGGAGGCGGAAAAGCCCCTGCAGGTGGCGGCCGTTGAC
AGCAGTGTACCCAGAACAGCTGAGCTGGCCGGCATCACAACCCTGGATGATCCCCTGG
GCCACATGCCTGAGAGGTTCGACGCTTTCATAAAGAAGGTTGCAAAAAAACCTACTAA
TAAGGCTCCCCATCCTAAGCAAGAGCCCCAAGAAATTAACTTTCCCGATGATCTTCCG
GGTTCTAACACGGCAGCCCCGGTGCAGGAGACCCTGCATGGTTGTCAACCCGTCACTC
AGGAGGACGGGAAAGAGTCTCGTATCTCCGTCCAGGAGAGACAG -continued Myd88 + CD40 cytoplasmic domain - human (SEQ ID NO: 20)

MAAGGPGAGSAAPVSSTSSLPLAALNMRVRRRLSLFLNVRTQVAADWTALAEEMDFEYL
EIRQLETQADPTGRLLDAWQGRPGASVGRLLELLTKLGRDDVLLELGPSIEEDCQKYILKQ
QQEEAEKPLQVAAVDSSVPRTAELAGITTLDDPLGHMPERFDAFIKKVAKKPTNKAPHPK
QEPQEINFPDDLPGSNTAAPVQETLHGCQPVTQEDGKESRISVQERQ

Myd88 cytoplasmic domain - human (SEQ ID NO: 21)

ATGGCGGCGGGCGGCCCGGCGCCGGAAGCGCCGCGCCAGTCTCATCTACGTCCAGTC
TGCCACTGGCTGCCCTGAACATGAGAGTGAGACGCCGTTTATCCCTCTTCCTGAATGTG
CGGACCCAGGTCGCCGCTGATTGGACCGCCCTGGCCGAAGAGATGGACTTTGAATACT
TGGAAATCAGACAGCTGGAAACACAGGCAGACCCAACCGGGAGACTGCTTGACGCCT
GGCAGGGACGCCCAGGGGCAAGTGTTGGTCGGTTACTGGAGCTTTTAACTAAGTTGGG
CCGCGATGACGTGCTGTTGGAGTTAGGACCCAGTATCGAGGAGGATTGTCAGAAATAC
ATCTTGAAACAGCAGCAGGAGGAGGCGGAAAAGCCCCTGCAGGTGGCGGCCGTTGAC
AGCAGTGTACCCAGAACAGCTGAGCTGGCCGGCATCACAACCCTGGATGATCCCCTGG
GCCACATGCCTGAGAGGTTCGACGCTTTCATA

Myd88 cytoplasmic domain - human (SEQ ID NO: 22)

MAAGGPGAGSAAPVSSTSSLPLAALNMRVRRRLSLFLNVRTQVAADWTALAEEMDFEYL
EIRQLETQADPTGRLLDAWQGRPGASVGRLLELLTKLGRDDVLLELGPSIEEDCQKYILKQ
QQEEAEKPLQVAAVDSSVPRTAELAGITTLDDPLGHMPERFDAFI

CD79a cytoplasmic domain - human (SEQ ID NO: 23)

AGGAAACGATGGCAGAACGAGAAGCTCGGGTTGGATGCCGGGGATGAATATGAAGAT
GAAAACCTTTATGAAGGCCTGAACCTGGACGACTGCTCCATGTATGAGGACATCTCCC
GGGGCCTCCAGGGCACCTACCAGGATGTGGGCAGCCTCAACATAGGAGATGTCCAGCT
GGAGAAGCCG

CD79a cytoplasmic domain - human (SEQ ID NO: 24)

RKRWQNEKLGLDAGDEYEDENLYEGLNLDDCSMYEDISRGLQGTYQDVGSLNIGDVQLE
KP

CD79b cytoplasmic domain - human (SEQ ID NO: 25)

CTGGACAAGGATGACAGCAAGGCTGGCATGGAGGAAGATCACACCTACGAGGGCCTG
GACATTGACCAGACAGCCACCTATGAGGACATAGTGACGCTGCGGACAGGGGAAGTG
AAGTGGTCTGTAGGTGAGCACCCAGGCCAGGAG

CD79b cytoplasmic domain - human (SEQ ID NO: 26)

LDKDDSKAGMEEDHTYEGLDIDQTATYEDIVTLRTGEVKWSVGEHPGQE

CD8 hinge domain - human (SEQ ID NO: 27)

TTCGTGCCTGTGTTCCTCCCAGCTAAGCCCACTACCACCCCCGCTCCAAGGCCGCCCAC
GCCCGCTCCTACTATTGCTAGTCAGCCTTTAAGTTTACGACCCGAAGCTTGCAGGCCCG
CCGCCGGCGGCGCTGTGCACACCAGGGGGCTTGATTTTGCCTGCGAC

CD8 hinge domain - human (SEQ ID NO: 28)

FVPVFLPAKPTTTPAPRPPTPAPTIASQPLSLRPEACRPAAGGAVHTRGLDFACD

Spacer with 3X strep II tag (SEQ ID NO: 29)

GGCGCTGGTAGTGGCGGTAACTGGAGCCACCCTCAATTTGAGAAGGGCGGGTCAGGC
GGATCAGGTGGTAGTGGTGGGTCCAACTGGAGCCATCCGCAATTTGAAAAGGGCGGA
AGCGGCGGTTCCGGCGGTTCAGGCGGTAGCAACTGGTCACATCCGCAATTTGAGAAAG
GCGGGTCAGGCGGCGGG

Spacer with 3X strep II tag (SEQ ID NO: 30)

GAGSGGNWSHPQFEKGGSGGSGGSGGSNWSHPQFEKGGSGGSGGSGGSNWSHPQFEKGG
SGGG human IgG1 Fc (transmembrane form)

(SEQ ID NO: 31)

CCCAAGAGCTGCGACAAGACCCACACCTGCCCCCCCTGCCCAGCCCCAGAGCTGCTGG
GCGGACCCTCCGTGTTCCTGTTCCCCCCCAAGCCCAAGGACACCCTGATGATCAGCAG
GACCCCCGAGGTGACCTGCGTGGTGGTGGACGTGAGCCACGAGGACCCAGAGGTGAA
GTTCAACTGGTACGTGGACGGCGTGGAGGTGCACAACGCCAAGACCAAGCCCAGAGA
GGAGCAGTACAACAGCACCTACAGGGTGGTGTCCGTGCTGACCGTGCTGCACCAGGAC
TGGCTGAACGGCAAGGAATACAAGTGCAAGGTCTCCAACAAGGCCCTGCCAGCCCCC
ATCGAAAAGACCATCAGCAAGGCCAAGGGCCAGCCACGGGAGCCCCAGGTGTACACC
CTGCCCCCCTCCCGGGAGGAGATGACCAAGAACCAGGTGTCCCTGACCTGTCTGGTGA
AGGGCTTCTACCCCAGCGACATCGCCGTGGAGTGGGAGAGCAACGGCCAGCCCGAGA

-continued

ACAACTACAAGACCACCCCCCCAGTGCTGGACAGCGACGGCAGCTTCTTCCTGTACAG
CAAGCTGACCGTGGACAAGTCCAGGTGGCAGCAGGGCAACGTGTTCAGCTGCAGCGT
GATGCACGAGGCCCTGCACAACCACTACACCCAGAAGAGCCTGAGCCTGTCCCCCGAG
CTGCAACTGGAGGAGAGCTGTGCGGAGGCGCAGGACGGGGAGCTGGACGGGCTGTGG
ACGACCATCACCATCTTCATCACACTCTTCCTGTTAAGCGTGTGCTACAGTGCCACCGT
CACCTTCTTCAAGGTGAAGTGGATCTTCTCCTCGGTGGTGGACCTGAAGCAGACCATC
ATCCCCGACTACAGGAACATGATCGGACAGGGGGCCTGA human IgG1 Fc (transmembrane form)

(SEQ ID NO: 32)

PKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPELQLEESCAEAQ
DGELDGLWTTITIFITLFLLSVCYSATVTFFKVKWIFSSVVDLKQTIIPDYRNMIGQGA anti-huPSMA scFv (SEQ ID NO: 33)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAA anti-huPSMA scFv (SEQ ID NO: 34)

EVQLVQSGAE VKKPGASVKV SCKTSGYTFT EYTIHWVRQA PGQSLEWMGN
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IK anti-Sarcoglycan scFv (SEQ ID NO: 35)

GAAGTCCAATTGGTTGAAAGCGGTGGTGGACTCGTCAAACCTGGCGGTAGCCTTAAAC
TTTCATGTGCCGCAAGCGGCTTCACGTTTAGTAACTATGCTATGAGTTGGGTCCGCCAA
AGTCCAGAAAAGCGCCTCGAATGGGTGGCGGAGATCTCTGGAGGAGGAACATATACA
TATTATCCAGACACCATGACCGGTAGGTTTACAATCTCAAGAGACAACGCTAAGAACA
CCCTGTACCTGGAAATGTCAAGCCTGAGATCAGAAGATACGGCCATGTATTATTGTAC
GCGCCTACTCGACTATTGGGGTCAAGGAACTTCCGTGACGGTGTCAAGCGGAGGAGGT
GGGAGCGGAGGAGGCGGAAGTGGCGGTGGTGGCTCTGGTGGCGGTGGAAGTGATATA
GTGATGACGCAAGCTGCCTTTTCAAACCCTGTTACTTTGGGGACTAGCGCATCAATCTC
CTGTAGGTCCAGCAAATCTTTGCTGCACAGTAATGGAATCACCTATCTTTTCTGGTATT
TGCAAAAGCCTGGGCAGAGCCCGCAACTGCTGATCTATCAAATGTCAAATCTTGCTTC
CGGAGTTCCAGACCGCTTCTCAAGTTCCGGGTCCGGCACTGATTTTACCTTGAGAATTT
CTAGGGTCGAAGCTGAAGACGTCGGTGTCTATTATTGCGCGCAAAACCTTGAGCTTCC
ATACACCTTCGGGGGGGGCACAAAACTTGAGATCAAG anti-Sarcoglycan scFv (SEQ ID NO: 36)

EVQLVESGGGLVKPGGSLKLSCAASGFTFSNYAMSWVRQSPEKRLEWVAEISGGGTYTYY
PDTMTGRFTISRDNAKNTLYLEMSSLRSEDTAMYYCTRLLDYWGQGTSVTVSSGGGGSG
GGGSGGGGSGGGGSDIVMTQAAFSNPVTLGTSASISCRSSKSLLHSNGITYLFWYLQKPGQ
SPQLLIYQMSNLASGVPDRESSSGSGTDFTLRISRVEAEDVGVYYCAQNLELPYTFGGGTK
LEIK anti-hu GPC3 scFv (SEQ ID NO: 37)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGGTGCAGCTG
GTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAA
GGGGCTGGAGTGGGTCTCAGTTATTTATAGCGGTGGTAGTAGCACATACTATGCAGAC
TCCGTGAAGGGCCGGTTCACCATCTCCAGAGATAATTCCAAGAACACGCTGTATCTGC
AAATGAACAGCCTGAGAGCCGAGGACACGGCCGTATATTACTGTGCGCGCACTTCTTA
CCTGAACCATGGTGATTACTGGGGTCAAGGTACTCTGGTGACCGTGTCTAGCGCCGCT
GCA

-continued anti-hu GPC3 scFv (SEQ ID NO: 38)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGSRGGGGSGGG
GSGGGGSLEMAQVQLVESGGGLVQPGGSLRLSCAASGFTFSSYAMSWVRQAPGKGLEWV
SVIYSGGSSTYYADSVKGRFTISRDNSKNTLYLQMNSLRAEDTAVYYCARTSYLNHGDYW
GQGTLVTVSSAAA pWF-82

(SEQ ID NO: 39)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGCAGCGGGCTTTAGTCTT
GCGGCGTAAACGTAAAAGAATGACAGATCCAACTCGCAGGTTCTTCAAAGTGACCCCC
CCACCTGGGTCCGGACCGCAGAACCAATATGGGAATGTCCTGTCTCTGCCTACGCCTA
CAAGTGGACTGGGTAGGGCTCAGAGGTGGGCTGCCGGTCTCGGCGGAACTGCGCCATC
TTACGGAAATCCCTCCTCCGACGTTCAGGCAGACGGGGCCCTGGGGTCTCGATCCCCG
CCTGGTGTTGGACCAGAAGAGGAAGAGGGCGAGGGCTACGAAGAGCCCGACTCCGAA
GAGGACAGTGAGTTTTACGAGAACGACAGCAACCTGGGGCAGGATCAGCTGTCACAG
GATGGCTCAGGATATGAAAACCCTGAGGACGAGCCTTTGGGGCCTGAAGATGAGGAC
TCCTTTTCTAATGCAGAGTCATATGAGAATGAGGACGAAGAATTGACTCAACCCGTGG
CAAGAACAATGGATTTCCTCAGTCCACACGGGAGTGCATGGGACCCCTCCAGAGAGGC
TACTAGCCTCGGTTCTCAAAGCTATGAGGACATGAGGGGTATTCTGTACGCAGCGCCT
CAGTTGAGGTCCATCCGCGGCCAGCCAGGCCCAAACCATGAGGAAGATGCCGATTCTT
ACGAAAACATGGACAACCCCGATGGTCCTGACCCCGCATGGGGGGGGGGGGGAGGA
TGGGCACCTGGTCTACTCGCTAG pWF-82

(SEQ ID NO: 40)

EVQLVQSGAE VKKPGASVKV SCKTSGYTFT EYTIHWVRQA PGQSLEWMGN
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IKFVPVFLPA KPTTTPAPRP
PTPAPTIASQ PLSLRPEACR PAAGGAVHTR GLDFACDFWV LVVVGGVLAC
YSLLVTVAFI IFWVQRALVL RRKRKRMTDP TRRFFKVTPP PGSGPQNQYG NVLSLPTPTS
GLGRAQRWAA GLGGTAPSYG NPSSDVQADG ALGSRSPPGV GPEEEEGEGY
EEPDSEEDSE FYENDSNLGQ DQLSQDGSGY ENPEDEPLGP EDEDSFSNAE SYENEDEELT
QPVARTMDFL SPHGSAWDPS REATSLGSQS YEDMRGILYA APQLRSIRGQ
PGPNHEEDAD SYENMDNPDG PDPAWGGGGR MGTWSTRpWF-83

(SEQ ID NO: 41)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGCTGGACAAGGATGACAG
CAAGGCTGGCATGGAGGAAGATCACACCTACGAGGGCCTGGACATTGACCAGACAGC
CACCTATGAGGACATAGTGACGCTGCGGACAGGGGAAGTGAAGTGGTCTGTAGGTGA
GCACCCAGGCCAGGAGTGA pWF-83

(SEQ ID NO: 42)

EVQLVQSGAE VKKPGASVKV SCKTSGYTFT EYTIHWVRQA PGQSLEWMGN

-continued

```
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IKFVPVFLPA KPTTTPAPRP
PTPAPTIASQ PLSLRPEACR PAAGGAVHTR GLDFACDFWV LVVVGGVLAC
YSLLVTVAFI IFWVLDKDDS KAGMEEDHTY EGLDIDQTAT YEDIVTLRTG
EVKWSVGEHP GQE-
```

pWF-84:

(SEQ ID NO: 43)

```
GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGAAGAAGGTTGCAAAAA
AACCTACTAATAAGGCTCCCCATCCTAAGCAAGAGCCCCAAGAAATTAACTTTCCCGA
TGATCTTCCGGGTTCTAACACGGCAGCCCCGGTGCAGGAGACCCTGCATGGTTGTCAA
CCCGTCACTCAGGAGGACGGGAAAGAGTCTCGTATCTCCGTCCAGGAGAGACAGGAC
AAGGACGATAGTAAAGCAGGGATGGAGGAGGACCATACATACGAGGGACTGGATATC
GATCAGACAGCCACGTACGAAGACATTGTGACACTGAGAACTGGCGAGGTGAAGTGG
TCAGTGGGAGAACATCCGGGGCAGGAATAA
```

pWF-84:

(SEQ ID NO: 44)

```
EVQLVQSGAE VKKPGASVKV SCKTSGYTFT EYTIHWVRQA PGQSLEWMGN
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IKFVPVFLPA KPTTTPAPRP
PTPAPTIASQ PLSLRPEACR PAAGGAVHTR GLDFACDFWV LVVVGGVLAC
YSLLVTVAFI IFWVKKVAKK PTNKAPHPKQ EPQEINFPDD LPGSNTAAPV
QETLHGCQPV TQEDGKESRI SVQERQDKDD SKAGMEEDHT YEGLDIDQTA
TYEDIVTLRT GEVKWSVGEH PGQE-
```

pWF-85:

(SEQ ID NO: 45)

```
GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGAAGAAGGTTGCAAAAA
AACCTACTAATAAGGCTCCCCATCCTAAGCAAGAGCCCCAAGAAATTAACTTTCCCGA
TGATCTTCCGGGTTCTAACACGGCAGCCCCGGTGCAGGAGACCCTGCATGGTTGTCAA
CCCGTCACTCAGGAGGACGGGAAAGAGTCTCGTATCTCCGTCCAGGAGAGACAGAAA
AGAGGCCGAAAAAAGCTGCTGTACATCTTCAAACAACCCTTCATGCGACCTGTTCAGA
CGACACAGGAGGAGGACGGCTGCAGCTGTAGGTTTCCCGAAGAAGAGGAGGGAGGAT
GCGAACTTTAA
```

pWF-85:

(SEQ ID NO: 46)

```
EVQLVQSGAE VKKPGASVKV SCKTSGYTFT EYTIHWVRQA PGQSLEWMGN
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IKFVPVFLPA KPTTTPAPRP
PTPAPTIASQ PLSLRPEACR PAAGGAVHTR GLDFACDFWV
LVVVGGVLAC YSLLVTVAFI IFWVKKVAKK PTNKAPHPKQ EPQEINFPDD
```

-continued

LPGSNTAAPV QETLHGCQPV TQEDGKESRI SVQERQKRGR KKLLYIFKQP
FMRPVQTTQE EDGCSCRFPE EEEGGCELpWF-86

(SEQ ID NO: 150)

GAGGTTCAACTTGTTCAATCTGGGGCAGAAGTGAAGAAGCCCGGGGCATCTGTGAAA
GTATCATGCAAAACATCCGGCTATACGTTTACCGAATACACCATTCACTGGGTCAGA
CAGGCTCCCGGTCAAAGCCTCGAATGGATGGGAAATATTAACCCTAACAATGGCGGA
ACCACATATAATCAGAAATTCCAAGGCCGAGTGACGATAACTGTCGATAAGAGTACG
TCCACAGCTTACATGGAACTCAGCTCTTTGAGATCCGAAGACACTGCAGTTTATTATT
GTGCAGCTGGATGGAACTTCGACTATTGGGGACAAGGGACTCTTGTTACGGTGTCCA
GTGGCAAACCAGGTAGTGGTAAACCCGGAAGCGGCAAGCCCGGGAGCGGTAAACCT
GGTAGCGACATCGTCATGACTCAAAGCCCTGACTCACTCGCCGTGAGCCTGGGAGAG
CGTGCAACGCTATCTTGTCGGGCCTCTCAGGATGTCGGAACTGCTGTAGACTGGTATC
AACAGAAACCTGACCAATCACCAAAACTCCTGATTTATTGGGCCTCAACACGTCACA
CAGGAGTGCCAGATAGGTTCACAGGTAGTGGCAGTGGAACTGATTTTACTTTGACAA
TTAGCAGCCTGCAAGCCGAAGATGTAGCCGTTTACTTCTGTCAACAATATAACTCATA
CCCACTAACGTTCGGTGCCGGGACGAAGGTAGAGATTAAATTCGTGCCTGTGTTCCT
CCCAGCTAAGCCCACTACCACCCCCGCTCCAAGGCCGCCCACGCCCGCTCCTACTATT
GCTAGTCAGCCTTTAAGTTTACGACCCGAAGCTTGCAGGCCCGCCGCCGGCGGCGCT
GTGCACACCAGGGGGCTTGATTTTGCCTGCGACTTTTGGGTATTGGTAGTGGTGGGCG
GAGTTTTAGCCTGCTACAGCCTCCTGGTAACAGTGGCTTTTATCATCTTTTGGGTGAA
GAAGGTTGCAAAAAAACCTACTAATAAGGCTCCCCATCCTAAGCAAGAGCCCCAAG
AAATTAACTTTCCCGATGATCTTCCGGGTTCTAACACGGCAGCCCCGGTGCAGGAGA
CCCTGCATGGTTGTCAACCCGTCACTCAGGAGGACGGGAAAGAGTCTCGTATCTCCG
TCCAGGAGAGACAGCGCAAAAAACGTATAAGCGCAAACTCTACAGATCCAGTAAAA
GCCGCGCAATTCGAGCCTCCCGGCCGCCAGATGATTGCAATACGGAAACGTCAACTG
GAGGAAACTAATAATGACTATGAGACGGCCGACGGTGGATACATGACCCTTAATCCC
CGCGCGCCAACCGACGATGATAAGAACATATATCTGACGCTCCCCCCTAACGATCAC
GTTAACAGTAATAATTAA pWF-86:

(SEQ ID NO: 47)

EVQLVQSGAE VKKPGASVKV SCKTSGYTFT EYTIHWVRQA PGQSLEWMGN
INPNNGGTTY NQKFQGRVTI TVDKSTSTAY MELSSLRSED TAVYYCAAGW
NFDYWGQGTL VTVSSGKPGS GKPGSGKPGS GKPGSDIVMT QSPDSLAVSL
GERATLSCRA SQDVGTAVDW YQQKPDQSPK LLIYWASTRH TGVPDRFTGS
GSGTDFTLTI SSLQAEDVAV YFCQQYNSYP LTFGAGTKVE IKFVPVFLPA KPTTTPAPRP
PTPAPTIASQ PLSLRPEACR PAAGGAVHTR GLDFACDFWV LVVVGGVLAC
YSLLVTVAFI IFWVKKVAKK PTNKAPHPKQ EPQEINFPDD LPGSNTAAPV
QETLHGCQPV TQEDGKESRI SVQERQKKR ISANSTDPVK AAQFEPPGRQ
MIAIRKRQLE ETNNDYETAD GGYMTLNPRA PTDDDKNIYL TLPPNDHVNS NNpWF-87:

(SEQ ID NO: 48)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGATGGCGGCGGGCGGGCC
CGGCGCCGGAAGCGCCGCGCCAGTCTCATCTACGTCCAGTCTGCCACTGGCTGCCCTG
AACATGAGAGTGAGACGCCGTTTATCCCTCTTCCTGAATGTGCGGACCCAGGTCGCCG
CTGATTGGACCGCCCTGGCCGAAGAGATGGACTTTGAATACTTGGAAATCAGACAGCT
GGAAACACAGGCAGACCCAACCGGGAGACTGCTTGACGCCTGGCAGGGACGCCCAGG
GGCAAGTGTTGGTCGGTTACTGGAGCTTTTAACTAAGTTGGGCCGCGATGACGTGCTG
TTGGAGTTAGGACCCAGTATCGAGGAGGATTGTCAGAAATACATCTTGAAACAGCAGC
AGGAGGAGGCGGAAAAGCCCCTGCAGGTGGCGGCCGTTGACAGCAGTGTACCCAGAA
CAGCTGAGCTGGCCGGCATCACAACCCTGGATGATCCCCTGGGCCACATGCCTGAGAG
GTTCGACGCTTTCATAAAGAAGGTTGCAAAAAAACCTACTAATAAGGCTCCCCATCCT
AAGCAAGAGCCCCAAGAAATTAACTTTCCCGATGATCTTCCGGGTTCTAACACGGCAG
CCCCGGTGCAGGAGACCCTGCATGGTTGTCAACCCGTCACTCAGGAGGACGGGAAAG
AGTCTCGTATCTCCGTCCAGGAGAGACAGTGA pWF-87:

(SEQ ID NO: 49)

EVQLVQSGAEVKKPGASVKVSCKTSGYTFTEYTIHWVRQAPGQSLEWMGNINPNNGGTT
YNQKFQGRVTITVDKSTSTAYMELSSLRSEDTAVYYCAAGWNFDYWGQGTLVTVSSGKP
GSGKPGSGKPGSGKPGSDIVMTQSPDSLAVSLGERATLSCRASQDVGTAVDWYQQKPDQS
PKLLIYWASTRHTGVPDRFTGSGSGTDFTLTISSLQAEDVAVYFCQQYNSYPLTFGAGTKV

-continued

EIKFVPVFLPAKPTTTPAPRPPTPAPTIASQPLSLRPEACRPAAGGAVHTRGLDFACDFWVL
VVVGGVLACYSLLVTVAFIIFWVMAAGGPGAGSAAPVSSTSSLPLAALNMRVRRRLSLFL
NVRTQVAADWTALAEEMDFEYLEIRQLETQADPTGRLLDAWQGRPGASVGRLLELLTKL
GRDDVLLELGPSIEEDCQKYILKQQQEEAEKPLQVAAVDSSVPRTAELAGITTLDDPLGHM
PERFDAFIKKVAKKPTNKAPHPKQEPQEINFPDDLPGSNTAAPVQETLHGCQPVTQEDGKE
SRISVQERQpWF-88:

(SEQ ID NO: 50)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGAGGAAACGATGGCAGA
ACGAGAAGCTCGGGTTGGATGCCGGGGATGAATATGAAGATGAAAACCTTTATGAAG
GCCTGAACCTGGACGACTGCTCCATGTATGAGGACATCTCCCGGGGCCTCCAGGGCAC
CTACCAGGATGTGGGCAGCCTCAACATAGGAGATGTCCAGCTGGAGAAGCCGTGA pWF-88:

(SEQ ID NO: 51)

EVQLVQSGAEVKKPGASVKVSCKTSGYTFTEYTIHWVRQAPGQSLEWMGNINPNNGGTT
YNQKFQGRVTITVDKSTSTAYMELSSLRSEDTAVYYCAAGWNFDYWGQGTLVTVSSGKP
GSGKPGSGKPGSGKPGSDIVMTQSPDSLAVSLGERATLSCRASQDVGTAVDWYQQKPDQS
PKLLIYWASTRHTGVPDRFTGSGSGTDFTLTISSLQAEDVAVYFCQQYNSYPLTFGAGTKV
EIKFVPVFLPAKPTTTPAPRPPTPAPTIASQPLSLRPEACRPAAGGAVHTRGLDFACDFWVL
VVVGGVLACYSLLVTVAFIIFWVRKRWQNEKLGLDAGDEYEDENLYEGLNLDDCSMYED
ISRGLQGTYQDVGSLNIGDVQLEKPpWF-89:

(SEQ ID NO: 52)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAATTCGTGCCTGTGTTCCTCCCAGCTAAGC
CCACTACCACCCCCGCTCCAAGGCCGCCCACGCCCGCTCCTACTATTGCTAGTCAGCCT
TTAAGTTTACGACCCGAAGCTTGCAGGCCCGCCGCCGGCGGCGCTGTGCACACCAGGG
GGCTTGATTTTGCCTGCGACTTTTGGGTATTGGTAGTGGTGGGCGGAGTTTTAGCCTGC
TACAGCCTCCTGGTAACAGTGGCTTTTATCATCTTTTGGGTGCTGGACAAGGATGACAG
CAAGGCTGGCATGGAGGAAGATCACACCTACGAGGGCCTGGACATTGACCAGACAGC
CACCTATGAGGACATAGTGACGCTGCGGACAGGGGAAGTGAAGTGGTCTGTAGGTGA
GCACCCAGGCCAGGAGTGA pWF-89:

(SEQ ID NO: 53)

EVQLVQSGAEVKKPGASVKVSCKTSGYTFTEYTIHWVRQAPGQSLEWMGNINPNNGGTT
YNQKFQGRVTITVDKSTSTAYMELSSLRSEDTAVYYCAAGWNFDYWGQGTLVTVSSGKP
GSGKPGSGKPGSGKPGSDIVMTQSPDSLAVSLGERATLSCRASQDVGTAVDWYQQKPDQS
PKLLIYWASTRHTGVPDRFTGSGSGTDFTLTISSLQAEDVAVYFCQQYNSYPLTFGAGTKV
EIKFVPVFLPAKPTTTPAPRPPTPAPTIASQPLSLRPEACRPAAGGAVHTRGLDFACDFWVL
VVVGGVLACYSLLVTVAFIIFWVLDKDDSKAGMEEDHTYEGLDIDQTATYEDIVTLRTGE
VKWSVGEHPGQE pWF-391:

(SEQ ID NO: 54)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA

-continued

AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAAGGCGCTGGTAGTGGCGGTAACTGGAGC
CACCCTCAATTTGAGAAGGGCGGGTCAGGCGGATCAGGTGGTAGTGGTGGGTCCAACT
GGAGCCATCCGCAATTTGAAAAGGGCGGAAGCGGCGGTTCCGGCGGTTCAGGCGGTA
GCAACTGGTCACATCCGCAATTTGAGAAAGGCGGGTCAGGCGGCGGGTTTTGGGCTCT
CGTGGTGGTGGCTGGAGTGCTTTTCTGCTATGGCCTGCTGGTAACCGTGGCCCTTTGTG
TAATCTGGACCGATAAAGACGATGGAAAAGCCGGGATGGAAGAAGACCATACCTACG
AGGGGCTCAATATTGATCAAACCGCCACGTATGAAGACATTGTAACACTGCGCACAGG
TGAGGTCAAGTGGTCCGTCGGTGAACACCCAGGACAAGAATAA pWF-391:

(SEQ ID NO: 55)

EVQLVQSGAEVKKPGASVKVSCKTSGYTFTEYTIHWVRQAPGQSLEWMGNINPNNGGTT
YNQKFQGRVTITVDKSTSTAYMELSSLRSEDTAVYYCAAGWNFDYWGQGTLVTVSSGKP
GSGKPGSGKPGSGKPGSDIVMTQSPDSLAVSLGERATLSCRASQDVGTAVDWYQQKPDQS
PKLLIYWASTRHTGVPDRFTGSGSGTDFTLTISSLQAEDVAVYFCQQYNSYPLTFGAGTKV
EIKGAGSGGNWSHPQFEKGGSGGSGGSGGSNWSHPQFEKGGSGGSGGSGGSNWSHPQFE
KGGSGGGFWALVVVAGVLFCYGLLVTVALCVIWTDKDDGKAGMEEDHTYEGLNIDQTA
TYEDIVTLRTGEVKWSVGEHPGQE pWF-394:

(SEQ ID NO: 56)

GAAGTCCAATTGGTTGAAAGCGGTGGTGGACTCGTCAAACCTGGCGGTAGCCTTAAAC
TTTCATGTGCCGCAAGCGGCTTCACGTTTAGTAACTATGCTATGAGTTGGGTCCGCCAA
AGTCCAGAAAAGCGCCTCGAATGGGTGGCGGAGATCTCTGGAGGAGGAACATATACA
TATTATCCAGACACCATGACCGGTAGGTTTACAATCTCAAGAGACAACGCTAAGAACA
CCCTGTACCTGGAAATGTCAAGCCTGAGATCAGAAGATACGGCCATGTATTATTGTAC
GCGCCTACTCGACTATTGGGGTCAAGGAACTTCCGTGACGGTGTCAAGCGGAGGAGGT
GGGAGCGGAGGAGGCGGAAGTGGCGGTGGTGGCTCTGGTGGCGGTGGAAGTGATATA
GTGATGACGCAAGCTGCCTTTTCAAACCCTGTTACTTTGGGGACTAGCGCATCAATCTC
CTGTAGGTCCAGCAAATCTTTGCTGCACAGTAATGGAATCACCTATCTTTTCTGGTATT
TGCAAAAGCCTGGGCAGAGCCCGCAACTGCTGATCTATCAAATGTCAAATCTTGCTTC
CGGAGTTCCAGACCGCTTCTCAAGTTCCGGGTCCGGCACTGATTTTACCTTGAGAATTT
CTAGGGTCGAAGCTGAAGACGTCGGTGTCTATTATTGCGCGCAAAACCTTGAGCTTCC
ATACACCTTCGGGGGGGGCACAAAACTTGAGATCAAGGGCGCTGGGAGCGGCGGGAA
TTGGAGTCATCCACAATTCGAAAAGGGTGGGTCCGGCGGCAGTGGTGGAAGCGGCGG
GAGTAACTGGTCACATCCCCAGTTTGAGAAAGGCGGTAGTGGTGGCAGCGGCGGTAGT
GGTGGCAGTAATTGGAGCCATCCCCAATTCGAAAAGGGCGGTTCCGGCGGCGGATTTT
GGGCTCTTGTTGTGGTGGCCGGAGTATTGTTTTGCTATGGCCTGCTCGTTACAGTGGCA
TTGTGCGTAATTTGGACTGATAAAGACGACGGCAAAGCCGGGATGGAAGAAGATCAC
ACCTATGAGGGGCTTAATATAGATCAAACAGCCACATATGAAGATATTGTGACTCTAA
GGACTGGAGAGGTTAAATGGAGTGTGGGTGAGCATCCAGGACAAGAATAA pWF-394:

(SEQ ID NO: 57)

EVQLVESGGGLVKPGGSLKLSCAASGFTFSNYAMSWVRQSPEKRLEWVAEISGGGTYTYY
PDTMTGRFTISRDNAKNTLYLEMSSLRSEDTAMYYCTRLLDYWGQGTSVTVSSGGGGSG
GGGSGGGGSGGGGSDIVMTQAAFSNPVTLGTSASISCRSSKSLLHSNGITYLFWYLQKPGQ
SPQLLIYQMSNLASGVPDRESSSGSGTDFTLRISRVEAEDVGVYYCAQNLELPYTFGGGTK
LEIKGAGSGGNWSHPQFEKGGSGGSGGSGGSNWSHPQFEKGGSGGSGGSGGSNWSHPQF
EKGGSGGGFWALVVVAGVLFCYGLLVTVALCVIWTDKDDGKAGMEEDHTYEGLNIDQT
ATYEDIVTLRTGEVKWSVGEHPGQE pWF-396:

(SEQ ID NO: 58)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGGTGCAGCTG
GTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAA
GGGGCTGGAGTGGGTCTCAGTTATTTATAGCGGTGGTAGTAGCACATACTATGCAGAC
TCCGTGAAGGGCCGGTTCACCATCTCCAGAGATAATTCCAAGAACACGCTGTATCTGC
AAATGAACAGCCTGAGAGCCGAGGACACGGCCGTATATTACTGTGCGCGCACTTCTTA
CCTGAACCATGGTGATTACTGGGGTCAAGGTACTCTGGTGACCGTGTCTAGCGCCGCT
GCATTCGTGCCTGTGTTCCTCCCAGCTAAGCCCACTACCACCCCCGCTCCAAGGCCGCC
CACGCCCGCTCCTACTATTGCTAGTCAGCCTTTAAGTTTACGACCCGAAGCTTGCAGGC
CCGCCGCCGGCGGCGCTGTGCACACCAGGGGGCTTGATTTTGCCTGCGACTTTTGGGT
ATTGGTAGTGGTGGGCGGAGTTTTAGCCTGCTACAGCCTCCTGGTAACAGTGGCTTTTA
TCATCTTTTGGGTGAGGAAACGATGGCAGAACGAGAAGCTCGGGTTGGATGCCGGGG
ATGAATATGAAGATGAAAACCTTTATGAAGGCCTGAACCTGGACGACTGCTCCATGTA
TGAGGACATCTCCCGGGGCCTCCAGGGCACCTACCAGGATGTGGCAGCCTCAACATA
GGAGATGTCCAGCTGGAGAAGCCGTGA

-continued pWF-396:

(SEQ ID NO: 59)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGSRGGGGSGGG
GSGGGGSLEMAQVQLVESGGGLVQPGGSLRLSCAASGFTFSSYAMSWVRQAPGKGLEWV
SVIYSGGSSTYYADSVKGRFTISRDNSKNTLYLQMNSLRAEDTAVYYCARTSYLNHGDYW
GQGTLVTVSSAAAFVPVFLPAKPTTTPAPRPPTPAPTIASQPLSLRPEACRPAAGGAVHTRG
LDFACDFWVLVVVGGVLACYSLLVTVAFIIFWVRKRWQNEKLGLDAGDEYEDENLYEGL
NLDDCSMYEDISRGLQGTYQDVGSLNIGDVQLEKP pWF-397:

(SEQ ID NO: 60)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGGTGCAGCTG
GTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAA
GGGGCTGGAGTGGGTCTCAGTTATTTATAGCGGTGGTAGTAGCACATACTATGCAGAC
TCCGTGAAGGGCCGGTTCACCATCTCCAGAGATAATTCCAAGAACACGCTGTATCTGC
AAATGAACAGCCTGAGAGCCGAGGACACGGCCGTATATTACTGTGCGCGCACTTCTTA
CCTGAACCATGGTGATTACTGGGGTCAAGGTACTCTGGTGACCGTGTCTAGCGCCGCT
GCATTCGTGCCTGTGTTCCTCCCAGCTAAGCCCACTACCACCCCCGCTCCAAGGCCGCC
CACGCCCGCTCCTACTATTGCTAGTCAGCCTTTAAGTTTACGACCCGAAGCTTGCAGGC
CCGCCGCCGGCGGCGCTGTGCACACCAGGGGGCTTGATTTTGCCTGCGACTTTTGGGT
ATTGGTAGTGGTGGGCGGAGTTTTAGCCTGCTACAGCCTCCTGGTAACAGTGGCTTTTA
TCATCTTTTGGGTGCTGGACAAGGATGACAGCAAGGCTGGCATGGAGGAAGATCACAC
CTACGAGGGCCTGGACATTGACCAGACAGCCACCTATGAGGACATAGTGACGCTGCGG
ACAGGGGAAGTGAAGTGGTCTGTAGGTGAGCACCCAGGCCAGGAGTGA pWF-397:

(SEQ ID NO: 61)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGSRGGGGSGGG
GSGGGGSLEMAQVQLVESGGGLVQPGGSLRLSCAASGFTFSSYAMSWVRQAPGKGLEWV
SVIYSGGSSTYYADSVKGRFTISRDNSKNTLYLQMNSLRAEDTAVYYCARTSYLNHGDYW
GQGTLVTVSSAAAFVPVFLPAKPTTTPAPRPPTPAPTIASQPLSLRPEACRPAAGGAVHTRG
LDFACDFWVLVVVGGVLACYSLLVTVAFIIFWVLDKDDSKAGMEEDHTYEGLDIDQTAT
YEDIVTLRTGEVKWSVGEHPGQE pWF-460:

(SEQ ID NO: 62)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGGTGCAGCTG
GTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAA
GGGGCTGGAGTGGGTCTCAGTTATTTATAGCGGTGGTAGTAGCACATACTATGCAGAC
TCCGTGAAGGGCCGGTTCACCATCTCCAGAGATAATTCCAAGAACACGCTGTATCTGC
AAATGAACAGCCTGAGAGCCGAGGACACGGCCGTATATTACTGTGCGCGCACTTCTTA
CCTGAACCATGGTGATTACTGGGGTCAAGGTACTCTGGTGACCGTGTCTAGCCCCAAG
AGCTGCGACAAGACCCACACCTGCCCCCCCTGCCCAGCCCCAGAGCTGCTGGGCGGAC
CCTCCGTGTTCCTGTTCCCCCCCAAGCCCAAGGACACCCTGATGATCAGCAGGACCCCC
GAGGTGACCTGCGTGGTGGTGGACGTGAGCCACGAGGACCCAGAGGTGAAGTTCAAC
TGGTACGTGGACGGCGTGGAGGTGCACAACGCCAAGACCAAGCCCAGAGAGGAGCAG
TACAACAGCACCTACAGGGTGGTGTCCGTGCTGACCGTGCTGCACCAGGACTGGCTGA
ACGGCAAGGAATACAAGTGCAAGGTCTCCAACAAGGCCCTGCCAGCCCCCATCGAAA
AGACCATCAGCAAGGCCAAGGGCCAGCCACGGGAGCCCCAGGTGTACACCCTGCCCC
CCTCCCGGGAGGAGATGACCAAGAACCAGGTGTCCCTGACCTGTCTGGTGAAGGGCTT
CTACCCCAGCGACATCGCCGTGGAGTGGGAGAGCAACGGCCAGCCCGAGAACAACTA
CAAGACCACCCCCCCAGTGCTGGACAGCGACGGCAGCTTCTTCCTGTACAGCAAGCTG
ACCGTGGACAAGTCCAGGTGGCAGCAGGGCAACGTGTTCAGCTGCAGCGTGATGCAC
GAGGCCCTGCACAACCACTACACCCAGAAGAGCCTGAGCCTGTCCCCCGAGCTGCAAC
TGGAGGAGAGCTGTGCGGAGGCGCAGGACGGGGAGCTGGACGGGCTGTGGACGACCA
TCACCATCTTCATCACACTCTTCCTGTTAAGCGTGTGCTACAGTGCCACCGTCACCTTCT
TCAAGGTGAAGTGGATCTTCTCCTCGGTGGTGGACCTGAAGCAGACCATCATCCCCGA
CTACAGGAACATGATCGGACAGGGGGCCTGA pWF-460:

(SEQ ID NO: 63)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGSRGGGGSGGG
GSGGGGSLEMAQVQLVESGGGLVQPGGSLRLSCAASGFTFSSYAMSWVRQAPGKGLEWV

-continued

SVIYSGGSSTYYADSVKGRFTISRDNSKNTLYLQMNSLRAEDTAVYYCARTSYLNHGDYW
GQGTLVTVSSPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPELQ
LEESCAEAQDGELDGLWTTITIFITLFLLSVCYSATVTFFKVKWIFSSVVDLKQTIIPDYRNM
IGQGA pWF-428:

(SEQ ID NO: 64)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTCAGCCCAAGGCCAACCC
CACTGTCACTCTGTTCCCGCCCTCCTCTGAGGAGCTCCAAGCCAACAAGGCCACACTA
GTGTGTCTGATCAGTGACTTCTACCCGGGAGCTGTGACAGTGGCCTGGAAGGCAGATG
GCAGCCCCGTCAAGGCGGGAGTGGAGACCACCAAACCCTCCAAACAGAGCAACAACA
AGTACGCGGCCAGCAGCTACCTGAGCCTGACGCCCGAGCAGTGGAAGTCCCACAGAA
GCTACAGCTGCCAGGTCACGCATGAAGGGAGCACCGTGGAGAAGACAGTGGCCCCTA
CAGAATGTTCA pWF-428:

(SEQ ID NO: 65)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGQPKANPTVTLF
PPSSEELQANKATLVCLISDFYPGAVTVAWKADGSPVKAGVETTKPSKQSNNKYAASSYL
SLTPEQWKSHRSYSCQVTHEGSTVEKTVAPTECS pWF-429:

(SEQ ID NO: 66)

CAGGTGCAGCTGGTGGAGTCTGGGGGAGGCTTGGTACAGCCTGGGGGGTCCCTGAGAC
TCTCCTGTGCAGCCTCTGGATTCACCTTTAGCAGCTATGCCATGAGCTGGGTCCGCCAG
GCTCCAGGGAAGGGGCTGGAGTGGGTCTCAGTTATTTATAGCGGTGGTAGTAGCACAT
ACTATGCAGACTCCGTGAAGGGCCGGTTCACCATCTCCAGAGATAATTCCAAGAACAC
GCTGTATCTGCAAATGAACAGCCTGAGAGCCGAGGACACGGCCGTATATTACTGTGCG
CGCACTTCTTACCTGAACCATGGTGATTACTGGGGTCAAGGTACTCTGGTGACCGTGTC
TAGCGCCTCCACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGG
GCACCCAGACCTACATCTGCAACGTGAACCACAAGCCCAGCAACACCAAGGTGGACA
AGAGAGTGGAGCCCAAGAGCTGCGACAAGACCCACACCTGCCCCCCCTGCCCAGCCCC
AGAGCTGCTGGGCGGACCCTCCGTGTTCCTGTTCCCCCCCAAGCCCAAGGACACCCTG
ATGATCAGCAGGACCCCCGAGGTGACCTGCGTGGTGGTGGACGTGAGCCACGAGGAC
CCAGAGGTGAAGTTCAACTGGTACGTGGACGGCGTGGAGGTGCACAACGCCAAGACC
AAGCCCAGAGAGGAGCAGTACAACAGCACCTACAGGGTGGTGTCCGTGCTGACCGTG
CTGCACCAGGACTGGCTGAACGGCAAGGAATACAAGTGCAAGGTCTCCAACAAGGCC
CTGCCAGCCCCCATCGAAAAGACCATCAGCAAGGCCAAGGGCCAGCCACGGGAGCCC
CAGGTGTACACCCTGCCCCCCTCCCGGGAGGAGATGACCAAGAACCAGGTGTCCCTGA
CCTGTCTGGTGAAGGGCTTCTACCCCAGCGACATCGCCGTGGAGTGGGAGAGCAACGG
CCAGCCCGAGAACAACTACAAGACCACCCCCCCAGTGCTGGACAGCGACGGCAGCTTC
TTCCTGTACAGCAAGCTGACCGTGGACAAGTCCAGGTGGCAGCAGGGCAACGTGTTCA
GCTGCAGCGTGATGCACGAGGCCCTGCACAACCACTACACCCAGAAGAGCCTGAGCCT
GTCCCCCGAGCTGCAACTGGAGGAGAGCTGTGCGGAGGCGCAGGACGGGGAGCTGGA
CGGGCTGTGGACGACCATCACCATCTTCATCACACTCTTCCTGTTAAGCGTGTGCTACA
GTGCCACCGTCACCTTCTTCAAGGTGAAGTGGATCTTCTCCTCGGTGGTGGACCTGAAG
CAGACCATCATCCCCGACTACAGGAACATGATCGGACAGGGGGCCTGA pWF-429:

(SEQ ID NO: 67)

QVQLVESGGGLVQPGGSLRLSCAASGFTFSSYAMSWVRQAPGKGLEWVSVIYSGGSSTYY
ADSVKGRFTISRDNSKNTLYLQMNSLRAEDTAVYYCARTSYLNHGDYWGQGTLVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPELQLEESCAEAQDGELDGLWTTITIFITLFLLSVCYSA
TVTFFKVKWIFSSVVDLKQTIIPDYRNMIGQGAmu CXCL13

(SEQ ID NO: 68)

ATGAGACTTTCAACAGCAACACTCCTCCTGTTGCTGGCTTCATGTCTGAGCCCTGGTCA
TGGTATTTTGGAGGCCCACTATACAAATCTCAAATGTCGGTGTTCAGGCGTAATATCCA
CCGTAGTCGGCCTGAACATTATCGATAGGATTCAGGTTACACCCCCCGGGAACGGATG
TCCTAAGACCGAGGTGGTGATTTGGACCAAGATGAAGAAGGTCATTTGTGTGAACCCA
CGGGCTAAATGGCTGCAGCGTCTTTTGCGACACGTGCAGTCCAAGAGCTTGTCCAGCA
CACCTCAGGCCCCAGTTAGCAAGCGACGTGCAGCC

-continued mu CXCL13

(SEQ ID NO: 69)
MRLSTATLLLLLASCLSPGHGILEAHYTNLKCRCSGVISTVVGLNIIDRIQVTPPGNGCPKTE
VVIWTKMKKVICVNPRAKWLQRLLRHVQSKSLSSTPQ APVSKRRAA mu FLT3LG (SEQ ID NO: 70)
ATGACAGTGCTGGCCCCCGCGTGGTCTCCCAATAGCTCACTCCTCCTCTTGCTGCTACT
GCTCAGCCCATGCCTCAGGGGCACCCCCGATTGTTACTTCAGCCACAGCCCAATCTCCT
CCAACTTCAAAGTGAAATTTAGGGAACTGACCGACCACCTGCTGAAAGATTATCCTGT
GACTGTGGCAGTGAACCTGCAAGACGAAAAGCATTGTAAGGCGCTATGGAGCCTCTTT
CTTGCCCAACGATGGATTGAGCAACTCAAAACTGTAGCCGGAAGCAAAATGCAGACG
CTACTGGAGGACGTGAATACTGAGATTCACTTCGTTACCAGTTGTACTTTCCAGCCACT
GCCAGAGTGTCTCAGGTTTGTGCAGACTAATATCAGCCACCTGCTGAAGGATACTTGC
ACCCAGCTCCTGGCTCTCAAGCCTTGTATAGGCAAGGCTTGTCAAAATTTTAGCAGGTG
TCTCGAAGTCCAGTGCCAGCCAGATTCATCCACACTGCTGCCGCCCCGAAGCCCTATC
GCACTCGAAGCGACAGAGTTGCCAGAGCCTCGTCCCAGACAGCTTCTGCTGCTGCTAC
TTCTGCTGCTGCCGCTAACTCTGGTGCTACTTGCTGCCGCCTGGGGCCTCAGATGGCAA
CGCGCCAGACGCCGAGGCGAACTCCACCCTGGGGTGCCACTGCCATCCCACCCA mu FLT3LG (SEQ ID NO: 71)
MTVLAPAWSPNSSLLLLLLLLSPCLRGTPDCYFSHSPISSNFKVKFRELTDHLLKDYPVTVA
VNLQDEKHCKALWSLFLAQRWIEQLKTVAGSKMQTLLEDVNTEIHFVTSCTFQPLPECLRF
VQTNISHLLKDTCTQLLALKPCIGKACQNFSRCLEVQCQPDSSTLLPPRSPIALEATELPEPR
PRQLLLLLLLLLPLTLVLLAAAWGLRWQRARRRGELHPGVPLPS HP mu XCL1

(SEQ ID NO: 72)
ATGCGACTCTTGTTGTTGACTTTTCTCGGAGTGTGCTGCCTGACACCCTGGGTCGTAGA
GGGAGTTGGCACTGAAGTACTAGAAGAGTCCTCCTGCGTTAACCTGCAGACACAGCGG
CTCCCAGTCCAGAAAATTAAGACCTACATTATATGGGAAGGAGCAATGCGAGCGGTGA
TTTTTGTGACCAAGAGAGGGGTCTCAAGATTTGCGCGGACCCTGAGGCCAAGTGGGTCAA
AGCAGCTATTAAGACAGTAGACGGAAGAGCCTCCACCAGGAAGAATATGGCAGAAAC
TGTACCGACCGGTGCGCAGCGGTCAACATCTACCGCAATCACACTCACCGGC mu XCL1

(SEQ ID NO: 73)
MRLLLLTFLGVCCLTPWVVEGVGTEVLEESSCVNLQTQRLPVQKIKTYIIWEGAMRAVIFV
TKRGLKICADPEAKWVKAAIKTVDGRASTRKNMAETVPTGAQRSTSTAI TLTG mu Tim4(ECD)-muIgG2a Fc (SEQ ID NO: 74)
ATGAGCAAGGGCCTTCTCCTGCTGTGGCTAGTAACTGAATTGTGGTGGTTGTACCTGAC
ACCTGCCGCTAGTGAGGACACCATCATTGGTTTCCTTGGGCAGCCCGTCACCCTCCCTT
GCCATTACCTAAGCTGGAGCCAGTCACGGAACTCTATGTGCTGGGGAAAGGGGTCATG
CCCTAATTCCAAGTGCAACGCCGAGCTGTTGCGCACGGACGGCACCAGAATAATCTCA
AGAAAGTCCACCAAGTATACGCTGCTCGGCAAGGTGCAATTCGGTGAAGTGAGCTTGA
CCATAAGTAACACCAACCGCGGTGACTCCGGAGTTTATTGTTGCAGGATCGAAGTGCC
AGGCTGGTTTAACGACGTGAAGAAAAACGTGCGGCTGGAACTGAGGAGGGCAACTAC
GACCAAGAAACCAACAACCACGACGAGACCTACCACCACTCCTTACGTGACAACCAC
GACACCGGAGCTGTTGCCAACTACCGTCATGACAACATCTGTGTTGCCAACTACCACC
CCCCCCCAAACGCTCGCGACAACTGCCTTTTCCACAGCCGTTACCACATGTCCTTCCAC
CACCCCAGGCTCTTTTTCTCAAGAAACTACCAAGGGATCAGCTTTTACCACCGAGTCTG
AAACTCTCCCAGCAAGTAATCACTCACAGCGGTCAATGATGACCATCAGCACAGACAT
CGCTGTCTTGAGACCTACTGGCAGCAATCCAGGCATTCTGCCCTCCACTTCACAGCTGA
CTACCCAAAAGACTACACTAACCACCAGCGAAAGTCTGCAGAAAACTACAAAGAGCC
ATCAAATAAACTCCCGGCAGACTCCCAGAGGGCCCACAATCAAGCCCTGTCCTCCATG
CAAATGCCCAGCACCTAACCTCTTGGGTGGACCATCCGTCTTCATCTTCCCTCCAAAGA
TCAAGGATGTACTCATGATCTCCCTGAGCCCCATAGTCACATGTGTGGTGGTGGATGTG
AGCGAGGATGACCCAGATGTCCAGATCAGCTGGTTTGTGAACAACGTGGAAGTACACA
CAGCTCAGACACAAACCCATAGAGAGGATTACAACAGTACTCTCCGGGTGGTCAGTGC
CCTCCCCATCCAGCACCAGGACTGGATGAGTGGCAAGGAGTTCAAATGCAAGGTCAAC
AACAAAGACCTCCCAGCGCCCATCGAGAGAACCATCTCAAAACCCAAAGGGTCAGTA
AGAGCTCCACAGGTATATGTCTTGCCTCCACCAGAAGAAGAGATGACTAAGAAACAG
GTCACTCTGACCTGCATGGTCACAGACTTCATGCCTGAAGACATTTACGTGGAGTGGA
CCAACAACGGGAAAACAGAGCTAAACTACAAGAACACTGAACCAGTCCTGGACTCTG
ATGGTTCTTACTTCATGTACAGCAAGCTGAGAGTGGAAAAGAAGAACTGGGTGGAAA
GAAATAGCTACTCCTGTTCAGTGGTCCACGAGGGTCTGCACAATCACCACACGACTAA
GAGCTTCTCCCGGACTCCGGGTAAA mu Tim4(ECD)-muIgG2a Fc (SEQ ID NO: 75)
MSKGLLLLWLVTELWWLYLTPAASEDTIIGFLGQPVTLPCHYLSWSQSRNSMCWGKGSCP
NSKCNAELLRTDGTRIISRKSTKYTLLGKVQFGEVSLTISNTNRGDSGVYCCRIEVPGWFND
VKKNVRLELRRATTTKKPTTTTRPTTTPYVTTTTPELLPTTVMTTSVLPTTTPPQTLATTAF
STAVTTCPSTTPGSFSQETTKGSAFTTESETLPASNHSQRSMMTISTDIAVLRPTGSNPGILPS
TSQLTTQKTTLTTSESLQKTTKSHQINSRQTPRGPTIKPCPPCKCPAPNLLGGPSVFIFPPKIK
DVLMISLSPIVTCVVVDVSEDDPDVQISWFVNNVEVHTAQTQTHREDYNSTLRVVSALPIQ
HQDWMSGKEFKCKVNNKDLPAPIERTISKPKGSVRAPQVYVLPPPEEEMTKKQVTLTCMV

-continued

TDFMPEDIYVEWTNNGKTELNYKNTEPVLDSDGSYFMYSKLRVEKKNWVERNSYSCSVV
HEGLHNHHTTKSFSRTPGK mu 4-1BB-L (SEQ ID NO: 76)

ATGGATCAGCATACACTGGACGTGGAAGATACAGCCGATGCCAGACACCCTGCTGGA
ACGTCCTGTCCCAGCGACGCTGCCCTGCTCAGAGACACCGGGCTGCTCGCAGATGCTG
CTCTGCTGAGTGATACCGTTCGGCCAACTAACGCGGCCCTACCCACAGATGCCGCATA
TCCCGCGGTAAATGTCAGGGACCGGGAAGCTGCCTGGCCACCGGCCCTCAATTTCTGC
TCTAGACATCCGAAACTGTACGGTCTGGTCGCACTGGTACTGCTGCTACTTATAGCAGC
TTGTGTTCCCATATTTACCCGCACTGAACCCAGACCCGCTCTCACTATTACAACTTCAC
CAAACTTGGGCACACGTGAAAACAATGCAGATCAGGTTACCCCTGTAAGTCATATTGG
ATGCCCCAACACCACACAACAGGGAAGTCCGGTGTTTGCAAAACTCCTTGCTAAGAAT
CAGGCTTCACTGTGTAACACTACTCTTAATTGGCACTCACAAGACGGGGCCGGGAGTA
GCTATCTCAGCCAAGGTCTCCGCTATGAAGAAGATAAGAAAGAGTTGGTGGTGGACAG
CCCAGGACTCTACTACGTCTTCCTGGAGCTAAAACTAAGCCCCACTTTTACTAACACTG
GACATAAGGTCCAAGGTTGGGTGTCCCTCGTACTTCAAGCTAAACCCCAGGTGGACGA
CTTCGATAACCTGGCGTTGACAGTTGAGCTCTTTCCTTGCTCTATGGAAAATAAGCTCG
TGGATCGGAGCTGGTCTCAACTGTTGCTGCTTAAAGCCGGTCATCGTCTGTCTGTTGGA
CTACGCGCATACTTGCATGGAGCCCAGGACGCATATCGTGATTGGGAACTGAGCTACC
CGAATACCACTAGCTTTGGACTATTTCTTGTTAAACCAGATAATCCTTGGGAG mu 4-1BB-L (SEQ ID NO: 77)

MDQHTLDVEDTADARHPAGTSCPSDAALLRDTGLLADAALLSDTVRPTNAALPTDAAYP
AVNVRDREAAWPPALNFCSRHPKLYGLVALVLLLLIAACVPIFTRTEPRPALTITTSPNLGT
RENNADQVTPVSHIGCPNTTQQGSPVFAKLLAKNQASLCNTTLNWHSQDGAGSSYLSQGL
RYEEDKKELVVDSPGLYYVFLELKLSPTFTNTGHKVQGWVSLVLQAKPQVDDFDNLALT
VELFPCSMENKLVDRSWSQLLLLKAGHRLSVGLRAYLHGAQDAYRDWELSYPNTTSFGL
FLVKPDNPWE mu LIGHT (cleavage-deficient mutant)

(SEQ ID NO: 78)

ATGGAGAGCGTAGTGCAACCCAGCGTATTTGTGGTGGATGGACAGACCGACATCCCAT
TCAGACGCTTGGAACAGAACCACCGAAGAAGGCGGTGCGGCACCGTCCAGGTGTCCCT
CGCTCTCGTGCTGCTGCTTGGTGCTGGCCTCGCAACACAAGGGTGGTTTCTTTTGAGAC
TCCATCAACGCTTGGGAGACATAGTGGCCCACCTGCCTGATGGTGGGAAGGGCTCTTG
GCAGGACCAGCGATCACACCAGGCTAACCCCGCCGCTCACCTGACAGGGGCGAATGC
CAGCTTGATCGGAATAGGTGGGCCGCTGCTGTGGGAAACTAGGCTTGGACTTGCCTTT
CTGAGAGGGCTTACATACCATGACGGAGCCCTCGTAACAATGGAGCCTGGTTATTACT
ACGTGTACAGTAAGGTGCAGCTTTCTGGAGTCGGGTGTCCCCAGGGGCTGGCTAACGG
ACTGCCCATCACTCATGGACTATACAAACGCACATCCAGATATCCTAAAGAGCTGGAA
CTGTTGGTGTCCCGTAGGAGCCCGTGTGGCAGGGCCAACTCTTCCCGTGTGTGGTGGG
ACTCCTCTTTTCTGGGCGGCGTGGTCCATCTGGAAGCTGGTGAGGAAGTCGTCGTAAG
AGTACCTGGAAACCGTCTGGTTCGCCCCCGCGATGGCACCAGGTCCTACTTCGGAGCT
TTCATGGTA mu LIGHT (cleavage-deficient mutant)

(SEQ ID NO: 79)

MESVVQPSVFVVDGQTDIPFRRLEQNHRRRRCGTVQVSLALVLLLGAGLATQGWFLLRLH
QRLGDIVAHLPDGGKGSWQDQRSHQANPAAHLTGANASLIGIGGPLLWETRLGLAFLRGL
TYHDGALVTMEPGYYYVYSKVQLSGVGCPQGLANGLPITHGLYKRTSRYPKELELLVSRR
SPCGRANSSRVWWDSSFLGGVVHLEAGEEVVVRVPGNRLVRPRDGTRSYFGAFMV mu IL12 (transmembrane form)

(SEQ ID NO: 80)

ATGTGCCCACAGAAACTCACAATTTCTTGGTTCGCAATCGTCCTGCTGGTGTCACCCCT
GATGGCAATGTGGGAGTTGGAAAAGGATGTATACGTCGTCGAGGTCGACTGGACACCT
GACGCTCCGGGTGAAACTGTCAACCTCACTTGCGATACTCCTGAAGAGGACGACATCA
CGTGGACGAGCGACCAGCGACATGGAGTGATAGGGTCTGGCAAGACGCTTACTATCAC
GGTTAAGGAATTTCTCGACGCAGGGCAGTACACATGTCACAAGGGCGGCGAGACTCTG
AGCCACTCCCATTTGCTGCTGCACAAGAAGGAGAATGGTATCTGGTCTACCGAAATCC
TGAAGAATTTTAAGAACAAGACTTTTCTGAAATGCGAGGCCCCAAATTATTCCGGACG
TTTCACTTGCAGTTGGCTCGTTCAAAGAAATATGGACTTGAAATTTAACATTAAATCCA
GCTCTTCATCTCCTGACAGCAGGGCCGTAACTTGTGGAATGGCTTCATTGTCAGCTGAG
AAAGTTACGCTTGACCAAAGGGATTATGAGAAATACAGCGTGAGTTGCCAGGAAGAT
GTGACATGTCCAACGGCAGAGGAAACGTTGCCAATTGAGCTCGCTTTGGAAGCTCGTC
AACAAAACAAGTATGAAAACTATAGTACTAGCTTCTTCATACGGGACATCATCAAACC
AGATCCACCTAAGAATTTGCAGATGAAGCCTCTGAAGAATTCACAAGTCGAGGTATCC
TGGGAATACCCAGATTCATGGTCCACTCCTCATAGTTACTTTAGCCTGAAATTCTTTGT
ACGCATACAGCGGAAGAAGGAGAAAATGAAGGAGACGGAAGAAGGCTGCAATCAGA
AAGGCGCTTTTCTTGTTGAAAAGACGAGCACTGAGGTTCAATGCAAAGGCGGGAATGT
ATGTGTTCAAGCCCAAGATAGGTATTATAATAGCTCCTGCTCTAAGTGGGCTTGCGTAC
CATGCAGAGTTAGAAGTGGCTCAACCTCAGGCTCCGGAAAACCTGGTTCCGGTGAAGG
TTCCACAAAAGGGCGTGTGATTCCTGTGTCCGGCCCAGCTAGGTGTCTCTCCCAGTCAC
GGAATCTCCTGAAAACCACGGATGACATGGTAAAGACAGCTAGGGAGAAACTCAAGC
ACTACTCCTGCACAGCTGAGGATATCGATCATGAGGACATCACCAGGGACCAGACATC
CACTCTGAAAACTTGCCTGCCTTTGGAACTCCACAAGAACGAATCTTGTCTGGCAACG
CGTGAAACGAGTTCTACTACAAGAGGGTCCTGTCTTCCCCCTCAAAAGACAAGCCTTA
TGATGACCTTGTGTCTCGGTAGCATTTATGAGGACCTAAAGATGTATCAAACCGAGTTT
CAGGCTATCAATGCAGCGCTCCAGAATCATAACCATCAGCAGATCATTCTTGACAAAG

-continued

GAATGCTCGTGGCCATTGATGAACTAATGCAGAGCCTAAACCACAATGGCGAGACTCT
TCGACAGAAACCGCCTGTGGGCGAGGCCGATCCATATAGAGTCAAAATGAAACTGTGT
ATTCTCCTGCATGCATTTAGTACTCGTGTAGTGACTATTAACAGAGTGATGGGTTACCT
TTCCTCAGCTAATACACTTGTCCTCTTTGGCGCTGGGTTCGGCGCCGTCATAACGGTTG
TTGTCATCGTGGTAATAATCAAGTGCTTTTGCAAGCACAGGTCTTGTTTTCGCAGGAAT
GAAGCCTCTAGAGAAACAAATAATTCACTGACCTTTGGCCCCGAAGAAGCTCTTGCAG
AGCAAACGGTGTTTCTC mu IL12 (transmembrane form)

(SEQ ID NO: 81)

MCPQKLTISWFAIVLLVSPLMAMWELEKDVYVVEVDWTPDAPGETVNLTCDTPEEDDIT
WTSDQRHGVIGSGKTLTITVKEFLDAGQYTCHKGGETLSHSHLLLHKKENGIWSTEILKNF
KNKTFLKCEAPNYSGRFTCSWLVQRNMDLKFNIKSSSSSPDSRAVTCGMASLSAEKVTLD
QRDYEKYSVSCQEDVTCPTAEETLPIELALEARQQNKYENYSTSFFIRDIIKPDPPKNLQMK
PLKNSQVEVSWEYPDSWSTPHSYFSLKFFVRIQRKKEKMKETEEGCNQKGAFLVEKTSTE
VQCKGGNVCVQAQDRYYNSSCSKWACVPCRVRSGSTSGSGKPGSGEGSTKGRVIPVSGPA
RCLSQSRNLLKTTDDMVKTAREKLKHYSCTAEDIDHEDITRDQTSTLKTCLPLELHKNESC
LATRETSSTTRGSCLPPQKTSLMMTLCLGSIYEDLKMYQTEFQAINAALQNHNHQQIILDK
GMLVAIDELMQSLNHNGETLRQKPPVGEADPYRVKMKLCILLHAFSTRVVTINRVMGYLS
SANTLVLFGAGFGAVITVVVIVVIIKCFCKHRSCFRRNEASRETNNSLTFGPEEALAEQTVF
L mu IL12 (secreted form)

(SEQ ID NO: 82)

ATGTGTCAGTCACGCTATCTTCTCTTCCTTGCTACTCTGGCCTTGCTCAATCACTTGTCC
CTTGCTCGTGTGATTCCTGTGTCCGGCCCAGCTAGGTGTCTCTCCCAGTCACGGAATCT
CCTGAAAACCACGGATGACATGGTAAAGACAGCTAGGGAGAAACTCAAGCACTACTC
CTGCACAGCTGAGGATATCGATCATGAGGACATCACCAGGGACCAGACATCCACTCTG
AAAACTTGCCTGCCTTTGGAACTCCACAAGAACGAATCTTGTCTGGCAACGCGTGAAA
CGAGTTCTACTACAAGAGGGTCCTGTCTTCCCCCTCAAAAGACAAGCCTTATGATGAC
CTTGTGTCTCGGTAGCATTTATGAGGACCTAAAGATGTATCAAACCGAGTTTCAGGCTA
TCAATGCAGCGCTCCAGAATCATAACCATCAGCAGATCATTCTTGACAAAGGAATGCT
CGTGGCCATTGATGAACTAATGCAGAGCCTAAACCACAATGGCGAGACTCTTCGACAG
AAACCGCCTGTGGGCGAGGCCGATCCATATAGAGTCAAAATGAAACTGTGTATTCTCC
TGCATGCATTTAGTACTCGTGTAGTGACTATTAACAGAGTGATGGGTTACCTTTCCTCA
GCTGGAAGCGGCGCCACCAACTTCTCCCTGCTGAAGCAGGCCGGCGACGTGGAGGAG
AACCCCGGCCCCATGTGCCCACAGAAACTCACAATTTCTTGGTTCGCAATCGTCCTGCT
GGTGTCACCCCTGATGGCAATGTGGGAGTTGGAAAAGGATGTATACGTCGTCGAGGTC
GACTGGACACCTGACGCTCCGGGTGAAACTGTCAACCTCACTTGCGATACTCCTGAAG
AGGACGACATCACGTGGACGAGCGACCAGCGACATGGAGTGATAGGGTCTGGCAAGA
CGCTTACTATCACGGTTAAGGAATTTCTCGACGCAGGGCAGTACACATGTCACAAGGG
CGGCGAGACTCTGAGCCACTCCCATTTGCTGCTGCACAAGAAGGAGAATGGTATCTGG
TCTACCGAAATCCTGAAGAATTTTAAGAACAAGACTTTTCTGAAATGCGAGGCCCCAA
ATTATTCCGGACGTTTCACTTGCAGTTGGCTCGTTCAAAGAAATATGGACTTGAAATTT
AACATTAAATCCAGCTCTTCATCTCCTGACAGCAGGGCCGTAACTTGTGGAATGGCTTC
ATTGTCAGCTGAGAAAGTTACGCTTGACCAAAGGGATTATGAGAAATACAGCGTGAGT
TGCCAGGAAGATGTGACATGTCCAACGGCAGAGGAAACGTTGCCAATTGAGCTCGCTT
TGGAAGCTCGTCAACAAAACAAGTATGAAAACTATAGTACTAGCTTCTTCATACGGGA
CATCATCAAACCAGATCCACCTAAGAATTTGCAGATGAAGCCTCTGAAGAATTCACAA
GTCGAGGTATCCTGGGAATACCCAGATTCATGGTCCACTCCTCATAGTTACTTTAGCCT
GAAATTCTTTGTACGCATACAGCGGAAGAAGGAGAAAATGAAGGAGACGGAAGAAGG
CTGCAATCAGAAAGGCGCTTTTCTTGTTGAAAAGACGAGCACTGAGGTTCAATGCAAA
GGCGGGAATGTATGTGTTCAAGCCCAAGATAGGTATTATAATAGCTCCTGCTCTAAGT
GGGCTTGCGTACCATGCAGAGTTAGAAGT mu IL12 (secreted form)

(SEQ ID NO: 83)

MCQSRYLLFLATLALLNHLSLARVIPVSGPARCLSQSRNLLKTTDDMVKTAREKLKHYSC
TAEDIDHEDITRDQTSTLKTCLPLELHKNESCLATRETSSTTRGSCLPPQKTSLMMTLCLGSI
YEDLKMYQTEFQAINAALQNHNHQQIILDKGMLVAIDELMQSLNHNGETLRQKPPVGEAD
PYRVKMKLCILLHAFSTRVVTINRVMGYLSSAGSGATNFSLLKQAGDVEENPGPMCPQKL
TISWFAIVLLVSPLMAMWELEKDVYVVEVDWTPDAPGETVNLTCDTPEEDDITWTSDQRH
GVIGSGKTLTITVKEFLDAGQYTCHKGGETLSHSHLLLHKKENGIWSTEILKNFKNKTFLK
CEAPNYSGRFTCSWLVQRNMDLKFNIKSSSSSPDSRAVTCGMASLSAEKVTLDQRDYEKY
SVSCQEDVTCPTAEETLPIELALEARQQNKYENYSTSFFIRDIIKPDPPKNLQMKPLKNSQVE
VSWEYPDSWSTPHSYFSLKFFVRIQRKKEKMKETEEGCNQKGAFLVEKTSTEVQCKGGNV
CVQ AQDRYYNSSCSKWACVPCRV RS mu IFN alpha A2

(SEQ ID NO: 84)

ATGGCCAGGCTTTGCGCTTTTCTCGTCATGCTGATCGTCATGAGTTACTGGTCCATTTG
CAGCCTCGGATGTGATCTGCCCCACACCTACAACCTGCGCAACAAACGAGCTCTCAAA
GTGTTGGCCCAAATGAGGCGGTTGCCCTTCCTTTCCTGTCTCAAAGACAGGCAAGATTT
TGGATTTCCACTAGAGAAAGTAGACAATCAACAGATACAGAAAGCTCAAGCTATCCCC
GTGTTGAGGGACTTGACTCAACAGACGTTGAATCTATTTACTAGCAAGGCCAGCTCTG
CTGCTTGGAATGCCACCCTTCTTGACTCATTTTGCAATGACCTACATCAACAACTGAAT
GATCTCCAAACATGTTTGATGCAGCAGGTAGGTGTCCAAGAACCCCCGCTTACTCAGG
AAGACGCCCTTCTGGCTGTCCGCAAGTACTTTCACAGAATCACAGTGTACCTGCGCGA
AAAGAAACACTCCCCCTGCGCTTGGGAAGTGGTCAGGGCCGAGGTTTGGCGAGCCCTG
AGTAGCTCCGTCAATCTCCTTCCTCGGTTGTCCGAGGAGAAAGAG

-continued

```
mu IFN alpha A2
                                                         (SEQ ID NO: 85)
MARLCAFLVMLIVMSYWSICSLGCDLPHTYNLRNKRALKVLAQMRRLPFLSCLKDRQDF
GFPLEKVDNQQIQKAQAIPVLRDLTQQTLNLFTSKASSAAWNATLLDSFCNDLHQQLNDL
QTCLMQQVGVQEPPLTQEDALLAVRKYFHRITVYLREKKHSPCAWEVVRAEVWRALSSS
VNLLPRLSEEKE

mu CD80
                                                         (SEQ ID NO: 86)
ATGGCTTGCAACTGTCAGCTCATGCAAGATACTCCCCTGCTTAAGTTTCCCTGCCCTAG
ACTCATTCTCCTCTTCGTCCTTCTCATTCGCCTAAGCCAGGTGAGTTCCGATGTGGATG
AACAACTGAGTAAATCTGTCAAGGATAAAGTTCTGCTCCCATGCCGCTACAATAGCCC
CCATGAGGACGAGTCCGAAGATAGGATTTACTGGCAGAAACATGATAAGGTGGTGCT
ATCCGTCATTGCCGGTAAATTGAAGGTGTGGCCCGAATATAAGAATAGAACCCTGTAT
GACAACACAACTTATAGCCTAATCATCCTCGGTCTCGTACTGAGCGACCGAGGTACTT
ACTCATGCGTTGTGCAGAAGAAGGAGCGCGGAACATACGAAGTCAAGCACCTTGCATT
GGTGAAATTGTCAATAAAAGCTGACTTTTCAACTCCTAATATTACTGAATCAGGTAACC
CTTCCGCAGACACTAAAAGAATTACATGCTTCGCCTCTGGCGGGTTTCCCAAACCACG
GTTCTCTTGGCTAGAGAATGGAGAGAACTTCCAGGTATCAATACAACCATCTCTCAA
GACCCAGAATCAGAACTGTACACCATCTCCAGCCAACTCGATTTCAATACCACAAGAA
ATCATACAATAAAATGTCTGATAAAGTACGGAGATGCACATGTCTCTGAAGATTTCAC
ATGGGAGAAACCACCAGAGGACCCGCCAGACAGCAAGAATACACTTGTCCTCTTTGGC
GCTGGGTTCGGCGCCGTCATAACGGTTGTTGTCATCGTGGTAATAATCAAGTGCTTTTG
CAAGCACAGGTCTTGTTTTCGCAGGAATGAAGCCTCTAGAGAAACAAATAATTCACTG
ACCTTTGGCCCCGAAGAAGCTCTTGCAGAGCAAACGGTGTTTCTC

mu CD80
                                                         (SEQ ID NO: 87)
MACNCQLMQDTPLLKFPCPRLILLFVLLIRLSQVSSDVDEQLSKSVKDKVLLPCRYNSPHE
DESEDRIYWQKHDKVVLSVIAGKLKVWPEYKNRTLYDNTTYSLIILGLVLSDRGTYSCVV
QKKERGTYEVKHLALVKLSIKADFSTPNITESGNPSADTKRITCFASGGFPKPRFSWLENGR
ELPGINTTISQDPESELYTISSQLDFNTTRNHTIKCLIKYGDAHVSEDFTWEKPPEDPPDSKN
TLVLFGAGFGAVITVVVIVVIIKCFCKHRSCFRR NEASRETNNS LTFGPEEALAEQTVFL

mu CD40-L
                                                         (SEQ ID NO: 88)
ATGATCGAAACTTATTCCCAACCCTCACCGCGCTCAGTAGCAACTGGCCTACCAGCCA
GCATGAAGATATTCATGTACCTCTTGACTGTATTCTTGATCACGCAAATGATTGGTAGT
GTTTTGTTCGCCGTTTATCTCCACAGGCGCCTGGATAAAGTTGAAGAAGAGGTTAATCT
CCATGAAGACTTCGTGTTCATTAAGAAACTCAAAAGATGTAACAAAGGTGAGGGATCT
CTGTCTCTTCTGAACTGTGAGGAGATGCGACGGCAATTCGAGGACCTCGTAAAAGACA
TAACTCTCAACAAAGAAGAGAAGAAAGAAAACTCTTTCGAGATGCAACGGGGCGACG
AGGACCCTCAAATTGCCGCACATGTCGTTTCTGAAGCGAATTCCAATGCCGCGTCCGT
GCTCCAGTGGGCGAAGAAGGGATACTACACGATGAAGAGCAACCTTGTGATGCTTGA
AAATGGCAAGCAGCTCACAGTTAAACGCGAGGGACTCTACTATGTATACACCCAAGTG
ACCTTTTGTTCCAACCGGGAGCCAAGTAGCCAACGCCCGTTCATCGTTGGGCTGTGGCT
CAAGCCTTCTTCAGGGAGTGAACGAATCCTTCTCAAGGCAGCCAACACGCATTCCAGC
AGCCAACTGTGTGAGCAACAATCCGTGCATCTTGGCGGGGTCTTTGAGCTGCAAGCGG
GCGCCTCTGTGTTCGTGAATGTTACCGAAGCCAGCCAGGTTATCCACCGCGTGGGTTTC
AGTAGTTTTGGCCTGCTCAAGCTG

mu CD40-L
                                                         (SEQ ID NO: 89)
MIETYSQPSPRSVATGLPASMKIFMYLLTVFLITQMIGSVLFAVYLHRRLDKVEEEVNLHED
FVFIKKLKRCNKGEGSLSLLNCEEMRRQFEDLVKDITLNKEEKKENSFEMQRGDEDPQIAA
HVVSEANSNAASVLQWAKKGYYTMKSNLVMLENGKQLTVKREGLYYVYTQVTFCSNRE
PSSQRPFIVGLWLKPSSGSERILLKAANTHSSSQLCEQQSVHLGGVFELQAGASVFVNVTEA
SQVIHRVGFSSFGLLKL

mu IL21
                                                         (SEQ ID NO: 90)
ATGGAGCGTACTCTGGTCTGCCTTGTTGTGATATTCTTGGGGACAGTTGCACACAAATC
ATCACCCCAAGGACCGGATAGACTCCTCATACGCCTGCGCCATCTGATTGACATTGTC
GAGCAGTTGAAGATTTATGAGAACGACCTGGACCCTGAACTATTGAGCGCGCCTCAAG
ACGTCAAAGGGCATTGCGAGCATGCTGCATTTGCATGTTTTCAGAAAGCTAAGCTCAA
ACCAAGTAATCCCGGTAACAATAAAACATTCATCATCGACCTGGTGGCCCAACTAAGA
CGCCGGTTGCCGGCGCGCCGGGGTGGTAAGAAACAGAAACATATTGCTAAATGCCCCT
CTTGCGACTCTTACGAGAAAAGGACACCTAAGGAATTCCTCGAACGATTGAAATGGTT
GTTGCAGAAGATGATCCATCAACATCTGAGC

mu IL21
                                                         (SEQ ID NO: 91)
MERTLVCLVVIFLGTVAHKSSPQGPDRLLIRLRHLIDIVEQLKIYENDLDPELLSAPQDVKG
HCEHAAFACFQKAKLKPSNPGNNKTFIIDLVAQLRRRLPARRGGKKQK
HIAKCPSCDSYEKRTPKEFLERLKWLLQKM IHQHLS

mu CCL21
                                                         (SEQ ID NO: 92)
ATGGCACAAATGATGACACTGTCCCTACTTAGTCTAGTTCTAGCTTTGTGTATTCCCTG
GACTCAAGGCAGTGACGGAGGAGGACAAGACTGCTGCCTCAAATATTCTCAAAAGAA
AATCCCTTATTCTATAGTCCGAGGTTACCGTAAGCAAGAACCGAGTCTAGGTTGTCCTA
```

-continued

TCCCCGCAATCCTCTTTCTACCACGGAAACATAGCAAACCAGAATTGTGCGCCAACCC
AGAAGAGGGTTGGGTCCAAAATTTGATGAGGCGCCTTGACCAACCACCGGCCCCGGGT
AAACAATCACCGGGGTGTCGGAAGAATAGGGGTACATCCAAATCCGGGAAGAAAGGG
AAGGGGAGTAAGGGCTGTAAGAGAACGGAACAAACTCAACCTAGCAGAGGT mu CCL21

(SEQ ID NO: 93)

MAQMMTLSLLSLVLALCIPWTQGSDGGGQDCCLKYSQKKIPYSIVRGYRKQEPSLGCPIPA
ILFLPRKHSKPELCANPEEGWVQNLMRRLDQPPAPGKQSPGCRKNRGTSKSGKKGKGSKG
CKRTEQTQPSRG anti-mu CD3 scFv-transmembrane (SEQ ID NO: 94)

ATGGAAACCGACACATTGCTCCTCTGGGTTCTCCTTCTATGGGTCCCCGGTTCCACCGG
AGATATCCAAATGACACAATCACCCAGCAGCCTGCCTGCCTCTCTGGGCGACCGCGTT
ACCATCAATTGTCAAGCTTCCCAAGATATAAGTAATTATCTCAACTGGTACCAGCAAA
AGCCCGGTAAAGCGCCTAAATTGCTGATTTATTATACTAATAAACTCGCAGATGGAGT
TCCTAGTAGATTTTCTGGTTCAGGGAGTGGACGGGACTCCAGTTTTACCATATCAAGTC
TGGAATCCGAGGATATCGGCAGCTACTATTGCCAGCAATATTATAATTACCCTTGGACT
TTTGGACCCGGGACTAAACTTGAGATCAAAAGAGGCGGAGGAGGCAGTGGTGGTGGT
GGATCAGGCGGCGGTGGTAGTGAGGTACAACTCGTGGAATCAGGCGGCGGACTGGTC
CAACCCGGCAAGAGCCTTAAACTCTCTTGTGAGGCCAGTGGATTTACATTCAGCGGTT
ATGGAATGCACTGGGTGAGACAAGCTCCCGGCAGGGGCCTAGAATCAGTGGCGTACA
TCACCAGCTCATCAATAAACATTAAATACGCTGATGCAGTCAAGGGCCGGTTTACTGT
ATCCCGCGACAACGCTAAGAATCTTCTCTTTCTGCAAATGAACATACTTAAGAGCGAG
GATACTGCCATGTATTATTGTGCCCGCTTCGATTGGGATAAGAATTATTGGGGACAAG
GCACCATGGTTACCGTTAGTAGTCCAAACATCACATCAAATAATAGCAACCCCGTGGA
AGGGGACGACTCTGTTTCACTCACCTGTGATTCCTATACCGATCCTGATAATATCAACT
ATCTATGGTCTCGTAACGGTGAAAGTCTCAGCGAAGGCGACCGGTTGAAACTCTCCGA
AGGTAACAGAACCCTTACGCTTCTGAACGTCACCCGGAACGATACCGGGCCCTATGTT
TGCGAAACTAGGAACCCTGTTAGCGTGAATCGTAGCGACCCTTTCTCCCTAAATAATA
CTCTAGTGCTATTCGGAGCGGGATTCGGTGCCGTCATCACAGTAGTCGTTATTGTAGTC
ATTATTAAATGCTTTTGTAAACATAGGTCTTGCTTCAGAAGAAATGAGGCCAGCCGTG
AAACTAATAATTCCCTGACCTTTGGGCCCGAAGAAGCTTTGGCTGAACAGACTGTGTTT
CTC anti-mu CD3 scFv-transmembrane (SEQ ID NO: 95)

METDTLLLWVLLLWVPGSTGDIQMTQSPSSLPASLGDRVTINCQASQDISNYLNWYQQKP
GKAPKLLIYYTNKLADGVPSRFSGSGSGRDSSFTISSLESEDIGSYYCQQYYNYPWTFGPGT
KLEIKRGGGGSGGGGSGGGGSEVQLVESGGGLVQPGKSLKLSCEASGFTFSGYGMHWVR
QAPGRGLESVAYITSSSINIKYADAVKGRFTVSRDNAKNLLFLQMNILKSEDTAMYYCARF
DWDKNYWGQGTMVTVSSPNITSNNSNPVEGDDSVSLTCDSYTDPDNINYLWSRNGESLSE
GDRLKLSEGNRTLTLLNVTRNDTGPYVCETRNPVSVNRSDPFSLNNTLVLFGAGFGAVITV
VVIVVIIKCFCKHRSCFRRNEASRETNNSLTFGPEEALAEQTVFL mu TSLP (SEQ ID NO: 96)

ATGGTTCTTCTCAGGAGCCTCTTCATCCTGCAAGTACTAGTACGGATGGGGCTAACTTA
CAACTTTTCTAACTGCAACTTCACGTCAATTACGAAAATATATTGTAACATAATTTTTC
ATGACCTGACTGGAGATTTGAAAGGGGCTAAGTTCGAGCAAATCGAGGACTGTGAGA
GCAAGCCAGCTTGTCTCCTGAAAATCGAGTACTATACTCTCAATCCTATCCCTGGCTGC
CCTTCACTCCCCGACAAAACATTTGCCCGGAGAACAAGAGAAGCCCTCAATGACCACT
GCCCAGGCTACCCTGAAACTGAGAGAAATGACGGTACTCAGGAAATGGCACAAGAAG
TCCAAAACATCTGCCTGAATCAAACCTCACAAATTCTAAGATTGTGGTATTCCTTCATG
CAATCTCCAGAA mu TSLP (SEQ ID NO: 97)

MVLLRSLFILQVLVRMGLTYNFSNCNFTSITKIYCNIIFHDLTGDLKGAKFEQIEDCESKPAC
LLKIEYYTLNPIPGCPSLPDKTFARRTREALNDHCPGYPETERNDGTQEMAQEVQNICLNQ
TSQILRLWYSFMQSPE mu GM-CSF (SEQ ID NO: 98)

ATGTGGCTGCAGAATTTACTTTTCCTGGGCATTGTGGTCTACAGCCTCTCAGCACCCAC
CCGCTCACCCATCACTGTCACCCGGCCTTGGAAGCATGTAGAGGCCATCAAAGAAGCC
CTGAACCTCCTGGATGACATGCCTGTCACGTTGAATGAAGAGGTAGAAGTCGTCTCTA
ACGAGTTCTCCTTCAAGAAGCTAACATGTGTGCAGACCCGCCTGAAGATATTCGAGCA
GGGTCTACGGGGCAATTTCACCAAACTCAAGGGCGCCTTGAACATGACAGCCAGCTAC
TACCAGACATACTGCCCCCCAACTCCGGAAACGGACTGTGAAACACAAGTTACCACCT
ATGCGGATTTCATAGACAGCCTTAAAACCTTTCTGACTGATATCCCCTTTGAATGCAAA
AAACCAGGCCAAAAA mu GM-CSF (SEQ ID NO: 99)

MWLQNLLFLGIVVYSLSAPTRSPITVTRPWKHVEAIKEALNLLDDMPVTLNEEVEVVSNEF
SFKKLTCVQTRLKIFEQGLRGNFTKLKGALNMTASYYQTYCPPTPETDCETQVTTYADFID
SLKTFLTDIPFECKKPGQK

-continued mu IFN gamma
(SEQ ID NO: 100)
ATGAACGCTACACACTGCATCTTGGCTTTGCAGCTCTTCCTCATGGCTGTTTCTGGCTG
TTACTGCCACGGCACAGTCATTGAAAGCCTAGAAAGTCTGAATAACTATTTTAACTCA
AGTGGCATAGATGTGGAAGAAAAGAGTCTCTTCTTGGATATCTGGAGGAACTGGCAAA
AGGATGGTGACATGAAAATCCTGCAGAGCCAGATTATCTCTTTCTACCTCAGACTCTTT
GAAGTCTTGAAAGACAATCAGGCCATCAGCAACAACATAAGCGTCATTGAATCACACC
TGATTACTACCTTCTTCAGCAACAGCAAGGCGAAAAAGGATGCATTCATGAGTATTGC
CAAGTTTGAGGTCAACAACCCACAGGTCCAGCGCCAAGCATTCAATGAGCTCATCCGA
GTGGTCCACCAGCTGTTGCCGGAATCCAGCCTCAGGAAGCGGAAAAGGAGTCGCTGC mu IFN gamma
(SEQ ID NO: 101)
MNATHCILALQLFLMAVSGCYCHGTVIESLESLNNYFNSSGIDVEEKSLFLDIWRNWQKDG
DMKILQSQIISFYLRLFEVLKDNQAISNNISVIESHLITTFFSNSKAKKDAFMSIAKFEVNNPQ
VQRQAFNELIRVVHQLLPESSLRKRKRSRC mu IL7
(SEQ ID NO: 102)
ATGTTCCATGTTTCTTTTAGATATATCTTTGGAATTCCTCCACTGATCCTTGTTCTGCTG
CCTGTCACATCATCTGAGTGCCACATTAAAGACAAAGAAGGTAAAGCATATGAGAGTG
TACTGATGATCAGCATCGATGAATTGGACAAAATGACAGGAACTGATAGTAATTGCCC
GAATAATGAACCAAACTTTTTTAGAAAACATGTATGTGATGATACAAAGGAAGCTGCT
TTTCTAAATCGTGCTGCTCGCAAGTTGAAGCAATTTCTTAAAATGAATATCAGTGAAGA
ATTCAATGTCCACTTACTAACAGTATCACAAGGCACACAAACACTGGTGAACTGCACA
AGTAAGGAAGAAAAAAACGTAAAGGAACAGAAAAAGAATGATGCATGTTTCCTAAAG
AGACTACTGAGAGAAATAAAAACTTGTTGGAATAAAATTTTGAAGGGCAGTATA mu IL7
(SEQ ID NO: 103)
MFHVSFRYIFGIPPLILVLLPVTSSECHIKDKEGKAYESVLMISIDELDKMTGTDSNCPNNEP
NFFRKHVCDDTKEAAFLNRAARKLKQFLKMNISEEFNVHLLTVSQGTQTLVNCTSKEEKN
VKEQKKNDACFLKRLLREIKTCWNKILKGSI mu ICOS-L
(SEQ ID NO: 104)
ATGCAGCTAAAGTGTCCCTGTTTTGTGTCCTTGGGAACCAGGCAGCCTGTTTGGAAGA
AGCTCCATGTTTCTAGCGGGTTCTTTTCTGGTCTTGGTCTGTTCTTGCTGCTGTTGAGCA
GCCTCTGTGCTGCCTCTGCAGAGACTGAAGTCGGTGCAATGGTGGGCAGCAATGTGGT
GCTCAGCTGCATTGACCCCCACAGACGCCATTTCAACTTGAGTGGTCTGTATGTCTATT
GGCAAATCGAAAACCCAGAAGTTTCGGTGACTTACTACCTGCCTTACAAGTCTCCAGG
GATCAATGTGGACAGTTCCTACAAGAACAGGGGCCATCTGTCCCTGGACTCCATGAAG
CAGGGTAACTTCTCTCTGTACCTGAAGAATGTCACCCCTCAGGATACCCAGGAGTTCA
CATGCCGGGTATTTATGAATACAGCCACAGAGTTAGTCAAGATCTTGGAAGAGGTGGT
CAGGCTGCGTGTGGCAGCAAACTTCAGTACACCTGTCATCAGCACCTCTGATAGCTCC
AACCCGGGCCAGGAACGTACCTACACCTGCATGTCCAAGAATGGCTACCCAGAGCCCA
ACCTGTATTGGATCAACACAACGGACAATAGCCTAATAGACACGGCTCTGCAGAATAA
CACTGTCTACTTGAACAAGTTGGGCCTGTATGATGTAATCAGCACATTAAGGCTCCCTT
GGACATCTCGTGGGGATGTTCTGTGCTGCGTAGAGAATGTGGCTCTCCACCAGAACAT
CACTAGCATTAGCCAGGCAGAAAGTTTCACTGGAAATAACACAAAGAACCCACAGGA
AACCCACAATAATGAGTTAAAAGTCCTTGTCCCCGTCCTTGCTGTACTGGCGGCAGCG
GCATTCGTTTCCTTCATCATATACAGACGCACGCGTCCCCACCGAAGCTATACAGGACC
CAAGACTGTACAGCTTGAACTTACAGACCACGCC mu ICOS-L
(SEQ ID NO: 105)
MQLKCPCFVSLGTRQPVWKKLHVSSGFFSGLGLFLLLLSSLCAASAETEVGAMVGSNVVL
SCIDPHRRHFNLSGLYVYWQIENPEVSVTYYLPYKSPGINVDSSYKNRGHLSLDSMKQGNF
SLYLKNVTPQDTQEFTCRVFMNTATELVKILEEVVRLRVAANFSTPVISTSDSSNPGQERTY
TCMSKNGYPEPNLYWINTTDNSLIDTALQNNTVYLNKLGLYDVISTLRLPWTSRGDVLCC
VENVALHQNITSISQAESFTGNNTKNPQETHNNELKVLVPVLAVLAAAAFVSFIIYRRTRPH
RSYTGPKTVQLELTD HA mu CD47
(SEQ ID NO: 106)
ATGTGGCCCTTGGCGGCGGCGCTGTTGCTGGGCTCCTGCTGCTGCGGTTCAGCTCAACT
ACTGTTTAGTAACGTCAACTCCATAGAGTTCACTTCATGCAATGAAACTGTGGTCATCC
CTTGCATCGTCCGTAATGTGGAGGCGCAAAGCACCGAAGAAATGTTTGTGAAGTGGAA
GTTGAACAAATCGTATATTTTCATCTATGATGGAAATAAAAATAGCACTACTACAGAT
CAAAACTTTACCAGTGCAAAAATCTCAGTCTCAGACTTAATCAATGGCATTGCCTCTTT
GAAAATGGATAAGCGCGATGCCATGGTGGGAAACTACACTTGCGAAGTGACAGAGTT
ATCCAGAGAAGGCAAAACAGTTATAGAGCTGAAAAACCGCACGGTTTCGTGGTTTTCT
CCAAATGAAAAGATCCTCATTGTTATTTTCCCAATTTTGGCTATACTCCTGTTCTGGGG
AAAGTTTGGTATTTTAACACTCAAATATAAATCCAGCCATACGAATAAGAGAATCATT
CTGCTGCTCGTTGCCGGGCTGGTGCTCACAGTCATCGTGGTTGTTGGAGCCATCCTTCT
CATCCCAGGAGAAAAGCCCGTGAAGAATGCTTCTGGACTTGGCCTCATTGTAATCTCT
ACGGGGATATTAATACTACTTCAGTACAATGTGTTTATGACAGCTTTTGGAATGACCTC
TTTCACCATTGCCATATTGATCACTCAAGTGCTGGGCTACGTCCTTGCTTTGGTCGGGC
TGTGTCTCTGCATCATGGCATGTGAGCCAGTGCACGGCCCCCTTTTGATTTCAGGTTTG -continued GGGATCATAGCTCTAGCAGAACTACTTGGATTAGTTTATATGAAGTTTGTCGCTTCCAA
CCAGAGGACTATCCAACCTCCTAGGAATAGG mu CD47

(SEQ ID NO: 107)

MWPLAAALLLGSCCCGSAQLLFSNVNSIEFTSCNETVVIPCIVRNVEAQSTEEMFVKWKLN
KSYIFIYDGNKNSTTTDQNFTSAKISVSDLINGIASLKMDKRDAMVGNYTCEVTELSREGK
TVIELKNRTVSWFSPNEKILIVIFPILAILLFWGKFGILTLKYKSSHTNKRIILLLVAGLVLTVI
VVVGAILLIPGEKPVKNASGLGLIVISTGILILLQYNVFMTAFGMTSFTIAILITQVLGYVLAL
VGLCLCIMACEPVHGPLLISGLGIIALAELLGLVYMKFVASNQRTIQPPRNR

Mu Sarcoglycan alpha:

(SEQ ID NO: 108)

ATGGCAGCAGCAGTAACTTGGATACCTCTCCTGGCAGGTCTCCTGGCAGGACTGAGGG
ACACCAAGGCCCAGCAGACAACTTTACACCTACTTGTGGGTCGTGTGTTTGTGCATCCT
TTGGAACATGCCACCTTCCTGCGCCTTCCAGAACACGTTGCGGTGCCACCCACTGTCCG
ACTCACCTACCACGCTCACCTCCAGGGACATCCAGACCTGCCCAGGTGGCTGCACTAC
ACACAGCGCAGTCCCTATAACCCTGGCTTCCTCTACGGCTCCCCCACTCCAGAAGATCG
TGGGTACCAAGTCATCGAGGTCACAGCCTACAATCGAGACAGTTTTGACACCACTAGA
CAGAGGCTGCTGCTGCTGATTGGGGACCCCGAAGGTCCCCGGTTGCCATACCAAGCTG
AGTTCCTGGTGCGCAGCCATGATGTGGAGGAGGTGCTGCCCACCACACCTGCCAACCG
CTTCCTCACCGCCTTGGGGGGACTGTGGGAGCCAGGAGAGCTTCAGCTGCTCAACATC
ACTTCCGCCTTGGACCGGGGAGGCCGAGTCCCTCTTCCTATTGAGGGACGGAAGGAAG
GGGTATACATTAAGGTAGGCTCTGCCACACCCTTCTCCACCTGCCTGAAGATGGTGGC
GTCGCCCGACAGCTATGCCCGTTGTGCCCAGGGACAGCCTCCACTACTGTCCTGCTACG
ACACTTTGGCACCCCACTTCCGCGTTGACTGGTGCAATGTGTCTCTGGTAGACAAGTCA
GTACCCGAGCCCCTGGATGAGGTACCTACTCCAGGCGATGGGATCTTGGAGCACGACC
CGTTCTTCTGCCCACCCACTGAAGCCACAGACCGAGACTTCCTGACAGATGCCTTGGTG
ACCCTCTTGGTGCCTTTGTTGGTGGCTCTGCTGCTTACTCTGTTGCTGGCTTACATCATG
TGCTTTCGGCGTGAAGGACGGCTGAAGAGAGACATGGCCACCTCTGACATCCAGATGT
TTCACCACTGTTCCATCCATGGGAATACAGAAGAGCTTCGGCAGATGGCAGCCAGCCG
AGAGGTGCCCCGGCCTCTTTCCACCTTGCCCATGTTTAATGTTCGTACAGGAGAGCGGT
TACCTCCCCGAGTAGACAGCGCACAGATGCCTCTTATCCTGGACCAGCAC

Mu Sarcoglycan alpha:

(SEQ ID NO: 109)

MAAAVTWIPLLAGLLAGLRDTKAQQTTLHLLVGRVFVHPLEHATFLRLPEHVAVPPTVRL
TYHAHLQGHPDLPRWLHYTQRSPYNPGFLYGSPTPEDRGYQVIEVTAYNRDSFDTTRQRL
LLLIGDPEGPRLPYQAEFLVRSHDVEEVLPTTPANRFLTALGGLWEPGELQLLNITSALDRG
GRVPLPIEGRKEGVYIKVGSATPFSTCLKMVASPDSYARCAQGQPPLLSCYDTLAPHFRVD
WCNVSLVDKSVPEPLDEVPTPGDGILEHDPFFCPPTEATDRDFLTDALVTLLVPLLVALLLT
LLLAYIMCFRREGRLKRDMATSDIQMFHHCSIHGNTEELRQMAASREVPRPLSTLPMFNVR
TGERLPPRVDSAQM PLILDQH

Mu FGF10

(SEQ ID NO: 110)

ATGTGGAAATGGATACTGACACATTGTGCCTCAGCCTTTCCCCACCTGCCGGGCTGCTG
TTGCTGCTTCTTGTTGCTCTTTTTGGTGTCTTCGTTCCCTGTCACCTGCCAAGCTCTTGGT
CAGGACATGGTGTCACAGGAGGCCACCAACTGCTCTTCTTCCTCCTCGTCCTTCTCCTC
TCCTTCCAGTGCGGGAAGGCATGTGCGGAGCTACAATCACCTCCAAGGAGATGTCCGC
TGGAGAAGGCTGTTCTCCTTCACCAAGTACTTTCTCACGATTGAGAAGAACGGCAAGG
TCAGCGGGACCAAGAATGAAGACTGTCCGTACAGTGTCCTGGAGATAACATCAGTGGA
AATCGGAGTTGTTGCCGTCAAAGCCATCAACAGCAACTATTACTTAGCCATGAACAAG
AAGGGGAAACTCTATGGCTCAAAAGAGTTTAACAACGACTGTAAGCTGAAAGAGAGA
ATAGAGGAAAATGGATACAACACCTATGCATCTTTTAACTGGCAGCACAATGGCAGGC
AAATGTATGTGGCATTGAATGGAAAAGGAGCTCCCAGGAGAGGACAAAAAACAAGAA
GGAAAAACACCTCTGCTCACTTCCTCCCCATGACGATCCAAACA

Mu FGF10

(SEQ ID NO: 111)

MWKWILTHCASAFPHLPGCCCCFLLLFLVSSFPVTCQALGQDMVSQEATNCSSSSSSFSSPS
SAGRHVRSYNHLQGDVRWRRLFSFTKYFLTIEKNGKVSGTKNEDCPYSVLEITSVEIGVVA
VKAINSNYYLAMNKKGKLYGSKEFNNDCKLKERIEENGYNTYASFNWQHNGRQMYVAL
NGKGAPRRGQKTRRKNTSAHFLPMTIQT

Mu Agrin (SEQ ID NO: 112)

ATGCCTCCTCTGCCACTGGAACACAGACCCAGGCAGCAGCCTGGTGCCTCCGTGCTGG
TTCGGTACTTCATGATCCCCTGCAACATCTGCTTGATCCTCTTGGCTACTTCTACGTTGG
GCTTTGCGGTGCTGCTTTTCCTCAGCAACTACAAACCTGGGATCCACTTCACAGCAGCG
CCTTCTATGCCTCCTGATGTGTGCAGGGGAATGTTATGTGGCTTTGGTGCTGTGTGTGA
ACCTAGTGTTGAGGATCCAGGCCGGGCCTCCTGTGTGTGCAAGAAGAATGTCTGCCCT
GCTATGGTAGCTCCTGTGTGTGGCTCAGATGCTTCCACCTATAGCAACGAGTGTGAGCT
ACAGCGTGCACAGTGCAACCAGCAACGGCGCATCCGCCTACTCCGCCAAGGGCCATGT
GGGTCCCGGGACCCCTGTGCCAATGTGACCTGCAGTTTCGGTAGTACCTGTGTACCTTC
AGCCGATGGACAGACCGCCTCGTGTCTGTGTCCTACAACCTGCTTTGGGGCCCCTGATG
GCACAGTGTGTGGCAGTGATGGTGTTGACTACCCTAGTGAGTGCCAGCTGCTCCGTCA
TGCCTGTGCCAACCAGGAGCACATCTTTAAGAAGTTCGATGGTCCTTGTGACCCCTGCC
AGGGCAGCATGTCAGACCTGAATCATATTTGCCGGGTGAACCCACGTACACGGCACCC
AGAAATGCTTCTGCGGCCTGAGAACTGCCCCGCCCAACACACACCTATCTGTGGAGAT
GATGGGGTCACCTATGAAAACGACTGTGTCATGAGCCGTATAGGTGCAGCCCGTGGCC

-continued

TGCTTCTCCAGAAAGTGCGCTCTGGTCAATGCCAGACTCGAGACCAGTGCCCGGAGAC
CTGCCAGTTTAACTCTGTATGCCTGTCCCGCCGCGGCCGTCCCCACTGTTCCTGCGATC
GCGTCACCTGTGATGGGGCTTACAGGCCAGTGTGTGCCCAGGATGGGCACACGTATGA
CAATGACTGTTGGCGCCAACAGGCCGAGTGTCGACAACAGCAGACCATTCCCCCCAAG
CACCAGGGCCCGTGTGACCAGACCCCATCCCCGTGCCGTGGAGCGCAGTGTGCATTTG
GGGCAACATGCACAGTGAAGAATGGGAAAGCTGTGTGCGAGTGCCAGCGGGTGTGCT
CGGGCGGCTACGATCCTGTGTGCGGCAGTGATGGTGTCACTTACGGCAGTGTGTGCGA
GCTGGAATCCATGGCCTGTACCCTTGGGCGGGAAATCCGAGTGGCCCGCAGAGGACCG
TGTGACCGATGTGGGCAGTGCCGGTTTGGATCCTTGTGCGAGGTGGAGACTGGACGCT
GTGTGTGCCCCTCTGAGTGTGTGGAGTCAGCCCAGCCCGTATGTGGCTCTGACGGACA
CACATATGCTAGTGAATGTGAGCTGCATGTCCACGCCTGTACACACCAGATCAGCCTA
TACGTGGCCTCAGCCGGACACTGCCAGACCTGTGGAGAAACAGTTTGTACCTTTGGGG
CTGTGTGCTCAGCTGGACAGTGTGTATGTCCCCGTTGTGAGCACCCCCCACCTGGCCCT
GTGTGCGGCAGTGATGGCGTCACCTACCTCAGTGCCTGTGAGCTCCGAGAGGCTGCCT
GTCAGCAGCAGGTACAAATTGAGGAGGCCCGTGCAGGGCCGTGTGAGCCGGCTGAGT
GTGGCTCAGGGGGCTCTGGGTCTGGGGAAGACAATGCGTGTGAGCAGGAGCTGTGTCG
GCAGCATGGTGGTGTCTGGGATGAGGACTCAGAAGACGGGCCGTGTGTCTGTGACTTT
AGTTGCCAGAGTGTCCTTAAAAGCCCAGTGTGTGGCTCAGATGGAGTCACCTATAGCA
CGGAGTGCCATCTGAAGAAGGCCAGATGTGAAGCGCGGCAAGAGCTGTACGTCGCTG
CTCAGGGAGCCTGCCGGGGCCCTACCTTGGCTCCACTGCTACCTATGGCCTCCCCACAC
TGTGCCCAAACCCCCTATGGCTGCTGCCAGGACAATGTCACTGCTGCCCAGGGTGTGG
GCTTGGCTGGCTGTCCCAGCACCTGCCATTGCAACCCACACGGCTCCTATAGCGGCACT
TGTGACCCAGTCACAGGGCAGTGCTCCTGCCGACCAGGTGTAGGAGGCCTCAGGTGTG
ATCGCTGTGAGCCTGGCTTCTGGAACTTCCGTGGCATTGTCACCGATGGACATAGTGGT
TGCACTCCCTGCAGCTGTGACCCTCGGGGTGCTGTAAGAGATGACTGTGAGCAGATGA
CTGGATTGTGTTCCTGTAGACCTGGTGTGGCTGGTCCCAAGTGTGGGCAGTGTCCAGAT
GGTCAAGCCCTGGGCCATCTTGGCTGTGAAGCAGATCCCACAACACCAGTGACTTGTG
TGGAAATGCACTGTGAGTTTGGCGCCTCCTGCGTAGAGGAGGCTGGTTTTGCCCAGTG
TGTCTGCCCAACTCTCACATGTCCAGAGGCTAACTCTACCAAGGTCTGTGGATCAGATG
GTGTCACATACGGCAATGAATGCCAGCTGAAGACCATTGCCTGCCGCCAGCGTCTGGA
CATCTCCATTCAGAGTCTTGGTCCATGCCGGGAGAGTGTTGCTCCTGGGGTTTCCCCTA
CATCTGCATCTATGACCACCCCAAGGCATATCCTGAGCAGGACACTGGCGTCTCCCCA
CAGCAGCCTTCCTCTGTCTCCCAGCACTACTGCCCATGATTGGCCCACCCCATTACCCA
CATCACCTCAGACCGTAGTCGGCACCCCCAGGAGCACTGCAGCCACACCCTCTGATGT
GGCCAGTCTTGCTACAGCGATCTTCAGGGAATCTGGCAGCACCAACGGCAGTGGCGAT
GAGGAGCTCAGTGGCGATGAGGAGGCCAGTGGGGGCGGGTCTGGGGGACTTGAGCCC
CCGGTGGGCAGCGTTGTGGTGACCCACGGGCCACCCATCGAGAGGGCTTCCTGTTACA
ACTCACCTTTGGGCTGCTGCTCAGATGGCAAGACACCCTCACTGGACTCAGAAGGCTC
CAACTGTCCAGCTACCAAGGCATTCCAGGGCGTGCTGGAGCTTGAGGGGGTCGAGGGA
CAGGAACTGTTCTACACACCAGAGATGGCTGACCCCAAGTCAGAGTTGTTTGGGGAGA
CTGCAAGGAGCATTGAGAGCACGCTGGACGACCTGTTCCGGAATTCGGATGTTAAGAA
GGACTTCTGGAGCATCCGCCTACGGGAACTGGGGCCTGGCAAATTAGTCCGTGCCATT
GTGGATGTTCACTTTGACCCCACCACAGCCTTCCAGGCACCAGATGTGGGTCAGGCCTT
GCTCCAACAGATCCAGGTATCCAGGCCGTGGGCCCTGGCAGTGAGGAGGCCTCTGCGG
GAGCATGTGCGATTCTTGGACTTTGACTGGTTTCCCACTTTTTTTACGGGAGCTGCAAC
AGGAACCACAGCTGCTGTGGCCACAGCCAGAGCCACCACTGTGAGCCGACTGTCTGCC
TCTTCTGTCACCCCACGAGTCTACCCCAGTTACACCAGCCGGCCTGTTGGCAGAACTAC
GGCACCGCTAACCACTCGCCGGCCACCAACCACTACCGCCAGTATTGACCGACCTCGG
ACTCCAGGCCCGCAACGGCCCCCAAAGTCCTGTGATTCCCAGCCTTGCCTCCACGGAG
GTACCTGCCAGGACCTGGATTCTGGCAAGGGTTTCAGCTGCAGCTGTACTGCAGGCAG
GGCTGGCACTGTCTGTGAGAAAGTGCAGCTCCCCTCTGTGCCAGCTTTTAAGGGCCACT
CCTTCTTGGCCTTCCCCACCCTCCGAGCCTACCACACGCTGCGTCTGGCACTAGAATTC
CGGGCGCTGGAGACAGAGGGACTGCTGCTCTACAATGGCAATGCACGTGGCAAAGAT
TTCCTGGCTCTGGCTCTGTTGGATGGTCATGTACAGTTCAGGTTCGACACGGGCTCAGG
GCCGGCGGTGCTAACAAGCTTAGTGCCAGTGGAACCGGGACGGTGGCACCGCCTCGA
GTTGTCACGGCATTGGCGGCAGGGCACACTTTCTGTGGATGGCGAGGCTCCTGTTGTA
GGTGAAAGTCCGAGTGGCACTGATGGCCTCAACTTGGACACGAAGCTCTATGTGGGTG
GTCTCCCAGAAGAACAAGTTGCCACGGTGCTTGATCGGACCTCTGTGGGCATCGGCCT
GAAAGGATGCATTCGTATGTTGGACATCAACAACCAGCAGCTGGAGCTGAGCGATTGG
CAGAGGGCTGTGGTTCAAAGCTCTGGTGTGGGGGAATGCGGAGACCATCCCTGCTCAC
CTAACCCCTGCCATGGCGGGGCCCTCTGCCAGGCCCTGGAGGCTGGCGTGTTCCTCTGT
CAGTGCCCACCTGGCCGCTTTGGCCCAACTTGTGCAGATGAAAAGAACCCCTGCCAAC
CGAACCCCTGCCACGGGTCAGCCCCCTGCCATGTGCTTTCCAGGGGTGGGGCCAAGTG
TGCGTGCCCCCTGGGACGCAGTGGTTCCTTCTGTGAGACAGTCCTGGAGAATGCTGGC
TCCCGGCCCTTCCTGGCTGACTTTAATGGCTTCTCCTACCTGGAACTGAAAGGCTTGCA
CACCTTCGAGAGAGACCTAGGGGAGAAGATGGCGCTGGAGATGGTGTTCTTGGCTCGT
GGGCCCAGTGGCTTACTCCTCTACAATGGGCAGAAGACGGATGGCAAGGGGGACTTTG
TATCCCTGGCCCTGCATAACCGGCACCTAGAGTTCCGCTATGACCTTGGCAAGGGGGC
TGCAATCATCAGGAGCAAAGAGCCCATAGCCCTGGGCACCTGGGTTAGGGTATTCCTG
GAACGAAATGGCCGCAAGGGTGCCCTTCAAGTGGGTGATGGGCCCCGTGTGCTAGGG
GAATCTCCGAAATCCCGCAAGGTCCCGCACACCATGCTCAACCTCAAGGAGCCCCTCT
ATGTGGGGGGAGCTCCTGACTTCAGCAAGCTGGCTCGGGGCGCTGCAGTGGCCTCCGG
CTTTGATGGTGCCATCCAGCTGGTGTCTCTAAGAGGCCATCAGCTGCTGACTCAGGAG
CATGTGTTGCGGGCAGTAGATGTAGCGCCTTTTGCAGGCCACCCTTGTACCCAGGCCGT
GGACAACCCCTGCCTTAATGGGGGCTCCTGTATCCCGAGGGAAGCCACTTATGAGTGC
CTGTGTCCTGGGGGCTTCTCTGGGCTGCACTGCGAGAAGGGGATAGTTGAGAAGTCAG
TGGGGGACCTAGAAACACTGGCCTTTGATGGGCGGACCTACATCGAGTACCTCAATGC
TGTGACTGAGAGCGAGCTGACCAATGAGATCCCAGCCCCCGAAACTCTGGATTCCCGG
GCCCTTTTCAGTGAGAAAGCGCTGCAGAGCAACCACTTTGAGCTGAGCTTACGCACTG
AGGCCACGCAGGGGCTGGTGCTGTGGATTGGAAAGGTTGGAGAACGTGCAGACTACA
TGGCTCTGGCCATTGTGGATGGGCACCTACAACTGAGCTATGACCTAGGCTCCCAGCC

-continued

AGTTGTGCTGCGCTCCACTGTGAAGGTCAACACCAACCGCTGGCTTCGAGTCAGGGCT
CACAGGGAGCACAGGGAAGGTTCCCTTCAGGTGGGCAATGAAGCCCCTGTGACTGGCT
CTTCCCCGCTGGGTGCCACACAATTGGACACAGATGGAGCCCTGTGGCTTGGAGGCCT
ACAGAAGCTTCCTGTGGGGCAGGCTCTCCCCAAGGCCTATGGCACGGGTTTTGTGGGC
TGTCTGCGGGACGTGGTAGTGGGCCATCGCCAGCTGCATCTGCTGGAGGACGCTGTCA
CCAAACCAGAGCTAAGACCCTGCCCCACTCTCTGA

Mu Agrin (SEQ ID NO: 113)

MPPLPLEHRPRQQPGASVLVRYFMIPCNICLILLATSTLGFAVLLFLSNYKPGIHFTAAPSMP
PDVCRGMLCGFGAVCEPSVEDPGRASCVCKKNVCPAMVAPVCGSDASTYSNECELQRAQ
CNQQRRIRLLRQGPCGSRDPCANVTCSFGSTCVPSADGQTASCLCPTTCFGAPDGTVCGSD
GVDYPSECQLLRHACANQEHIFKKFDGPCDPCQGSMSDLNHICRVNPRTRHPEMLLRPEN
CPAQHTPICGDDGVTYENDCVMSRIGAARGLLLQKVRSGQCQTRDQCPETCQFNSVCLSR
RGRPHCSCDRVTCDGAYRPVCAQDGHTYDNDCWRQQAECRQQQTIPPKHQGPCDQTPSP
CRGAQCAFGATCTVKNGKAVCECQRVCSGGYDPVCGSDGVTYGSVCELESMACTLGREI
RVARRGPCDRCGQCRFGSLCEVETGRCVCPSECVESAQPVCGSDGHTYASECELHVHACT
HQISLYVASAGHCQTCGETVCTFGAVCSAGQCVCPRCEHPPPGPVCGSDGVTYLSACELRE
AACQQQVQIEEARAGPCEPAECGSGGSGSGEDNACEQELCRQHGGVWDEDSEDGPCVCD
FSCQSVLKSPVCGSDGVTYSTECHLKKARCEARQELYVAAQGACRGPTLAPLLPMASPHC
AQTPYGCCQDNVTAAQGVGLAGCPSTCHCNPHGSYSGTCDPVTGQCSCRPGVGGLRCDR
CEPGFWNFRGIVTDGHSGCTPCSCDPRGAVRDDCEQMTGLCSCRPGVAGPKCGQCPDGQ
ALGHLGCEADPTTPVTCVEMHCEFGASCVEEAGFAQCVCPTLTCPEANSTKVCGSDGVTY
GNECQLKTIACRQRLDISIQSLGPCRESVAPGVSPTSASMTTPRHILSRTLASPHSSLPLSPST
TAHDWPTPLPTSPQTVVGTPRSTAATPSDVASLATAIFRESGSTNGSGDEELSGDEEASGGG
SGGLEPPVGSVVVTHGPPIERASCYNSPLGCCSDGKTPSLDSEGSNCPATKAFQGVLELEGV
EGQELFYTPEMADPKSELFGETARSIESTLDDLFRNSDVKKDFWSIRLRELGPGKLVRAIVD
VHFDPTTAFQAPDVGQALLQQIQVSRPWALAVRRPLREHVRFLDFDWFPTFFTGAATGTT
AAVATARATTVSRLSASSVTPRVYPSYTSRPVGRTTAPLTTRRPPTTTASIDRPRTPGPQRPP
KSCDSQPCLHGGTCQDLDSGKGFSCSCTAGRAGTVCEKVQLPSVPAFKGHSFLAFPTLRAY
HTLRLALEFRALETEGLLLYNGNARGKDFLALALLDGHVQFRFDTGSGPAVLTSLVPVEPG
RWHRLELSRHWRQGTLSVDGEAPVVGESPSGTDGLNLDTKLYVGGLPEEQVATVLDRTS
VGIGLKGCIRMLDINNQQLELSDWQRAVVQSSGVGECGDHPCSPNPCHGGALCQALEAGV
FLCQCPPGRFGPTCADEKNPCQPNPCHGSAPCHVLSRGGAKCACPLGRSGSFCETVLENAG
SRPFADFNGFSYLELKGLHTFERDLGEKMALEMVFLARGPSGLLLYNGQKTDGKGDFVSL
ALHNRHLEFRYDLGKGAAIIRSKEPIALGTWVRVFLERNGRKGALQVGDGPRVLGESPKSR
KVPHTMLNLKEPLYVGGAPDFSKLARGAAVASGFDGAIQLVSLRGHQLLTQEHVLRAVD
VAPFAGHPCTQAVDNPCLNGGSCIPREATYECLCPGGFSGLHCEKGIVEKSVGDLETLAFD
GRTYIEYLNAVTESELTNEIPAPETLDSRALFSEKALQSNHFELSLRTEATQGLVLWIGKVG
ERADYMALAIVDGHLQLSYDLGSQPVVLRSTVKVNTNRWLRVRAHREHREGSLQVGNEA
PVTGSSPLGATQLDTDGALWLGGLQKLPVGQALPKAYGTGFVGCLRDVVVGHRQLHLLE
DAVTKPELRPCPTL

Mu IL10

(SEQ ID NO: 114)

ATGCCTGGCTCAGCACTGCTATGCTGCCTGCTCTTACTGACTGGCATGAGGATCAGCAG
GGGCCAGTACAGCCGGGAAGACAATAACTGCACCCACTTCCCAGTCGGCCAGAGCCA
CATGCTCCTAGAGCTGCGGACTGCCTTCAGCCAGGTGAAGACTTTCTTTCAAACAAAG
GACCAGCTGGACAACATACTGCTAACCGACTCCTTAATGCAGGACTTTAAGGGTTACT
TGGGTTGCCAAGCCTTATCGGAAATGATCCAGTTTTACCTGGTAGAAGTGATGCCCCA
GGCAGAGAAGCATGGCCCAGAAATCAAGGAGCATTTGAATTCCCTGGGTGAGAAGCT
GAAGACCCTCAGGATGCGGCTGAGGCGCTGTCATCGATTTCTCCCCTGTGAAAATAAG
AGCAAGGCAGTGGAGCAGGTGAAGAGTGATTTTAATAAGCTCCAAGACCAAGGTGTC
TACAAGGCCATGAATGAATTTGACATCTTCATCAACTGCATAGAAGCATACATGATGA
TCAAAATGAAAAGCTAA

Mu IL10

(SEQ ID NO: 115)

MPGSALLCCLLLLTGMRISRGQYSREDNNCTHFPVGQSHMLLELRTAFSQVKTFFQTKDQ
LDNILLTDSLMQDFKGYLGCQALSEMIQFYLVEVMPQAEKHGPEIKEHLNSLGEKLKTLR
MRLRRCHRFLPCENKSKAVEQVKSDFNKLQDQGVYKAMNEFDIFINCIEAYMMIKMKS

Mu MYDGF (C19orf10)

(SEQ ID NO: 116)

ATGGCAGCCCCCAGCGGAGGCTTCTGGACTGCGGTGGTCCTGGCGGCCGCAGCGCTGA
AATTGGCCGCCGCTGTGTCCGAGCCCACCACCGTGCCATTTGACGTGAGGCCCGGAGG
GGTCGTGCATTCGTTCTCCCAGGACGTAGGACCCGGGAACAAGTTTACATGTACATTC
ACCTACGCTTCCCAAGGAGGGACCAACGAGCAATGGCAGATGAGCCTGGGGACAAGT
GAAGACAGCCAGCACTTTACCTGTACCATCTGGAGGCCCCAGGGGAAATCCTACCTCT
ACTTCACACAGTTCAAGGCTGAGTTGCGAGGTGCTGAGATCGAGTATGCCATGGCCTA
CTCCAAAGCCGCATTTGAGAGAGAGAGTGATGTCCCCCTGAAAAGTGAGGAGTTTGAA
GTGACCAAGACAGCAGTGTCTCACAGGCCTGGGGCCTTCAAAGCTGAGCTCTCCAAGC
TGGTGATCGTAGCCAAGGCGGCACGCTCGGAGCTGTGA

Mu MYDGF (C19orf10)

(SEQ ID NO: 117)

MAAPSGGFWTAVVLAAAALKLAAAVSEPTTVPFDVRPGGVVHSFSQDVGPGNKFTCTFT
YASQGGTNEQWQMSLGTSEDSQHFTCTIWRPQGKSYLYFTQFKAELRGAEIEYAMAYSK
AAFERESDVPLKSEEFEVTKTAVSHRPGAFKAELSKLVIVAKAARSEL

-continued pWF-521

(SEQ ID NO: 118)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTCAGCCCAAGGCCAACCC
CACTGTCACTCTGTTCCCGCCCTCCTCTGAGGAGCTCCAAGCCAACAAGGCCACACTA
GTGTGTCTGATCAGTGACTTCTACCCGGGAGCTGTGACAGTGGCCTGGAAGGCAGATG
GCAGCCCCGTCAAGGCGGGAGTGGAGACCACCAAACCCTCCAAACAGAGCAACAACA
AGTACGCGGCCAGCAGCTACCTGAGCCTGACGCCCGAGCAGTGGAAGTCCCACAGAA
GCTACAGCTGCCAGGTCACGCATGAAGGGAGCACCGTGGAGAAGACAGTGGCCCCTA
CAGAATGTTCAGGCGCCGGATCTGGTGGAAACTGGAGTCATCCCCAATTCGAGAAGGG
CGGAAGCGGTGGGAGTGGCGGGTCCGGTGGAAGCAACTGGTCACACCCACAATTCGA
GAAAGGCGGTTCTGGCGGATCTGGTGGATCTGGCGGAAGTAACTGGTCTCATCCTCAA
TTCGAAAAGGGCGGAAGCGGTGGCGGCAGGCTAGGTGGAGGCTCAGTGCAGGTGCAG
CTGGTGGAGTCTGGGGGAGGCTTGGTACAGCCTGGGGGGTCCCTGAGACTCTCCTGTG
CAGCCTCTGGATTCACCTTTAGCAGCTATGCCATGAGCTGGGTCCGCCAGGCTCCAGG
GAAGGGGCTGGAGTGGGTCTCAGTTATTTATAGCGGTGGTAGTAGCACATACTATGCA
GACTCCGTGAAGGGCCGGTTCACCATCTCCAGAGATAATTCCAAGAACACGCTGTATC
TGCAAATGAACAGCCTGAGAGCCGAGGACACGGCCGTATATTACTGTGCGCGCACTTC
TTACCTGAACCATGGTGATTACTGGGGTCAAGGTACTCTGGTGACCGTGTCTAGCGCCT
CCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCA
GACCTACATCTGCAACGTGAACCACAAGCCCAGCAACACCAAGGTGGACAAGAGAGT
GGAGCCCAAGAGCTGCGACAAGACCCACACCTGCCCCCCCTGCCCAGCCCCAGAGCTG
CTGGGCGGACCCTCCGTGTTCCTGTTCCCCCCCAAGCCCAAGGACACCCTGATGATCA
GCAGGACCCCCGAGGTGACCTGCGTGGTGGTGGACGTGAGCCACGAGGACCCAGAGG
TGAAGTTCAACTGGTACGTGGACGGCGTGGAGGTGCACAACGCCAAGACCAAGCCCA
GAGAGGAGCAGTACAACAGCACCTACAGGGTGGTGTCCGTGCTGACCGTGCTGCACCA
GGACTGGCTGAACGGCAAGGAATACAAGTGCAAGGTCTCCAACAAGGCCCTGCCAGC
CCCCATCGAAAAGACCATCAGCAAGGCCAAGGGCCAGCCACGGGAGCCCCAGGTGTA
CACCCTGCCCCCCTCCCGGGAGGAGATGACCAAGAACCAGGTGTCCCTGACCTGTCTG
GTGAAGGGCTTCTACCCCAGCGACATCGCCGTGGAGTGGGAGAGCAACGGCCAGCCC
GAGAACAACTACAAGACCACCCCCCCAGTGCTGGACAGCGACGGCAGCTTCTTCCTGT
ACAGCAAGCTGACCGTGGACAAGTCCAGGTGGCAGCAGGGCAACGTGTTCAGCTGCA
GCGTGATGCACGAGGCCCTGCACAACCACTACACCCAGAAGAGCCTGAGCCTGTCCCC
CGAGCTGCAACTGGAGGAGAGCTGTGCGGAGGCGCAGGACGGGGAGCTGGACGGGCT
GTGGACGACCATCACCATCTTCATCACACTCTTCCTGTTAAGCGTGTGCTACAGTGCCA
CCGTCACCTTCTTCAAGGTGAAGTGGATCTTCTCCTCGGTGGTGGACCTGAAGCAGACC
ATCATCCCCGACTACAGGAACATGATCGGACAGGGGGCCTGA pWF-521

(SEQ ID NO: 119)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGQPKANPTVTLF
PPSSEELQANKATLVCLISDFYPGAVTVAWKADGSPVKAGVETTKPSKQSNNKYAASSYL
SLTPEQWKSHRSYSCQVTHEGSTVEKTVAPTECSGAGSGGNWSHPQFEKGGSGGSGGSGG
SNWSHPQFEKGGSGGSGGSGGSNWSHPQFEKGGSGGGRLGGGSVQVQLVESGGGLVQPG
GSLRLSCAASGFTFSSYAMSWVRQAPGKGLEWVSVIYSGGSSTYYADSVKGRFTISRDNSK
NTLYLQMNSLRAEDTAVYYCARTSYLNHGDYWGQGTLVTVSSASTKGPSVFPLAPSSKST
SGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYT
QKSLSLSPELQLEESCAEAQDGELDGLWTTITIFITLFLLSVCYSATVTFFKVKWIFSSVVDL
KQTIIPDYRNMIGQGA pWF-533

(SEQ ID NO: 120)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAtcttcaGCCTCCACCAAGGGCCC
ATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTACATCTGCA
ACGTGAACCACAAGCCCAGCAACACCAAGGTGGACAAGAGAGTGGAGCCCAAGAGCT
GC pWF-533

(SEQ ID NO: 121)

QSVLTQPPSVSAAPGQRVTISCSGTRSNIGSDYVSWYQHLPGTAPKLLVYGDNLRPSGIPDR

-continued

FSASKSGTSATLGITGLQTGDEADYYCGTWDYTLNGVVFGGGTKLTVLSSASTKGPSVFPL
APSSKSTSGGTAALGCLVKDYFPEPVTVSWNSGALTSGVHTFPAVLQSSGLYSLSSVVTVP
SSSLGTQTYICNVNHKPSNTKVDKRVEPKSC pWF-534

(SEQ ID NO: 122)

CAGGTGCAGCTGGTGGAGTCTGGGGGAGGCTTGGTACAGCCTGGGGGGTCCCTGAGAC
TCTCCTGTGCAGCCTCTGGATTCACCTTTAGCAGCTATGCCATGAGCTGGGTCCGCCAG
GCTCCAGGGAAGGGGCTGGAGTGGGTCTCAGTTATTTATAGCGGTGGTAGTAGCACAT
ACTATGCAGACTCCGTGAAGGGCCGGTTCACCATCTCCAGAGATAATTCCAAGAACAC
GCTGTATCTGCAAATGAACAGCCTGAGAGCCGAGGACACGGCCGTATATTACTGTGCG
CGCACTTCTTACCTGAACCATGGTGATTACTGGGGTCAAGGTACTCTGGTGACCGTGTC
TAGCGCCTCCGTGGCTGCACCATCTGTCTTCATCTTCCCGCCATCTGATGAGCAGTTGA
AATCTGGAACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAGTGTCACAG
AGCAGGACAGCAAGGACAGCACCTACAGCCTCAGCAGCACCCTGACGCTGAGCAAAG
CAGACTACGAGAAACACAAAGTCTACGCCTGCGAAGTCACCCATCAGGGCCTGAGCTC
GCCCGTCACAAAGAGCTTCAACAGGGGAGAGTGTGACAAGACCCACACCTGCCCCCCC
TGCCCAGCCCCAGAGCTGCTGGGCGGACCCTCCGTGTTCCTGTTCCCCCCCAAGCCCAA
GGACACCCTGATGATCAGCAGGACCCCCGAGGTGACCTGCGTGGTGGTGGACGTGAGC
CACGAGGACCCAGAGGTGAAGTTCAACTGGTACGTGGACGGCGTGGAGGTGCACAAC
GCCAAGACCAAGCCCAGAGAGGAGCAGTACAACAGCACCTACAGGGTGGTGTCCGTG
CTGACCGTGCTGCACCAGGACTGGCTGAACGGCAAGGAATACAAGTGCAAGGTCTCCA
ACAAGGCCCTGCCAGCCCCCATCGAAAAGACCATCAGCAAGGCCAAGGGCCAGCCAC
GGGAGCCCCAGGTGTACACCCTGCCCCCCTCCCGGGAGGAGATGACCAAGAACCAGG
TGTCCCTGACCTGTCTGGTGAAGGGCTTCTACCCCAGCGACATCGCCGTGGAGTGGGA
GAGCAACGGCCAGCCCGAGAACAACTACAAGACCACCCCCCCAGTGCTGGACAGCGA
CGGCAGCTTCTTCCTGTACAGCAAGCTGACCGTGGACAAGTCCAGGTGGCAGCAGGGC
AACGTGTTCAGCTGCAGCGTGATGCACGAGGCCCTGCACAACCACTACACCCAGAAGA
GCCTGAGCCTGTCCCCCGAGCTGCAACTGGAGGAGAGCTGTGCGGAGGCGCAGGACG
GGGAGCTGGACGGGCTGTGGACGACCATCACCATCTTCATCACACTCTTCCTGTTAAG
CGTGTGCTACAGTGCCACCGTCACCTTCTTCAAGGTGAAGTGGATCTTCTCCTCGGTGG
TGGACCTGAAGCAGACCATCATCCCCGACTACAGGAACATGATCGGACAGGGGGCCT
GA pWF-534

(SEQ ID NO: 123)

QVQLVESGGGLVQPGGSLRLSCAASGFTFSSYAMSWVRQAPGKGLEWVSVIYSGGSSTYY
ADSVKGRFTISRDNSKNTLYLQMNSLRAEDTAVYYCARTSYLNHGDYWGQGTLVTVSSA
SVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGECDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPELQLEESCAEAQDGELDGLWTTITIFITLFLLSV
CYSATVTFFKVKWIFSSVVDLKQTIIPDYRNMIGQGA mu IL15

(SEQ ID NO: 124)

ATGAAAATTTTGAAACCATATATGAGGAATACATCCATCTCGTGCTACTTGTGTTTCCT
TCTAAACAGTCACTTTTTAACTGAGGCTGGCATTCATGTCTTCATTTTGGGCTGTGTCA
GTGTAGGTCTCCCTAAAACAGAGGCCAACTGGATAGATGTAAGATATGACCTGGAGAA
AATTGAAAGCCTTATTCAATCTATTCATATTGACACCACTTTATACACTGACAGTGACT
TTCATCCCAGTTGCAAAGTTACTGCAATGAACTGCTTTCTCCTGGAATTGCAGGTTATT
TTACATGAGTACAGTAACATGACTCTTAATGAAACAGTAAGAAACGTGCTCTACCTTG
CAAACAGCACTCTGTCTTCTAACAAGAATGTAGCAGAATCTGGCTGCAAGGAATGTGA
GGAGCTGGAGGAGAAAACCTTCACAGAGTTTTTGCAAAGCTTTATACGCATTGTCCAA
ATGTTCATCAACACGTCC mu IL15

(SEQ ID NO: 125)

MKILKPYMRNTSISCYLCFLLNSHFLTEAGIHVFILGCVSVGLPKTEANWIDVRYDLEKIESL
IQSIHIDTTLYTDSDFHPSCKVTAMNCFLLELQVILHEYSNMTLNETVRNVLYLANSTLSSN
KNVAESGCKECEELEEKTFTEFLQSFIRIVQMFINTS anti-human GPC3 CAR (79a)

(SEQ ID NO: 126)

CAGTCTGTGTTGACGCAGCCGCCCTCAGTGTCTGCGGCCCCAGGACAGAGGGTCACCA
TCTCCTGCTCTGGAACCAGGTCCAACATTGGGAGTGATTATGTTTCCTGGTACCAACAC
CTCCCAGGAACAGCCCCCAAACTCCTCGTTTATGGCGATAATCTGCGACCCTCAGGGA
TTCCTGACCGATTCTCTGCCTCCAAGTCTGGCACGTCAGCCACCCTGGGCATCACCGGA
CTCCAGACTGGGGACGAGGCCGATTATTACTGCGGCACATGGGATTACACCCTGAATG
GTGTGGTGTTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGGTGCAGCTG
GTGGAGTCTGGGGGAGGCTTGGTACAGCCTGGGGGGTCCCTGAGACTCTCCTGTGCAG
CCTCTGGATTCACCTTTAGCAGCTATGCCATGAGCTGGGTCCGCCAGGCTCCAGGGAA
GGGGCTGGAGTGGGTCTCAGTTATTTATAGCGGTGGTAGTAGCACATACTATGCAGAC
TCCGTGAAGGGCCGGTTCACCATCTCCAGAGATAATTCCAAGAACACGCTGTATCTGC
AAATGAACAGCCTGAGAGCCGAGGACACGGCCGTATATTACTGTGCGCGCACTTCTTA
CCTGAACCATGGTGATTACTGGGGTCAAGGTACTCTGGTGACCGTGTCTAGCGCCGCT
GCA*GTGGTCCCCGTGCTGCAGAAAGTTAATAGCACCACCACTAAACCTGTCCTGAGGACTCC*

-continued

*TAGTCCAGTGCACCCAACAGGGACCAGTCAGCCACAGAGACCGGAAGACTGCAGACCAAGA*
*GGTTCAGTGAAGGGAACCGGCCTGGATTTCGCCTGCGAT*TTTTGGGCCCTGGTCGTCGTC
GCAGGAGTTTTGTTTTGCTATGGACTGCTCGTCACAGTTGCTTTGTGTGTTATCTGGAC
*AAGGAAACGGTGGCAAAATGAGAAGTTTGGGGTGGACATGCCAGATGACTATGAAGATGAA*
*AATCTCTATGAGGGCCTGAACCTTGATGACTGTTCTATGTATGAGGACATCTCCAGGGGACT*
*CCAGGGCACCTACCAGGATGTGGGCAACCTCCACATTGGAGATGCCCAGCTGGAAAAGCCA*
*TGA* anti-human GPC3 CAR (79a)

(SEQ ID NO: 127)

QSVLTQPPSVSAAPGQRVTISCSGTRSNIGSDYVSWYQHLPGTAPKLLVYGDNLRPSGIPDR
FSASKSGTSATLGITGLQTGDEADYYCGTWDYTLNGVVFGGGTKLTVLGSRGGGGSGGG
GSGGGGSLEMAQVQLVESGGGLVQPGGSLRLSCAASGFTFSSYAMSWVRQAPGKGLEWV
SVIYSGGSSTYYADSVKGRFTISRDNSKNTLYLQMNSLRAEDTAVYYCARTSYLNHGDYW
GQGTLVTVSSAAA*VVPVLQKVNSTTTKPVLRTPSPVHPTGTSQPQRPEDCRPRGSVKGTGLDF*
*ACDF*WALVVVAGVLFCYGLLVTVALCVIWT*RKRWQNEKFGVDMPDDYEDENLYEGLNLD*
*DCSMYEDISRGLQGTYQDVGNLHIGDAQLEKP* anti-human PSMA(XENP14484) CAR 79a (SEQ ID NO: 128)

GAGGTTCAACTTGTTCAATCTGGGGCAGAAGTGAAGAAGCCCGGGGCATCTGTGAAAG
TATCATGCAAAACATCCGGCTATACGTTTACCGAATACACCATTCACTGGGTCAGACA
GGCTCCCGGTCAAAGCCTCGAATGGATGGGAAATATTAACCCTAACAATGGCGGAACC
ACATATAATCAGAAATTCCAAGGCCGAGTGACGATAACTGTCGATAAGAGTACGTCCA
CAGCTTACATGGAACTCAGCTCTTTGAGATCCGAAGACACTGCAGTTTATTATTGTGCA
GCTGGATGGAACTTCGACTATTGGGGACAAGGGACTCTTGTTACGGTGTCCAGTGGCA
AACCAGGTAGTGGTAAACCCGGAAGCGGCAAGCCCGGGAGCGGTAAACCTGGTAGCG
ACATCGTCATGACTCAAAGCCCTGACTCACTCGCCGTGAGCCTGGGAGAGCGTGCAAC
GCTATCTTGTCGGGCCTCTCAGGATGTCGGAACTGCTGTAGACTGGTATCAACAGAAA
CCTGACCAATCACCAAAACTCCTGATTTATTGGGCCTCAACACGTCACACAGGAGTGC
CAGATAGGTTCACAGGTAGTGGCAGTGGAACTGATTTTACTTTGACAATTAGCAGCCT
GCAAGCCGAAGATGTAGCCGTTTACTTCTGTCAACAATATAACTCATACCCACTAACG
TTCGGTGCCGGGACGAAGGTAGAGATTAAA*GTGGTCCCCGTGCTGCAGAAAGTTAATAG*
*CACCACCACTAAACCTGTCCTGAGGACTCCTAGTCCAGTGCACCCAACAGGGACCAGTCAG*
*CCACAGAGACCGGAAGACTGCAGACCAAGAGGTTCAGTGAAGGGAACCGGCCTGGATTTCG*
*CCTGCGAT*TTTTGGGCCCTGGTCGTCGTCGCAGGAGTTTTGTTTTGCTATGGACTGCTCG
TCACAGTTGCTTTGTGTGTTATCTGGACA*AGGAAACGGTGGCAAAATGAGAAGTTTGGGG*
*TGGACATGCCAGATGACTATGAAGATGAAAATCTCTATGAGGGCCTGAACCTTGATGACTGTT*
*CTATGTATGAGGACATCTCCAGGGGACTCCAGGGCACCTACCAGGATGTGGGCAACCTCCA*
*CATTGGAGATGCCCAGCTGGAAAAGCCATGA* anti-human PSMA(XENP14484) CAR 79a (SEQ ID NO: 129)

EVQLVQSGAEVKKPGASVKVSCKTSGYTFTEYTIHWVRQAPGQSLEWMGNINPNNGGTT
YNQKFQGRVTITVDKSTSTAYMELSSLRSEDTAVYYCAAGWNFDYWGQGTLVTVSSGKP
GSGKPGSGKPGSGKPGSDIVMTQSPDSLAVSLGERATLSCRASQDVGTAVDWYQQKPDQS
PKLLIYWASTRHTGVPDRFTGSGSGTDFTLTISSLQAEDVAVYFCQQYNSYPLTFGAGTKV
EIK*VVPVLQKVNSTTTKPVLRTPSPVHPTGTSQPQRPEDCRPRGSVKGTGLDFACD*FWALVVV
AGVLFCYGLLVTVALCVIWT*RKRWQNEKFGVDMPDDYEDENLYEGLNLDDCSMYEDISRGL*
*QGTYQDVGNLHIGDAQLEKP* mouse IL 12a-mouse IgG2a Fc (SEQ ID NO: 130)

ATGTGTCAGTCACGCTATCTTCTCTTCCTTGCTACTCTGGCCTTGCTCAATCACTTGTCC
CTTGCTCGTGTGATTCCTGTGTCCGGCCCAGCTAGGTGTCTCTCCCAGTCACGGAATCT
CCTGAAAACCACGGATGACATGGTAAAGACAGCTAGGGAGAAACTCAAGCACTACTC
CTGCACAGCTGAGGATATCGATCATGAGGACATCACCAGGGACCAGACATCCACTCTG
AAAACTTGCCTGCCTTTGGAACTCCACAAGAACGAATCTTGTCTGGCAACGCGTGAAA
CGAGTTCTACTACAAGAGGGTCCTGTCTTCCCCCTCAAAAGACAAGCCTTATGATGAC
CTTGTGTCTCGGTAGCATTTATGAGGACCTAAAGATGTATCAAACCGAGTTTCAGGCTA
TCAATGCAGCGCTCCAGAATCATAACCATCAGCAGATCATTCTTGACAAAGGAATGCT
CGTGGCCATTGATGAACTAATGCAGAGCCTAAACCACAATGGCGAGACTCTTCGACAG
AAACCGCCTGTGGGCGAGGCCGATCCATATAGAGTCAAAATGAAACTGTGTATTCTCC
TGCATGCATTTAGTACTCGTGTAGTGACTATTAACAGAGTGATGGGTTACCTTTCCTCA
GCTCCCAGAGGGCCCACAATCAAGCCCTGTCCTCCATGCAAATGCCCAGCACCTAACC
TCTTGGGTGGACCATCCGTCTTCATCTTCCCTCCAAAGATCAAGGATGTACTCATGATC
TCCCTGAGCCCCATAGTCACATGTGTGGTGGTGGATGTGAGCGAGGATGACCCAGATG
TCCAGATCAGCTGGTTTGTGAACAACGTGGAAGTACACACAGCTCAGACACAAACCCA
TAGAGAGGATTACAACAGTACTCTCCGGGTGGTCAGTGCCCTCCCCATCCAGCACCAG
GACTGGATGAGTGGCAAGGAGTTCAAATGCAAGGTCAACAACAAAGACCTCCCAGCG
CCCATCGAGAGAACCATCTCAAAACCCAAAGGGTCAGTAAGAGCTCCACAGGTATATG
TCTTGCCTCCACCAGAAGAAGAGATGACTAAGAAACAGGTCACTCTGACCTGCATGGT
CACAGACTTCATGCCTGAAGACATTTACGTGGAGTGGACCAACAACGGGAAAACAGA
GCTAAACTACAAGAACACTGAACCAGTCCTGGACTCTGATGGTTCTTACTTCATGTACA
GCAAGCTGAGAGTGGAAAAGAAGAACTGGGTGGAAAGAAATAGCTACTCCTGTTCAG
TGGTCCACGAGGGTCTGCACAATCACCACACGACTAAGAGCTTCTCCCGGACTCCGGG
TAAATAG mouse IL 12a-mouse IgG2a Fc (SEQ ID NO: 131)

MCQSRYLLFLATLALLNHLSLARVIPVSGPARCLSQSRNLLKTTDDMVKTAREKLKHYSC

-continued

TAEDIDHEDITRDQTSTLKTCLPLELHKNESCLATRETSSTTRGSCLPPQKTSLMMTLCLGSI
YEDLKMYQTEFQAINAALQNHNHQQIILDKGMLVAIDELMQSLNHNGETLRQKPPVGEAD
PYRVKMKLCILLHAFSTRVVTINRVMGYLSSAPRGPTIKPCPPCKCPAPNLLGGPSVFIFPPK
IKDVLMISLSPIVTCVVVDVSEDDPDVQISWFVNNVEVHTAQTQTHREDYNSTLRVVSALP
IQHQDWMSGKEFKCKVNNKDLPAPIERTISKPKGSVRAPQVYVLPPPEEEMTKKQVTLTC
MVTDFMPEDIYVEWTNNGKTELNYKNTEPVLDSDGSYFMYSKLRVEKKNWVERNSYSCS
VVHEGLHNHHTTKSFSRTPGK* mouse IL 12b-mouse IgG2a Fc (SEQ ID NO: 132)

ATGTGCCCACAGAAACTCACAATTTCTTGGTTCGCAATCGTCCTGCTGGTGTCACCCCT
GATGGCAATGTGGGAGTTGGAAAAGGATGTATACGTCGTCGAGGTCGACTGGACACCT
GACGCTCCGGGTGAAACTGTCAACCTCACTTGCGATACTCCTGAAGAGGACGACATCA
CGTGGACGAGCGACCAGCGACATGGAGTGATAGGTCTGGCAAGACGCTTACTATCAC
GGTTAAGGAATTTCTCGACGCAGGGCAGTACACATGTCACAAGGGCGGCGAGACTCTG
AGCCACTCCCATTTGCTGCTGCACAAGAAGGAGAATGGTATCTGGTCTACCGAAATCC
TGAAGAATTTTAAGAACAAGACTTTTCTGAAATGCGAGGCCCCAAATTATTCCGGACG
TTTCACTTGCAGTTGGCTCGTTCAAAGAAATATGGACTTGAAATTTAACATTAAATCCA
GCTCTTCATCTCCTGACAGCAGGGCCGTAACTTGTGGAATGGCTTCATTGTCAGCTGAG
AAAGTTACGCTTGACCAAAGGGATTATGAGAAATACAGCGTGAGTTGCCAGGAAGAT
GTGACATGTCCAACGGCAGAGGAAACGTTGCCAATTGAGCTCGCTTTGGAAGCTCGTC
AACAAAACAAGTATGAAAACTATAGTACTAGCTTCTTCATACGGGACATCATCAAACC
AGATCCACCTAAGAATTTGCAGATGAAGCCTCTGAAGAATTCACAAGTCGAGGTATCC
TGGGAATACCCAGATTCATGGTCCACTCCTCATAGTTACTTTAGCCTGAAATTCTTTGT
ACGCATACAGCGGAAGAAGGAGAAAATGAAGGAGACGGAAGAAGGCTGCAATCAGA
AAGGCGCTTTTCTTGTTGAAAAGACGAGCACTGAGGTTCAATGCAAAGGCGGGAATGT
ATGTGTTCAAGCCCAAGATAGGTATTATAATAGCTCCTGCTCTAAGTGGGCTTGCGTAC
CATGCAGAGTTAGAAGTCCCAGAGGGCCCACAATCAAGCCCTGTCCTCCATGCAAATG
CCCAGCACCTAACCTCTTGGGTGGACCATCCGTCTTCATCTTCCCTCCAAAGATCAAGG
ATGTACTCATGATCTCCCTGAGCCCCATAGTCACATGTGTGGTGGTGGATGTGAGCGA
GGATGACCCAGATGTCCAGATCAGCTGGTTTGTGAACAACGTGGAAGTACACACAGCT
CAGACACAAACCCATAGAGAGGATTACAACAGTACTCTCCGGGTGGTCAGTGCCCTCC
CCATCCAGCACCAGGACTGGATGAGTGGCAAGGAGTTCAAATGCAAGGTCAACAACA
AAGACCTCCCAGCGCCCATCGAGAGAACCATCTCAAAACCCAAAGGGTCAGTAAGAG
CTCCACAGGTATATGTCTTGCCTCCACCAGAAGAAGAGATGACTAAGAAACAGGTCAC
TCTGACCTGCATGGTCACAGACTTCATGCCTGAAGACATTTACGTGGAGTGGACCAAC
AACGGGAAAACAGAGCTAAACTACAAGAACACTGAACCAGTCCTGGACTCTGATGGT
TCTTACTTCATGTACAGCAAGCTGAGAGTGGAAAAGAAGAACTGGGTGGAAAGAAAT
AGCTACTCCTGTTCAGTGGTCCACGAGGGTCTGCACAATCACCACACGACTAAGAGCT
TCTCCCGGACTCCGGGTAAATAG mouse IL 12b-mouse IgG2a Fc (SEQ ID NO: 133)

MCPQKLTISWFAIVLLVSPLMAMWELEKDVYVVEVDWTPDAPGETVNLTCDTPEEDDIT
WTSDQRHGVIGSGKTLTITVKEFLDAGQYTCHKGGETLSHSHLLLHKKENGIWSTEILKNF
KNKTFLKCEAPNYSGRFTCSWLVQRNMDLKFNIKSSSSSPDSRAVTCGMASLSAEKVTLD
QRDYEKYSVSCQEDVTCPTAEETLPIELALEARQQNKYENYSTSFFIRDIIKPDPPKNLQMK
PLKNSQVEVSWEYPDSWSTPHSYFSLKFFVRIQRKKEKMKETEEGCNQKGAFLVEKTSTE
VQCKGGNVCVQAQDRYYNSSCSKWACVPCRVRSPRGPTIKPCPPCKCPAPNLLGGPSVFIF
PPKIKDVLMISLSPIVTCVVVDVSEDDPDVQISWFVNNVEVHTAQTQTHREDYNSTLRVVS
ALPIQHQDWMSGKEFKCKVNNKDLPAPIERTISKPKGSVRAPQVYVLPPPEEEMTKKQVTL
TCMVTDFMPEDIYVEWTNNGKTELNYKNTEPVLDSDGSYFMYSKLRVEKKNWVERNSYS
CSVVHEGLHNHHTTKSFSRTPGK mouse IL 12a-mouse IgG2a Fc (Silent)

(SEQ ID NO: 134)

ATGTGTCAGTCACGCTATCTTCTCTTCCTTGCTACTCTGGCCTTGCTCAATCACTTGTCC
CTTGCTCGTGTGATTCCTGTGTCCGGCCCAGCTAGGTGTCTCTCCCAGTCACGGAATCT
CCTGAAAACCACGGATGACATGGTAAAGACAGCTAGGGAGAAACTCAAGCACTACTC
CTGCACAGCTGAGGATATCGATCATGAGGACATCACCAGGGACCAGACATCCACTCTG
AAAACTTGCCTGCCTTTGGAACTCCACAAGAACGAATCTTGTCTGGCAACGCGTGAAA
CGAGTTCTACTACAAGAGGGTCCTGTCTTCCCCCTCAAAAGACAAGCCTTATGATGAC
CTTGTGTCTCGGTAGCATTTATGAGGACCTAAAGATGTATCAAACCGAGTTTCAGGCTA
TCAATGCAGCGCTCCAGAATCATAACCATCAGCAGATCATTCTTGACAAAGGAATGCT
CGTGGCCATTGATGAACTAATGCAGAGCCTAAACCACAATGGCGAGACTCTTCGACAG
AAACCGCCTGTGGGCGAGGCCGATCCATATAGAGTCAAAATGAAACTGTGTATTCTCC
TGCATGCATTTAGTACTCGTGTAGTGACTATTAACAGAGTGATGGGTTACCTTTCCTCA
GCTCCCAGAGGGCCCACAATCAAGCCCTGTCCTCCATGCAAATGCCCAGCACCTAACG
CTGCCGGTGGACCATCCGTCTTCATCTTCCCTCCAAAGATCAAGGATGTACTCATGATC
TCCCTGAGCCCCATAGTCACATGTGTGGTGGTGGATGTGAGCGAGGATGACCCAGATG
TCCAGATCAGCTGGTTTGTGAACAACGTGGAAGTACACACAGCTCAGACACAAACCCA
TAGAGAGGATTACAACAGTACTCTCCGGGTGGTCAGTGCCCTCCCCATCCAGCACCAG
GACTGGATGAGTGGCAAGGAGTTCAAATGCAAGGTCAACAACAAAGACCTCGGAGCG
CCCATCGAGAGAACCATCTCAAAACCCAAAGGGTCAGTAAGAGCTCCACAGGTATATG
TCTTGCCTCCACCAGAAGAAGAGATGACTAAGAAACAGGTCACTCTGACCTGCATGGT
CACAGACTTCATGCCTGAAGACATTTACGTGGAGTGGACCAACAACGGGAAAACAGA
GCTAAACTACAAGAACACTGAACCAGTCCTGGACTCTGATGGTTCTTACTTCATGTACA
GCAAGCTGAGAGTGGAAAAGAAGAACTGGGTGGAAAGAAATAGCTACTCCTGTTCAG
TGGTCCACGAGGGTCTGCACAATCACCACACGACTAAGAGCTTCTCCCGGACTCCGGG
TAAATGA

-continued mouse IL 12a-mouse IgG2a Fc (Silent)

(SEQ ID NO: 135)

MCQSRYLLFLATLALLNHLSLARVIPVSGPARCLSQSRNLLKTTDDMVKTAREKLKHYSC
TAEDIDHEDITRDQTSTLKTCLPLELHKNESCLATRETSSTTRGSCLPPQKTSLMMTLCLGSI
YEDLKMYQTEFQAINAALQNHNHQQIILDKGMLVAIDELMQSLNHNGETLRQKPPVGEAD
PYRVKMKLCILLHAFSTRVVTINRVMGYLSSAPRGPTIKPCPPCKCPAPNAAGGPSVFIFPP
KIKDVLMISLSPIVTCVVVDVSEDDPDVQISWFVNNVEVHTAQTQTHREDYNSTLRVVSAL
PIQHQDWMSGKEFKCKVNNKDLGAPIERTISKPKGSVRAPQVYVLPPPEEEMTKKQVTLT
CMVTDFMPEDIYVEWTNNGKTELNYKNTEPVLDSDGSYFMYSKLRVEKKNWVERNSYSC
SVVHEGLHNHHTTKSFSRTPGK* mouse IL 12b-mouse IgG2a Fc (Silent)

(SEQ ID NO: 136)

ATGTGCCCACAGAAACTCACAATTTCTTGGTTCGCAATCGTCCTGCTGGTGTCACCCCT
GATGGCAATGTGGGAGTTGGAAAAGGATGTATACGTCGTCGAGGTCGACTGGACACCT
GACGCTCCGGGTGAAACTGTCAACCTCACTTGCGATACTCCTGAAGAGGACGACATCA
CGTGGACGAGCGACCAGCGACATGGAGTGATAGGGTCTGGCAAGACGCTTACTATCAC
GGTTAAGGAATTTCTCGACGCAGGGCAGTACACATGTCACAAGGGCGGCGAGACTCTG
AGCCACTCCCATTTGCTGCTGCACAAGAAGGAGAATGGTATCTGGTCTACCGAAATCC
TGAAGAATTTTAAGAACAAGACTTTTCTGAAATGCGAGGCCCCAAATTATTCCGGACG
TTTCACTTGCAGTTGGCTCGTTCAAAGAAATATGGACTTGAAATTTAACATTAAATCCA
GCTCTTCATCTCCTGACAGCAGGGCCGTAACTTGTGGAATGGCTTCATTGTCAGCTGAG
AAAGTTACGCTTGACCAAAGGGATTATGAGAAATACAGCGTGAGTTGCCAGGAAGAT
GTGACATGTCCAACGGCAGAGGAAACGTTGCCAATTGAGCTCGCTTTGGAAGCTCGTC
AACAAAACAAGTATGAAAACTATAGTACTAGCTTCTTCATACGGGACATCATCAAACC
AGATCCACCTAAGAATTTGCAGATGAAGCCTCTGAAGAATTCACAAGTCGAGGTATCC
TGGGAATACCCAGATTCATGGTCCACTCCTCATAGTTACTTTAGCCTGAAATTCTTTGT
ACGCATACAGCGGAAGAAGGAGAAAATGAAGGAGACGGAAGAAGGCTGCAATCAGA
AAGGCGCTTTTCTTGTTGAAAAGACGAGCACTGAGGTTCAATGCAAAGGCGGGAATGT
ATGTGTTCAAGCCCAAGATAGGTATTATAATAGCTCCTGCTCTAAGTGGGCTTGCGTAC
CATGCAGAGTTAGAAGTCCCAGAGGGCCCACAATCAAGCCCTGTCCTCCATGCAAATG
CCCAGCACCTAACGCTGCCGGTGGACCATCCGTCTTCATCTTCCCTCCAAAGATCAAGG
ATGTACTCATGATCTCCCTGAGCCCCATAGTCACATGTGTGGTGGTGGATGTGAGCGA
GGATGACCCAGATGTCCAGATCAGCTGGTTTGTGAACAACGTGGAAGTACACACAGCT
CAGACACAAACCCATAGAGAGGATTACAACAGTACTCTCCGGGTGGTCAGTGCCCTCC
CCATCCAGCACCAGGACTGGATGAGTGGCAAGGAGTTCAAATGCAAGGTCAACAACA
AAGACCTCGGAGCGCCCATCGAGAGAACCATCTCAAAACCCAAAGGGTCAGTAAGAG
CTCCACAGGTATATGTCTTGCCTCCACCAGAAGAAGAGATGACTAAGAAACAGGTCAC
TCTGACCTGCATGGTCACAGACTTCATGCCTGAAGACATTTACGTGGAGTGGACCAAC
AACGGGAAAACAGAGCTAAACTACAAGAACACTGAACCAGTCCTGGACTCTGATGGT
TCTTACTTCATGTACAGCAAGCTGAGAGTGGAAAAGAAGAACTGGGTGGAAAGAAAT
AGCTACTCCTGTTCAGTGGTCCACGAGGGTCTGCACAATCACCACACGACTAAGAGCT
TCTCCCGGACTCCGGGTAAATGA mouse IL 12b-mouse IgG2a Fc (Silent)

(SEQ ID NO: 137)

MCPQKLTISWFAIVLLVSPLMAMWELEKDVYVVEVDWTPDAPGETVNLTCDTPEEDDIT
WTSDQRHGVIGSGKTLTITVKEFLDAGQYTCHKGGETLSHSHLLLHKKENGIWSTEILKNF
KNKTFLKCEAPNYSGRFTCSWLVQRNMDLKFNIKSSSSSPDSRAVTCGMASLSAEKVTLD
QRDYEKYSVSCQEDVTCPTAEETLPIELALEARQQNKYENYSTSFFIRDIIKPDPPKNLQMK
PLKNSQVEVSWEYPDSWSTPHSYFSLKFFVRIQRKKEKMKETEEGCNQKGAFLVEKTSTE
VQCKGGNVCVQAQDRYYNSSCSKWACVPCRVRSPRGPTIKPCPPCKCPAPNAAGGPSVFI
FPPKIKDVLMISLSPIVTCVVVDVSEDDPDVQISWFVNNVEVHTAQTQTHREDYNSTLRVV
SALPIQHQDWMSGKEFKCKVNNKDLGAPIERTISKPKGSVRAPQVYVLPPPEEEMTKKQV
TLTCMVTDFMPEDIYVEWTNNGKTELNYKNTEPVLDSDGSYFMYSKLRVEKKNWVERNS
YSCSVVHEGLHNHHTTKSFSRTPGK

CD3 zeta cytoplasmic domain-human (SEQ ID NO: 138)

RVKFSRSADAPAYQQGQNQLYNELNLGRREEYDVLDKRRGRDPEMGGKPQRRKNPQEGL
YNELQKDKMAEAYSEIGMKGERRRGKGHDGLYQGLSTATKDTYDALHMQALPPR

CD3 zeta cytoplasmic domain-human (SEQ ID NO: 139)

AGAGTGAAGTTCAGCAGGAGCGCAGACGCCCCCGCGTACCAGCAGGGCCAGAACCAG
CTCTATAACGAGCTCAATCTAGGACGAAGAGAGGAGTACGATGTTTTGGACAAGAGAC
GTGGCCGGGACCCTGAGATGGGGGGAAAGCCGCAGAGAAGGAAGAACCCTCAGGAA
GGCCTGTACAATGAACTGCAGAAAGATAAGATGGCGGAGGCCTACAGTGAGATTGGG
ATGAAAGGCGAGCGCCGGAGGGGCAAGGGGCACGATGGCCTTTACCAGGGTCTCAGT
ACAGCCACCAAGGACACCTACGACGCCCTTCACATGCAGGCCCTGCCCCCTCGCTAA pWF-506

(SEQ ID NO: 140)

METDTLLLWVLLLWVPGSTGQSVLTQPPSVSAAPGQRVTISCSGTRSNIGSDYVSWYQHLP
GTAPKLLVYGDNLRPSGIPDRFSASKSGTSATLGITGLQTGDEADYYCGTWDYTLNGVVF
GGGTKLTVLGSRGGGGSGGGGSGGGGSLEMAQVQLVESGGGLVQPGGSLRLSCAASGFT
FSSYAMSWVRQAPGKGLEWVSVIYSGGSSTYYADSVKGRFTISRDNSKNTLYLQMNSLRA
EDTAVYYCARTSYLNHGDYWGQGTLVTVSSPKSCDKTHTCPPCPAPELLGGPSVFLFPPKP
KDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCS

-continued

VMHEALHNHYTQKSLSLSPELQLEESCAEAQDGELDGLWTTITIFITLFLLSVCYSATVTFF
KVKWIFSSVVDLKQTIIPDYRNMIGQGA pWF-506

(SEQ ID NO: 141)

ATGGAAACCGATACACTGCTGCTGTGGGTGCTGCTGCTGTGGGTGCCAGGATCTACCG
GTCAGTCTGTGTTGACGCAGCCGCCCTCAGTGTCTGCGGCCCCAGGACAGAGGGTCAC
CATCTCCTGCTCTGGAACCAGGTCCAACATTGGGAGTGATTATGTTTCCTGGTACCAAC
ACCTCCCAGGAACAGCCCCCAAACTCCTCGTTTATGGCGATAATCTGCGACCCTCAGG
GATTCCTGACCGATTCTCTGCCTCCAAGTCTGGCACGTCAGCCACCCTGGGCATCACCG
GACTCCAGACTGGGGACGAGGCCGATTATTACTGCGGCACATGGGATTACACCCTGAA
TGGTGTGGTGTTCGGCGGAGGGACCAAGCTGACCGTCCTAGGTTCTAGAGGTGGTGGT
GGTAGCGGCGGCGGCGGCTCTGGTGGTGGTGGATCCCTCGAGATGGCCCAGGTGCAGC
TGGTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGG
AAGGGGCTGGAGTGGGTCTCAGTTATTTATAGCGGTGGTAGTAGCACATACTATGCAG
ACTCCGTGAAGGGCCGGTTCACCATCTCCAGAGATAATTCCAAGAACACGCTGTATCT
GCAAATGAACAGCCTGAGAGCCGAGGACACGGCCGTATATTACTGTGCGCGCACTTCT
TACCTGAACCATGGTGATTACTGGGGTCAAGGTACTCTGGTGACCGTGTCTAGCCCCA
AGAGCTGCGACAAGACCCACACCTGCCCCCCCTGCCCAGCCCCAGAGCTGCTGGGCGG
ACCCTCCGTGTTCCTGTTCCCCCCCAAGCCCAAGGACACCCTGATGATCAGCAGGACC
CCCGAGGTGACCTGCGTGGTGGTGGACGTGAGCCACGAGGACCCAGAGGTGAAGTTC
AACTGGTACGTGGACGGCGTGGAGGTGCACAACGCCAAGACCAAGCCCAGAGAGGAG
CAGTACAACAGCACCTACAGGGTGGTGTCCGTGCTGACCGTGCTGCACCAGGACTGGC
TGAACGGCAAGGAATACAAGTGCAAGGTCTCCAACAAGGCCCTGCCAGCCCCCATCG
AAAAGACCATCAGCAAGGCCAAGGGCCAGCCACGGGAGCCCCAGGTGTACACCCTGC
CCCCCTCCCGGGAGGAGATGACCAAGAACCAGGTGTCCCTGACCTGTCTGGTGAAGGG
CTTCTACCCCAGCGACATCGCCGTGGAGTGGGAGAGCAACGGCCAGCCCGAGAACAA
CTACAAGACCACCCCCCCAGTGCTGGACAGCGACGGCAGCTTCTTCCTGTACAGCAAG
CTGACCGTGGACAAGTCCAGGTGGCAGCAGGGCAACGTGTTCAGCTGCAGCGTGATGC
ACGAGGCCCTGCACAACCACTACACCCAGAAGAGCCTGAGCCTGTCCCCCGAGCTGCA
ACTGGAGGAGAGCTGTGCGGAGGCGCAGGACGGGGAGCTGGACGGGCTGTGGACGAC
CATCACCATCTTCATCACACTCTTCCTGTTAAGCGTGTGCTACAGTGCCACCGTCACCT
TCTTCAAGGTGAAGTGGATCTTCTCCTCGGTGGTGGACCTGAAGCAGACCATCATCCCC
GACTACAGGAACATGATCGGACAGGGGGCCTGA pWF-507:

(SEQ ID NO: 142)

METDTLLLWVLLLWVPGSTGQSVLTQPPSVSAAPGQRVTISCSGTRSNIGSDYVSWYQHLP
GTAPKLLVYGDNLRPSGIPDRFSASKSGTSATLGITGLQTGDEADYYCGTWDYTLNGVVF
GGGTKLTVLGQPKANPTVTLFPPSSEELQANKATLVCLISDFYPGAVTVAWKADGSPVKA
GVETTKPSKQSNNKYAASSYLSLTPEQWKSHRSYSCQVTHEGSTVEKTVAPTECS pWF-507:

(SEQ ID NO: 143)

ATGGAAACCGATACACTGCTGCTGTGGGTGCTGCTGCTGTGGGTGCCAGGATCTACCG
GTCAGTCTGTGTTGACGCAGCCGCCCTCAGTGTCTGCGGCCCCAGGACAGAGGGTCAC
CATCTCCTGCTCTGGAACCAGGTCCAACATTGGGAGTGATTATGTTTCCTGGTACCAAC
ACCTCCCAGGAACAGCCCCCAAACTCCTCGTTTATGGCGATAATCTGCGACCCTCAGG
GATTCCTGACCGATTCTCTGCCTCCAAGTCTGGCACGTCAGCCACCCTGGGCATCACCG
GACTCCAGACTGGGGACGAGGCCGATTATTACTGCGGCACATGGGATTACACCCTGAA
TGGTGTGGTGTTCGGCGGAGGGACCAAGCTGACCGTCCTAGGTCAGCCCAAGGCCAAC
CCCACTGTCACTCTGTTCCCGCCCTCCTCTGAGGAGCTCCAAGCCAACAAGGCCACACT
AGTGTGTCTGATCAGTGACTTCTACCCGGGAGCTGTGACAGTGGCCTGGAAGGCAGAT
GGCAGCCCCGTCAAGGCGGGAGTGGAGACCACCAAACCCTCCAAACAGAGCAACAAC
AAGTACGCGGCCAGCAGCTACCTGAGCCTGACGCCCGAGCAGTGGAAGTCCCACAGA
AGCTACAGCTGCCAGGTCACGCATGAAGGGAGCACCGTGGAGAAGACAGTGGCCCCT
ACAGAATGTTCATAG pWF-508:

(SEQ ID NO: 144)

MVFTPQILGLMLFWISASRGQVQLVESGGGLVQPGGSLRLSCAASGFTFSSYAMSWVRQA
PGKGLEWVSVIYSGGSSTYYADSVKGRFTISRDNSKNTLYLQMNSLRAEDTAVYYCARTS
YLNHGDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPELQLEESCAEAQDGELD
GLWTTITIFITLFLLSVCYSATVTFFKVKWIFSSVVDLKQTIIPDYRNMIGQGA pWF-508:

(SEQ ID NO: 145)

ATGGTGTTTACACCGCAAATATTGGGGCTCATGCTTTTCTGGATCAGTGCAAGCAGGG
GACAGGTGCAGCTGGTGGAGTCTGGGGGAGGCTTGGTACAGCCTGGGGGGTCCCTGA
GACTCTCCTGTGCAGCCTCTGGATTCACCTTTAGCAGCTATGCCATGAGCTGGGTCCGC
CAGGCTCCAGGGAAGGGGCTGGAGTGGGTCTCAGTTATTTATAGCGGTGGTAGTAGCA
CATACTATGCAGACTCCGTGAAGGGCCGGTTCACCATCTCCAGAGATAATTCCAAGAA
CACGCTGTATCTGCAAATGAACAGCCTGAGAGCCGAGGACACGGCCGTATATTACTGT
GCGCGCACTTCTTACCTGAACCATGGTGATTACTGGGGTCAAGGTACTCTGGTGACCGT
GTCTAGCGCCTCCACCAAGGGCCCATCGGTCTTCCCCCTGGCACCCTCCTCCAAGAGCA

-continued

```
CCTCTGGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTT
GGGCACCCAGACCTACATCTGCAACGTGAACCACAAGCCCAGCAACACCAAGGTGGA
CAAGAGAGTGGAGCCCAAGAGCTGCGACAAGACCCACACCTGCCCCCCCTGCCCAGC
CCCAGAGCTGCTGGGCGGACCCTCCGTGTTCCTGTTCCCCCCCAAGCCCAAGGACACC
CTGATGATCAGCAGGACCCCCGAGGTGACCTGCGTGGTGGTGGACGTGAGCCACGAG
GACCCAGAGGTGAAGTTCAACTGGTACGTGGACGGCGTGGAGGTGCACAACGCCAAG
ACCAAGCCCAGAGAGGAGCAGTACAACAGCACCTACAGGGTGGTGTCCGTGCTGACC
GTGCTGCACCAGGACTGGCTGAACGGCAAGGAATACAAGTGCAAGGTCTCCAACAAG
GCCCTGCCAGCCCCCATCGAAAAGACCATCAGCAAGGCCAAGGGCCAGCCACGGGAG
CCCCAGGTGTACACCCTGCCCCCCTCCCGGGAGGAGATGACCAAGAACCAGGTGTCCC
TGACCTGTCTGGTGAAGGGCTTCTACCCCAGCGACATCGCCGTGGAGTGGGAGAGCAA
CGGCCAGCCCGAGAACAACTACAAGACCACCCCCCCAGTGCTGGACAGCGACGGCAG
CTTCTTCCTGTACAGCAAGCTGACCGTGGACAAGTCCAGGTGGCAGCAGGGCAACGTG
TTCAGCTGCAGCGTGATGCACGAGGCCCTGCACAACCACTACACCCAGAAGAGCCTGA
GCCTGTCCCCCGAGCTGCAACTGGAGGAGAGCTGTGCGGAGGCGCAGGACGGGGAGC
TGGACGGGCTGTGGACGACCATCACCATCTTCATCACACTCTTCCTGTTAAGCGTGTGC
TACAGTGCCACCGTCACCTTCTTCAAGGTGAAGTGGATCTTCTCCTCGGTGGTGGACCT
GAAGCAGACCATCATCCCCGACTACAGGAACATGATCGGACAGGGGGCCTGA
```

pWF-509:

(SEQ ID NO: 146)

```
METDTLLLWVLLLWVPGSTGQSVLTQPPSVSAAPGQRVTISCSGTRSNIGSDYVSWYQHLP
GTAPKLLVYGDNLRPSGIPDRFSASKSGTSATLGITGLQTGDEADYYCGTWDYTLNGVVF
GGGTKLTVLGSRGGGGSGGGGSGGGGSLEMAQVQLVESGGGLVQPGGSLRLSCAASGFT
FSSYAMSWVRQAPGKGLEWVSVIYSGGSSTYYADSVKGRFTISRDNSKNTLYLQMNSLRA
EDTAVYYCARTSYLNHGDYWGQGTLVTVSSAAAFVPVFLPAKPTTTPAPRPPTPAPTIASQ
PLSLRPEACRPAAGGAVHTRGLDFACDFWVLVVVGGVLACYSLLVTVAFIIFWVLDKDDS
KAGMEEDHTYEGLDIDQTATYEDIVTLRTGEVKWSVGEHPGQE
```

pWF-509:

(SEQ ID NO: 147)

```
ATGGAAACCGATACACTGCTGCTGTGGGTGCTGCTGCTGTGGGTGCCAGGATCTACCG
GTCAGTCTGTGTTGACGCAGCCGCCCTCAGTGTCTGCGGCCCCAGGACAGAGGGTCAC
CATCTCCTGCTCTGGAACCAGGTCCAACATTGGGAGTGATTATGTTTCCTGGTACCAAC
ACCTCCCAGGAACAGCCCCCAAACTCCTCGTTTATGGCGATAATCTGCGACCCTCAGG
GATTCCTGACCGATTCTCTGCCTCCAAGTCTGGCACGTCAGCCACCCTGGGCATCACCG
GACTCCAGACTGGGGACGAGGCCGATTATTACTGCGGCACATGGGATTACACCCTGAA
TGGTGTGGTGTTCGGCGGAGGGACCAAGCTGACCGTCCTAGGTTCTAGAGGTGGTGGT
GGTAGCGGCGGCGGCGGCTCTGGTGGTGGTGGATCCCTCGAGATGGCCCAGGTGCAGC
TGGTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGG
AAGGGGCTGGAGTGGGTCTCAGTTATTTATAGCGGTGGTAGTAGCACATACTATGCAG
ACTCCGTGAAGGGCCGGTTCACCATCTCCAGAGATAATTCCAAGAACACGCTGTATCT
GCAAATGAACAGCCTGAGAGCCGAGGACACGGCCGTATATTACTGTGCGCGCACTTCT
TACCTGAACCATGGTGATTACTGGGGTCAAGGTACTCTGGTGACCGTGTCTAGCGCCG
CTGCATTCGTGCCTGTGTTCCTCCCAGCTAAGCCCACTACCACCCCCGCTCCAAGGCCG
CCCACGCCCGCTCCTACTATTGCTAGTCAGCCTTTAAGTTTACGACCCGAAGCTTGCAG
GCCCGCCGCCGGCGGCGCTGTGCACACCAGGGGGCTTGATTTTGCCTGCGACTTTTGG
GTATTGGTAGTGGTGGGCGGAGTTTTAGCCTGCTACAGCCTCCTGGTAACAGTGGCTTT
TATCATCTTTTGGGTGCTGGACAAGGATGACAGCAAGGCTGGCATGGAGGAAGATCAC
ACCTACGAGGGCCTGGACATTGACCAGACAGCCACCTATGAGGACATAGTGACGCTGC
GGACAGGGGAAGTGAAGTGGTCTGTAGGTGAGCACCCAGGCCAGGAGTGA
```

pWF-510:

(SEQ ID NO: 148)

```
METDTLLLWVLLLWVPGSTGQSVLTQPPSVSAAPGQRVTISCSGTRSNIGSDYVSWYQHLP
GTAPKLLVYGDNLRPSGIPDRFSASKSGTSATLGITGLQTGDEADYYCGTWDYTLNGVVF
GGGTKLTVLGSRGGGGSGGGGSGGGGSLEMAQVQLVESGGGLVQPGGSLRLSCAASGFT
FSSYAMSWVRQAPGKGLEWVSVIYSGGSSTYYADSVKGRFTISRDNSKNTLYLQMNSLRA
EDTAVYYCARTSYLNHGDYWGQGTLVTVSSAAAFVPVFLPAKPTTTPAPRPPTPAPTIASQ
PLSLRPEACRPAAGGAVHTRGLDFACDFWVLVVVGGVLACYSLLVTVAFIIFWVRKRWQ
NEKLGLDAGDEYEDENLYEGLNLDDCSMYEDISRGLQGTYQDVGSLNIGDVQLEKP
```

pWF-510:

(SEQ ID NO: 149)

```
ATGGAAACCGATACACTGCTGCTGTGGGTGCTGCTGCTGTGGGTGCCAGGATCTACCG
GTCAGTCTGTGTTGACGCAGCCGCCCTCAGTGTCTGCGGCCCCAGGACAGAGGGTCAC
CATCTCCTGCTCTGGAACCAGGTCCAACATTGGGAGTGATTATGTTTCCTGGTACCAAC
ACCTCCCAGGAACAGCCCCCAAACTCCTCGTTTATGGCGATAATCTGCGACCCTCAGG
GATTCCTGACCGATTCTCTGCCTCCAAGTCTGGCACGTCAGCCACCCTGGGCATCACCG
GACTCCAGACTGGGGACGAGGCCGATTATTACTGCGGCACATGGGATTACACCCTGAA
TGGTGTGGTGTTCGGCGGAGGGACCAAGCTGACCGTCCTAGGTTCTAGAGGTGGTGGT
GGTAGCGGCGGCGGCGGCTCTGGTGGTGGTGGATCCCTCGAGATGGCCCAGGTGCAGC
TGGTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGG
AAGGGGCTGGAGTGGGTCTCAGTTATTTATAGCGGTGGTAGTAGCACATACTATGCAG
ACTCCGTGAAGGGCCGGTTCACCATCTCCAGAGATAATTCCAAGAACACGCTGTATCT
GCAAATGAACAGCCTGAGAGCCGAGGACACGGCCGTATATTACTGTGCGCGCACTTCT
TACCTGAACCATGGTGATTACTGGGGTCAAGGTACTCTGGTGACCGTGTCTAGCGCCG
```

-continued

```
CTGCATTCGTGCCTGTGTTCCTCCCAGCTAAGCCCACTACCACCCCCGCTCCAAGGCCG
CCCACGCCCGCTCCTACTATTGCTAGTCAGCCTTTAAGTTTACGACCCGAAGCTTGCAG
GCCCGCCGCCGGCGGCGCTGTGCACACCAGGGGGCTTGATTTTGCCTGCGACTTTTGG
GTATTGGTAGTGGTGGGCGGAGTTTTAGCCTGCTACAGCCTCCTGGTAACAGTGGCTTT
TATCATCTTTTGGGTGAGGAAACGATGGCAGAACGAGAAGCTCGGGTTGGATGCCGGG
GATGAATATGAAGATGAAAACCTTTATGAAGGCCTGAACCTGGACGACTGCTCCATGT
ATGAGGACATCTCCCGGGGCCTCCAGGGCACCTACCAGGATGTGGGCAGCCTCAACAT
AGGAGATGTCCAGCTGGAGAAGCCGTGA
```

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The following examples, including the experiments conducted and results achieved, are provided for illustrative purposes only and are not to be construed as limiting the present invention.

EXAMPLES

Example 1—Chimeric Antigen Receptor for B Cells (CAR-B) Constructs to Bind PSMA DNA Constructs. Exemplary CAR-B constructs were designed to recognize Prostate Specific Membrane Antigen ("PSMA"). PSMA is an antigen that is expressed more highly on prostate cancer cells than on other non-cancerous cells. Various construct were made comprising an extracellular domain that comprised an scFv specific for PSMA, an extracellular hinge region from CD8, a CD28 transmembrane domain, and various intracellular signaling domains. A list of the constructs is provided in Table 6:

TABLE 6

| Construct | Description |
|---|---|
| pWF-82 | pTLPW-SFFV-XENP14484 scFv-hCD8H-hCD28M-hCD19E (SEQ ID NOS. 39 and 40) |
| pWF-83 | pTLPW-SFFV-XENP14484 scFv-hCD8H-hCD28M-hCD40E (SEQ ID NOS. 41 and 42) |
| pWF-84 | pTLPW-SFFV-XENP14484 scFv-hCD8H-hCD28M-h(CD40 + CD79b)E (SEQ ID NOS. 43 and 44) |
| pWF-85 | pTLPW-SFFV-XENP14484 scFv-hCD8H-hCD28M-h(CD40 + CD137)E (SEQ ID NOS. 45 and 46) |
| pWF-86 | pTLPW-SFFV-XENP14484 scFv-hCD8H-hCD28M-h(CD40 + Fcγr2a)E (SEQ ID NOS. 47) |
| pWF-87 | TLPW-SFFV-XENP14484 scFv-hCD8H-hCD28M-h(hMyd88 + CD40)E (SEQ ID NOS. 48 and 49) |
| pWF-88 | pTLPW-SFFV-XENP14484 scFv-hCD8H-hCD28M-hCD79aE (SEQ ID NOS. 50 and 51) |
| pWF-89 | pTLPW-SFFV-XENP14484 scFv-hCD8H-hCD28M-hCD79bE (SEQ ID NOS. 52 and 53) |

Figure 5:
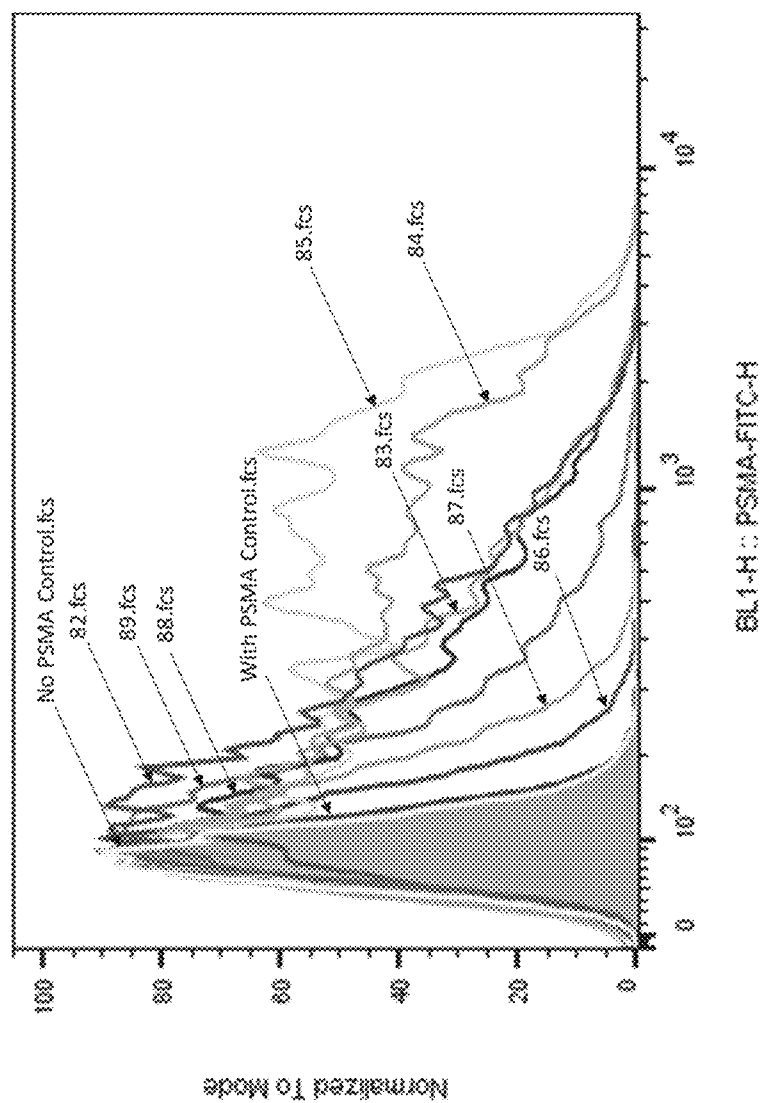
FIG. 5 sets forth expression of various anti-PSMA CARs on the surface of HEK-293 cells.

Expression of anti-PSMA CAR-B on HEK-293 Cells. The constructs encoding pWF82 to pWF89 were used to prepare lentivirus in Lentix cells using the Takara lentivirus preparation kit. Expression of the various CAR-B constructs was measured using flow cytometry using antibodies specific for PSMA (biotin-PSMA, Sinobiological and is depicted in FIG. 5.

Expression of anti-PSMA CAR-B in Human B Cells. To measure expression and binding of anti-PSMA CAR-B's in B cells, two additional constructs were made:

TABLE 7

| Construct | Description |
|---|---|
| pWF-391 | pMMLV(LTR)-hEF1a promoter-anti hPSMA(XENP14484)-CBCR (SEQ ID NOS. 54 and 55) |
| pWF-394 | MMLV(LTR)-hEF1a promoter-anti sarcoglycan CBCR1 (SEQ ID NOS. 56 and 57) |

A MMLV based vector was used for the preparation of the retrovirus. The retrovirus was used to infect mouse B cells isolated from the spleen. After transduction, B cells were further expanded on feeder cells expressing CD40L and soluble IL-4. The expression of anti-PSMA CAR-B was detected by using recombinant biotin-PSMA. PE-labeled streptavidin was used to detect PSMA binding in HEK-293 cells.

Figure 6C:
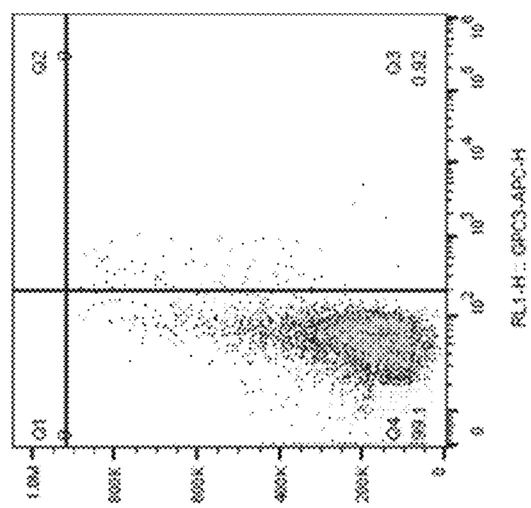
FIGS. 6A-6C set forth a FACS Plot illustrating interrogation of binding of anti-PSMA CAR and of anti-sarcoglycan CAR to PSMA. B cells expressing anti-PSMA CAR-B constructs pWF396 and pWF397 bound PSMA whereas the B cells expressing pWF398 (anti-sarcoglycan CAR-B) did not bind PSMA.
Figure 6B:
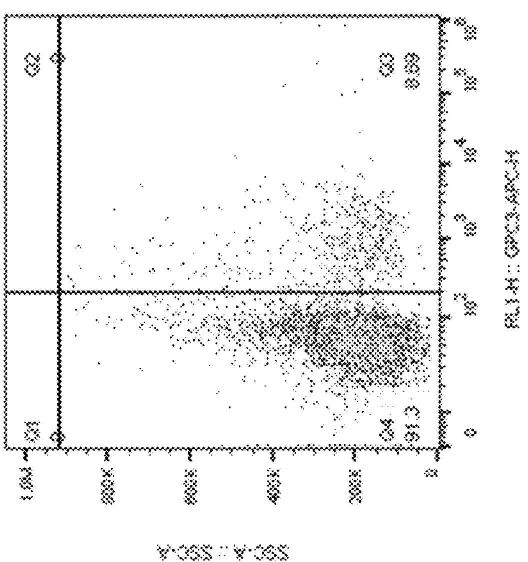
Figure 6A:
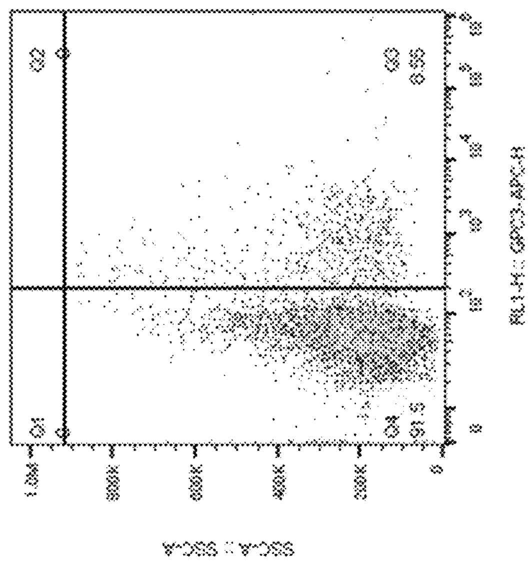
Figure 7:
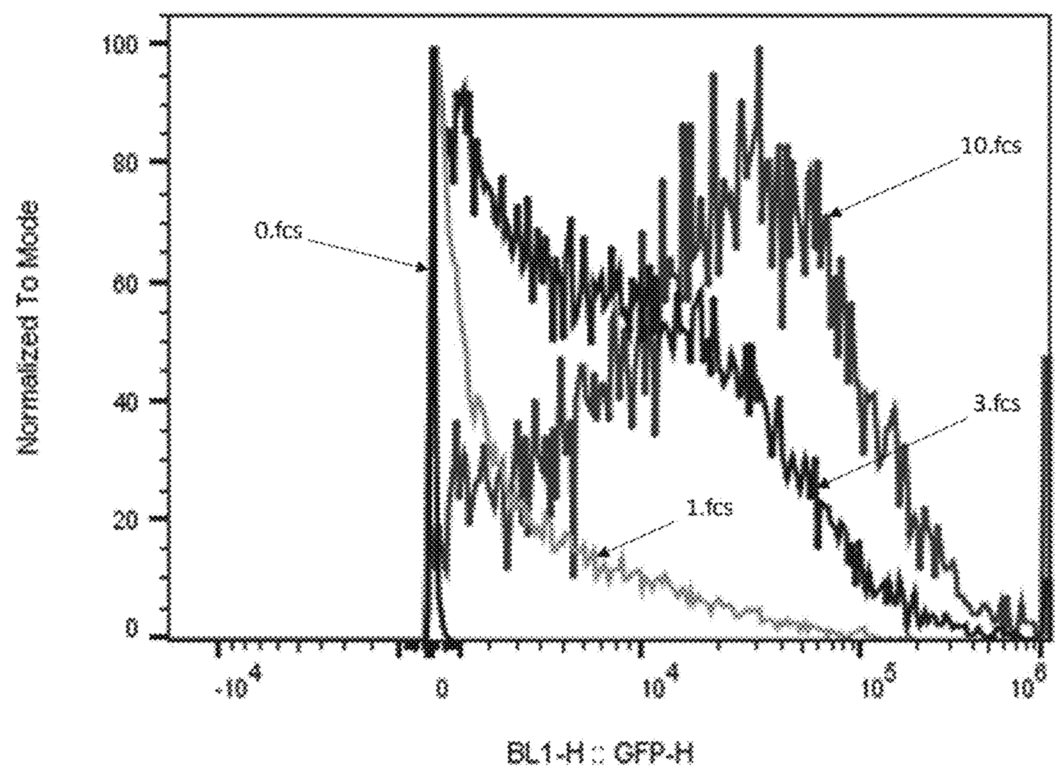
FIG. 7 illustrates the ability of adenovirus F35 encoding GFP to transduce human B cells. Human B cells were isolated from peripheral blood. The B cells were infected with adenovirus encoding GFP. 0, 1, 3, 10 ul, representing the microliter volume of the adenovirus preparation used to infect human B cells. The titer of the adenovirus preparations were approximately $1\times e^{12}$ particles/ml.

Results. The results of this experiment are depicted in FIG. 6 and demonstrate that it is possible to create mouse B cell that expresses a CAR-B that can bind with specificity to an antigen. For example, B cells expressing pWF396 or pWF397 bound to PSMA whereas the B cells expressing pWF394 did not bind PSMA pWF398 was designed to bind sarcoglycan not PSMA).

Example 2—Chimeric Antigen Receptor on B Cells (CAR-B) Constructs to Bind GPC3

DNA Construct. Exemplary CAR constructs were designed to recognize glypican-3 (GPC-3). Glypican-3 is expressed on hepatocellular carcinoma cells among other tumor types, but not on most non-cancer cells. GPC3 can be used to target an anti-GPC3 CAR to hepatocellular carcinoma, as well as other cancers in which GPC3 is expressed (e.g. ovarian clear cell carcinoma, pediatric cancers, lung cancers (i.e. lung adenocarcinoma and lung squamous cell carcinoma), urothelial carcinoma, thyroid cancer, gastric cancer, and others). Various construct were made comprising an extracellular domain that comprised an scFv specific for GPC-3, an extracellular hinge region from CD8, a CD28 transmembrane domain, and various intracellular signaling domains. An additional anti-PSMA CAR-B was constructed as a control for these experiments. A list of the constructs is provided in Table 8.

TABLE 8

| Construct | Description |
|---|---|
| pWF-396 | pMMLV(LTR)-hEF1a promoter-anti-GPC3 scFv-hCD8H-hCD28M-hCD79aE (SEQ ID NOS. 58 and 59) |
| pWF-397 | MMLV(LTR)-hEF1a promoter-anti-GPC3 scFv-hCD8H-hCD28M-hCD79bE (SEQ IDNOS. 60 and 61) |
| pWF-398 | pMMLV(LTR)-hEF1a promoter-anti-hPSMA(XENP14484) scFv-hCD8H-hCD28M-hCD79aE (SEQ ID NOS. 62 and 63) |

Expression of anti-GPC-3 on HEK-293 Cell. Lentiviral transductions were used to express GPC3 CAR-B proteins on the surface of HEK293 cells. Expression was determined by flow cytometry with an anti-idiotype antibody specific for GPC-3 (Eureka Therapeutics).

Expression of anti-GPC-3 CAR-B in Human B Cells. pWF 396, 397 and 398 encoding CAR constructs were used to prepare MMLV retrovirus. This retrovirus was used to transduce mouse B cells isolated by negative selection (Stem Cell Technologies) and activated for 24 hours by co-culture with HeLa cells expressing CD40L and the addition of soluble IL-4. 48 hours post-transduction, expression was confirmed using flow cytometry. The expression of the CAR-B was detected using an anti-idiotype antibody against human GPC3. The anti-idiotype antibody was obtained from Eureka Therapeutics.

Results. Mouse B cells expressing anti-GPC-3 CAR-Bs, pWF-396 and 397, were expressed and specifically bound by anti-GPC3 idiotype antibody.

Example 3—Adenovirus Variant F35 Expressing GFP

Adenovirus variant F35 expressing GFP was demonstrated to efficiently infect human B cells. Human B cells were isolated from the peripheral blood. The B cells were infected with adenovirus encoding GFP at volumes of 0, 1, 3, 10 μL. The titer of the adenovirus preparations were approximately $1\times e^{12}$ particles/ml.

Example 4—Delivering Payloads to Tumor Cells

Figure 8:
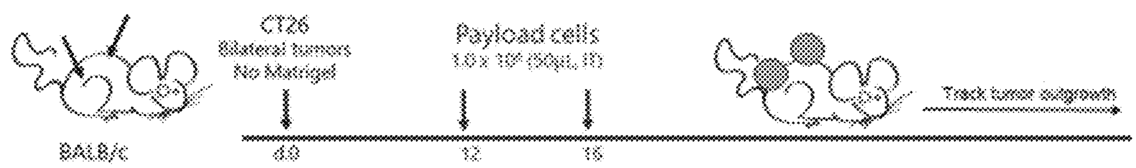
FIG. 8 describes an experiment where BALB/c mice were injected with CT26 bilateral tumors at day zero. At day 12 and day 16, tumor-bearing mice were injected intra-tumorally with payload-expressing cells at a volume of $10^6$ in 50 μL.

A large screening study was conducted to examine the effect of payloads on NIH3T3 fibroblasts in a CT26 Model. Payloads included various immunomodulators, including cytokines and chemokines. First, BALB/c mice were injected with CT26 tumors into their left and right flank. See FIG. 8. Twelve and sixteen days later, mice were injected into the right flank tumor, with various combinations of 4-5 payloads. Tumor volume was measured for up to 35 days.

Generation of the BALB/C CT26 tumor model. A total of 139 mice were injected with CT26 tumors into their left and right flanks.

Selection of Payload. Twelve peptides were identified for their potential to (i) recruit and activate dendritic cells; (ii) initiate homing and guidance of dendritic cells and T cells into the tumor site; and (iii) activate effector T cells. The payloads screened are listed in Table 9.

TABLE 9

| Payload | SEQ ID NO. |
|---|---|
| FLT3L | 70, 71 |
| XCL1 | 72, 73 |
| TIM4-Fc | 74, 75 |
| CXCL13 | 68, 69 |
| mCCL21 | 92, 93 |
| mCD80 - membrane bound | 86, 87 |
| mCD40L - membrane bound | 88, 89 |
| mIFNa A2 | 84, 85 |
| mIL-12 | 80, 81 |
| mIL-21 | 90, 91 |
| mLIGHT mutant | 78, 79 |
| M4-1BBL-membrane bound | 76, 77 |
| mIL-15 | 124, 125 |

Each was either given a combination of 4-5 payloads, all 12 payloads, or 3T3 cells (without payload) or saline as a control. In total, there were twenty-seven groups (n=5 mice/group). The experimental groups are identified in Table 10.

TABLE 10

| Group # | Treatment |
|---|---|
| 1 | FLT3L, XCL1, CXCL13, TIM4-Fc, TLR |
| 2 | FLT3L, XCL1, CXCL13, CD80-MB |
| 3 | FLT3L, XCL1, CXCL13, CD40L-MB, TLR |
| 4 | FLT3L, XCL1, CXCL13, IL-12 and TM |
| 5 | FLT3L, XCL1, CXCL13, 4-1BBL-MB |
| 6 | FLT3L, XCL1, CXCL13, IFNa A2 |
| 7 | FLT3L, XCL1, LIGHT, TIM4-Fc |
| 8 | FLT3L, XCL1, LIGHT, CD80-MB |
| 9 | FLT3L, XCL1, LIGHT, CD40L-MB, TLR |
| 10 | FLT3L, XCL1, LIGHT, IL-12 and TM |
| 11 | FLT3L, XCL1, LIGHT, 4-1BBL-MB |
| 12 | FLT3L, XCL1, LIGHT, IFNa A2 |
| 13 | FLT3L, XCL1, IL-21, TIM4-Fc |
| 14 | FLT3L, XCL1, IL-21, CD80-MB |
| 15 | FLT3L, XCL1, IL-21, CD40L-MB |
| 16 | FLT3L, XCL1, IL-21, IL-12 and TM |
| 17 | FLT3L, XCL1, IL-21, 4-1BBL-MB |
| 18 | FLT3L, XCL1, IL-21, IFNa A2 |
| 19 | FLT3L, XCL1, CCL21, TIM4-Fc |
| 20 | FLT3L, XCL1, CCL21, CD80-MB |
| 21 | FLT3L, XCL1, CCL21, CD40L-MB |
| 22 | FLT3L, XCL1, CCL21, IL-12 and TM |
| 23 | FLT3L, XCL1, CCL21, 4-1BBL-MB |
| 24 | FLT3L, XCL1, CCL21, IFNa A2 |
| 25 | All Payloads |
| 26 | Saline |
| 27 | 3t3 cells (no payload) |

Dosing. Tumor volume was between 100 $mm^3$ and 150 $mm^3$ at the time of the first injection. For the groups receiving 4 payloads, each pay load was delivered at $2.5\times10^5$ cells per injection for a total of $10^6$ cells. For the groups receiving 5 payloads, each pay load was delivered at [x] cells per injection for a total of $3\times10^6$ cells. The fifth payload was co-administered with Poly(I:C), which is a ds-RNA analog. Payloads were administered by intra-tumor injection. The volume of administration was 50 HI, for all groups except the poly (I:C) group and the large 12-way group, where the volume was 150 μL.

Payload Administration Procedures. Cells were harvested with versene (not in the presences of trypsin). Once collected, the cells were counted, spun and resuspended in a volume that could be adjusted to $20\times10^6$/ml after the cells are recounted. TLR agonist (Invivogen Cat #ODN:1826) by resuspending lyophilized powder in water provided. TLR agonist was resuspended at 10 mg/ml and heated to 70 deg C. and then let to sit at RT for 1 hour prior to using. The dose of TLR agonist is 50 μg in 50 μl.

Figure 9:
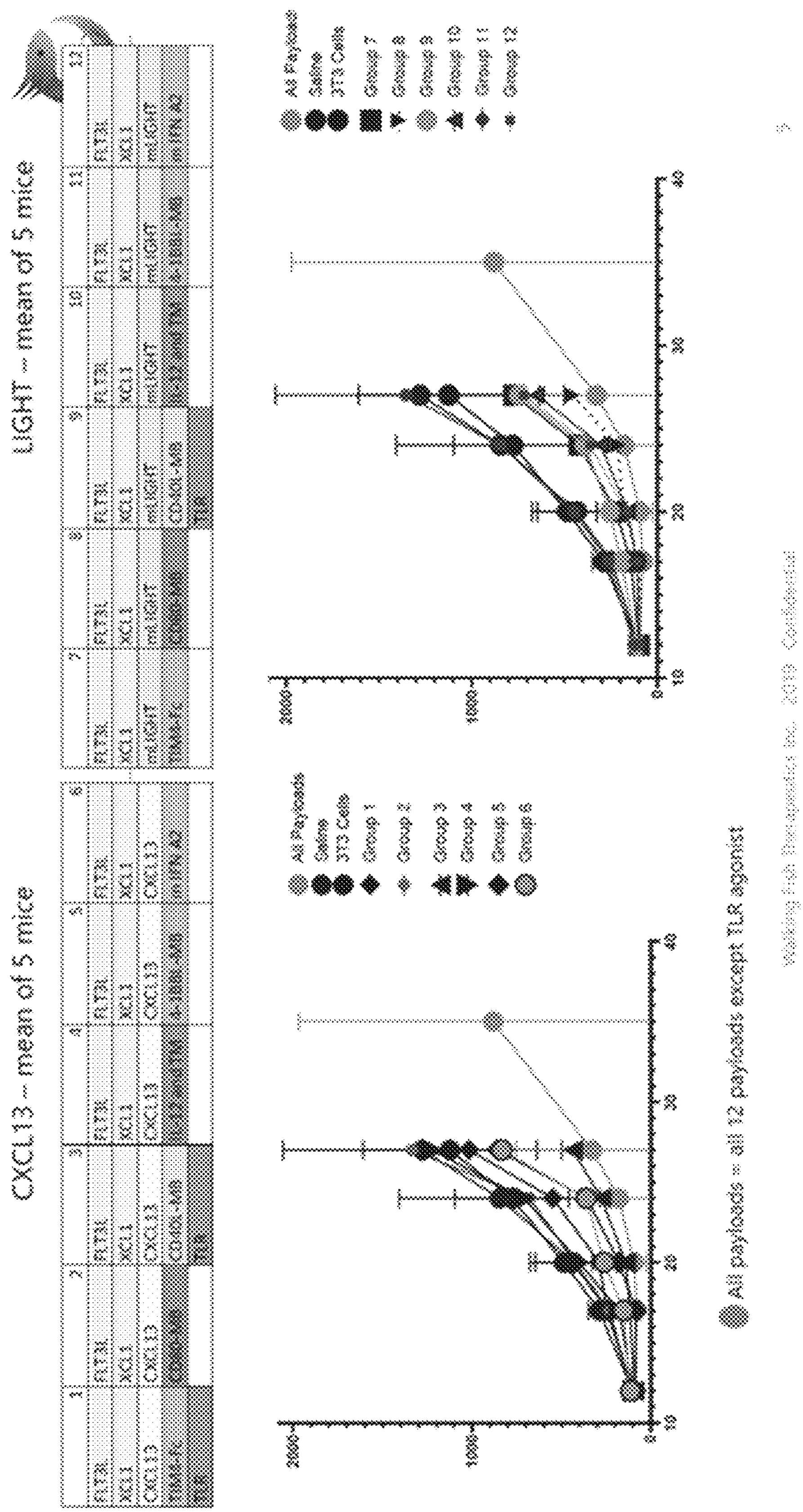
FIG. 9 illustrates the effect of 12 different combinations of payloads injected intra-tumorally on tumor volume over 30-35 days as compared to saline and 3T3 cells (without a payload).
Figure 10:
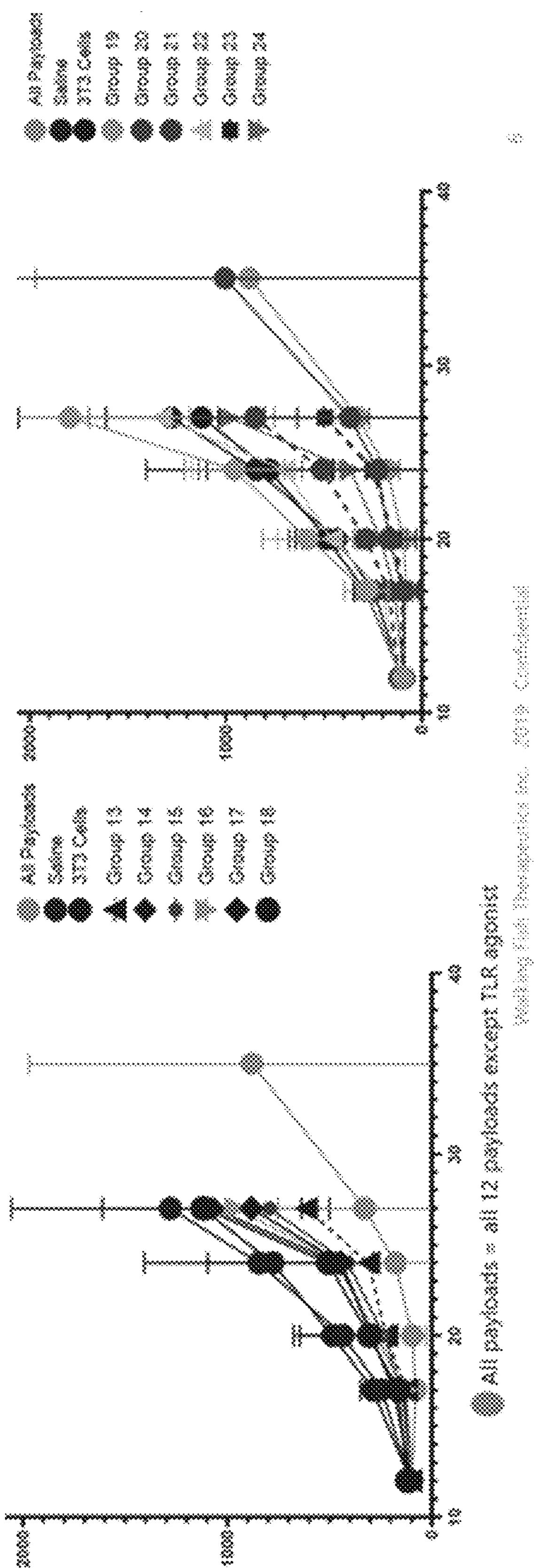
FIG. 10 illustrates the effect of 12 different combinations of payloads injected intra-tumorally on tumor volume over 30-35 days as compared to saline and 3T3 cells (without a payload).
Figure 11C:
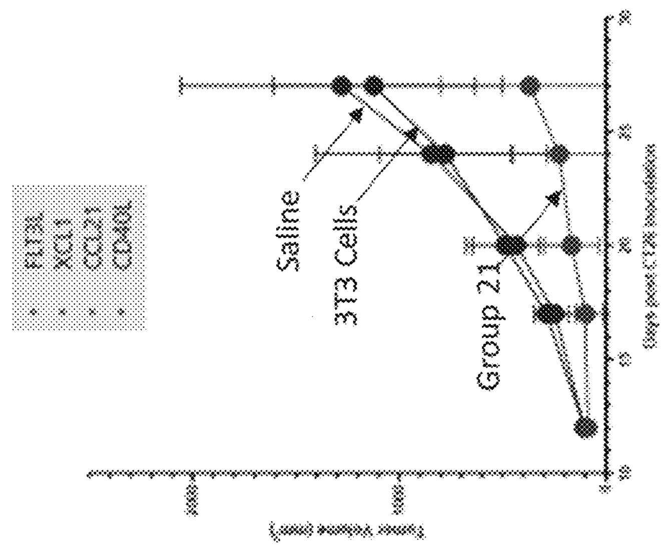
FIGS. 11A-11C illustrate the effect of the top three combinations of payloads injected intra-tumorally on tumor volume over 30 days as compared to saline and 3T3 cells (without a payload).
Figure 11B:
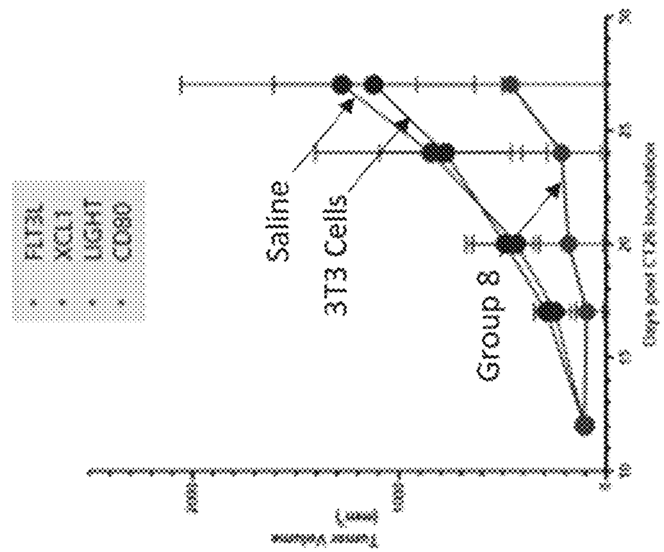
Figure 11A:
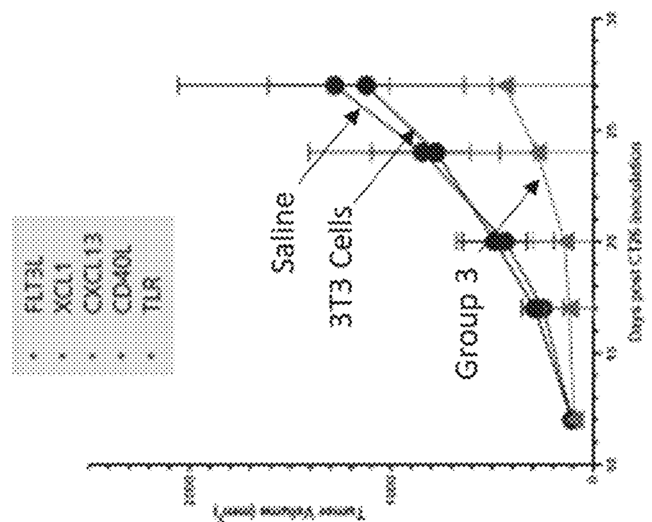

Results. The results are depicted in FIGS. 9-11. Several combinations of payloads injected ipsilaterally demonstrated antitumor activity in the contralateral tumors manifested as delayed tumor growth in this model. Groups 3, 8 and 21 showed the most significant impairment of tumor growth over 30 days.

Example 5—Modified B Cells that Express and Secrete Payloads

Experimental Design. A BALB/c mouse CT26 tumor model was used to evaluate the efficacy of modified B cells expressing various payload on tumor volume and survival. Mice were injected with tumor cells at a volume of 100 μL. On day 6 once tumors had reached a volume of 175 $mm^3$, mice were injected with modified B cells expressing various payloads as described below. Tumor volume and survival were measured for 17 days.

Isolation of Mouse PBMCs. Mouse PBMCs or splenocytes are isolated from blood or spleen, respectively. PBMCs are isolated using Lympholyte-M (CedarLane, Cat #CL5030). Splenocytes are isolated by manual cell separation through a 70 micron nylon cell strainer. B cells are then isolated from PBMCs or splenocytes via immunomagnetic negative selection using EasySep® Mouse B cell Isolation Kit (Stem Cell Technologies, Cat #19854).

Selection of Payloads. Nucleic acid sequences expressing payload peptides or proteins are transfected or transduced into isolated B cells. The following twelve peptides were identified for their potential to (i) recruit and activate dendritic cells; (ii) initiate homing and guidance of dendritic cells and T cells into the tumor site; and (iii) activate effector T cells. The payloads screened are listed in Table 9.

Each mouse was either given a combination of 4-5 payloads, or isolated B cells (without payload) or saline as a control. In total, there were twenty-seven groups (n=5 mice/group). The experimental groups are identified in Table 11.

TABLE 11

| Group # | Treatment |
|---|---|
| 3 | FLT3L, XCL1, CXCL13, CD40L-MB, TLR |
| 8 | FLT3L, XCL1, mLIGHT, CD80-MB |
| 21 | FLT3L, XCL1, CCL21, CD40L-MB |
| 26 | Saline |
| 27 | B cells (no payload) |

Generation of Payload Expressing B Cells. For transfection, purified or cultured B cells are washed and suspended in Cytoporation Medium T (BTX, Cat #47-0002) at $5\times10^6$ to $25\times10^6$ cells per ml and mixed with 7.5 μg to 50 μg RNA (RNA constructs are designed and prepped in house or purchased from TriLink using CleanCap® and fully substituted with Pseudo-U). 200 μL cell/RNA suspension electroporated using BTX Agilpulse® Electroporation System.

Dosing. Tumor volume was between 100 $mm^3$ and 150 $mm^3$ at the time of the first injection. For the groups receiving 4 payloads, each payload was delivered at $2.5\times10^5$ cells per injection for a total of $10^6$ cells delivered. For the groups receiving 5 payloads, each pay load was delivered at $2.5\times10^5$ cells per injection for a total of $1.25\times10^6$ cells delivered. Payloads were injected intra-tumor. The volume of administration was 50 μL for groups receiving 4 payloads, the volume of administration was 100 HI, for groups receiving 5 payloads.

Payload Administration Procedures. Cells were harvested with versene (not in the presence of trypsin). Once collected, the cells were counted, spun and resuspended in a volume that could be adjusted to $20\times10^6$/ml. TLR agonist (InvivoGen Cat #ODN:1826) by resuspending lyophilized powder in water provided. TLR agonist was resuspended at 10 mg/ml and heated to 70° C. and then let to sit at RT for 1 hour prior to using. The dose of TLR agonist is 50 μg in 50 μl.

Example 6—Anti-Tumor Activity of Intratumorally Injected B Cells

Mouse splenocytes were obtained and isolated via manual cell separation utilizing a 70 micron nylon cell strainer. Autologous (BALB/c) or allogeneic (C57Bl/6) donor mice were used (data shown utilized allogeneic B cells). B cells were isolated from the splenocytes above using immunomagnetic negative selection via the EasySep® Mouse B Cell Isolation Kit (Stem Cell Technologies®, Cat #19854).

Figure 12:
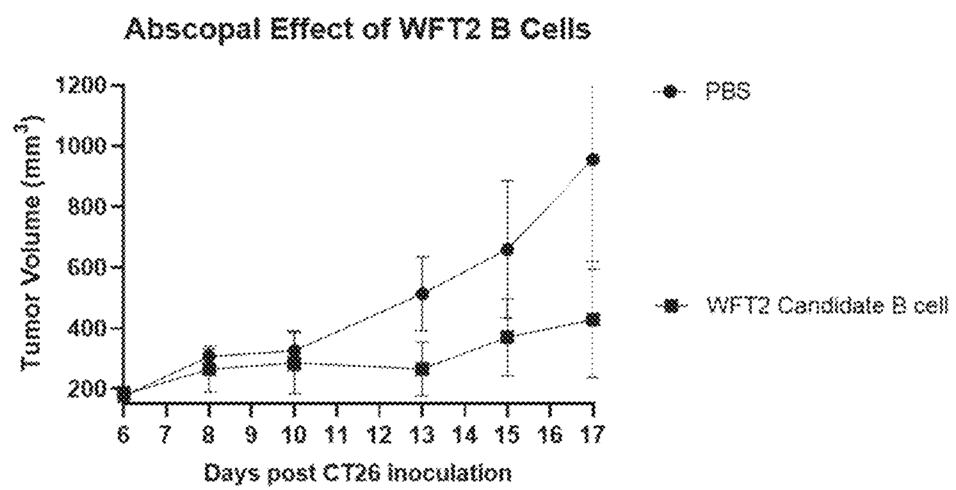
FIG. 12 illustrates the abscopal effect of intratumorally injected B cells. B cells were then injected either (i) fresh or (ii) first stimulated for 16-24 hours in growth media (RPMI, 10% FBS, 1% Pen/Strep, 5 ng/ml recombinant mouse IL-4, 100 uM beta-mercaptoethanol) with 5 μg/ml Lipopolysaccharide. $5\times10^6$ B cells were then intratumorally injected into the CT26 mouse model, and anti-tumor responses in the distal (abscopal) tumor where measured. Tumors were implanted at day 0, and at day 6 palpable tumor mass was observed. Treatment was initiated on day 6 intratumorally.

B cells were then injected either (i) fresh or (ii) first stimulated for 16-24 hours in growth media (RPMI, 10% FBS, 1% Pen/Strep, 5 ng/ml recombinant mouse IL-4, 100 uM beta-mercaptoethanol) with 5 μg/ml Lipopolysaccharide. $5\times10^6$ B cells were then intratumorally injected into the CT26 mouse model, and anti-tumor responses in the distal (abscopal) tumor where measured. Tumors were implanted at day 0, and at day 6 palpable tumor mass was observed. Treatment was initiated on day 6 intratumorally. The results are set forth in FIG. 12.

Example 7—Expression of Chimeric Antigen Receptor (CAR) in B Cells Using RNA Electroporation to Make CAR B Cells Mouse PBMCs or splenocytes were isolated from blood or spleen as follows. Mouse PBMCs were isolated using Lympholyte-M (CedarLane, Cat #CL5030), and splenocytes were isolated by manual cell separation via passage through a 70 micron nylon cell strainer. B cells were then isolated from PBMCs or splenocytes, respectively, via immunomagnetic negative selection using the EasySep® Mouse B Cell Isolation Kit (Stem Cell Technologies, Cat #19854).

B cells were then stimulated for 16-24 hours in growth media (RPMI, 10% FBS, 1% Pen/Strep, 5 ng/ml recombinant mouse IL-4, and 100 uM beta-mercaptoethanol) with 5-15 ug/ml lipopolysaccharide. B cells were then transduced or transfected using known techniques (viral transfection or electroporation) to achieve either stable or transient expression of CAR-B. A strep II tag was incorporated for post-translational detection. Representative CAR-Bs depicted are as follows:

1. XENP PSMA CBCR (3× strep II tag)
2. HyHEL10 CBCR (3× strep II tag)
3. D1.3-M3 HEL CBCR (3× strep II tag)

Figures 13A, 13B, 13C:
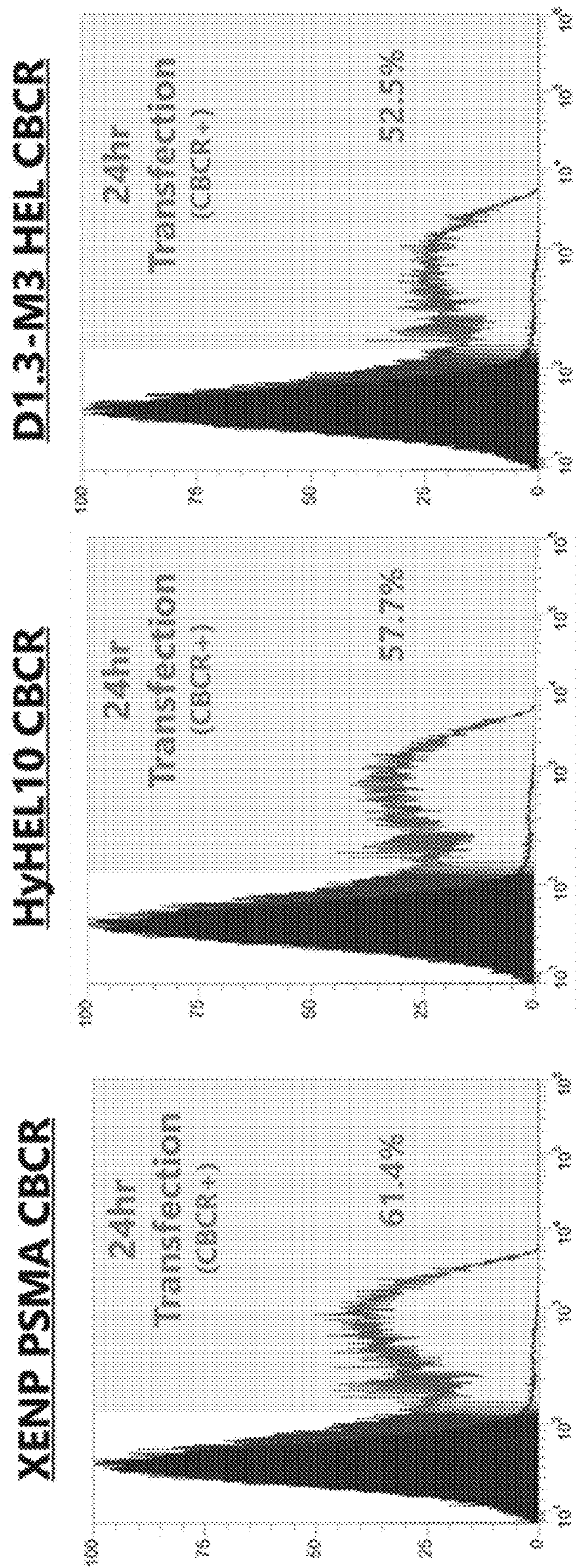
FIGS. 13A-13C illustrates expression of three CAR-B receptors (also referred to as CAR-B receptors) in mouse B cells 24 hours post transfection.

For transfection, purified or cultured B cells were washed and suspended in Cytoporation Medium T (BTX, Cat #47-0002) at $5\times10^6$ to $25\times10^6$ cells per ml and mixed with 7.5 ug to 50 ug RNA (RNA constructs were designed and prepped either in-house or purchased from TriLink using CleanCap® and fully substituted with Pseudo-U). A 200 ul cell/RNA suspension was obtained and electroporated using the BTX AgilePulse® Electroporation System. Cells were then washed in PBS and prepped for IV injection into immune-incompetent mice with established HepG2 tumor cells that express respective antigen (e.g. GPC3, HEL, PSMA). Translation and expression of protein of interest was then measured using an anti-Strep II tag antibody. The results are set forth in FIG. 13. In FIG. 13, the X axis shows strength of expression signal as measured by flow cytometry, and the Y axis sets forth percent of cells expressing the desired protein of interest (PSMA, HEL).

This experiment demonstrates that the desired RNA sequence/s are successfully transfected or transduced (accordingly), the RNA is successfully translated, and the desired protein of interest is expressed on the cell surface.

Example 8—Modified B Cells Expressing Integrins and Homing Receptors

Nucleic acid constructs expressing an integrin, a homing receptor, or both are constructed using known techniques. Mouse and Human B cells are transfected or transduced (accordingly) with the nucleic acid constructs to express the integrin, the homing receptor, or both. These modified cells are administered intravenously into mice or a human host. Time-lapse imaging will measure accumulation of the modified B cells at the site/target of interest, such as a homing or target tissue, an inflammatory site in a specific location or tissue, or a tumor or tumor microenvironment, to establish that expression of an integrin and/or a homing receptor of defined homing specificity endows the B cells with the ability to home to and accumulate at the site/target of interest where delivery of therapeutic payloads is desirable. A screening study is conducted according to the techniques of Example 5 to examine delivery and effect of payloads at the site/target of interest.

Example 9—Altering B Cell Trafficking

Isolated B cells are cultured with a specific concentration of all-trans-retinoic acid (ATRA) or derivatives thereof that induce expression of $\alpha4\beta7$ integrin and the homing receptor CCR9. Thereafter, the B cells are harvested and administered intravenously into mice. There are two experimental groups of the recipient mice. The first group of mice are pre-treated with DSS or TNBS to induce gut inflammation. The second group of mice are not treated with DSS or TNBS. Inflammation similar to that observed in human intestinal bowl diseases is induced by pretreatment with DSS or TNBS. Administered B cells treated with ATRA or derivative thereof will home to areas of inflammation consistent with their homing potential due to increased expression of $\alpha4\beta7$ integrin and the homing receptor CCR9.

Example 10—Modified B Cells Expressing Immune Inhibitory Molecules

Nucleic acid constructs expressing an immune inhibitory molecule selected from IL-10, TGF-β, PD-L1, PD-L2, LAG-3, and TIM-3, or any combinations thereof, are constructed using known techniques. Mouse and Human B cells are transfected or transduced (accordingly) with the nucleic acid constructs to express one or more of the immune inhibitory molecules listed above. These modified cells are administered intravenously into mice or a human host or elsewhere near or at sites of inflammation. Time-lapse imaging will measure accumulation of the modified B cells at a site/target of interest, such as a homing or target tissue, an inflammatory site in a specific location or tissue, or a tumor or tumor microenvironment, to establish that inflammation at the site and autoimmune activity of the B cells localized to the site are decreased, thereby leading to a positive therapeutic response.

Example 11—Activation of B Cells with TLRs

B cells are treated with TLR agonists and/or modified to express a constitutively active TLR for use in potentiating B cells for immune responses and producing potent effector B cells to increase antigen-specific immune responses in a subject. Isolated mouse or human B cells are treated in vitro with a TLR agonist at the same time or in advance of the administration of the B cells. In some instances, the mouse or human B cells are treated with more than one TLR agonists.

A modified B cell, transfected or transduced with or without a CAR-B construct of the foregoing examples, is engineered to express one or more constitutively active TLRs. Each TLR is introduced into the modified B cell (transduced or transfected using known techniques) as a DNA construct under the control of a constitutively activated transcriptional pathway. A modified B cell, expressing one or more constitutively active TLRs (with or without a CAR-B construct), is also treated with one or more TLR agonists at the same time or in advance of the administration of the modified B cells to a subject or patient in need thereof. Time-lapse imaging and other known techniques will measure accumulation of the modified B cells in the desired location and confirm expression of the TLR(s) and any expressed CAR-B of a defined specificity.

This experiment will demonstrate that the desired DNA sequence/s encoding specific TLR(s) of interest are successfully transfected or transduced (accordingly) into B cells with or without a CAR-B construct and treated with or without TLR agonist(s), the RNA is successfully translated, the desired TLR(s) are expressed in the B cells for producing potent effector B cells potentiating B cells for immune responses.

Example 12—Antigen Presentation Both in HLA Class I and Class II Molecules Using RNA Electroporated B Cells mRNA Constructs. Exemplary mRNA constructs are designed by fusing a specific antigen, e.g., a tumor antigen or an infectious disease antigen, to the targeting signal of a the lysosomal protein LAMP1, to target the specific antigen to the lysosomes and present the antigen simultaneously and efficiently in both HLA class I and class II molecules. Tumor antigens and infectious disease antigens are well known in the art and can include any antigen of interest against which an immune response is desired. Various mRNA constructs are made encoding at least one specific antigen of interest fused to the targeting signal of LAMP1 that is capable of presenting the specific antigen simultaneously and efficiently by both HLA class I and class II molecules when transfected into a suitable immune cell.

Experimental Design. Isolated mouse or human B cells are electroporated in vitro with an mRNA construct described above (i.e., encoding a specific antigen of interest fused to the targeting signal of LAMP1) using known mRNA electroporation techniques. In some instances, the mouse or human B cells are also transduced or transfected using known techniques with a CAR-B construct according to any of the foregoing examples. The mRNA electroporated B cells, transduced with or without a CAR-B construct of interest, are introduced intravenously into mice or a human host. Time-lapse imaging will measure accumulation of the modified B cells in the desired location and also confirm expression of CAR-B of a defined specificity. Translation and expression of the specific tumor antigens or infectious disease antigens of interest are measured using known techniques to establish that the antigens of interest are targeted to the lysosomes and presented simultaneously and efficiently by both HLA class I and class II molecules.

This experiment will demonstrate that the desired mRNA sequence/s encoding specific antigens of interest fused to a targeting signal are successfully transfected into B cells (which, if desired, are also transduced with a CAR-B construct), the mRNA is successfully translated, and the electroporated and modified B cells simultaneously and efficiently present the specific antigen of interest by both HLA class I and class II molecules for increasing antigen-specific immune responses in a subject.

Figure 14:
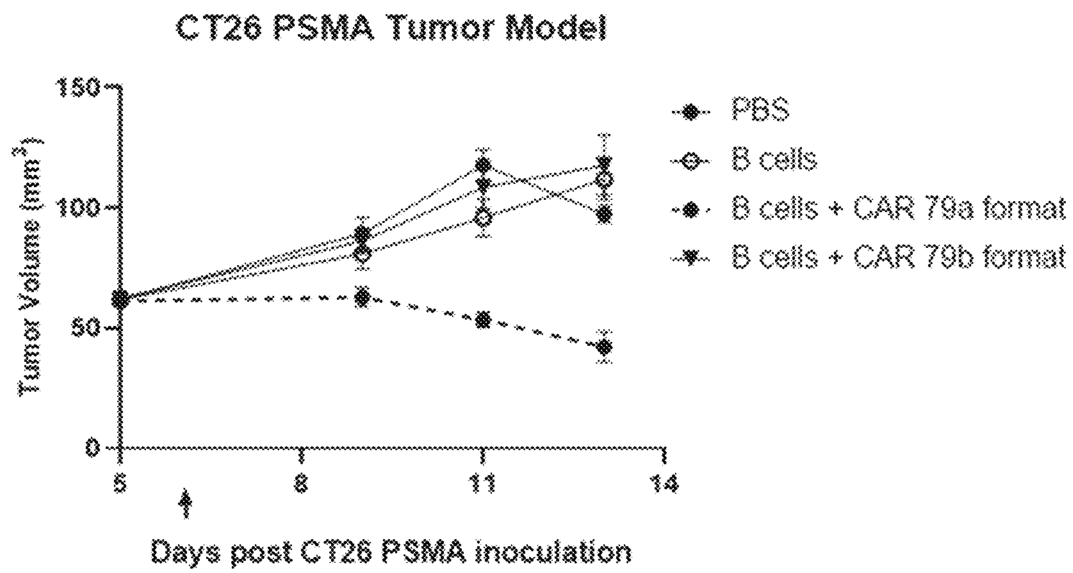
FIG. 14 illustrates the efficacy of PSMA-specific CAR engineered murine B cells on tumor volume and survival in BALB/c mice with CT26-PSMA tumors.

Example 13—B Cells Expressing a PSMA-Specific CAR Reduce Tumor Growth in CT26-PSMA Tumors Mouse Tumor Model. A BALB/c CT26-PSMA tumor model engineered to express human PSMA was used to evaluate the efficacy of PSMA-specific CAR engineered murine B cells on tumor volume and survival. Eight-week-old BALB/c mice were injected on one hind flank with $1.0\times10^6$ CT26-PSMA tumor cells in a volume of 50 μl. On day 5 when the tumor volume reached approximately 60 $mm^3$ the mice were distributed equally into 3 groups of 10 mice. Treatment of mice was started on day 6 using murine B cells engineered with mRNA encoding two different PSMA-specific CAR formats or un-engineered B cells administered intravenously at a dose of $1.5\times10^6$ cells in 100 μl, or saline on day 6. Tumor volume was measured using calipers on day 5, 9, 11, and 13. There was a statistically significant tumor reduction of 57% in the PSMA-CAR group (format 79a) relative to saline on day 13. There was not a significant reduction of tumor volume on day 13 in the PSMA-CAR treatment group (format 79b) relative to saline (FIG. 14).

Engineering of Murine B Cells. Mouse splenocytes were isolated from BALB/c donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, 5 ng/ml recombinant mouse IL-4, 100 μM beta-mercaptoethanol) with anti-CD40 (250 ng/ml). Cells were then electroporated with 20 μg CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 μl of cell suspension were used per dose.

PSMA construct CD79a: pmRNA_d7_13_anti hPSMA(X-ENP14484) scFv-mCD8H-mCD28M-mCD79aE #ab-1

PSMA construct CD79b: pmRNA_d7_13_anti hPSMA(X-ENP14484) scFv-mCD8H-mCD28M-mCD79bE #ac-1

Figure 15:
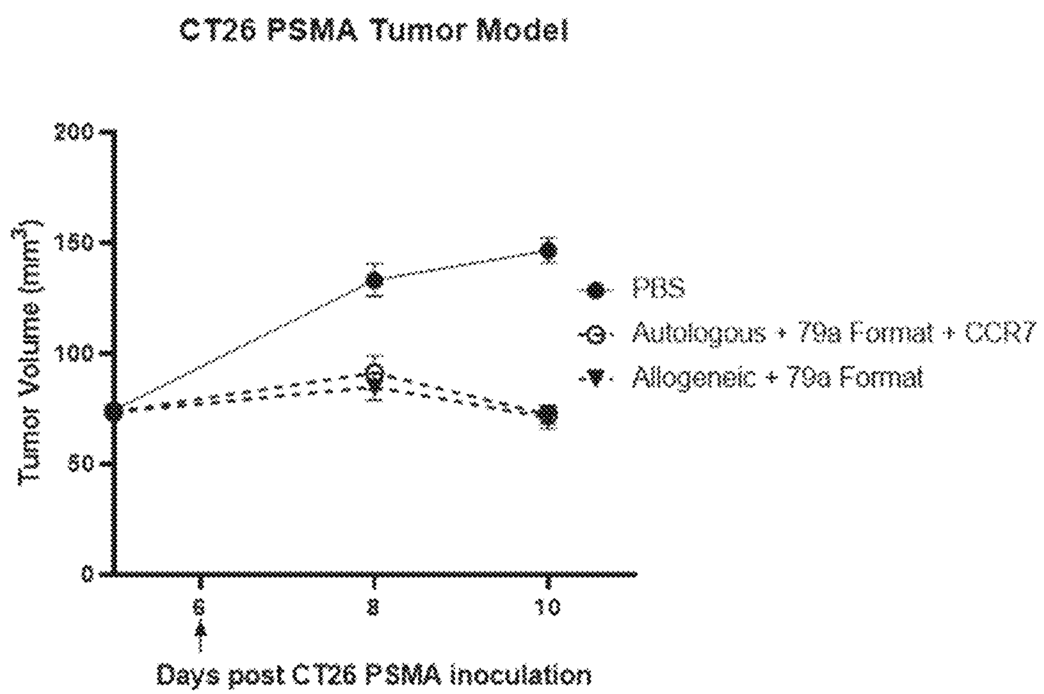
FIG. 15 illustrates the efficacy of PSMA-specific CAR engineered allogenic B cells on tumor volume and survival in BALB/c mice with CT26-PSMA tumors.

Example 14—Allogenic B Cells Expressing a PSMA-Specific CAR Reduce Tumor Growth in CT26-PSMA Tumors Mouse Tumor Model. A BALB/c CT26-PSMA tumor model engineered to express human PSMA was used to evaluate the efficacy of PSMA-specific CAR engineered allogeneic murine B cells on tumor volume and survival. Eight-week-old BALB/c mice were injected on one hind flank with $1.0\times10^6$ CT26-PSMA tumor cells in a volume of 50 μl. On day 5 when the tumor volume reached approximately 70 $mm^3$ the mice were distributed equally into 3 groups of 10 mice. Treatment of mice was started on day 6 using autologous murine B cells engineered with mRNA encoding a PSMA-specific CAR and an mRNA encoding CCR7 or allogeneic murine B cells engineered with mRNA encoding a PSMA-specific CAR administered intravenously at a dose of $1.5\times10^6$ cells in 100 μl, or saline. Tumor volume was measured using calipers on day 5, 8, and 10. There was a statistically significant tumor reduction of 51% in the allogeneic and autologous engineered B cell groups relative to saline on day 10 (FIG. 15). ($p<0.005$).

Engineering of Murine B Cells. Mouse splenocytes were isolated from autologous BALB/c and allogeneic C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, recombinant mouse IL-4, 100 μM beta-mercaptoethanol) with anti-CD40 (250 ng/ml). Cells were then electroporated with 20 ug CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 μl of cell suspension were used per dose.

Example 15—the Antitumor Activity of PSMA-CAR-Engineered B Cells Depends on an Intact Host Immune System Mouse Tumor Models. The effect of antitumor PSMA-CAR B cells was studied in WT and immunocompromised NSG mice.

WT Mice. A BALB/c CT26-PSMA tumor model engineered to express human PSMA was used to evaluate the efficacy of PSMA-specific CAR engineered murine B cells on tumor volume and survival in WT mice. Eight-week-old BALB/c mice were injected on one hind flank with $1.0\times10^6$ CT26-PSMA tumor cells in a volume of 50 μl. On day 5 when the tumor volume reached approximately 60 $mm^3$ the mice were distributed equally into 4 groups of 10 mice. Treatment of mice was started on day 6 using murine B cells engineered with mRNA encoding two different PSMA-specific CAR formats or un-engineered B cells administered intravenously at a dose of $1.5\times10^6$ cells in 1004 or saline on day 6. Tumor volume was measured using calipers on day 5, 9, 11, and 13. There was a statistically significant tumor reduction of 57% in the PSMA-CAR group (format 79a) relative to saline on day 13. There was not a significant reduction of tumor volume on day 13 in the PSMA-CAR treatment group (format 79b) or un-engineered B cells, relative to saline (FIG. 14).

Figure 16:
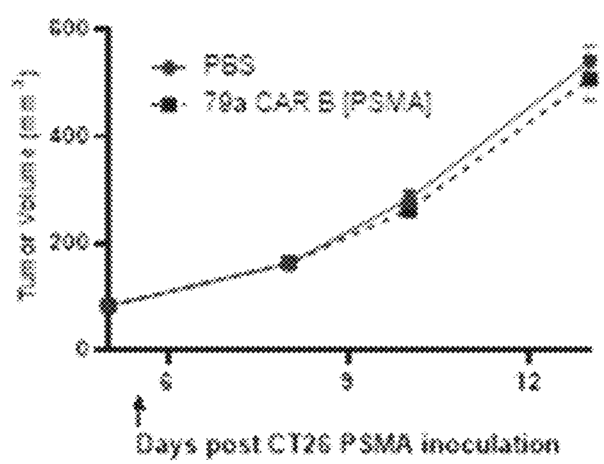
FIG. 16 illustrates the efficacy of PSMA-specific CAR engineered murine B cells on immunocompromised BALB/c mice with CT26-PSMA tumors.

NSG Mice. A BALB/c CT26-PSMA tumor model engineered to express human PSMA was used to evaluate the efficacy of PSMA-specific CAR engineered murine B cells on tumor volume and survival in immunocompromised mice. Eight-week-old NSG mice were injected on one hind flank with $1.0\times10^6$ CT26-PSMA tumor cells in a volume of 50 μl. On day 5 when the tumor volume reached approximately 60 $mm^3$ the mice were distributed equally into 2 groups of mice. Treatment of mice was started on day 6 using murine B cells engineered with mRNA encoding a PSMA-specific CAR format administered intravenously at a dose of $1.5\times10^6$ cells in 1004 or saline on day 6. Tumor volume was measured using calipers on day 5, 8, 10, and 13. There was no significant reduction in tumor volume in the PSMA-CAR group (format 79a) relative to saline on day 13 (FIG. 16B).

Engineering of Murine B Cells. Mouse splenocytes were isolated from autologous BALB/c and allogeneic C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, recombinant mouse IL-4, 100 μM beta-mercaptoethanol) with anti-CD40 (250 ng/ml). Cells were then electroporated with 20 ug CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 μl of cell suspension were used per dose.

PSMA construct CD79a: pmRNA_d7_13_anti hPSMA(XENP14484) scFv-mCD8H-mCD28M-mCD79aE #ab-1

PSMA construct CD79b: pmRNA_d7_13_anti hPSMA(XENP14484) scFv-mCD8H-mCD28M-mCD79bE #ac-1

Figure 17:
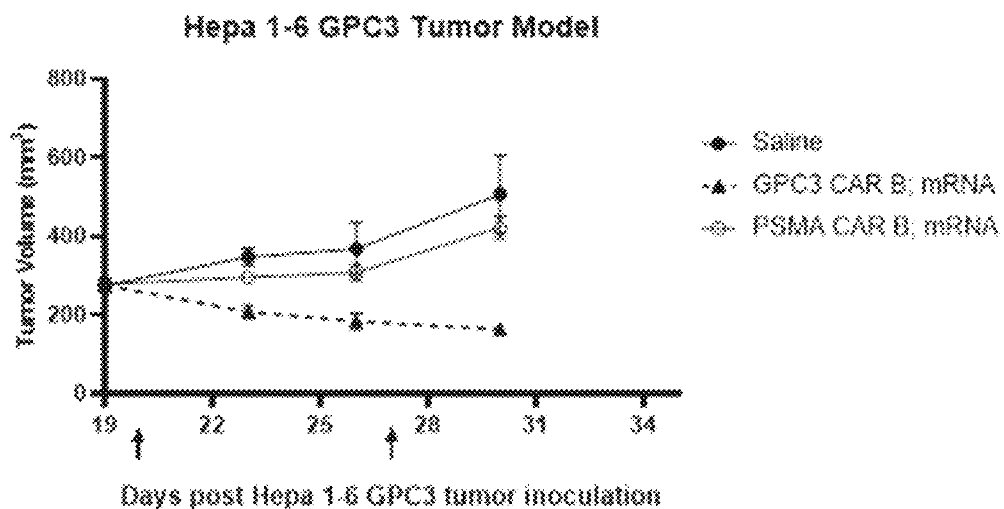
FIG. 17 illustrates the efficacy of murine B cells on tumor volume and survival in C57Bl/6 mice with HEPA 1-6 GPC3 tumors.

Example 16—B Cells Expressing a GPC3-Specific CAR Reduce Tumor Growth in HEPA 1-6 GPC3 Tumors Mouse Tumor Model. A C57Bl/6 HEPA 1-6 tumor model engineered to express human GPC3 (HEPA 1-6-GPC3) was used to evaluate the efficacy of murine B cells on tumor volume and survival. Eight-week-old C57Bl/6 mice were injected on one hind flank with $5.0\times10^6$ HEPA 1-6-GPC3 tumor cells at a volume of 200 μl. On day 19 when the tumors volume reached approximately 250 $mm^3$ the mice were distributed equally into 3 groups of 10 mice. Treatment of mice was started on day 20 using murine B cells engineered with mRNA encoding a GPC3-specific CAR or a PSMA-specific CAR administered intravenously at a dose of $1.5\times10^6$ cells in 1000, or saline on day 20 and day 27. Tumor volume was measured using calipers on day 19, 23, 26, and 30. There was a statistically significant tumor reduction of 68% in the GPC3-CAR group relative to saline on day 30. There was not a significant reduction of tumor volume on day 30 in the PSMA-CAR treatment group relative to saline. (note: this study is still in progress on Jan. 19, 2021) (FIG. 17).

Engineering of Murine B Cells. Mouse splenocytes were isolated from C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, 5 ng/ml recombinant mouse IL-4, 100 μM beta-mercaptoethanol) with anti-CD40 (250 ng/ml). Cells were then electroporated with 20 μg CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 μl of cell suspension were used per dose.

GPC3 mRNA construct: pmRNA_d7_13_anti-hGPC3 scFv-mCD8H-mCD28M-mCD79aE #15-1

PSMA construct: pmRNA_d7_13_anti hPSMA (XENP14484) scFv-mCD8H-mCD28M-mCD79aE #ab-1

Example 17—Multimerized GPC3 can Activate NFκB Expression of Luciferase in Cells Expressing a GPC3 CAR in a Dose-Responsive Manner CAR-B Construct Design. Five CAR-B constructs were designed using three basic formats (i) CAR 2 (an scFv, a hinge domain, a transmembrane domain and a signaling domain (see FIG XA)); (ii) CAR 3 (a multimerized receptor complex with 2 of each of the following: an scFv, a hinge domain, an FC domain, a transmembrane domain and a cytoplasmic tail (see FIG XB)); (iii) CAR 4 (a multimerized receptor complex with 2 of each of the following: (a FAB domain, a hinge domain, an FC domain, a transmembrane domain and a cytoplasmic tail (see FIG XC). The five CAR-B constructs are as follows:

TABLE 12

| | |
|---|---|
| pWF-506 (SEQ ID NO. 140/141) | pmRNA__d7__13__anti-hGPC3 scFv-hIgG1 Fc [TM + cyto] A-1 (CAR 3) |
| pWF-507 (SEQ ID NO. 142/143)/ pWF-508 (SEQ ID NO. 144/145) | pmRNA__d7__13__anti-hGPC3 vl-hcLamda/ pmRNA__d7__13__anti-hGPC3 vH-hlgHg1 [TM + cyto] (CAR 4) |
| pWF-509 (SEQ ID NO. 146/147) | pmRNA__d7__13__anti-hGPC3 scFv-hCD8H-hCD28M-hCD79bE (CAR 2) |
| pWF-510 (SEQ ID NO. 148/149) | pmRNA__d7__13__anti-hGPC3 scFv-hCD8H-hCD28M-hCD79aE (CAR 2) |

Figure 18:
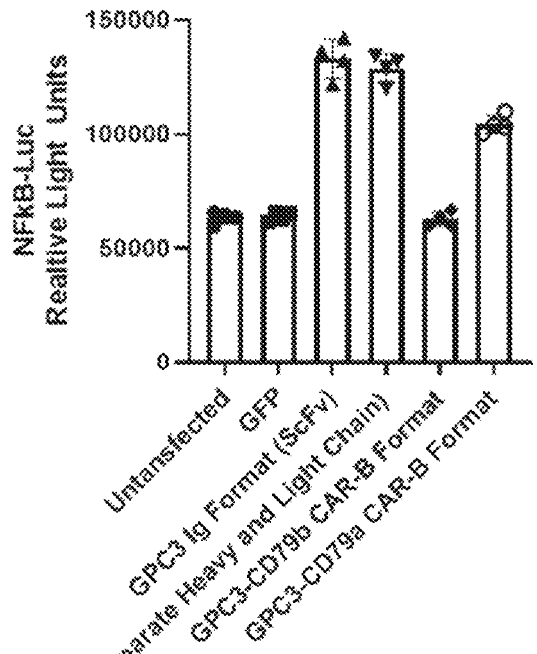
FIG. 18 illustrates NFKb signaling in luciferase reporter cells in B cells engineered with four different CAR constructs that recognized GPC3, using GFP as a control.

NFκB Reporter Assay: Antigen induced signaling. Ramos NFκB-luciferase reporter cells were transduced with mRNA coding for one of the CAR-B constructs listed above. Ramos NFκB-luciferase reporter cells were transfected at 280 V and 1 msec with 10 μg of RNA in 200 μL of electroporation buffer followed by culturing overnight in growth medium. The cells were left at room temperature for 4 hours to quiesce the cells to reduce background. 30,000 of the transfected cells were transferred to each well in a multi-well plate in a volume of 30 μL per well. The transfected Ramos cells were then incubated with GPC3 protein multimerized with streptavidin, streptavidin control or GPC3-Fc protein for 3 hours in growth medium. 30 μL of Bioglo substrate (Promega) was added to each well and the plate was read within 5 minutes using a luminometer. As demonstrated in FIG. 18, multimerized GPC3 was capable of activating NFκB expression of luciferase in cells expressing three of the four GPC3 CAR-Bs except pWF-509 (GPC3-CD79b). All four constructs displayed good binding to GPC3 in FACS assays. Therefore, CD79b was an example where a CAR, which had good binding affinity, did not signal.

Figure 19:
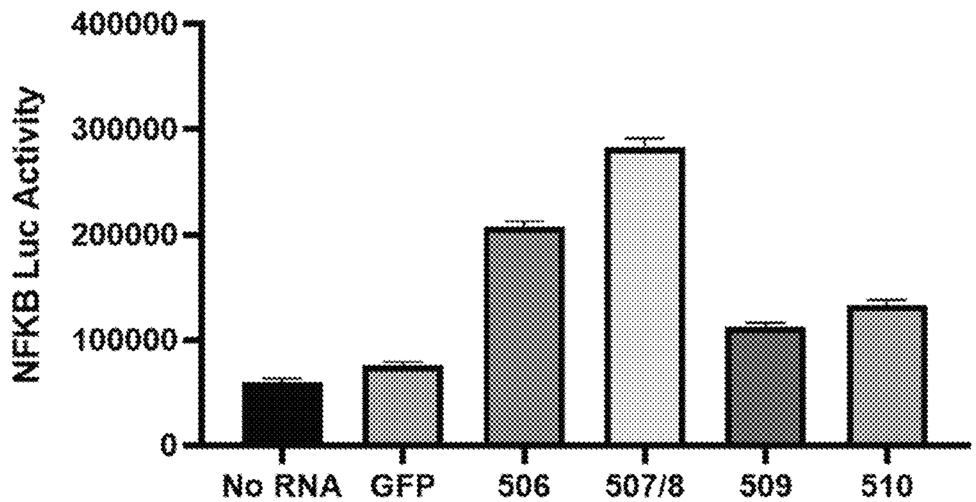
FIG. 19 illustrates basal or tonic NFKb activity in the absence of cognate target antigen in CAR constructs expressed in human B cell reporter line.

NFκB Reporter Assay: Tonic Signaling. Tonic signaling was also assessed, using the NFκB Reporter Assay. CAR constructs, which induced elevated tonic signaling in the absence of cognate antigen binding, were generated. FIG. 19 shows that the four CAR-B constructs were expressed in a human B cell reporter line and NFκB luciferase activity was measured in the absence of cognate target antigen. Each construct displayed significant tonic signaling activity. Engineered B cells with tonic signaling CAR Bs remained at a high number in vivo and led to high and durable expression of replacement factors or other payloads.

Figure 20:
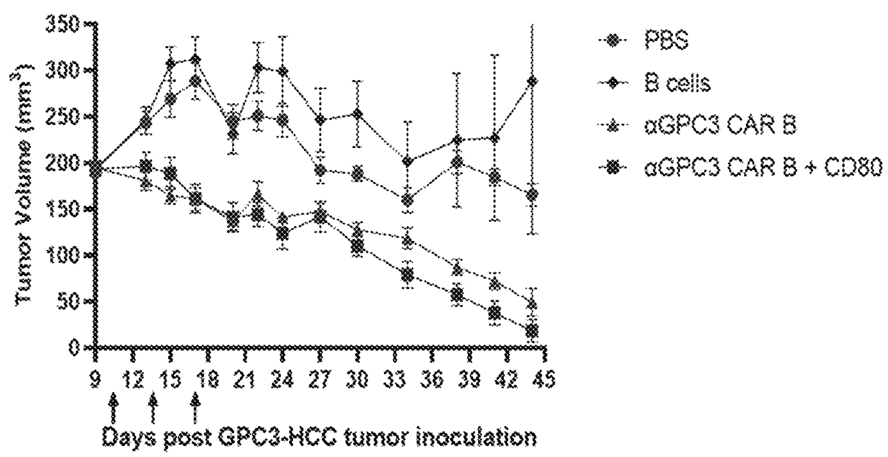
FIG. 20 illustrates the efficacy of murine B cells electroporated with anti-GPC3CAR-CD79a and a CD80 payload mRNAs in syngeneic C57Bl/6 mice with HEPA1-6GPC3 tumors.

Example 18—a CD80 Payload Enhances the Antitumor Activity of Anti-GPC3CAR-CD79a B Cells Experimental Design. A syngeneic C57Bl/6 mouse HEPA1-6GPC3 tumor is a model of human HCC engineered to express human GPC3. This model was used to evaluate the efficacy of murine B cells electroporated with anti-GPC3CAR-CD79a and a CD80 payload mRNAs. Mice were injected on one hind flank with $5.0\times10^{6}$ HEPA1-6GPC3 tumor cells at a volume of 200 ul in matrigel. On day 11, 14, and 17 the mice were administered a 200 ul IV dose of $1.5\times10^{6}$ B cells, B cells engineered with anti-GPC3CAR-CD79a, B cells engineered with anti-GPC3CAR-CD79a and CD80, or saline as indicated in FIG. 20. The B cells were engineered with mRNA as described below. Tumor volume was monitored on multiple days as indicated in FIG. 20.

Figures 21A, 21B, 21C:
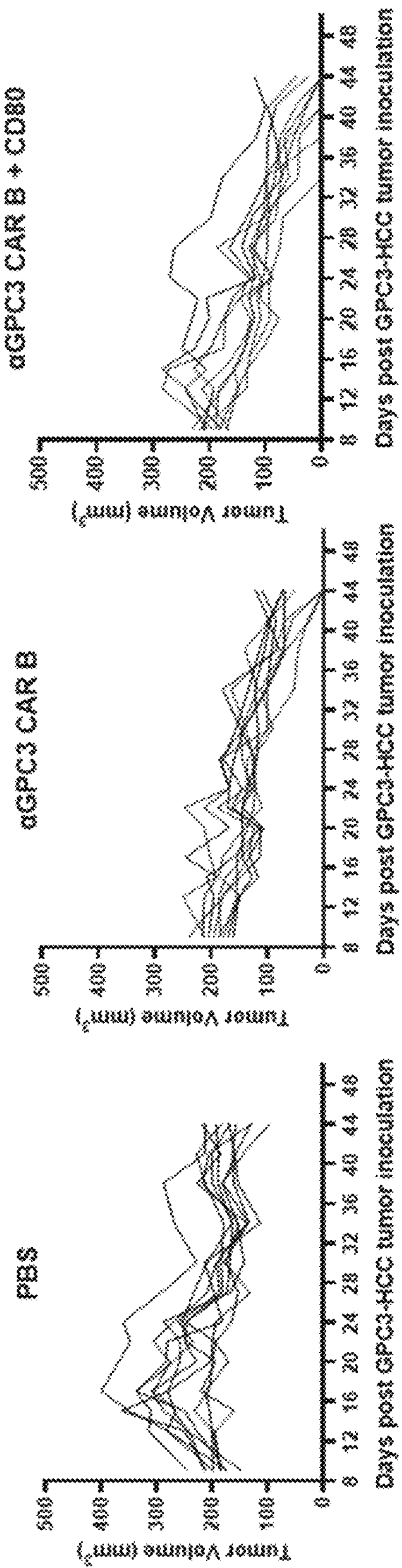
FIGS. 21A-21C illustrate the responses of the saline control, anti-GPC3CAR-CD79a, and anti-GPC3CAR-CD79a plus CD80 combo B cell groups.

In FIG. 20, both the anti-GPC3CAR-CD79a, and anti-GPC3CAR-CD79a plus CD80 combo displayed a statistically significant effect relative to saline or un-engineered B cells on day 44 and at multiple earlier time points. Additionally, by day 44 there were no complete responses in the saline control or B cell control groups but the anti-GPC3CAR-CD79a, and anti-GPC3CAR-CD79a plus CD80 combo resulted in 4 and 7 complete responses, respectively, as indicated in FIGS. 21A-21C. These data demonstrate that inclusion of the CD80 payload as mRNA potentiated the antitumor activity of B cells co-electroporated with an antigen-specific GPC3 CAR.

B Cell preparation. Mouse splenocytes were isolated from C57Bl/6 donor spleens by mechanical cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 1% Pen/Strep, 5 ng/ml recombinant mouse IL-4, 100 uM beta-mercaptoethanol) with 250 ng/ml CD40 antibody (anti-murine CD40 Ab). Cells were then electroporated with 20 ug mRNA per $1.0\times10^{7}$ B cells using BTX AgilePulse electroporation system set at 400V for 1 ms, 2 ms interval for 5 pulses. When two mRNA's were cotransfected, 20 ug of each mRNA was used. Immediately after electroporation, the cells were washed in PBS and prepared for IV administration at a dose of $1.0\times10^{7}$ per 200 ul. The electroporated cells were administered to mice within 90 minutes after electroporation.

Figures 22A, 22B, 22C:
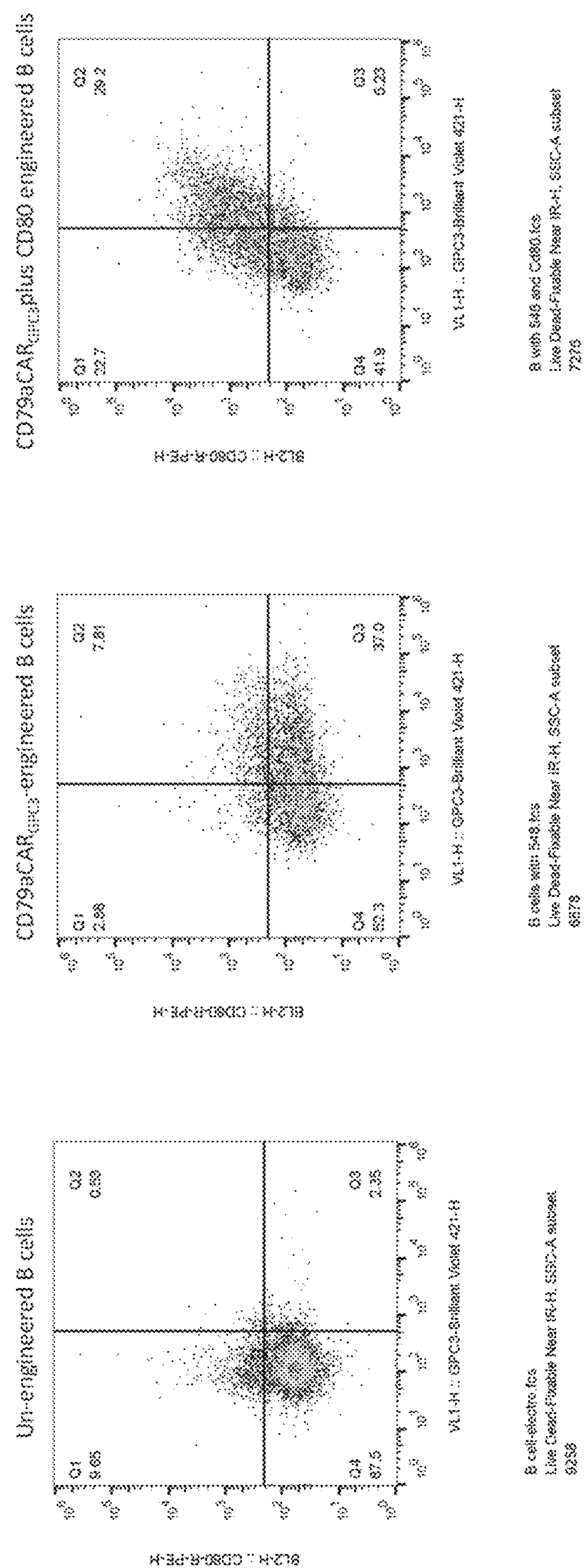
FIGS. 22A-22C illustrate the expression of the GPC3 CAR post-electroporation, using FACS plots.

Twelve hours after electroporation, a small aliquot of the cells were stained for expression of anti-GPC3CAR-CD79a and CD80 expression. For detection of anti-GPC3CAR-CD79a expression, GPC3-Avitag and Streptavidin-BV421 were used. CD80 expression was measured with an anti-CD80-PE FACS antibody. The FACS plots in FIGS. 22A-22C show expression of the GPC3 CAR post-electroporation. CD80 was expressed at a basal level in un-engineered B cells, thus accounting for the ~10% positivity. This level remained in the CAR sample, but was increased dramatically in the CAR+CD80 sample. The latter suggested efficient expression of CD80.

What is claimed:

1. A method for treating cancer by stimulating or enhancing an immune response in a subject, comprising administering to the subject a population of modified B cells comprising a chimeric receptor, wherein said chimeric receptor comprises:

a) an extracellular domain comprising an extracellular binding domain specific to a target antigen associated with cancer;

b) a transmembrane domain; and c) a cytoplasmic domain comprising:

(i) a cytoplasmic tail comprising a native B cell receptor C-terminus, or (ii) at least one signaling domain, wherein, upon the binding of the extracellular binding domain to the target antigen, a signal is induced that activates at least one effector function of the modified B cells to stimulate or enhance an immune response in the subject, and wherein the at least one effector function comprises antigen presentation.

2. The method of claim 1, where the at least one effector function further comprises at least one effector function selected from the group consisting of activation, proliferation, protein expression or secretion, antibody expression or secretion, receptor expression or secretion, integrin expression, transcription induction, RNA translation, dendritic cell activation or recruitment, T cell activation, initiation of dendritic cell or T cell homing to a site/target of interest, and tertiary lymphoid structure formation.

3. The method of claim 2, wherein the at least one effector function further comprises expression or secretion of a payload, and wherein the payload is not naturally expressed in a B cell or is expressed at higher levels than is naturally expressed in a B cell.

4. The method of claim 1, wherein the at least one effector function comprises presentation of the target antigen or protein, or an epitope derived from the target antigen or protein in an HLA or MHC complex.

5. The method of claim 1, wherein the at least one effector function comprises presentation of an antigen or protein, or an epitope derived from an antigen or protein in an HLA or MHC complex.

6. The method of claim 1, wherein the modified B cell is administered intra-tumorally, intravenously, subcutaneously, intradermally, or within an inflammatory lesion.

7. The method of claim 1, further comprising administering one or more checkpoint inhibitors, with or without an additional chemotherapeutic agent.

8. The method of claim 7, wherein the checkpoint inhibitor is capable of inhibiting a checkpoint molecule selected from the group consisting of: PD-1, PD-L1, CTLA-4, LAG3, TIM-3 and NKG2A.

9. The method of claim 1, further comprising administering a T cell co stimulatory molecule.

10. The method of claim 9, wherein the T cell costimulatory molecule is selected from the group consisting of: CD80, CD86, ICOSL, 4-1BBL, OX40L, CD27, and LIGHT.

11. The method of claim 1, wherein said extracellular binding domain is a single chain variable fragment (scFv), or a full-length antibody or an antibody fragment, or the extracellular domain of a receptor or ligand.

12. The method of claim 1, wherein said cytoplasmic domain comprises a domain that is selected from the group consisting of: CD79a (Immunoglobulin α), CD79b (Immunoglobulin ß), CD40, CD19, CD137, Fcγr2a, MyD88, CD21, Syk, FYN, LYN, P13K, BTK PLCγ2, CD3ζ, and BLNK.

13. The method of claim 1, wherein said at least one signaling domain comprises an immunoreceptor tyrosine-based activation motif (ITAM) of a CD79a.

14. The method of claim 3, wherein the payload is an antibody, antibody fragment, antigen-binding fragment, F(ab')2, Fab, Fab', scFv, or Fc fragment.

15. The method of claim 14, wherein modified B cell of claim 14, wherein the payload is secreted or membrane bound.

16. The method of claim 3, wherein said payload is selected from a group of cytokines, chemokines, T cell costimulatory molecules, and checkpoint molecules, the group consisting of: IL-1, IL-7, IL-8, IL-10, IL-12, IL-13, IL-17, IL-18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), GM-CSF, an anti-FAP antibody, a TGF-β trap, decoy or other inhibitory molecule; an anti-BMP antibody; a BMP trap, decoy or other inhibitory molecule.

17. The method of claim 3, wherein said B cell expresses more than one payload.

* * * * *